US011390649B2

(12) United States Patent
Kawaoka et al.

(10) Patent No.: US 11,390,649 B2
(45) Date of Patent: Jul. 19, 2022

(54) INFLUENZA VIRUS REPLICATION FOR VACCINE DEVELOPMENT

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Jihui Ping, Nanjing (CN)

(73) Assignee: Wisconsin Alumni Research Foundation (WARF), Madison, WI (US)

(*) Notice: Subject to any disclaimer, the term of this patent is extended or adjusted under 35 U.S.C. 154(b) by 75 days.

(21) Appl. No.: 16/865,194

(22) Filed: May 1, 2020

(65) Prior Publication Data

US 2021/0061862 A1 Mar. 4, 2021

Related U.S. Application Data

(60) Provisional application No. 62/841,491, filed on May 1, 2019.

(51) Int. Cl.

| | |
|---|---|
| ***A61K 39/145*** | (2006.01) |
| ***A61K 39/00*** | (2006.01) |
| ***A61K 39/12*** | (2006.01) |
| ***C12N 7/00*** | (2006.01) |
| ***C07K 14/005*** | (2006.01) |
| ***A61P 31/16*** | (2006.01) |
| ***A61K 9/00*** | (2006.01) |

(52) U.S. Cl.

CPC ............ *C07K 14/005* (2013.01); *A61K 9/007* (2013.01); *A61K 9/0019* (2013.01); *A61K 39/145* (2013.01); *A61P 31/16* (2018.01); *C12N 7/00* (2013.01); *A61K 2039/54* (2013.01); *A61K 2039/544* (2013.01); *C12N 2760/16121* (2013.01); *C12N 2760/16122* (2013.01); *C12N 2760/16134* (2013.01); *C12N 2760/16152* (2013.01)

(58) Field of Classification Search

CPC ............ C12N 7/00; C12N 2760/16134; A61K 39/145; A61K 39/12; A61P 31/16

See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,716,821 | A | 2/1998 | Wertz et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,872,395 | B2 | 3/2005 | Kawaoka |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,226,774 | B2 | 6/2007 | Kawaoka |
| 7,312,064 | B2 | 12/2007 | Hoffmann |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,670,837 | B2 | 3/2010 | Schwartz |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | De Wit et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,048,430 | B2 | 11/2011 | Yang et al. |
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"Australian Application Serial No. 2001255336, Examiner's First Report dated Feb. 16, 2005", 2 pgs.

(Continued)

*Primary Examiner* — Barry A Chestnut

(74) *Attorney, Agent, or Firm* — Schwegman Lundberg & Woessner, P.A.

(57) ABSTRACT

An isolated recombinant influenza virus is provided having PA, PB1, PB2, NP, NS, M, NA and HA viral segments, wherein the PB1 viral segment encodes a PB1 with a residue other than isoleucine at position 711 or the M viral segment encodes a M1 with a residue other than methionine at position 128, wherein the recombinant influenza virus has enhanced replication relative to a corresponding influenza virus having a PB1 viral segment that encodes a PB1 with an isoleucine at position 711 or having a M viral segment that encodes a M1 with methionine at position 128, as well as methods of making and using the virus.

20 Claims, 64 Drawing Sheets

Specification includes a Sequence Listing.

(56) References Cited

U.S. PATENT DOCUMENTS

| | | | |
|---|---|---|---|
| 8,119,388 | B2 | 2/2012 | Schwartz et al. |
| 8,309,099 | B2 | 11/2012 | Hoffmann |
| 8,354,114 | B2 | 1/2013 | Lu et al. |
| 8,357,376 | B2 | 1/2013 | Liu et al. |
| 8,409,843 | B2 | 4/2013 | Kemble et al. |
| 8,460,914 | B2 | 6/2013 | Gregersen |
| 8,475,806 | B2 | 7/2013 | Kawaoka |
| 8,524,497 | B2 | 9/2013 | Reiter et al. |
| 8,546,123 | B2 | 10/2013 | Lewis |
| 8,574,591 | B2 | 11/2013 | Hoffmann et al. |
| 8,574,593 | B2 | 11/2013 | Yang et al. |
| 8,580,277 | B2 | 11/2013 | Yang et al. |
| 8,591,914 | B2 | 11/2013 | Yang et al. |
| 9,109,013 | B2 | 8/2015 | Kawaoka et al. |
| 9,254,318 | B2 | 2/2016 | Kawaoka et al. |
| 9,284,533 | B2 | 3/2016 | Bilsel et al. |
| 9,474,798 | B2 | 10/2016 | Watanabe et al. |
| 9,757,446 | B2 | 9/2017 | LeFebvre et al. |
| 9,890,363 | B2 | 2/2018 | Kawaoka |
| 9,926,535 | B2 | 3/2018 | Kawaoka et al. |
| 9,950,057 | B2 | 4/2018 | Kawaoka et al. |
| 10,053,671 | B2 | 8/2018 | Kawaoka et al. |
| 10,059,925 | B2 | 8/2018 | Kawaoka et al. |
| 10,119,124 | B2 | 11/2018 | Watanabe et al. |
| 10,130,697 | B2 | 11/2018 | Watanabe |
| 10,172,934 | B2 | 1/2019 | Kawaoka et al. |
| 10,246,686 | B2 | 4/2019 | Kawaoka et al. |
| 2002/0164770 | A1 | 11/2002 | Hoffmann |
| 2002/0197705 | A1 | 12/2002 | Kawaoka |
| 2003/0035814 | A1 | 2/2003 | Kawaoka et al. |
| 2003/0044962 | A1 | 3/2003 | Makizumi et al. |
| 2003/0073223 | A1 | 4/2003 | Groner et al. |
| 2003/0119183 | A1 | 6/2003 | Groner |
| 2003/0194694 | A1 | 10/2003 | Kawaoka |
| 2004/0002061 | A1 | 1/2004 | Kawaoka |
| 2004/0063141 | A1 | 4/2004 | Lok |
| 2004/0077086 | A1 | 4/2004 | Reiter et al. |
| 2004/0219170 | A1 | 11/2004 | Kawaoka |
| 2005/0003349 | A1 | 1/2005 | Kawaoka |
| 2005/0037487 | A1 | 2/2005 | Kawaoka et al. |
| 2005/0118140 | A1 | 6/2005 | Vorlop et al. |
| 2005/0158342 | A1 | 7/2005 | Kemble et al. |
| 2005/0186563 | A1 | 8/2005 | Hoffmann |
| 2005/0202553 | A1 | 9/2005 | Groner et al. |
| 2005/0232950 | A1 | 10/2005 | Kawaoka |
| 2005/0266026 | A1 | 12/2005 | Hoffmann et al. |
| 2006/0057116 | A1 | 3/2006 | Kawaoka et al. |
| 2006/0166321 | A1 | 7/2006 | Kawaoka et al. |
| 2006/0188977 | A1 | 8/2006 | Schwartz et al. |
| 2006/0246092 | A1 | 11/2006 | Neirynck et al. |
| 2007/0231348 | A1 | 10/2007 | Kawaoka et al. |
| 2008/0233560 | A1 | 9/2008 | Hoffmann |
| 2008/0254067 | A1 | 10/2008 | Trepanier et al. |
| 2008/0274141 | A1 | 11/2008 | Groner et al. |
| 2008/0311148 | A1 | 12/2008 | Hoffmann |
| 2008/0311149 | A1 | 12/2008 | Hoffmann |
| 2009/0074812 | A1 | 3/2009 | Watanabe et al. |
| 2009/0081252 | A1 | 3/2009 | Gregersen |
| 2009/0181446 | A1 | 7/2009 | Nouchi et al. |
| 2010/0112000 | A1 | 5/2010 | Schwartz |
| 2010/0183671 | A1 | 7/2010 | Gregersen et al. |
| 2010/0247572 | A1 | 9/2010 | Kawaoka |
| 2011/0027314 | A1 | 2/2011 | Broeker |
| 2011/0045022 | A1 | 2/2011 | Tsai |
| 2011/0110978 | A1 | 5/2011 | Kawaoka et al. |
| 2011/0236417 | A1 | 9/2011 | Watanabe et al. |
| 2012/0020997 | A1 | 1/2012 | Hoffman et al. |
| 2012/0034600 | A1 | 2/2012 | Gregersen |
| 2012/0115206 | A1 | 5/2012 | Schwartz et al. |
| 2012/0156241 | A1 | 6/2012 | De Wit et al. |
| 2012/0207785 | A1 | 8/2012 | Fabry et al. |
| 2013/0095135 | A1 | 4/2013 | Collignon et al. |
| 2013/0183741 | A1 | 7/2013 | Park et al. |
| 2013/0316434 | A1 | 11/2013 | Reiter et al. |
| 2014/0227310 | A1 | 8/2014 | Li et al. |
| 2015/0017205 | A1 | 1/2015 | Kawaoka et al. |
| 2015/0368621 | A1 | 12/2015 | Kawaoka et al. |
| 2016/0024479 | A1 | 1/2016 | Kawaoka et al. |
| 2016/0208223 | A1 | 7/2016 | Kawaoka et al. |
| 2016/0355790 | A1 | 12/2016 | Kawaoka et al. |
| 2017/0067029 | A1 | 3/2017 | Kawaoka et al. |
| 2017/0096645 | A1 | 4/2017 | Watanabe et al. |
| 2017/0258888 | A1 | 9/2017 | Kawaoka |
| 2017/0354730 | A1 | 12/2017 | Kawaoka et al. |
| 2018/0245054 | A1 | 8/2018 | Kawaoka et al. |
| 2018/0340152 | A1 | 11/2018 | Kawaoka et al. |
| 2019/0032023 | A1 | 1/2019 | Kawaoka et al. |
| 2019/0048324 | A1 | 2/2019 | Kawaoka et al. |
| 2019/0117759 | A1 | 4/2019 | Wantanabe et al. |

FOREIGN PATENT DOCUMENTS

| | | | |
|---|---|---|---|
| AU | 2014290203 | B2 | 12/2020 |
| CN | 1826407 | B | 9/2013 |
| CN | 109477074 | A | 3/2019 |
| EP | 0702085 | A1 | 3/1996 |
| EP | 1201760 | A1 | 5/2002 |
| EP | 2010557 | B1 | 2/2014 |
| EP | 1631663 | B1 | 8/2016 |
| IL | 171831 | A | 5/2015 |
| JP | 2004-500842 | A | 1/2004 |
| JP | 2004-531232 | A | 10/2004 |
| JP | 2005-523698 | A | 8/2005 |
| JP | 2005-245302 | A | 9/2005 |
| JP | 2005-535288 | A | 11/2005 |
| JP | 2007-518395 | A | 7/2007 |
| JP | 2009-532352 | A | 9/2009 |
| JP | 4927290 | B2 | 5/2012 |
| JP | 2013-507990 | A | 3/2013 |
| JP | 2014-039551 | A | 3/2014 |
| JP | 2014-131516 | A | 7/2014 |
| JP | 2016-521553 | A | 7/2016 |
| JP | 2016-144463 | A | 8/2016 |
| JP | 2016-524915 | A | 8/2016 |
| JP | 2016-169225 | A | 9/2016 |
| JP | 6352974 | B2 | 6/2018 |
| JP | 6375329 | B2 | 7/2018 |
| JP | 2019-510481 | A | 4/2019 |
| JP | 2020-010711 | A | 1/2020 |
| MX | 285206 | | 3/2011 |
| NO | 341506 | | 11/2017 |
| WO | WO-96/10631 | A1 | 4/1996 |
| WO | WO-96/10632 | A1 | 4/1996 |
| WO | WO-96/40955 | A1 | 12/1996 |
| WO | WO-97/37000 | A1 | 10/1997 |
| WO | WO-98/02530 | A1 | 1/1998 |
| WO | WO-98/53078 | A1 | 11/1998 |
| WO | WO-99/28445 | A1 | 6/1999 |
| WO | WO-00/53786 | A1 | 9/2000 |
| WO | WO-00/60050 | A2 | 10/2000 |
| WO | WO-00/60050 | A3 | 1/2001 |
| WO | WO-0179273 | A2 | 10/2001 |
| WO | WO-0183794 | A2 | 11/2001 |
| WO | WO-02064757 | A2 | 8/2002 |
| WO | WO-03/068923 | A2 | 8/2003 |
| WO | WO-03/076462 | A1 | 9/2003 |
| WO | WO-03/091401 | A2 | 11/2003 |
| WO | WO-04/094466 | A2 | 11/2004 |
| WO | WO-04/112831 | A2 | 12/2004 |
| WO | WO-2005/062820 | A2 | 7/2005 |
| WO | WO-2007/126810 | A2 | 11/2007 |
| WO | WO-2007/126810 | A3 | 11/2007 |
| WO | WO-2008/156778 | A2 | 12/2008 |
| WO | WO-2008/156778 | A3 | 12/2008 |
| WO | WO-2008/157583 | A1 | 12/2008 |
| WO | WO-2008/156778 | A9 | 2/2009 |
| WO | WO-2011/056591 | A1 | 5/2011 |
| WO | WO-2012/177924 | A2 | 12/2012 |
| WO | WO-2013/034069 | A1 | 3/2013 |
| WO | WO-2014/195920 | A2 | 12/2014 |
| WO | WO-2015/009743 | A1 | 1/2015 |
| WO | WO-2015/196150 | A2 | 12/2015 |
| WO | WO-2015/196150 | A3 | 12/2015 |

(56) References Cited

FOREIGN PATENT DOCUMENTS

WO WO-2017/007839 A1 1/2017
WO WO-2017/143236 A1 8/2017
WO WO-2020/223699 A1 11/2020

OTHER PUBLICATIONS

"Australian Application Serial No. 2001255336, Response filed Aug. 23, 2005 to Examiner's First Report dated Feb. 16, 2005", 10 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Respojnse filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Australian Application Serial No. 2014290203, First Examination Report dated Oct. 10, 2019", 4 pgs.
"Australian Application Serial No. 2014290203, Response filed Mar. 13, 2020 to First Examination Report dated Oct. 10, 2019", 16 pgs.
"Australian Application Serial No. 2014290203, Response filed Jun. 24, 2020 to Subsequent Examiners Report dated Mar. 23, 2020", 16 pgs.
"Australian Application Serial No. 2014290203, Response filed Sep. 29, 2020 to Subsequent Examiners Report dated Jul. 21, 2020", 25 pgs.
"Australian Application Serial No. 2014290203, Response filed Dec. 9, 2020 to Subsequent Examiners Report dated Oct. 6, 2020", 14 pgs.
"Australian Application Serial No. 2014290203, Subsequent Examiners Report dated Mar. 23, 2020", 6 pgs.
"Australian Application Serial No. 2014290203, Subsequent Examiners Report dated Jul. 21, 2020", 5 pgs.
"Australian Application Serial No. 2014290203, Subsequent Examiners Report dated Oct. 6, 2020", 4 pgs.
"Australian Application Serial No. 2021201844, Voluntary Amendment filed Dec. 6, 2021", 17 pgs.
"Brazilian Application Serial No. PI0410702-0, Office Action dated Feb. 23, 2012", w/ English Translation, 4 pgs.
"Brazilian Application Serial No. PI0410702-0, Response filed May 7, 2012 to Office Action dated Feb. 23, 2012", w/ English Claims, 11 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office Action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 7, 2012 to Office Action dated Nov. 10, 2011", 11 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,406,180, Response dated Jun. 10, 2011 to Office Action dated Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2,525,953, Amendment and Response filed Feb. 1, 2017 to Office Action dated Aug. 1, 2016", 28 pgs.
"Canadian Application Serial No. 2,525,953, Office Action dated Jan. 21, 2016", 6 pgs.
"Canadian Application Serial No. 2,525,953, Office Action dated Jan. 29, 2020", 4 pgs.
"Canadian Application Serial No. 2,525,953, Office Action dated Apr. 28, 2021", 7 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Oct. 3, 2017", 4 pgs.
"Canadian Application Serial No. 2,525,953, Office Action dated Nov. 2, 2018", 6 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Response filed Jan. 31, 2013 to Office Action dated Jul. 31, 2012", 11 pgs.
"Canadian Application Serial No. 2,525,953, Response filed Feb. 1, 2017 to Office Action dated Aug. 1, 2016", 28 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Apr. 3, 2018 to Office Action dated Oct. 3, 2017", 46 pgs.
"Canadian Application Serial No. 2,525,953, Response filed May 1, 2015 to Office Action dated Nov. 6, 2014", 23 pgs.
"Canadian Application Serial No. 2,525,953, Response filed May 2, 2019 to Office Action dated Nov. 2, 2018", 31 pgs.
"Canadian Application Serial No. 2,525,953, Response filed May 25, 2020 to Office Action dated Jan. 29, 2020", 35 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Dec. 22, 2011 to Office Action dated Jun. 22, 2011", 17 pgs.
"Canadian Application Serial No. 2,647,985, Response filed Sep. 30, 2013 to Office Action dated May 15, 2013", 20 pgs.
"Canadian Application Serial No. 2,647,985, Office Action dated May 15, 2013", 3 pgs.

(56) References Cited

OTHER PUBLICATIONS

"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9 Office Action dated Sep. 11, 2009", (English Translation), 7 pgs.
"Chinese Application Serial No. 200480021259.9 Response filed Aug. 20, 2010 to Office Acton dated May 6, 2010", (w/ English Translation of Claims), 26 pgs.
"Chinese Application Serial No. 200480021259.9, First Offiice Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w/ English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action dated Sep. 4, 2008", (w/ English Translation of Claims), 14 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication dated Oct. 12, 2006", 4 pgs.
"European Application Serial 17709236.8 , Response filed Apr. 26, 2019 to Communication Pursuant to Rules 161(1) and 162 EPC dated Oct. 19, 2018", 9 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons To Attend Oral Proceedings mailed Aug. 3, 2011", 13 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.

(56) References Cited

OTHER PUBLICATIONS

"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.
"European Application Serial No. 04776133.3, Response filed Sep. 18, 2015 to Examination Notification Art. 94(3) dated Jul. 28, 2015", 47 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC dated Apr. 4, 2018", 7 pgs.
"European Application Serial No. 10777154.5, Communication Pursuant to Article 94(3) EPC dated Jun. 11, 2019", 3 pgs.
"European Application Serial No. 10777154.5, Communication Pursuant to Article 94(3) EPC dated Oct. 12, 2017", 7 pgs.
"European Application Serial No. 10777154.5, Examination Notification Art. 94(3) dated Oct. 6, 2014", 7 pgs.
"European Application Serial No. 10777154.5, Office Action dated May 2, 2016", 6 pgs.
"European Application Serial No. 10777154.5, Office Action dated Jul. 4, 2012", 2 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jan. 14, 2013 to Office Action dated Jul. 4, 2012", 12 pgs.
"European Application Serial No. 10777154.5, Response filed Feb. 21, 2018 to Communication Pursuant to Article 94(3) EPC dated Oct. 12, 2017", 12 pgs.
"European Application Serial No. 10777154.5, Response filed Jul. 29, 2019 to Communication Pursuant to Article 94(3) EPC dated Jun. 11, 2019", 57 pgs.
"European Application Serial No. 10777154.5, Response filed Sep. 7, 2018 to Communication Pursuant to Article 94(3) EPC dated Apr. 4, 2018", 18 pgs.
"European Application Serial No. 10777154.5, Response filed Sep. 8, 2016 to Office Action dated May 2, 2016", 69 pgs.
"European Application Serial No. 10777154.5, Summons to Attend Oral Proceedings dated Jan. 7, 2019", 5 pgs.
"European Application Serial No. 14745060.5, Communication Pursuant to Article 94(3) EPC dated Feb. 6, 2018", 5 pgs.
"European Application Serial No. 14745060.5, Communication Pursuant to Article 94(3) EPC dated Mar. 12, 2020", 4 pgs.
"European Application Serial No. 14745060.5, Communication Pursuant to Article 94(3) EPC dated Jul. 18, 2019", 5 pgs.
"European Application Serial No. 14745060.5, Communication Pursuant to Article 94(3) EPC dated Sep. 15, 2021", 4 pgs.
"European Application Serial No. 14745060.5, Communication Pursuant to Article 94(3) EPC dated Sep. 18, 2018", 4 pgs.
"European Application Serial No. 14745060.5, Communication Pursuant to Article 94(3) EPC dated Nov. 9, 2020", 4 pgs.
"European Application Serial No. 14745060.5, Office Action dated Feb. 23, 2016", 2 pgs.
"European Application Serial No. 14745060.5, Response filed Jan. 28, 2020 to Communication Pursuant to Article 94(3) EPC dated Jul. 18, 2019", 9 pgs.
"European Application Serial No. 14745060.5, Response filed Mar. 27, 2019 to Communication Pursuant to Article 94(3) EPC dated Sep. 18, 2018", 13 pgs.
"European Application Serial No. 14745060.5, Response filed May 12, 2021 to Communication Pursuant to Article 94(3) EPC dated Nov. 9, 2020", 12 pgs.
"European Application Serial No. 14745060.5, Response filed Jun. 15, 2018 to Communication Pursuant to Article 94(3) EPC dated Feb. 6, 2018", 14 pgs.
"European Application Serial No. 14745060.5, Response filed Jul. 17, 2020 to Communication Pursuant to Article 94(3) EPC dated Mar. 12, 2020", 52 pgs.
"European Application Serial No. 14745060.5, Response filed Dec. 22, 2016 to Communication pursuant to Rules 161(1) and 162 EPC dated Feb. 23, 2016", 6 pgs.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Result 17, NCBI Blast nucleotide search of SEQ ID No. 2, database "nr"", (Jul. 18, 2006), 3 pgs.
"Result 7, NCBI Blast nucleotide search of SEQ ID: 1, database "nr"", (Jul. 18, 2006), 3 pgs.
"Result 1, NCBI Blast nucleotide search of SEQ ID No. 3, database "nr"; Result 4, NCBI Blast nucleotide search of SEQ ID No. 4, database "nr"", (Jul. 22, 2006), 11 pgs.
"Result 2, NCBI Blast nucleotide search of SEQ ID No. 5, database "nr"; Result 4, NCBI Blast nucleotide search of SEQ ID No. 6, database "nr"", (Jul. 22, 2006), 6 pgs.
"Results 1, NCBI Blast nucleotide search of SEQ ID No. 7, database "nr"; Result 1, NCBI Blast nucleotide search of SEQ ID No. 8, database "nr"", (Jul. 23, 2006), 8 pgs.
"FLUMIST™ Package Insert Template", [Online]. Retrieved from the Internet: http://www.fda.gov/downloads/BiologicsBioodVaccines!Vaccines/ApprovedProducts/UCM294307.pdf, (Mar. 1, 2012), 26 pgs.
"1.A.32 The Type B influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu./tcdb/tcfamilybrowse.php?tcname=1.A.32, (Archived Jan. 31, 2003), 1 pg.
"Adaptation of Egg-Grown and Transfectant Influenza Viruses for Growth in Mammalian Cells: Selection of Hemagglutinin Mutants with Elevated pH of Membrane Fusion", Virology, vol. 233, Issue. 2, [Online] retrieved from the Internet: <URL: http://www.sciencedirect.com/science/article/pii/S0042682297986268>, (1997), 402-410.
"Evaluation of Medicines for human Use", EMEA/CPMP/BWP/2289/01, London, The European Agency for the Evaluation of

(56) References Cited

OTHER PUBLICATIONS

Medicinal Products, Committee for Proprietary Medicinal Products (CPMP), (Feb. 20, 2003), 14 pgs.
"FLUZONE® Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 x Texas/1/1977) (H1N1))], (2012), 2 pgs.
"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"Influenza B/lee/40, neuraminidase & nb (seg 6) rna", Database EM_VI E.B.I. Hinxton U.K., (Jun. 13, 1985), 10 pgs.
"Polymerase acidic [influenza A virus (A/swine/Shizuoka/120/97(H3N2))]", GenBank AAO15329.1, (2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Polymerase acidic protein {ECO:0000256|RuleBase;RU361280, ECO: 0000256|SAAS-:SAAS00262764}", XP002744257, retrieved from EBI Accession No. UNIPR0T:A3R6C9 Database accession No. A3R6C9 the whole document, (Apr. 3, 2007), 1 pgs.
"RecName: Full=Polymerase acidic protein {ECO:0000256|RuleBase;RU361280, ECO:0000256|SAAS:SAAS00262764}", XP002744258, retrieved from EBI accession No. UNIPROT:U3S198 Database accession No. U3S198 the whole document, (Dec. 11, 2013), 1 pg.
"The Influenza Virus: Structure and Replication", Rapid Reference to Influenza. Elsevier Ltd, [Online]. Retrieved from the Internet: <URL: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
Air, Gillian M., et al., "Antigenic, Sequence, and Crystal Variation in Influenza B Neuraminidase", Virology, 177(2), (1990), 578-587.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem ceil transplant recipients", Bone Marrow Transplant, (2005), 411-415.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 (Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4, (2010), 1425-1427.
Bourmakina, S. V, et al., "Reverse genetics studies on the Filamentous morphology of influenza A Virus", Journal of General Virology (2003) 84,, (2003), 517-527.
Bowie, J. U., et al., "Deciphering the Message in Protein Sequences: Tolerance to Amino Acid Substitutions", Science, 247(4948), (1990), 1306-1310.
Boyer, J. C., et al., "Infectious transcripts and cDNA clones of RNA viruses", Virology, 198(2), (Feb. 1994), 415-426.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Brooke, C B, "Biological activities of 'noninfectious' influenza A virus particles", Future Virol 9(1), (Jan. 2014), 41-51.
Brown, E. G., et al., "Genetic analysis of mouse-adapted influenza A virus identifies roles for the NA, PB1, and PB2 genes in virulence", Virus Research, 61(1), (May 1999), 63-76.
Buchholz, U. J., et al., "Generation of Bovine Respiratory Syncytial Virus (BRSV) From cDNA: BRSV NS2 is Not Essentiiai for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Cao, S., et al., "Characterization of the Nucleocytoplasmic Shuttle of the Matrix Protein of Influenza B Virus", Journal of Virology., 88(13), (Jul. 2014), 7464-7473.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations

(56) References Cited

OTHER PUBLICATIONS on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Dunham, Eleca J., et al., "Different Evolutionary trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P. et al., "Recovery of infectious human parainfluenza virus type 3 from cDNA", Virology, 235(2), (Sep. 1, 1997), 323-332.
Elhefnawi, M, et al., "Identification of novel conserved functional motifs across most Influenza A viral strains", Virology Journal, 8:44, (2011), 10 pages.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., et al., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Fischer, W. B, et al., "Viral ion channels: structure and function.", Biochim Biophys Acta., 1561(1), (Mar. 19, 2002), 27-45.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Gao, Qinshan, et al., "A Nine-Segment In?uenza A Virus Carrying Subtype H1 and H3 Hemagglutinins†", Journal of Virology, 84(16), (Aug. 2010), 8062-8071.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garcia-Sastre, A., et al., "Genetic Manipulation of Negative-Strand RNA Virus Genomes", Annu. Rev. Microbiol., 47, (1993), 765-790.
Garcin, D. et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Giddings, A M, et al., "The matrix protein of HIV-1 is not sufficient for assembly and release of virus-like particles", Virology, 248(1), (1998), 108-16.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Govorkova, E A, et al., "Replication of Influenza A Viruses in a Green Monkey Kidney Continuous Cell Line (Vero)", J. Infect. Dis. 172(1), (1995), 250-253.

(56) References Cited

OTHER PUBLICATIONS

Grambas, S., et al., "Influence of amantadine resistance mutations on the pH regulatory function of the M2 protein of influenza A viruses", Virology, 191(2), (Dec. 1992), 541-549.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Hai, Rong, et al., "Influenza B Virus NS1-Truncated Mutants: Live-Attenuated Vaccine Approach", Journal of Virology, 82(21), (2008), 10580-10590.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza A Virus NS1 Protein to dsRNA in vitro", Journal of General Virology, 73, (1992), 3325-3329.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Holsinger, L. J., et al., "Influenza A Virus M2 Ion Channel Protein: a Structure-Function Analysis", Journal of Virology, 68 (3), (1994), pp. 1551-1563.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Huang, T.-S., et al., "Determination of Influenza Virus Proteins Required for Genome Replication", Journal of Virology, 64(11), (1990), 5669-5673.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, D., et al., "A reverse genetics approach for recovery of recombinant influenza B viruses entirely from cDNA.", J Virol., 76(22), (Nov. 2002), 11744-7.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Jiang, H, et al., "Influenza virus genome C4 promoter/origin attenuates its transcription and replication activity by the low polymerase recognition activity", Virology, 408(2), (2010), 190-196.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y, et al., "Sequence requirements for cleavage activation of influenza virus hemagglutinin expressed in mammalian cells", Proc Natl Acad Sci., 85(2), (1988), 324-328.
Kawaoka, Y., "Mutant Cells With Altered Sialic Acid", U.S. Appl. No. 11/644,179, filed Dec. 22, 2006, 51 pgs.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kimura, N., et al., "An In Vivo Study of the Replication Origin in the Influenza Virus Complementary RNA", The Journal of Biochemistry, 113(1), (1993), 88-92.
Kimura, N. et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.

(56) References Cited

OTHER PUBLICATIONS

Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an In?uenza A Virus Vector Expressing Biologically Active Human Interleukin-2 from the NS Gene Segment", Journal of Virology, 79(16), (Aug. 2005), 10672-10677.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Konarska, M. M., et al., "Structure of RNAs Replicated by the DNA-Dependent T7 RNA Polymerase", Cell, 63(2), (1990), 609-618.
Kovacova, A., et al., "Sequence similarities and evolutionary relationships of influenza virus A hemagglutinins.", Virus Genes, 24(1), (2002), 57-63.
Kovacova, Andrea, et al., "Sequence Similarities and Evolutionary Relationships of Influenza Vrus A Hemagglutinins", Virus Genes, 24(1), (2002), 57-63.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990).
Kunkel, T. A., "Rapid and Efficient Site-Specific Mutagenesis Without Phenotypic Selection", Proc. Natl. Acad. Sci. USA, 82, (1985), 488-492.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Lawson, N. D., "Recombinant Vesicular Stomatitis Viruses From DNA", Proc. Natl. Acad. Sci. USA, 92(10), (1995), 4477-4481.
Lazarovits, Janette, et al., "Endocytosis or Chimeric Influenza Virus Hemaggulutinin Proteins That Lack a Cytoplasmic Recognition Feature for Coated Pits", The Journal of Cell Biology, vol. 134, No. 2, (1996), 339-348.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, Dong-Hun, et al., "Progress and hurdles in development of influenza virus-like particle vaccines for veterinary use", Korean Vaccine Society, (2014), 133-139.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6Nl avian influenza viruses isolated in Taiwan between 1972 and 2005", Avian Diseases, 50(4), (Dec. 2006), 561-571.
Levis, R., et al., "Deletion Mapping of Sindbis Virus DI RNAs Derived From cDNAs Defines the Sequences Essential for Replication and Packaging", Cell, 44, (1986), 137-145.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5Nl influenza virus in eastern Asia", Nature, 430(6996), (Jul. 8, 2004), 209-213.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.
Liu, Bo, et al., "[Comparison of three methods in construction fusion gene of influenza A virus Nucleoprotein].", (English Abstract), Zhonghua Shi Yan He Lin Chuang Bing Du Xue Za Zhi, 26(1), 70-74, (Feb. 2012), 1 pg.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.
Manz, Benjamin, et al., "Disruption of the Viral Polymerase Complex Assembly as a Novel Approach to Attenuate Influenza A Virus", The Journal of Biological Chemistry, 286(10), (20111), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21), (2014), 12364-12373.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McCullers, Jonathan A., et al., "A single amino acid change in the C-terminal domain of the matrix protein M1 of influenza B virus confers mouse adaption and virulence", Virology, 336(2), (Jun. 5, 2005), 318-326.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of Biologically Active Influenza Virus Core Proteins Using a Vaccinia Virus-T7 RNA Polymerase Expression System", Journal of General Virology, 75, (1994), 2109-2114.

(56) References Cited

OTHER PUBLICATIONS

Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Monto, Arnold S, et al., "Comparative efficacy of inactivated and live attenuated influenza vaccines.", N Engl J Med., 361(13), (Sep. 24, 2009), 1260-7.
Moyer, S. A., et al., "Assembly and Transcription of Synthetic Vesicular Stomatitis Virus Nucleocapsids", Journal of Virology, 65(5), (1991), 2170-2178.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3" Noncoding Regions on the Neuraminidase Gene is Attenuated in Mice", Proc. Natl. Acad. Sci. USA, 88, (1991), 5177-5181.
Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "An improved reverse genetics system for influenza A virus generation and its implications for vaccine production", Proc. Natl. Acad. Sci. USA. 102(46), (2005), 16825-16829.
Neumann, G., et al., "Emergence and pandemic potential of swine-origin HlN1 influenza virus", Nature (London), 459(7249), (Jun. 2009), 931-939.
Neumann, G., et al., "Generation of influenza A virus from cloned cDNAs—historical perspective and outlook for the new millenium. ", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Mutational analysis of influenza virus promoter elements in vivo", Journal of General Virology, 76, (1995), 1709-1717.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Noda, Takeshi, et al., "Three-dimensional analysis of ribonucleoprotein complexes in influenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990).
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al. "Rescue of Newcastle Disease Virus From Cloned cDNA: Evidence That Cleavability of the Fusion Protein Is a Major Determinant for Virulence", Journal of Virology, 73(6), (1999), 5001-5009.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Percy, N., et al., "Expression of a Foreign Protein by Influenza A Virus", Journal of Virology, 68(7), (1994), 4486-4492.
Perez, Jasmine T., et al., "Unit 15G.4—Insertion of a GFP Reporter Gene in Influenza Virus", Curr Protoc Microbiol., (2013), 20 pgs.
Piller, S C., et al., "Vpr protein of human immunodeficiency virus type 1 forms cation-selective channels in planar lipid bilayers", PNAS, 93, (1996), 111-1115.
Ping. J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.com/article-assets/npg/ncomms/2015/150902/ncomms9148/extref/ncomms9148-sl.pdf>, (Sep. 2, 2015).
Pinto, L. H., et al., "Influenza Virus M2 Protein Has Ion Channel Activity", Cell, 69, (May 1992), pp. 517-528.
Plant, E P, et al., "Mutations to A/PuertoRico/8/34 PB1 gene improves seasonal reassortant influenza A virus growth kinetics", Vaccine, vol. 31, No. 1, (Dec. 1, 2012), 207-212 pgs.
Pleschka, S., et al., "A Plasmid-Based Reverse Genetics System for Influenza A Virus", Journal of Virology, 70(6), (1996), 4188-4192.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.

(56) References Cited

OTHER PUBLICATIONS

Ramanunninair, Manojkumar, et al., "Molecular Signature of High Yield (Growth) Influenza A Virus Reassortants Prepared as Candidate Vaccine Seeds", PLoS ONE, 8(6): e65955, (2013), 1-16.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Roberts, A., et al., "Minireview—Recovery of Negative-Strand RNA Viruses From Plasmid DNAs: A Positive Approach Revitalizes a Negative Field", Virology, 247(1), (1998), 1-6.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 ( Pt 4), (Apr. 1984), 799-802.
Ruigrok, R W, et al., "Structural Characterization and Membrane Binding Properties of the Matrix Protein VP40 of Ebola Virus", Journal of Molecular Biology, 300(1), (2000), 103-112.
Sansom, M. S., et al., "Influenza virus M2 Protein: a molecular modelling study of the ion channel", Protein Engineering, 6 (1), (1993), pp. 65-74.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Schotsaert, M, et al., "Universal M2 ectodomain-based influenza A vaccines: preclinical and clinical developments", Expert Rev V accines. Apr. 2009;8(4):, 499-508.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Skehel, J. J., et al., "On the Mechanism of Inhibition of Influenza Virus Replication by Amantadine Hydrochloride", The Journal of General Virology, 38 (1), (1977), pp. 97-110.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Takeda, M., et al., "Influenza a virus M2 ion channel activity is essential for efficient replication in tissue culture.", J Virol., 76(3), (Feb. 2002), 1391-9.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Tobler, K, et al., "Effect of cytoplasmic tail truncations on the activity of the M(2) ion channel of influenza A virus", J Virol., 73(12), (Dec. 1999), 9695-9701.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Verma, I. M, et al., "Gene Therapy—Promises, Problems and Prospects", Nature, 389, (1997), 239-242.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Wagner, R., et al., "Interdependence of hemagglutinin glycosylation and neuraminidase as regulators of influenza virus arowth: a study by reverse genetics", Journal of Virology, 74 (14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Wenlig, et al., "Robust Immunity and Heterologous Protection against Influenza in Mice Elicited by a Novel Recombinant NP-M2e Fusion Protein Expressed in *E. coli*", PLoS ONE 7(12): e52488, (Dec. 2012), 1-13.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Watanabe, S., et al., "Influenza A Virus Lacking M2 Protein as a Live Attenuated Vaccine", Journal of Virology, 83(11), (2009), 5947-5950.
Watanabe, T., et al., "Influenza A virus can undergo multiple cycles of replication without M2 ion channel activity", J Virol., 75(12), (Jun. 2001), 5656-62.

(56) References Cited

OTHER PUBLICATIONS

Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Wei, Hung-Ju, et al., "Fabrication of influenza virus-like particles using M2 fusion proteins for imaging single viruses and designing vaccines", Vaccine, 29, (2011), 7163-7172.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wilson, Julie A, et al., "Epitopes Involved in Antibody-Mediated Protection from Ebola Virus", Science, 287(5458), (Mar. 2000), 1664-1666.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Rui, et al., "A live bivalent influenza vaccine based on a H9N2 virus strain", Vaccine, 28, (2010), 673-680.
Xu, X., et al., "Reassortment and evolution of current human influenza A and B viruses", Virus Research, 103, (2004), 55-60.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yannarell, Dean A., et al., "Factors affecting the yield of cold-adapted influenza virus vaccine", Journal of Virological Methods, vol. 64, 161-169, (1997), 1 pg.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zobel, A., et al., "RNA Polymerase I Catalysed Transcription of Insert Viral cDNA", Nucleic Acids Research, 21(16), (1993), 3607-3614.
U.S. Appl. No. 14/332,121 U.S. Pat. No. 9,950,057, filed Jul. 15, 2014, High Titer Recombinant Influenza Viruses With Enhanced Replication in MDCK or Vero Cells or Eggs.
U.S. Appl. No. 15/593,039 U.S. Pat. No. 10,172,934, filed May 11, 2017, High Titer Recombinant Influenza Viruses With Enhanced Replication in MDCK or Vero Cells or Eggs.
U.S. Appl. No. 15/203,581 U.S. Pat. No. 9,890,363, filed Jul. 6, 2016, Influenza Virus Replication for Vaccine Development.
U.S. Appl. No. 15/865,364 U.S. Pat. No. 10,246,686, filed Jan. 9, 2018, Influenza Virus Replication for Vaccine Development.
U.S. Appl. No. 16/284,020, filed Feb. 25, 2019, Influenza Virus Replication for Vaccine Development.
"U.S. Appl. No. 09/834,095, Advisory Action dated Jan. 8, 2004", 3 pgs.
"U.S. Appl. No. 09/834,095, Final Office Action dated Aug. 26, 2003", 12 pgs.
"U.S. Appl. No. 09/834,095, Non-Final Office Action dated Nov. 4, 2002", 12 pgs.
"U.S. Appl. No. 09/834,095, Notice of Allowance dated Sep. 27, 2004", 13 pgs.
"U.S. Appl. No. 09/834,095, Office Action dated Apr. 20, 2004", 11 pgs.
"U.S. Appl. No. 09/834,095, Response filed Feb. 4, 2003 to Office Action dated Nov. 4, 2002", 14 pgs.
"U.S. Appl. No. 09/834,095, Response filed Jun. 12, 2003 to Restriction Requirement dated Apr. 22, 2003", 2 pgs.
"U.S. Appl. No. 09/834,095, Response filed Jun. 18, 2004 to Office Action dated Apr. 20, 2004", 11 pgs.
"U.S. Appl. No. 09/834,095, Response filed Aug. 1, 2002 to Restriction Requirement dated Jul. 1, 2002", 3 pgs.
"U.S. Appl. No. 09/834,095, Response filed Nov. 26, 2003 to Final Office Action dated Aug. 26, 2003", 10 pgs.
"U.S. Appl. No. 09/834,095, Restriction Requirement dated Apr. 22, 2003", 5 pgs.
"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", 20 Pgs.
"U.S. Appl. No. 10/855,875, Final Office Action dated Aug. 2, 2006", 34 pgs.
"U.S. Appl. No. 10/855,875, Final Office Action dated Dec. 10, 2010", 15 pgs.

(56) References Cited

OTHER PUBLICATIONS

"U.S. Appl. No. 10/855,875, Non-Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated May 3, 2007", 13 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non-Final Office Action dated Feb. 19, 2010", 20 pgs.
"U.S. Appl. No. 10/855,875, Response filed Dec. 7, 2009 to Non-Final Office Action dated Aug. 7, 2009", 15 pgs.
"U.S. Appl. No. 10/855,875, Response filed Mar. 31, 2009 to Non-Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to Final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007", 16 pgs.
"U.S. Appl. No. 11/043,768, Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non-Final Office Action dated Feb. 23, 2010", 9 pgs.
"U.S. Appl. No. 11/043,768, Response filed Jun. 23, 2009 to Non-Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non-Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non-Final Office Action dated Feb. 18, 2015", 13 pgs.
"U.S. Appl. No. 11/729,557, Non-Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non-Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non-Final Office Action dated Jan. 30, 2009", 18 pgs.
"U.S. Appl. No. 11/729,557, Response filed May 22, 2014 to Non-Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non-Final Office Action dated Feb. 22, 2010", 16 pgs.
"U.S. Appl. No. 11/729,557, Response filed Jun. 22, 2015 to Non-Final Office Action dated Feb. 18, 2015", 13 pgs.
"U.S. Appl. No. 11/729,557, Response filed Oct. 28, 2010 to Non-Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"U.S. Appl. No. 12/214,414, Advisory Action dated Feb. 2, 2016", 5 pgs.
"U.S. Appl. No. 12/214,414, Advisory Action dated Apr. 15, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.
"U.S. Appl. No. 12/214,414, Final Office Action dated Nov. 18, 2015", 17 pgs.
"U.S. Appl. No. 12/214,414, Non-Final Office Action dated Jun. 12, 2014", 28 pgs.
"U.S. Appl. No. 12/214,414, Non-Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.

(56) References Cited

OTHER PUBLICATIONS

"U.S. Appl. No. 12/214,414, Response filed May 3, 2011 to Non-Final Office Action dated Dec. 10, 2010", 12 pgs.
"U.S. Appl. No. 12/214,414, Response filed Jul. 20, 2015 to Advisory Action dated Apr. 15, 2015", 14 pgs.
"U.S. Appl. No. 12/214,414, Response filed Aug. 31, 2010 to Non-Final Office Action dated Mar. 2, 2010", 11 pgs.
"U.S. Appl. No. 12/214,414, Response filed Oct. 3, 2011 to Non-Final Office Action dated Aug. 2, 2011", 9 pgs.
"U.S. Appl. No. 12/214,414, Response filed Oct. 14, 2014 to Non-Final Office Action dated Jun. 12, 2014", 16 pgs.
"U.S. Appl. No. 12/214,414, Response filed Dec. 21, 2011 to Advisory Action dated Oct. 21, 2011", 10 pgs.
"U.S. Appl. No. 12/467,492, Restriction Requirement dated Nov. 22, 2010", 6 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non-Final Office Action dated Jun. 7, 2013", 8 pgs.
"U.S. Appl. No. 12/912,411, Non-Final Office Action dated Sep. 24, 2014", 11 pgs.
"U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Mar. 16, 2015 to Final Office Action dated Jan. 14, 2015", 9 pgs.
"U.S. Appl. No. 12/912,411, Response filed Oct. 7, 2013 to Non-Final Office Action dated Jun. 7, 2013", 10 pgs.
"U.S. Appl. No. 12/912,411, Response filed Dec. 31, 2014 to Non-Final Office Action dated Sep. 24, 2014", 12 pgs.
"U.S. Appl. No. 12/912,411, Restriction Requirement dated Oct. 17, 2012", 9 pgs.
"U.S. Appl. No. 13/070,110 Response filed Feb. 14, 2017 to Final Office Action dated Sep. 14, 2016", 8 pgs.
"U.S. Appl. No. 13/070,110, Advisory Action dated Mar. 3, 2017", 5 pgs.
"U.S. Appl. No. 13/070,110, Examiner Interview Summary dated Jan. 16, 2018", 3 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.
"U.S. Appl. No. 13/070,110, Final Office Action dated Sep. 14, 2016", 12 pgs.
"U.S. Appl. No. 13/070,110, Non-Final Office Action dated Jul. 21, 2017", 14 pgs.
"U.S. Appl. No. 13/070,110, Non-Final Office Action dated Oct. 2, 2014", 24 pgs.
"U.S. Appl. No. 13/070,110, Non-Final Office Action dated Dec. 11, 2015", 19 pgs.
"U.S. Appl. No. 13/070,110, Non-Final Office Action dated Dec. 21, 2012", 7 pgs.
"U.S. Appl. No. 13/070,110, Notice of Allowance dated Mar. 26, 2018", 6 pgs.
"U.S. Appl. No. 13/070,110, Notice of Allowance dated Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication dated Aug. 15, 2018", 2 pgs.
"U.S. Appl. No. 13/070,110, Response filed Jan. 22, 2018 to Non-Final Office Action dated Jul. 21, 2017", 10 pgs.
"U.S. Appl. No. 13/070,110, Response filed Mar. 22, 2013 to Non-Final Office Action dated Dec. 21, 2012", 8 pgs.
"U.S. Appl. No. 13/070,110, Response filed May 27, 2016 to Non-Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed Sep. 3, 2014 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 12, 2013 to Final Office Action dated Jun. 12, 2013", 9 pgs.
"U.S. Appl. No. 13/070,110, Response filed Dec. 30, 2014 to Non-Final Office Action dated Oct. 2, 2014", 13 pgs.
"U.S. Appl. No. 13/070,110, Restriction Requirement dated Jul. 8, 2014", 7 pgs.
"U.S. Appl. No. 14/332,121, Non-Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non-Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Non-Final Office Action dated Feb. 2, 2017", 14 pgs.
"U.S. Appl. No. 14/745,236, Notice of Allowability dated Jul. 5, 2018", 4 pgs.
"U.S. Appl. No. 14/745,236, Notice of Allowance dated Feb. 5, 2018", 9 pgs.
"U.S. Appl. No. 14/745,236, PTO Response to Rule 312 Communication dated Jul. 10, 2018", 2 pgs.
"U.S. Appl. No. 14/745,236, Response filed May 2, 2017 to Non-Final Office Action dated Feb. 2, 2017", 10 pgs.
"U.S. Appl. No. 14/745,236, Response filed Nov. 6, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"U.S. Appl. No. 14/745,236, Response filed Dec. 23, 2016 to Restriction Requirement dated Sep. 23, 2016", 8 pgs.
"U.S. Appl. No. 14/745,236, Restriction Requirement dated Sep. 23, 2016", 8 pgs.
"U.S. Appl. No. 14/816,807, Non-Final Office Action dated Oct. 3, 2017", 7 pgs.
"U.S. Appl. No. 14/816,807, Notice of Allowance dated Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication dated Jul. 6, 2018", 2 pgs.

(56) References Cited

OTHER PUBLICATIONS

"U.S. Appl. No. 14/816,807, Response filed Jan. 3, 2018 to Non-Final Office Action dated Oct. 3, 2017", 8 pgs.
"U.S. Appl. No. 14/816,807, Response filed May 1, 2017 to Restriction Requirement dated Nov. 1, 2016", 9 pgs.
"U.S. Appl. No. 14/816,807, Restriction Requirement dated Nov. 1, 2016", 8 pgs.
"U.S. Appl. No. 15/000,851, Non-Final Office Action dated Jan. 26, 2017", 15 pgs.
"U.S. Appl. No. 15/000,851, Notice of Allowance dated Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non-Final Office Action dated Jan. 26, 2017", 16 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/170,556, Final Office Action dated Jul. 30, 2019", 6 pgs.
"U.S. Appl. No. 15/170,556, Non-Final Office Action dated Feb. 8, 2019", 11 pgs.
"U.S. Appl. No. 15/170,556, Non-Final Office Action dated Jul. 27, 2018", 10 pgs.
"U.S. Appl. No. 15/170,556, Notice of Allowance dated Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement dated Feb. 16, 2018", 8 pgs.
"U.S. Appl. No. 15/170,556, Response filed Oct. 29, 2018 to Non-Final Office Action dated Jul. 27, 2018", 9 pgs.
"U.S. Appl. No. 15/170,556, Response filed Nov. 18, 2019 to Final Office Action dated Jul. 30, 2019", 8 pgs.
"U.S. Appl. No. 15/170,556, Response filed Apr. 15, 2019 to Non-Final Office Action dated Feb. 8, 2019", 9 pgs.
"U.S. Appl. No. 15/170,556, Restriction Requirement dated Feb. 16, 2018", 7 pgs.
"U.S. Appl. No. 15/203,581, Examiners Interview Summary dated Sep. 11, 2017", 1 pg.
"U.S. Appl. No. 15/203,581, Notice of Allowance dated Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication dated Dec. 27, 2017", 2 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/292,595, Non-Final Office Action dated Sep. 25, 2017", 13 pgs.
"U.S. Appl. No. 15/292,595, Notice of Allowance dated Feb. 28, 2018", 9 pgs.
"U.S. Appl. No. 15/292,595, Notice of Allowance dated Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non-Final Office Action dated Sep. 25, 2017", 9 pgs.
"U.S. Appl. No. 15/436,245, Non0Final Office Action dated Apr. 19, 2019", 9 pgs.
"U.S. Appl. No. 15/436,245, Preliminary Amendment filed May 5, 2017", 3 pgs.
"U.S. Appl. No. 15/436,245, Response filed Jul. 29, 2019 to Non-Final Office Action dated Apr. 19, 2019", 11 pgs.
"U.S. Appl. No. 15/436,245, Restriction Requirement dated Oct. 11, 2018", 9 pgs.
"U.S. Appl. No. 15/593,039, Non-Final Office Action dated Feb. 6, 2018", 8 pgs.
"U.S. Appl. No. 15/593,039, Notice of Allowance dated Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication dated Oct. 9, 2018", 2 pgs.
"U.S. Appl. No. 15/593,039, Response filed Apr. 30, 2018 to Non-Final Office Action dated Feb. 4, 2018", 8 pgs.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance dated Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement dated Jan. 3, 2019", 6 pgs.
"U.S. Appl. No. 16/046,250, Restriction Requirement dated Jul. 25, 2019", 7 pgs.

Figure 1A:
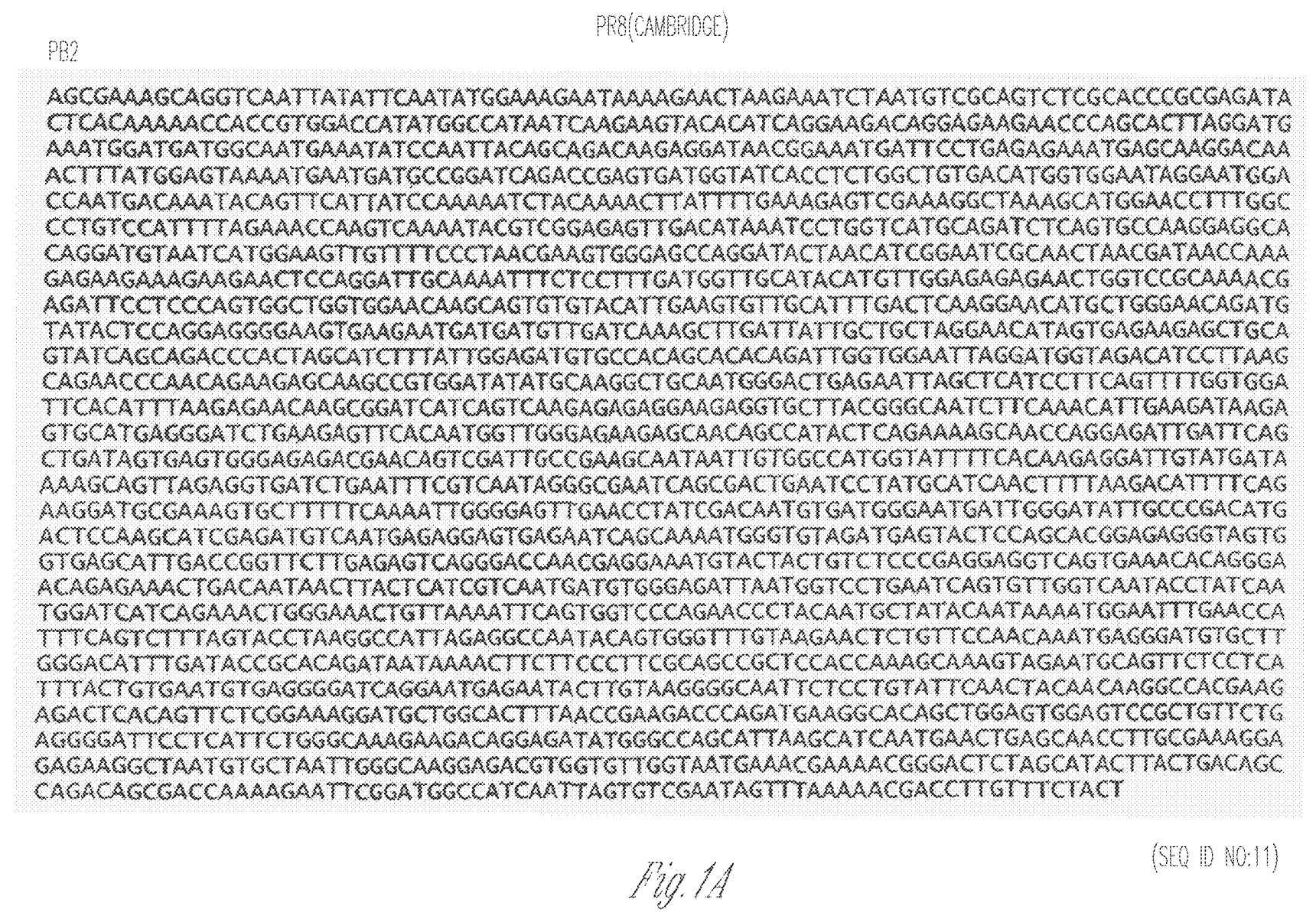

PR8(CAMBRIDGE)

PB2

AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGAACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTATTGGAGATGTGCCACAGCACACAGATTGGTGGAATTAGGATGGTAGACATCCTTAAG
CAGAACCCAACAGAAGAGCAAGCCGTGGATATATGCAAGGCTGCAATGGGACTGAGAATTAGCTCATCCTTCAGTTTTGGTGGA
TTCACATTTAAGAGAACAAGCGGATCATCAGTCAAGAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGACGAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACAATGTGATGGGAATGATTGGGATATTGCCCGACATG
ACTCCAAGCATCGAGATGTCAATGAGAGGAGTGAGAATCAGCAAAATGGGTGTAGATGAGTACTCCAGCACGGAGAGGGTAGTG
GTGAGCATTGACCGGTTCTTGAGAGTCAGGGACCAACGAGGAAATGTACTACTGTCTCCCGAGGAGGTCAGTGAAACACAGGGA
ACAGAGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGAACCA
TTTCAGTCTTTAGTACCTAAGGCCATTAGAGGCCAATACAGTGGGTTTGTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGAAAGGATGCTGGCACTTTAACCGAAGACCCAGATGAAGGCACAGCTGGAGTGGAGTCCGCTGTTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGACTCTAGCATACTTACTGACAGC
CAGACAGCGACCAAAAGAATTCGGATGGCCATCAATTAGTGTCGAATAGTTTAAAAACGACCTTGTTTCTACT (SEQ ID NO:11)

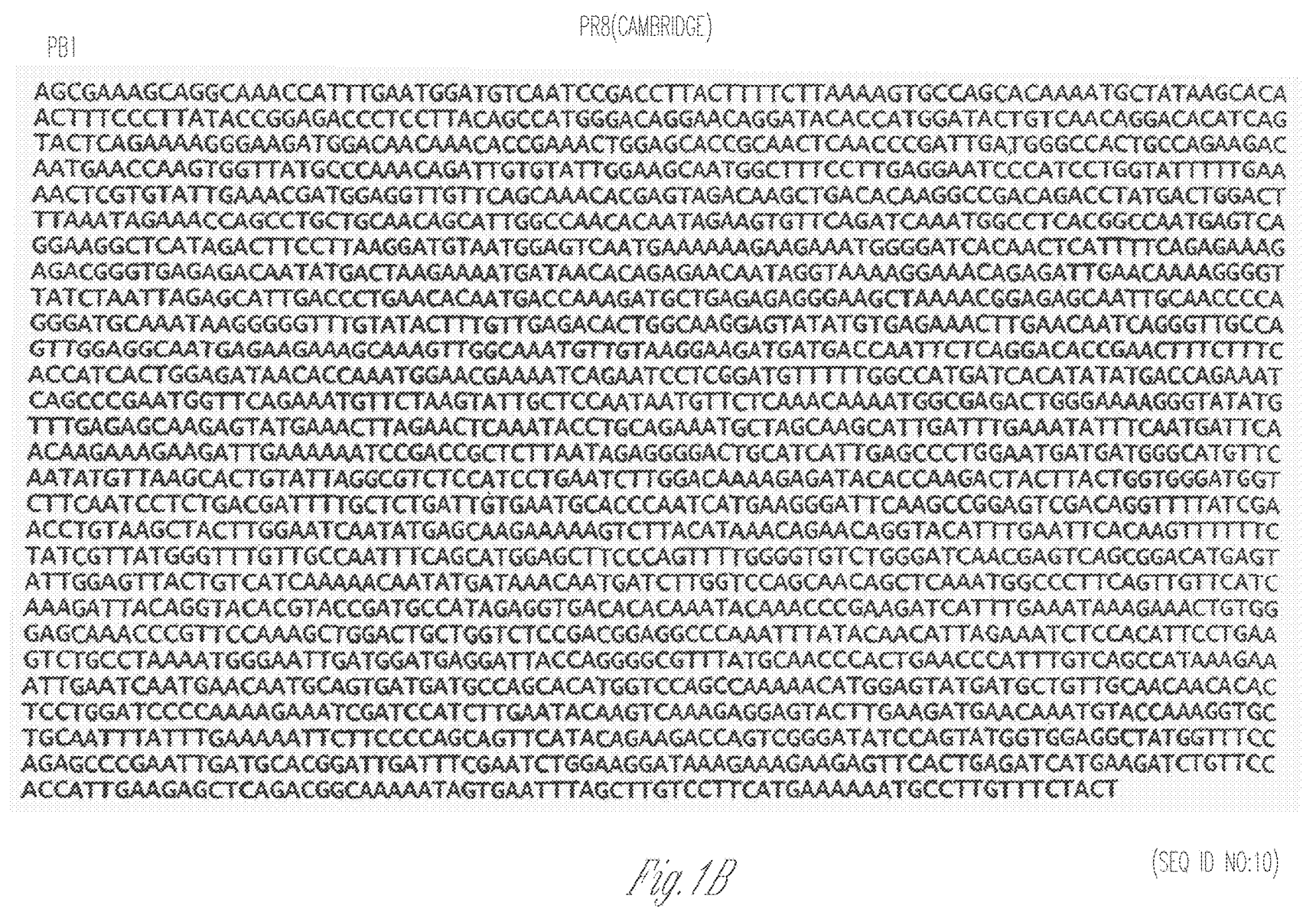

PR8(CAMBRIDGE)

AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTTGAA
AACTCGTGTATTGAAACGATGGAGGTTGTTCAGCAAACACGAGTAGACAAGCTGACACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAAGAAGAAATGGGGATCACAACTCATTTTCAGAGAAAG
AGACGGGTGAGAGACAATATGACTAAGAAAATGATAACACAGAGAACAATAGGTAAAAGGAAACAGAGATTGAACAAAAGGGGT
TATCTAATTAGAGCATTGACCCTGAACACAATGACCAAAGATGCTGAGAGAGGGAAGCTAAAACGGAGAGCAATTGCAACCCCA
GGGATGCAAATAAGGGGGTTTGTATACTTTGTTGAGACACTGGCAAGGAGTATATGTGAGAAACTTGAACAATCAGGGTTGCCA
GTTGGAGGCAATGAGAAGAAAGCAAAGTTGGCAAATGTTGTAAGGAAGATGATGACCAATTCTCAGGACACCGAACTTTCTTTC
ACCATCACTGGAGATAACACCAAATGGAACGAAAATCAGAATCCTCGGATGTTTTTGGCCATGATCACATATATGACCAGAAAT
CAGCCCGAATGGTTCAGAAATGTTCTAAGTATTGCTCCAATAATGTTCTCAAACAAAATGGCGAGACTGGGAAAAGGGTATATG
TTTGAGAGCAAGAGTATGAAACTTAGAACTCAAATACCTGCAGAAATGCTAGCAAGCATTGATTTGAAATATTTCAATGATTCA
ACAAGAAAGAAGATTGAAAAAATCCGACCGCTCTTAATAGAGGGGACTGCATCATTGAGCCCTGGAATGATGATGGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTGACGATTTTGCTCTGATTGTGAATGCACCCAATCATGAAGGGATTCAAGCCGGAGTCGACAGGTTTTATCGA
ACCTGTAAGCTACTTGGAATCAATATGAGCAAGAAAAAGTCTTACATAAACAGAACAGGTACATTTGAATTCACAAGTTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAGAAACTGTGG
GAGCAAACCCGTTCCAAAGCTGGACTGCTGGTCTCCGACGGAGGCCCAAATTTATACAACATTAGAAATCTCCACATTCCTGAA
GTCTGCCTAAAATGGGAATTGATGGATGAGGATTACCAGGGGCGTTTATGCAACCCACTGAACCCATTTGTCAGCCATAAAGAA
ATTGAATCAATGAACAATGCAGTGATGATGCCAGCACATGGTCCAGCCAAAAACATGGAGTATGATGCTGTTGCAACAACACAC
TCCTGGATCCCCAAAAGAAATCGATCCATCTTGAATACAAGTCAAAGAGGAGTACTTGAAGATGAACAAATGTACCAAAGGTGC
TGCAATTTATTTGAAAAATTCTTCCCCAGCAGTTCATACAGAAGACCAGTCGGGATATCCAGTATGGTGGAGGCTATGGTTTCC
AGAGCCCGAATTGATGCACGGATTGATTTCGAATCTGGAAGGATAAAGAAAGAAGAGTTCACTGAGATCATGAAGATCTGTTCC
ACCATTGAAGAGCTCAGACGGCAAAAATAGTGAATTTAGCTTGTCCTTCATGAAAAAATGCCTTGTTTCTACT (SEQ ID NO:10)

Fig. 1B

PR8(CAMBRIDGE)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTCCACTTCATCAATGAGCAAGGCGAGTCAATAATCGTAGAACTTGGTGATCCTAATGCACTTTTGAAGCACAGATTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAAATAGATTCATCGAAATTGGAGTAACAAGGAGAGAAGTTCACATATACTATCTG
GAAAAGGCCAATAAAATTAAATCTGAGAAAACACACATCCACATTTTCTCGTTCACTGGGGAAGAAATGGCCACAAGGGCCGAC
TACACTCTCGATGAAGAAAGCAGGGCTAGGATCAAAACCAGGCTATTCACCATAAGACAAGAAATGGCCAGCAGAGGCCTCTGG
GATTCCTTTCGTCAGTCCGAGAGAGGAGAAGAGACAATTGAAGAAAGGTTTGAAATCACAGGAACAATGCGCAAGCTTGCCGAC
CAAAGTCTCCCGCCGAACTTCTCCAGCCTTGAAAATTTTAGAGCCTATGTGGATGGATTCGAACCGAACGGCTACATTGAGGGC
AAGCTGTCTCAAATGTCCAAAGAAGTAAATGCTAGAATTGAACCTTTTTTGAAAACAACACCACGACCACTTAGACTTCCGAAT
GGGCCTCCCTGTTCTCAGCGGTCCAAATTCCTGCTGATGGATGCCTTAAAATTAAGCATTGAGGACCCAAGTCATGAAGGAGAG
GGAATACCGCTATATGATGCAATCAAATGCATGAGAACATTCTTTGGATGGAAGGAACCCAATGTTGTTAAACCACACGAAAAG
GGAATAAATCCAAATTATCTTCTGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAAGGTAGACTTTGACGACTGT
AAAGATGTAGGTGATTTGAAGCAATATGATAGTGATGAACCAGAATTGAGGTCGCTTGCAAGTTGGATTCAGAATGAGTTCAAC
AAGGCATGCGAACTGACAGATTCAAGCTGGATAGAGCTTGATGAGATTGGAGAAGATGTGGCTCCAATTGAACACATTGCAAGC
ATGAGAAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAGAAGTACTGTGTTCTTGAGATAGGAGATATGCTTCTAAGAAGT
GCCATAGGCCAGGTTTCAAGGCCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAAGCTGAGTCCTCTGTCAAAGAGAAAGACATGACC
AAAGAGTTCTTTGAGAACAAATCAGAAACATGGCCCATTGGAGAGTCTCCCAAAGGAGTGGAGGAAAGTTCCATTGGGAAGGTC
TGCAGGACTTTATTAGCAAAGTCGGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGGCTATATGAAGCAATTGAGGAG
TGCCTAATTAATGATCCCTGGGTTTTGCTTAATGCTTCTTGGTTCAACTCCTTCCTTACACATGCATTGAGTTAGTTGTGGCAG
TGCTACTATTTGCTATCCATACTGTCCAAAAAAGTACCTTGTTTCTACT (SEQ ID NO:12)

PR8(CAMBRIDGE)

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTGGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGGCGCCAAGCTAATAAT
GGTGACGATGCAACGGCTGGTCTGACTCACATGATGATCTGGCATTCCAATTTGAATGATGCAACTTATCAGAGGACAAGGGCT
CTTGTTCGCACCGGAATGGATCCCAGGATGTGCTCTCTGATGCAAGGTTCAACTCTCCCTAGGAGGTCTGGAGCCGCAGGTGCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAAGCA
ATGATGGATCAAGTGAGAGAGAGCCGGAACCCAGGGAATGCTGAGTTCGAAGATCTCACTTTTCTAGCACGGTCTGCACTCATA
TTGAGAGGGTCGGTTGCTCACAAGTCCTGCCTGCCTGCCTGTGTGTATGGACCTGCCGTAGCCAGTGGGTACGACTTTGAAAGA
GAGGGATACTCTCTAGTCGGAATAGACCCTTTCAGACTGCTTCAAAACAGCCAAGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGGTCCCAAGAGGGAAGCTTTCCACTAGAGGAGTTCAAATTGCTTCCAATGAAAATATGGAGACTATGGAATCAAGT
ACACTTGAACTGAGAAGCAGGTACTGGGCCATAAGGACCAGAAGTGGAGGAAACACCAATCAACAGAGGGCATCTGCGGGCCAA
ATCAGCATACAACCTACGTTCTCAGTACAGAGAAATCTCCCTTTTGACAGAACAACCGTTATGGCAGCATTCACTGGGAATACA
GAGGGGAGAACATCTGACATGAGGACCGAAATCATAAGGATGATGGAAAGTGCAAGACCAGAAGATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTATTTCTTC
GGAGACAATGCAGAGGAGTACGACAATTAAAGAAAAATACCCTTGTTTCTACT (SEQ ID NO:13)

*Fig.1D*

PR8(CAMBRIDGE)

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAAAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG
GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT (SEQ ID NO:14)

NS

AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAGAAAGTGGCAGGCCCTCTTTGTATCAGAATGGACCAGGCGATCATGGATAAAAACATCATACTGAAAG
CGAACTTCAGTGTGATTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTGAGCAAATAACATTTATGCAAGCCTTACATCTATTGCTTGAAGTGGAGCAAGAGATAAGA
ACTTTCTCATTTCAGCTTATTTAATAATAAAAAACACCCTTGTTTCTACT (SEQ ID NO:15)

*Fig. 1E*

Summary of HA assay of 1434 individual clones

| Groups | Numbers of clone | Fold change | % |
|---|---|---|---|
| WT HA titer = $2^7$ | - | - | - |
| HA titer =$2^{>9-9.5}$ | 8 | >4 | 0.6% |
| HA titer =$2^{>8.5-9}$ | 23 | >2.8 - 4 | 1.6% |
| HA titer =$2^{7-8.5}$ | 748 | 1 - 2.8 | 52.2% |
| HA titer < $2^7$ | 655 | <1 | 45.6% |
| Total | 1434 | - | 100% |

*FIG. 3*

Recombinant viruses generated from dominant mutations

| Viruses | Gene backbone | | | | | | | | Virus stock titer | |
|---|---|---|---|---|---|---|---|---|---|---|
| | HA | NA | PB2 | PB1 | PA | NP | M | NS | $2^n$ | Pfu/ml |
| WT | Indo/NC /09 delHA | Indo/NC /09 NA | PR8-wt | PR8-wt | PR8-wt | PR8-wt | PR8-wt | PR8-wt | 7 | 3.0E+07 |
| 1 | | | M202L F323L | M507V V644A | | I116L | | K55E | 9~9.5 | 2.0E+08 |
| 2 | | | M202L F323L | Q247H | R401K | | | T49A | 9 | 1.0E+08 |
| 3 | | | I504V | M507V V644A | I550L | R74K N417D | | K55E | 8~8.5 | 5.7E+07 |
| 4 | | | I505V | E112G | I550L | R74K | | S161T | 9 | 1.6E+08 |
| 5 | | | M202L F323L | E112G | | | | S161T | 8.5 | 1.3E+08 |
| 6 | | | M66R | M40I G180W | | R74K | | S161T | 8~8.5 | 2.3E+07 |

*FIG. 4*

PB1 Mutants

- ■ WT
- ─╀─ R327K
- ─╁─ V336I
- ─╀─ L473V, L598P
- ─●─ F2 N66S ✷
- ─□─ F2 K73R ✷
- ─△─ F2 V76A
- ─▷─ F2 R79Q
- ─◇─ F2 L82S
- ─○─ F2 E87Q

Virus yield ($Log_{10}$ pfu/ml) vs Hours of postinfection (12, 24, 36, 48)

Confirmed high replicative mutations

| Gene | Screened from viruses libraries | Described in literature |
|---|---|---|
| PB2 | M202L F323L, I504V, M66R | A44S, E158G, E158A, D236N, D256G, R368K, E391Q, I504V, Q591K, V613T, A661T, D701N, D701N S714R |
| PB1 | M507V V644A, V644A, R54I, Q247H, E112G, M40I G180W, I667T M714T | R327K, V336I, L473V L598P |
| PB1 F2 | - | N66S, K73R, V76A, R79Q, L82S, E87Q |
| PA | F105C, R401K | T97I, K142N, S225C, S149PP T357K, K356R, A404S, S421I |
| NP | R293M, I116L, N224I, R74K, R74K N417D, | R293K, R305K, E372D, R422K, T442A, D455E, I109V, N101G, N319K |
| M | P90S | V97A, Y100H, V97A Y100H |
| NS | A30P, T49A, R140Q, S161T, A223E | K55E |

FIG. 6

Recombinant viruses generated by RGS

| Virus # | Gene backbone | | | | | | | | Virus stock titer | |
|---|---|---|---|---|---|---|---|---|---|---|
| | HA | NA | PB2 | PB1 | PA | NP | M | NS | $2^n$ | Pfu/ml |
| wt | Inda/NC/09 delHA | Indo/NC/09 NA | wt | wt | wt | wt | wt | wt | 7 | 3.0E+07 |
| 1 | | | M202L F323L | M507V V644A | | I116L | | K55E | 9~9.5 | 2.0E+08 |
| 4 | | | M202L F323L | M507V V644A | K356R | T442A | V97A Y100H | K55E | 10~10.5 | 1.6E+08 |
| 36 | | | I504V | E112G | I550L | I112L | Y100H | R140Q | 9.5 | 1.3E+08 |
| 38 | | | M202L F323L | M507V V644A | | I116L | Y100H | K55E | 10~10.5 | 2.3E+08 |
| HY-#17 | | | I504V | E112G | S225C | R74K N417D | V97A Y100H | K55E | 9.5~10 | 5.8E+08 |
| HY-#61 | | | M202L F323L | Q247H | K142N | R74K | V97A Y100H | K55E | 10~10.5 | 2.0E+08 |
| HY-#26 | | | M202L F323L | M40L G180W | S225C | R422K | V97A Y100H | K55E | 10 | 3.0E+08 |

FIG. 7A

Total viral protein yield: 4.2 fold

Mutant virus generates much more M1 and HA1 proteins than wild type.

Wild type VS. mutant

| # | Gene backbone | | | | | | | | Virus stock titer | |
|---|---|---|---|---|---|---|---|---|---|---|
| | HA | NA | PB2 | PB1 | PA | NP | M | NS | HA titer ($2^n$) | Pfu/ml |
| WT | Indo/NC/09 delHA | Indo/NC/09 NA | PR8-wt | PR8-wt | PR8-wt | PR8-wt | PR8-wt | PR8-wt | 7 | 3.0E+07 |
| 4 | | | M202L F323L | M507V V644A | K356R | T442A | V97A Y100H | K55E | 10~10.5 | 1.6E+08 |

*FIG. 9A*

CANIS FAMILIARIS [gbmam]: 1194 CDS's (559501 CODONS)

FIELDS: [TRIPLET] [AMINO ACID] [FRACTION] [FREQUENCY: PER THOUSAND] ([NUMBER])

| | | | | | | | | | | | | | | | | | | | |
|---|---|---|---|---|---|---|---|---|---|---|---|---|---|---|---|---|---|---|---|
| UUU | F | 0.41 | 17.1 | ( 9540) | UCU | S | 0.18 | 13.8 | ( 7723) | UAU | Y | 0.40 | 11.5 | ( 6456) | UGU | C | 0.42 | 10.1 | ( 5665) |
| UUC | F | 0.59 | 24.4 | (13671) | UCC | S | 0.24 | 18.4 | (10299) | UAC | Y | 0.60 | 17.5 | ( 9786) | UGC | C | 0.58 | 13.8 | ( 7723) |
| UUA | L | 0.06 | 5.8 | ( 3270) | UCA | S | 0.13 | 9.8 | ( 5487) | UAA | * | 0.27 | 0.6 | ( 325) | UGA | * | 0.53 | 1.1 | ( 642) |
| UUG | L | 0.12 | 11.8 | ( 6627) | UCG | S | 0.06 | 4.6 | ( 2584) | UAG | * | 0.21 | 0.5 | ( 254) | UGG | W | 1.00 | 13.8 | ( 7704) |
| CUU | L | 0.12 | 11.7 | ( 6523) | CCU | P | 0.27 | 15.6 | ( 8713) | CAU | H | 0.39 | 9.0 | ( 5039) | CGU | R | 0.07 | 3.9 | ( 2163) |
| CUC | L | 0.22 | 21.8 | (12224) | CCC | P | 0.35 | 20.4 | (11422) | CAC | H | 0.61 | 14.1 | ( 7888) | CGC | R | 0.20 | 10.6 | ( 5943) |
| CUA | L | 0.06 | 6.5 | ( 3644) | CCA | P | 0.25 | 14.6 | ( 8157) | CAA | Q | 0.25 | 11.0 | ( 6149) | CGA | R | 0.11 | 5.6 | ( 3155) |
| CUG | L | 0.43 | 42.8 | (23966) | CCG | P | 0.12 | 7.0 | ( 3892) | CAG | Q | 0.75 | 32.6 | (18244) | CGG | R | 0.21 | 11.0 | ( 6132) |
| AUU | I | 0.32 | 15.5 | ( 8662) | ACU | T | 0.22 | 12.3 | ( 6886) | AAU | N | 0.43 | 16.5 | ( 9253) | AGU | S | 0.14 | 10.8 | ( 6029) |
| AUC | I | 0.53 | 25.7 | (14391) | ACC | T | 0.39 | 21.4 | (11979) | AAC | N | 0.57 | 21.6 | (12104) | AGC | S | 0.25 | 18.9 | (10595) |
| AUA | I | 0.15 | 7.2 | ( 4017) | ACA | T | 0.26 | 14.2 | ( 7972) | AAA | K | 0.40 | 22.2 | (12410) | AGA | R | 0.20 | 10.5 | ( 5847) |
| AUG | M | 1.00 | 22.7 | (12717) | ACG | T | 0.13 | 7.2 | ( 4005) | AAG | K | 0.60 | 33.9 | (18967) | AGG | R | 0.21 | 11.1 | ( 6228) |
| GUU | V | 0.14 | 9.3 | ( 5189) | GCU | A | 0.25 | 17.2 | ( 9609) | GAU | D | 0.43 | 19.7 | (11012) | GGU | G | 0.16 | 11.3 | ( 6298) |
| GUC | V | 0.27 | 17.2 | ( 9607) | GCC | A | 0.44 | 30.3 | (16927) | GAC | D | 0.57 | 26.2 | (14655) | GGC | G | 0.35 | 24.2 | (13513) |
| GUA | V | 0.10 | 6.5 | ( 3660) | GCA | A | 0.20 | 13.7 | ( 7651) | GAA | E | 0.40 | 26.4 | (14776) | GGA | G | 0.24 | 16.9 | ( 9465) |
| GUG | V | 0.48 | 31.0 | (17366) | GCG | A | 0.11 | 7.9 | ( 4431) | GAG | E | 0.60 | 40.3 | (22552) | GGG | G | 0.25 | 17.4 | ( 9718) |

CODING GC 53.16% 1ST LETTER GC 55.35% 2ND LETTER GC 41.92% 3RD LETTER GC 62.22%

GENETIC CODE 1: STANDARD

AGCGAAAGCAGGTCAATTATATTCAATATGGAAAGAATAAAAGAACTACGAAATCTAATGTCGCAGTCTCGCACCCGCGA
GATACTCACAAAAACCACCGTGGACCATATGGCCATAATCAAGAAGTACACATCAGGAAGACAGGAGAAGAACCCAGCAC
TTAGGATGAAATGGATGATGGCAATGAAATATCCAATTACAGCAGACAAGAGGATAACGGAAATGATTCCTGAGAGAAAT
GAGCAAGGACAAACTTTATGGAGTAAAATGAATGATGCCGGATCAGACCGAGTGATGGTATCACCTCTGGCTGTGACATG
GTGGAATAGGAATGGACCAATAACAAATACAGTTCATTATCCAAAAATCTACAAAACTTATTTTGAAAGAGTCGAAAGGC
TAAAGCATGGAACCTTTGGCCCTGTCCATTTTAGAAACCAAGTCAAAATACGTCGGAGAGTTGACATAAATCCTGGTCAT
GCAGATCTCAGTGCCAAGGAGGCACAGGATGTAATCATGGAAGTTGTTTTCCCTAACGAAGTGGGAGCCAGGATACTAAC
ATCGGAATCGCAACTAACGATAACCAAAGAGAAGAAAGAAGAACTCCAGGATTGCAAAATTTCTCCTTTGATGGTTGCAT
ACATGTTGGAGAGAGAACTGGTCCGCAAAACGAGATTCCTCCCAGTGGCTGGTGGAACAAGCAGTGTGTACATTGAAGTG
TTGCATTTGACTCAAGGAACATGCTGGGAACAGATGTATACTCCAGGAGGGGAAGTGAGGAATGATGATGTTGATCAAAG
CTTGATTATTGCTGCTAGGAACATAGTGAGAAGAGCTGCAGTATCAGCAGATCCACTAGCATCTTTATTGGAGATGTGCC
ACAGCACACAGATTGGTGGAATTAGGATGGTAGACATCCTTAGGCAGAACCCAACAGAAGAGCAAGCCGTGGATATATGC
AAGGCTGCAATGGGACTGAGAATTAGCTCATCCTTCAGTTTTGGTGGATTCACATTTAAGAGAACAAGCGGATCATCAGT
CAAGAGAGAGGAAGAGGTGCTTACGGGCAATCTTCAAACATTGAAGATAAGAGTGCATGAGGGATATGAAGAGTTCACAA
TGGTTGGGAGAAGAGCAACAGCCATACTCAGAAAAGCAACCAGGAGATTGATTCAGCTGATAGTGAGTGGGAGAGACGAA
CAGTCGATTGCCGAAGCAATAATTGTGGCCATGGTATTTTCACAAGAGGATTGTATGATAAAAGCAGTCAGAGGTGATCT
GAATTTCGTCAATAGGGCGAATCAACGATTGAATCCTATGCATCAACTTTTAAGACATTTTCAGAAGGATGCGAAAGTGC
TTTTTCAAAATTGGGGAGTTGAACCTATCGACAATGTGATGGGAATGATTGGGATATTGCCCGACATGACTCCAAGCATC
GAGATGTCAATGAGAGGAGTGAGAATCAGCAAAATGGGTGTAGATGAGTACTCCAGCACGGAGAGGGTAGTGGTGAGCAT
TGACCGTTTTTTGAGAATCCGGGACCAACGAGGAAATGTACTACTGTCTCCCGAGGAGGTCAGTGAAACACAGGGAACAG
AGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGA
ACCATTTCAGTCTTTAGTACCTAAGGCCATTAGAGGCCAATACAGTGGGTTTGTAAGAACTCTGTTCCAACAAATGAGGG
ATGTGCTTGGGACATTTGATACCGCACAGATAATAAAACTTCTTCCCTTCGCAGCCGCTCCACCAAAGCAAAGTAGAATG
CAGTTCTCCTCATTTACTGTGAATGTGAGGGGATCAGGAATGAGAATACTTGTAAGGGGCAATTCTCCTGTATTCAACTA
TAACAAGGCCACGAAGAGACTCACAGTTCTCGGAAAGGATGCTGGCACTTTAACTGAAGACCCAGATGAAGGCACAGCTG
GAGTGGAGTCCGCTGTTCTGAGGGGATTCCTCATTCTGGGCAAAGAAGACAAGAGATATGGGCCAGCACTAAGCATCAAT
GAACTGAGCAACCTTGCGAAAGGAGAGAAGGCTAATGTGCTAATTGGGCAAGGAGACGTGGTGTTGGTAATGAAACGGAA
ACGGGACTCTAGCATACTTACTGACAGCCAGACAGCGACCAAAAGAATTCGGATGGCCATCAATTAGTGTCGAATAGTTT
AAAAACGACCTTGTTTCTACT (SEQ ID NO:3)

FIG. 10F

Canine codon optimized PR8-PB2:

AGCGAAAGCAGGTCAATTATATTCAATATGGAAAGAATAAAAGAACTACGAAATCTAATGTCGCAGTCTCGCACCCGCGA

GATACTCACAAAAACCACCGTGGACCATATGGCCATAATCAAGAAGTACACATCAGGAAGACAGGAGAAGAACCCAGCAC

TGAGGATGAAATGGATGATGGCAATGAAATATCCAATTACAGCAGACAAGAGGATCACCGAAATGATTCCTGAGAGAAAT

GAGCAGGGACAGACTCTGTGGAGTAAAATGAATGATGCCGGATCAGACCGAGTGATGGTGTCACCTCTGGCTGTGACATG

GTGGAATAGGAATGGACCAATCACAAATACAGTGCATTATCCAAAAATCTACAAAACTTATTTTGAAAGAGTCGAAAGGC

TGAAGCATGGAACCTTTGGCCCTGTCCATTTTAGAAACCAGGTCAAAATCCGGCGGAGAGTGGACATCAATCCTGGTCAT

GCAGATCTCAGTGCCAAGGAGGCACAGGATGTGATCATGGAAGTGGTGTTCCCTAACGAAGTGGGAGCCAGGATTCTGAC

ATCCGAATCCCAGCTGACCATTACCAAAGAGAAGAAAGAAGAACTCCAGGATTGCAAAATTTCTCCTCTGATGGTGGCAT

ACATGCTGGAGAGAGAACTGGTCCGCAAAACAAGATTCCTCCCAGTGGCTGGTGGAACAAGCAGTGTGTACATTGAAGTG

CTGCATCTGACTCAGGGAACATGCTGGGAACAGATGTATACTCCAGGAGGGGAAGTGAGGAATGATGATGTGGATCAGAG

CCTGATTATTGCTGCTAGGAACATTGTGAGAAGAGCTGCAGTGTCAGCAGATCCACTGGCATCTCTGCTGGAGATGTGCC

ACAGCACACAGATTGGTGGAATTAGGATGGTGGACATCCTGAGGCAGAACCCAACAGAAGAGCAGGCCGTGGATATTTGC

AAGGCTGCAATGGGACTGAGAATTAGCTCATCCTTCAGTTTTGGTGGATTCACATTTAAGAGAACAAGCGGATCATCAGT

CAAGAGAGAGGAAGAGGTGCTGACCGGCAATCTGCAGACACTGAAGATCAGAGTGCATGAGGGATATGAAGAGTTCACAA

TGGTGGGGAGAAGAGCAACAGCCATCCTCAGAAAAGCAACCAGGAGACTGATTCAGCTGATCGTGAGTGGGAGAGACGAA

CAGTCCATTGCCGAAGCAATTATTGTGGCCATGGTGTTTTCACAGGAGGATTGTATGATTAAAGCAGTCAGAGGTGATCT

GAATTTCGTCAATAGGGCCAATCAGCGACTGAATCCTATGCATCAGCTGCTGAGACATTTTCAGAAGGATGCCAAAGTGC

TGTTTCAGAATTGGGGAGTGGAACCTATCGACAATGTGATGGGAATGATTGGGATCCTGCCCGACATGACTCCAAGCATC

GAGATGTCAATGAGAGGAGTGAGAATCAGCAAAATGGGTGTGGATGAGTACTCCAGCACCGAGAGGGTCGTGGTGAGCAT

TGACAGATTTCTGAGAATCCGGGACCAGCGAGGAAATGTGCTCCTGTCTCCCGAGGAGGTCAGTGAAACACAGGGAACAG

AGAAACTGACAATTACTTACTCATCCTCAATGATGTGGGAGATTAATGGTCCTGAATCAGTGCTGGTCAATACCTATCAG

TGGATCATCAGAAACTGGGAAACTGTGAAAATTCAGTGGTCCCAGAACCCTACAATGCTGTACAATAAAATGGAATTTGA

ACCATTTCAGTCTCTGGTGCCTAAGGCCATTAGAGGCCAGTACAGTGGGTTTGTGAGAACTCTGTTCCAGCAGATGAGGG

ATGTGCTGGGGACATTTGATACCGCACAGATTATTAAACTGCTGCCCTTCGCAGCCGCTCCACCAAAGCAGAGTAGAATG

CAGTTCTCCTCATTTACTGTGAATGTGAGGGGATCAGGAATGAGAATCCTGGTGAGGGGCAATTCTCCTGTGTTCAACTA

TAACAAGGCCACCAAGAGACTCACAGTGCTCGGAAAGGATGCTGGCACTCTGACTGAAGACCCAGATGAAGGCACAGCTG

GAGTGGAGTCCGCTGTGCTGAGGGGATTCCTCATTCTGGGCAAAGAAGACAAGAGATATGGGCCAGCACTGAGCATCAAT

GAACTGAGCAACCTGGCCAAAGGAGAGAAGGCTAATGTGCTAATTGGGCAAGGAGACGTGGTGTTGGTAATGAAACGGAA

ACGGGACTCTAGCATACTTACTGACAGCCAGACAGCGACCAAAAGAATTCGGATGGCCATCAATTAGTGTCGAATAGTTT

AAAAACGACCTTGTTTCTACT (SEQ ID NO:16)

AGCGAAAGCAGGCAAACCATTTGAATGGATGTCAATCCGACCTTACTTTTCTTAAAAGTGCCAGCACAAAATGCTATAAG
CACAACTTTCCCTTATACTGGAGACCCTCCTTACAGCCATGGGACAGGAACAGGATACACCATGGATACTGTCAACAGGA
CACATCAGTACTCAGAAAAGGGAAGATGGACAACAAACACCGAAACTGGAGCACCGCAACTCAACCCGATTGATGGGCCA
CTGCCAGAAGACAATGAACCAAGTGGTTATGCCCAAACAGATTGTGTATTGGAGGCGATGGCTTTCCTTGAGGAATCCCA
TCCTGGTATTTTTGAAAACTCGTGTATTGAAACGATGGAGGTTGTTCAGCAAACACGAGTAGACAAGCTGACACAAGGCC
GACAGACCTATGACTGGACTCTAAATAGAAACCAACCTGCTGCAACAGCATTGGCCAACACAATAGAAGTGTTCAGATCA
AATGGCCTCACGGCCAATGAGTCTGGAAGGCTCATAGACTTCCTTAAGGATGTAATGGAGTCAATGAACAAAGAAGAAAT
GGGGATCACAACTCATTTTCAGAGAAAGAGACGGGTGAGAGACAATATGACTAAGAAAATGATAACACAGAGAACAATGG
GTAAAAAGAAGCAGAGATTGAACAAAAGGAGTTATCTAATTAGAGCATTGACCCTGAACACAATGACCAAAGATGCTGAG
AGAGGGAAGCTAAAACGGAGAGCAATTGCAACCCCAGGGATGCAAATAAGGGGGTTTGTATACTTTGTTGAGACACTGGC
AAGGAGTATATGTGAGAAACTTGAACAATCAGGGTTGCCAGTTGGAGGCAATGAGAAGAAAGCAAAGTTGGCAAATGTTG
TAAGGAAGATGATGACCAATTCTCAGGACACCGAACTTTCTTTCACCATCACTGGAGATAACACCAAATGGAACGAAAAT
CAGAATCCTCGGATGTTTTTGGCCATGATCACATATATGACCAGAAATCAGCCCGAATGGTTCAGAAATGTTCTAAGTAT
TGCTCCAATAATGTTCTCAAACAAAATGGCGAGACTGGGAAAAGGGTATATGTTTGAGAGCAAGAGTATGAAACTTAGAA
CTCAAATACCTGCAGAAATGCTAGCAAGCATCGATTTGAAATATTTCAATGATTCAACAAGAAAGAAGATTGAAAAAATC
CGACCGCTCTTAATAGAGGGGACTGCATCATTGAGCCCTGGAATGATGATGGGCATGTTCAATATGTTAAGCACTGTATT
AGGCGTCTCCATCCTGAATCTTGGACAAAAGAGATACACCAAGACTACTTACTGGTGGGATGGTCTTCAATCCTCTGACG
ATTTTGCTCTGATTGTGAATGCACCCAATCATGAAGGGATTCAAGCCGGAGTCGACAGGTTTTATCGAACCTGTAAGCTA
CTTGGAATCAATATGAGCAAGAAAAAGTCTTACATAAACAGAACAGGTACATTTGAATTCACAAGTTTTTTCTATCGTTA
TGGGTTTGTTGCCAATTTCAGCATGGAGCTTCCCAGTTTTGGGGTGTCTGGGATCAACGAGTCAGCGGACATGAGTATTG
GAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATATAGGTGACACACAAATACAAACCCGAAGATCATTTGAAATAAAGAAACT
GTGGGAGCAAACCCGTTCCAAAGCTGGACTGCTGGTCTCCGACGGAGGCCCAAATTTATACAACATTAGAAATCTCCACA
TTCCTGAAGTCTGCCTAAAATGGGAATTGATGGATGAGGATTACCAGGGGCGTTTATGCAACCCACTGAACCCATTTGTC
AGCCATAAAGAAATTGAATCAATGAACAATGCAGTGATGATGCCAGCACATGGTCCAGCCAAAAACATGGAGTATGATGC
TGTTGCAACAACACACTCCTGGATCCCCAAAAGAAATCGATCCATCTTGAATACAAGTCAAAGAGGAGTACTTGAGGATG
AACAAATGTACCAAAGGTGCTGCAATTTATTTGAAAAATTCTTCCCCAGCAGTTCATACAGAAGACCAGTCGGGATATCC
AGTATGGTGGAGGCTATGGTTTCCAGAGCCCGAATTGATGCACGGATTGATTTCGAATCTGGAAGGATAAAGAAAGAAGA
GTTCACTGAGATCATGAAGATCTGTTCCACCATTGAAGAGCTCAGACGGCAAAAATAGTGAATTTAGCTTGTCCTTCATG
AAAAAATGCCTTGTTTCTACT (SEQ ID NO:2)

FIG. 10H

Canine codon optimized PR8 PB1:

AGCGAAAGCAGGCAAACCATTTGAATGGATGTCAATCCGACCTTACTTTTCTTAAAAGTGCCAGCACAAAATGCTATAAG

CACAACTTTCCCTTATACTGGAGACCCTCCTTACAGCCATGGGACAGGAACAGGATACACCATGGATACTGTCAACAGGA

CACATCAGTACTCAGAAAAGGGAAGATGGACAACAAACACCGAAACTGGAGCACCGCAACTCAACCCGATTGATGGGCCA

CTGCCAGAAGACAATGAACCAAGTGGTTATGCCCAAACAGATTGTGTATTGGAGGCGATGGCTTTCCTTGAGGAATCCCA

TCCTGGTATTTTTGAAAACTCGTGTATTGAAACGATGGAGGTTGTTCAGCAAACACGAGTGGACAAGCTGACACAGGGCC

GACAGACCTATGACTGGACTCTGAATAGAAACCAGCCTGCTGCAACAGCACTGGCCAACACAATCGAAGTGTTCAGATCA

AATGGCCTCACCGCCAATGAGTCTGGAAGGCTCATCGACTTCCTGAAGGATGTGATGGAGTCAATGAACAAAGAAGAAAT

GGGGATCACAACTCATTTTCAGAGAAAGAGACGGGTGAGAGACAATATGACTAAGAAAATGATTACACAGAGAACAATGG

GTAAAAAGAAGCAGAGACTGAACAAAAGGAGTTATCTGATTAGAGCACTGACCCTGAACACAATGACCAAAGATGCTGAG

AGAGGGAAGCTGAAACGGAGAGCAATTGCAACCCCAGGGATGCAGATTAGGGGGTTTGTGTACTTTGTGGAGACACTGGC

AAGGAGTATTTGTGAGAAACTGGAACAGTCAGGGCTGCCAGTGGGAGGCAATGAGAAGAAAGCAAAGCTGGCAAATGTGG

TGAGGAAGATGATGACCAATTCTCAGGACACCGAACTGTCTTTCACCATCACTGGAGATAACACCAAATGGAACGAAAAT

CAGAATCCTCGGATGTTTCTGGCCATGATCACATATATGACCAGAAATCAGCCCGAATGGTTCAGAAATGTGCTGAGTAT

TGCTCCAATTATGTTCTCAAACAAAATGGCCAGACTGGGAAAAGGGTATATGTTTGAGAGCAAGAGTATGAAACTGAGAA

CTCAGATTCCTGCAGAAATGCTGGCAAGCATCGATCTGAAATATTTCAATGATTCAACAAGAAAGAAGATTGAAAAAATC

CGACCCCTCCTGATTGAGGGGACTGCATCACTGAGCCCTGGAATGATGATGGGCATGTTCAATATGCTGAGCACTGTGCT

GGGCGTCTCCATCCTGAATCTGGGACAGAAGAGATACACCAAGACTACTTACTGGTGGGATGGTCTGCAGTCCTCTGACG

ATTTTGCTCTGATTGTGAATGCACCCAATCATGAAGGGATTCAGGCCGGAGTCGACAGGTTTTATCGAACCTGTAAGCTG

CTGGGAATCAATATGAGCAAGAAAAAGTCTTACATCAACAGAACAGGTACATTTGAATTCACAAGTTTTTTCTATCGCTA

TGGGTTTGTGGCCAATTTCAGCATGGAGCTGCCCAGTTTTGGGGTGTCTGGGATCAACGAGTCAGCCGACATGAGTATTG

GAGTGACTGTCATCAAAAACAATATGATCAACAATGATCTGGGTCCAGCAACAGCTCAGATGGCCCTGCAGCTGTTCATC

AAAGATTACAGGTACACCTACCGATGCCATATCGGTGACACACAGATTCAGACCCGAAGATCATTTGAAATCAAGAAACT

GTGGGAGCAGACCCGCTCCAAAGCTGGACTGCTGGTCTCCGACGGAGGCCCAAATCTGTACAACATTAGAAATCTCCACA

TTCCTGAAGTCTGCCTGAAATGGGAACTGATGGATGAGGATTACCAGGGGCGCCTGTGCAACCCACTGAACCCATTTGTC

AGCCATAAAGAAATTGAATCAATGAACAATGCAGTGATGATGCCAGCACATGGTCCAGCCAAAAACATGGAGTATGATGC

TGTGGCAACAACACACTCCTGGATCCCCAAAAGAAATCGATCCATCCTGAATACAAGTCAGAGAGGAGTGCTGGAGGATG

AACAGATGTACCAGAGGTGCTGCAATCTGTTTGAAAAATTCTTCCCCAGCAGTTCATACAGAAGACCAGTCGGGATCTCC

AGTATGGTGGAGGCTATGGTGTCCAGAGCCCGAATTGATGCACGGATTGATTTCGAATCTGGAAGGATCAAGAAAGAAGA

GTTCACTGAGATCATGAAGATCTGTTCCACCATTGAAGAGCTCAGACGGCAAAAATAGTGAATTTAGCTTGTCCTTCATG

AAAAAATGCCTTGTTTCTACT (SEQ ID NO:17)

AGCGAAAGCAGGTACTGATCCAAAATGGAAGATTTTGTGCGACAATGCTTCAATCCGATGATTGTCGAGCTTGCGGAAAA
AACAATGAAAGAGTATGGGGAGGACCTGAAAATCGAAACAAACAAATTTGCAGCAATATGCACTCACTTGGAAGTATGCT
TCATGTATTCAGATTTTCACTTCATCAATGAGCAAGGCGAGTCAATAATCGTAGAACTTGGTGATCCAAATGCACTTTTG
AAGCACAGATTTGAAATAATCGAGGGAAGAGATCGCACAATGGCCTGGACAGTAGTAAACAGTATTTGCAACACTACAGG
GGCTGAGAAACCAAAGTTTCTACCAGATTTGTATGATTACAAGGAGAATAGATTCATCGAAATTGGAGTAACAAGGAGAG
AAGTTCACATATACTATCTGGAAAAGGCCAATAAAATTAAATCTGAGAAAACACACATCCACATTTTCTCGTTCACTGGG
GAAGAAATGGCCACAAAGGCAGACTACACTCTCGATGAAGAAAGCAGGGCTAGGATCAAAACCAGACTATTCACCATAAG
ACAAGAAATGGCCAGCAGAGGCCTCTGGGATTCCTTTCGTCAGTCCGAGAGAGGAGAAGAGACAATTGAAGAAAGGTTTG
AAATCACAGGAACAATGCGCAAGCTTGCCGACCAAAGTCTCCCGCCGAACTTCTCCAGCCTTGAAAATTTTAGAGCCTAT
GTGGATGGATTCGAACCGAACGGCTACATTGAGGGCAAGCTGTCTCAAATGTCCAAAGAAGTAAATGCTAGAATTGAACC
TTTTTTGAAAACAACACCACGACCACTTAGACTTCCGAATGGGCCTCCCTGTTCTCAGCGGTCCAAATTCCTGCTGATGG
ATGCCTTAAAATTAAGCATTGAGGACCCAAGTCATGAAGGAGAGGGAATACCGCTATATGATGCAATCAAATGCATGAGA
ACATTCTTTGGATGGAAGGAACCCAATGTTGTTAAACCACACGAAAAGGGAATAAATCCAAATTATCTTCTGTCATGGAA
GCAAGTACTGGCAGAACTGCAGGACATTGAGAATGAGGAGAAAATTCCAAAGACTAAAAATATGAAGAAAACAAGTCAGC
TAAAGTGGGCACTTGGTGAGAACATGGCACCAGAAAAGGTAGACTTTGACGACTGTAAAGATGTAGGTGATTTGAAGCAA
TATGATAGTGATGAACCAGAATTGAGGTCGCTTGCAAGTTGGATTCAGAATGAGTTTAACAAGGCATGCGAACTGACAGA
TTCAAGCTGGATAGAGCTCGATGAGATTGGAGAAGATGTGGCTCCAATTGAACACATTGCAAGCATGAGAAGGAATTATT
TCACATCAGAGGTGTCTCACTGCAGAGCCACAGAATACATAATGAAGGGAGTGTACATCAATACTGCCTTGCTTAATGCA
TCTTGTGCAGCAATGGATGATTTCCAATTAATTCCAATGATAAGCAAGTGTAGAACTAAGGAGGGAAGGCGAAAGACCAA
CTTGTATGGTTTCATCATAAAAGGAAGATCCCACTTAAGGAATGACACCGACGTGGTAAACTTTGTGAGCATGGAGTTTT
CTCTCACTGACCCAAGACTTGAACCACATAAATGGGAGAAGTACTGTGTTCTTGAGATAGGAGATATGCTTATAAGAAGT
GCCATAGGCCAGGTTTCAAGGCCCATGTTCTTGTATGTGAGAACAAATGGAACCTCAAAAATTAAAATGAAATGGGGAAT
GGAGATGAGGCGTTGCCTCCTCCAGTCACTTCAACAAATTGAGAGTATGATTGAAGCTGAGTCCTCTGTCAAAGAGAAAG
ACATGACCAAAGAGTTCTTTGAGAACAAATCAGAAACATGGCCCATTGGAGAGTCCCCCAAAGGAGTGGAGGAAAGTTCC
ATTGGGAAGGTCTGCAGGACTTTATTAGCAAAGTCGGTATTCAACAGCTTGTATGCATCTCCACAACTAGAAGGATTTTC
AGCTGAATCAAGAAAACTGCTTCTTATCGTTCAGGCTCTTAGGGACAACCTGGAACCTGGGACCTTTGATCTTGGGGGGC
TATATGAAGCAATTGAGGAGTGCCTGATTAATGATCCCTGGGTTTTGCTTAATGCTTCTTGGTTCAACTCCTTCCTTACA
CATGCATTGAGTTAGTTGTGGCAGTGCTACTATTTGCTATCCATACTGTCCAAAAAAGTACCTTGTTTCTACT (SEQ ID NO:1)

FIG. 10J

Canine codon optimized PR8 PA:

AGCGAAAGCAGGTACTGATCCAAAATGGAAGATTTTGTGCGACAATGCTTCAATCCGATGATTGTCGAGCTTGCGGAAAA

AACAATGAAAGAGTATGGGGAGGACCTGAAAATCGAAACAAACAAATTTGCAGCAATATGCACTCACTTGGAAGTATGCT

TCATGTATTCAGATTTTCACTTCATCAATGAGCAAGGCGAGTCAATAATCGTAGAACTTGGTGATCCAAATGCACTTTTG

AAGCACAGATTTGAAATAATCGAGGGAAGAGATCGCACAATGGCCTGGACAGTAGTAAACAGTATTTGCAACACTACAGG

GGCTGAGAAACCAAAGTTTCTACCAGATTTGTATGATTACAAGGAGAATAGATTCATCGAAATTGGAGTAACAAGGAGAG

AAGTTCACATATACTATCTGGAAAAGGCCAATAAAATTAAATCTGAGAAAACACACATCCACATTTTCTCGTTCACTGGG

GAAGAAATGGCCACAAAGGCAGACTACACTCTCGATGAAGAAAGCAGGGCTAGGATCAAAACCAGACTATTCACCATAAG

ACAAGAAATGGCCAGCAGAGGCCTCTGGGATTCCTTTCGTCAGTCCGAGAGAGGAGAAGAGACAATTGAAGAAAGGTTTG

AAATCACAGGAACAATGCGCAAGCTTGCCGACCAAAGTCTCCCGCCGAACTTCTCCAGCCTTGAAAATTTTAGAGCCTAT

GTGGATGGATTCGAACCGAACGGCTACATTGAGGGCAAGCTGTCTCAAATGTCCAAAGAAGTAAATGCTAGAATTGAACC

TTTTCTGAAAACAACACCACGACCACTGAGACTGCCCAATGGGCCTCCCTGTTCTCAGCGGTCCAAATTCCTGCTGATGG

ATGCCCTGAAACTGAGCATTGAGGACCCAAGTCATGAAGGAGAGGGAATTCCCCTGTATGATGCAATCAAATGCATGAGA

ACATTCTTTGGATGGAAGGAACCCAATGTGGTGAAACCACACGAAAAGGGAATCAATCCAAATTATCTGCTGTCATGGAA

GCAGGTGCTGGCAGAACTGCAGGACATTGAGAATGAGGAGAAAATTCCAAAGACTAAAAATATGAAGAAAACAAGTCAGC

TGAAGTGGGCACTGGGTGAGAACATGGCACCAGAAAAGGTGGACTTTGACGACTGTAAAGATGTGGGTGATCTGAAGCAG

TATGATAGTGATGAACCAGAACTGAGGTCCCTGGCAAGTTGGATTCAGAATGAGTTTAACAAGGCATGCGAACTGACAGA

TTCAAGCTGGATTGAGCTCGATGAGATTGGAGAAGATGTGGCTCCAATTGAACACATTGCAAGCATGAGAAGGAATTATT

TCACATCAGAGGTGTCTCACTGCAGAGCCACAGAATACATCATGAAGGGAGTGTACATCAATACTGCCCTGCTGAATGCA

TCTTGTGCAGCAATGGATGATTTCCAGCTGATTCCAATGATCAGCAAGTGTAGAACTAAGGAGGGAAGGCGAAAGACCAA

CCTGTATGGTTTCATCATCAAAGGAAGATCCCACCTGAGGAATGACACCGACGTGGTGAACTTTGTGAGCATGGAGTTTT

CTCTCACTGACCCAAGACTGGAACCACATAAATGGGAGAAGTACTGTGTGCTGGAGATTGGAGATATGCTGATCAGAAGT

GCCATTGGCCAGGTGTCAAGGCCCATGTTCCTGTATGTGAGAACAAATGGAACCTCAAAAATTAAAATGAAATGGGGAAT

GGAGATGAGGCGCTGCCTCCTCCAGTCACTGCAGCAGATTGAGAGTATGATTGAAGCTGAGTCCTCTGTCAAAGAGAAAG

ACATGACCAAAGAGTTCTTTGAGAACAAATCAGAAACATGGCCCATTGGAGAGTCCCCCAAAGGAGTGGAGGAAAGTTCC

ATTGGGAAGGTCTGCAGGACTCTGCTGGCAAAGTCCGTGTTCAACAGCCTGTATGCATCTCCACAGCTGGAAGGATTTTC

AGCTGAATCAAGAAAACTGCTGCTGATCGTGCAGGCTCTGAGGGACAACCTGGAACCTGGGACCTTTGATCTGGGGGGGC

TGTATGAAGCAATTGAGGAGTGCCTGATTAATGATCCCTGGGTGCTGCTGAATGCTTCTTGGTTCAACTCCTTCCTTACA

CATGCATTGAGTTAGTTGTGGCAGTGCTACTATTTGCTATCCATACTGTCCAAAAAAGTACCTTGTTTCTACT (SEQ ID NO:18)

AGCAAAAGCAGGGTAGATAATCACTCACTGAGTGACATCAAAATCATGGCGTCTCAAGGCACCAAACGATCTTACGAACA

GATGGAGACTGATGGAGAACGCCAGAATGCCACTGAAATCAGAGCATCCGTCGGAAAAATGATTGGTGGAATTGGACGAT

TCTACATCCAAATGTGCACCGAACTCAAACTCAGTGATTATGAGGGACGGTTGATCCAAAACAGCTTAACAATAGAGAGA

ATGGTGCTCTCTGCTTTTGACGAAAGGAGAAATAAATACCTTGAAGAACATCCCAGTGCGGGGAAAGATCCTAAGAAAAC

TGGAGGACCTATATACAGGAGAGTAAACGGAAAGTGGATGAGAGAACTCATCCTTTATGACAAAGAAGAAATAAGGCGAA

TCTGGCGCCAAGCTAATAATGGTGACGATGCAACGGCTGGTCTGACTCACATGATGATCTGGCATTCCAATTTGAATGAT

GCAACTTATCAGAGGACAAGAGCTCTTGTTCGCACCGGAATGGATCCCAGGATGTGCTCTCTGATGCAAGGTTCAACTCT

CCCTAGGAGGTCTGGAGCCGCAGGTGCTGCAGTCAAAGGAGTTGGAACAATGGTGATGGAATTGGTCAGAATGATCAAAC

GTGGGATCAATGATCGGAACTTCTGGAGGGGTGAGAATGGACGAAAAACAAGAATTGCTTATGAAAGAATGTGCAACATT

CTCAAAGGGAAATTTCAAACTGCTGCACAAAAAGCAATGATGGATCAAGTGAGAGAGAGCCGGAACCCAGGGAATGCTGA

GTTCGAAGATCTCACTTTTCTAGCACGGTCTGCACTCATATTGAGAGGGTCGGTTGCTCACAAGTCCTGCCTGCCTGCCT

GTGTGTATGGACCTGCCGTAGCCAGTGGGTACGACTTTGAAAGGGAGGGATACTCTCTAGTCGGAATAGACCCTTTCAGA

CTGCTTCAAAACAGCCAAGTGTACAGCCTAATCAGACCAAATGAGAATCCAGCACACAAGAGTCAACTGGTGTGGATGGC

ATGCCATTCTGCCGCATTTGAAGATCTAAGAGTATTAAGCTTCATCAAAGGGACGAAGGTGCTCCCAAGAGGGAAGCTTT

CCACTAGAGGAGTTCAAATTGCTTCCAATGAAAATATGGAGACTATGGAATCAAGTACACTTGAACTGAGAAGCAGGTAC

TGGGCCATAAGGACCAGAAGTGGAGGAAACACCAATCAACAGAGGGCATCTGCGGGCCAAATCAGCATACAACCTACGTT

CTCAGTACAGAGAAATCTCCCTTTTGACAGAACAACCATTATGGCAGCATTCAATGGGAATACAGAGGGGAGAACATCTG

ACATGAGGACCGAAATCATAAGGATGATGGAAAGTGCAAGACCAGAAGATGTGTCTTTCCAGGGGCGGGGAGTCTTCGAG

CTCTCGGACGAAAAGGCAGCGAGCCCGATCGTGCCTTCCTTTGACATGAGTAATGAAGGATCTTATTTCTTCGGAGACAA

TGCAGAGGAGTACGACAATTAAAGAAAAATACCCTTGTTTCTACT (SEQ ID NO:4)

*FIG. 10L*

Canine codon optimized NP:

AGCAAAAGCAGGGTAGATAATCACTCACTGAGTGACATCAAAATCATGGCGTCTCAAGGCACCAAACGATCTTACGAACA

GATGGAGACTGATGGAGAACGCCAGAATGCCACTGAAATCAGAGCATCCGTCGGAAAAATGATTGGTGGAATTGGACGAT

TCTACATCCAGATGTGCACCGAACTCAAACTCAGTGATTATGAGGGACGGCTGATCCAGAACAGCCTGACAATCGAGAGA

ATGGTGCTCTCTGCTTTTGACGAAAGGAGAAATAAATACCTGGAAGAACATCCCAGTGCCGGGAAAGATCCTAAGAAAAC

TGGAGGACCTATCTACAGGAGAGTGAACGGAAAGTGGATGAGAGAACTCATCCTGTATGACAAAGAAGAAATCAGGCGAA

TCTGGCGCCAGGCTAATAATGGTGACGATGCAACCGCTGGTCTGACTCACATGATGATCTGGCATTCCAATCTGAATGAT

GCAACTTATCAGAGGACAAGAGCTCTGGTGCGCACCGGAATGGATCCCAGGATGTGCTCTCTGATGCAGGGTTCAACTCT

CCCTAGGAGGTCTGGAGCCGCAGGTGCTGCAGTCAAAGGAGTGGGAACAATGGTGATGGAACTGGTCAGAATGATCAAAA

GAGGGATCAATGATCGGAACTTCTGGAGGGGTGAGAATGGACGAAAAACAAGAATTGCTTATGAAAGAATGTGCAACATT

CTCAAAGGGAAATTTCAGACTGCTGCACAGAAAGCAATGATGGATCAGGTGAGAGAGAGCCGGAACCCAGGGAATGCTGA

GTTCGAAGATCTCACTTTTCTGGCACGGTCTGCACTCATCCTGAGAGGGTCCGTGGCTCACAAGTCCTGCCTGCCTGCCT

GTGTGTATGGACCTGCCGTGGCCAGTGGGTACGACTTTGAAAGGGAGGGATACTCTCTGGTCGGAATTGACCCTTTCAGA

CTGCTGCAGAACAGCCAGGTGTACAGCCTGATCAGACCAAATGAGAATCCAGCACACAAGAGTCAGCTGGTGTGGATGGC

ATGCCATTCTGCCGCATTTGAAGATCTGAGAGTGCTGAGCTTCATCAAAGGGACCAAGGTGCTCCCAAGAGGGAAGCTGT

CCACTAGAGGAGTGCAGATTGCTTCCAATGAAAATATGGAGACTATGGAATCAAGTACACTGGAACTGAGAAGCAGGTAC

TGGGCCATCAGGACCAGAAGTGGAGGAAACACCAATCAGCAGAGGGCATCTGCCGGCCAGATCAGCATTCAGCCTACCTT

CTCAGTGCAGAGAAATCTCCCTTTTGACAGAACAACCATTATGGCAGCATTCAATGGGAATACAGAGGGGAGAACATCTG

ACATGAGGACCGAAATCATCAGGATGATGGAAAGTGCAAGACCAGAAGATGTGTCTTTCCAGGGGCGGGGAGTCTTCGAG

CTCTCGGACGAAAAGGCAGCGAGCCCGATCGTGCCTTCCTTTGACATGAGTAATGAAGGATCTTATTTCTTCGGAGACAA

TGCAGAGGAGTACGACAATTAAAGAAAAATACCCTTGTTTCTACT (SEQ ID NO:19)

FIG. 10M

Nucleotide mutation in position 4 of each gene of PR8 and Indo/NC/09.

| Genes | Position 4 of vRNA | |
|---|---|---|
| PR8 PB2 | C | |
| PR8 PB1 | C | |
| PR8 PA | C | |
| PR8 NP | | U |
| PR8 M | | U |
| PR8 NS | | U |
| Inda/NC/09 HA | | U |
| Inda/NC/09 NA | | U |

FIG. 11A

All 3'C4U mutant

| Genes | Position 4 of vRNA | |
|---|---|---|
| PR8 PB2 | | U |
| PR8 PB1 | | U |
| PR8 PA | | U |
| PR8 NP | | U |
| PR8 M | | U |
| PR8 NS | | U |
| Inda/NC/09 HA | | U |
| Inda/NC/09 NA | | U |

HA atgaacactcaaatcctggtattcgctctgattgcgatcattccaacaaatgcagacaaaatctgcctcggacatcatgccgtgtcaaacggaaccaaagtaaa
cacattaactgaaagaggagtggaagtcgtcaatgcaactgaaacagtggaacgaacaaacatccccaggatctgctcaaaagggaaaaggacagttgacc
tcggtcaatgtggactcctggggacaatcactggaccacctcaatgtgaccaattcctagaattttcagccgatttaattattgagaggcgagaaggaagtgatg
tctgttatcctgggaaattcgtgaatgaagaagctctgaggcaaattctcagagaatcaggcggaattgacaaggaagcaatgggattcacatacagtggaat
aagaactaatggagcaaccagtgcatgtaggagatcaggatcttcattctatgcagaaatgaaatggctcctgtcaaacacagataatgctgcattcccgcaga
tgactaagtcatataaaaatacaagaaaaagcccagctctaatagtatggggggatccatcattccgtatcaactgcagagcaaaccaagctatatgggagtgg
aaacaaactggtgacagttgggagttctaattatcaacaatcttttgtaccgagtccaggagcgagaccacaagttaatggtctatctggaagaattgactttcat
tggctaatgctaaatcccaatgatacagtcactttcagtttcaatggggctttcatagctccagaccgtgcaagcttcctgagaggaaaatctatgggaatccag
agtggagtacaggttgatgccaattgtgaaggggactgctatcatagtggagggacaataataagtaacttgccatttcagaacatagatagcagggcagttg
gaaaatgtccgagatatgttaagcaaaggagtctgctgctagcaacagggatgaagaatgttcctgagattccaaagggaagaggcctatttggtgctatagc
gggtttcattgaaaatggatgggaaggcctaattgatggttggtatggtttcagacaccagaatgcacagggagagggaactgctgcagattacaaaagcact
caatcggcaattgatcaaataacaggaaaattaaaccggcttatagaaaaaaccaaccaacaatttgagttgatagacaatgaattcaatgaggtagagaag
caaatcggtaatgtgataaattggaccagagattctataacagaagtgtggtcatacaatgctgaactcttggtagcaatggagaaccagcatacaattgatct
ggctgattcagaaatggacaaactgtacgaacgagtgaaaagacagctgagagagaatgctgaagaagatggcactggttgctttgaaatatttcacaagtgt
gatgatgactgtatggccagtattagaaataacacctatgatcacagcaaatacagggaagaggcaatgcaaaatagaatacagattgacccagtcaaacta
agcagcggctacaaagatgtgatactttggtttagcttcggggcatcatgtttcatacttctagccattgtaatgggccttgtcttcatatgtgtaaagaatggaaa
catgcggtgcactatttgtatataa (SEQ ID NO:20)

MNTQILVFAL IAIIPTNADK ICLGHHAVSN GTKVNTLTER GVEVVNATET VERTNIPRIC
SKGKRTVDLG QCGLLGTITG PPQCDQFLEF SADLIIERRE GSDVCYPGKF VNEEALRQIL
RESGGIDKEA MGFTYSGIRT NGATSACRRS GSSFYAEMKW LLSNTDNAAF PQMTKSYKNT
RKSPALIVWG IHHSVSTAEQ TKLYGSGNKL VTVGSSNYQQ SFVPSPGARP QVNGLSGRID
FHWLMLNPND TVTFSFNGAF IAPDRASFLR GKSMGIQSGV QVDANCEGDC YHSGGTIISN
LPFQNIDSRA VGKCPRYVKQ RSLLLATGMK NVPEIPKGRG LFGAIAGFIE NGWEGLIDGW
YGFRHQNAQG EGTAADYKST QSAIDQITGK LNRLIEKTNQ QFELIDNEFN EVEKQIGNVI
NWTRDSITEV WSYNAELLVA MENQHTIDLA DSEMDKLYER VKRQLRENAE EDGTGCFEIF
HKCDDDCMAS IRNNTYDHSK YREEAMQNRI QIDPVKLSSG YKDVILWFSF GASCFILLAI
VMGLVFICVK NGNMRCTICI (SEQ ID NO:21)

NA atgaatccaaatcagaagattctatgcacttcagccactgctatcataataggcgcaatcgcagtactcattggaatagcaaacctaggattgaacataggact
gcatctaaaaccgggctgcaattgctcacactcacaacctgaaacaaccaacacaagccaaacaataataaacaactattataatgaaacaaacatcaccaa
catccaaatggaagagagaacaagcaggaatttcaataacttaactaaagggctctgtactataaattcatggcacatatatgggaaagacaatgcagtaaga
attggagagagctcggatgttttagtcacaagagaaccctatgtttcatgcgacccagatgaatgcaggttctatgctctcagccaaggaacaacaatcagagg
gaaacactcaaacggaacaatacacgataggtcccagtatcgcgccctgataagctggccactatcatcaccgcccacagtgtacaacagcagggtggaatg
cattgggtggtcaagtactagttgccatgatggcaaatccaggatgtcaatatgtatatcaggaccaaacaacaatgcatctgcagtagtatggtacaacagaa
ggcctgttgcagaaattaacacatgggcccgaaacatactaagaacacaggaatctgaatgtgtatgccacaacggcgtatgcccagtagtgttcaccgatgg
gtctgccactggacctgcagacacaagaatatactatttaaagaggggaaaatattgaaatgggagtctctgactggaactgctaagcatattgaagaatgct
catgttacggggaacgaacaggaattacctgcacatgcagggacaattggcagggctcaaatagaccagtgattcagatagacccagtagcaatgacacaca
ctagtcaatatatatgcagtcctgttcttacagacaatccccgaccgaatgacccaaatataggtaagtgtaatgacccttatccaggtaataataacaatggag
tcaagggattctcatacctggatggggctaacacttggctagggaggacaataagcacagcctcgaggtctggatacgagatgttaaaagtgccaaatgcatt
gacagatgatagatcaaagcccattcaaggtcagacaattgtattaaacgctgactggagtggttacagtggatctttcatggactattgggctgaaggggact
gctatcgagcgtgtttttatgtggagttgatacgtggaagacccaaggaagataaagtgtggtggaccagcaatagtatagtatcgatgtgttccagtacagaat
tcctgggacaatggaactggcctgatggggctaaaatagagtacttcctctaa (SEQ ID NO:22)

MNPNQKILCTSATAIIIGAIAVLIGIANLGLNIGLHLKPGCNCSHSQPETTNTSQTIINNYYNETNITNIQMEERTSRNFNNLTKGL
CTINSWHIYGKDNAVRIGESSDVLVTREPYVSCDPDECRFYALSQGTTIRG KHSNGTIHDRSQYRALISWPLSSPPTVYNSRVECI
GWSSTSCHDGKSRMSICISGPNNNASAVVWYNRRPVAEINTWARNILRTQESECVCHNGVCPVVFTDGSATGPADTRIYYFK

FIG. 12A

EGKILKWESLTGTAKHIEECSCYGERTGITCTCRDNWQGSNRPVIQIDPVAMTHTSQYICSPVLTDNPRPNDPNIGKCNDPYPG
NNNNGVKGFSYLDGANTWLGRTISTASRSGYEMLKVPNALTDDRSKPIQGQTIVLNADWSGYSGSFMDYWAEGDCYRACF
Y VELIRGRPKEDKVWWTSNSIVSMCSSTEFLGQWNWPDGAKIEYFL (SEQ ID NO:23)

HA atgaacactcaaatcctggtattcgctctgattgcgatcattccaacaaatgcagacaaaatctgcctcggacatcatgctgtgtcaaacggaaccaaagtaaa
cacattaactgaaagaggagtggaagtcgtcaatgcaactgaaacagtggaacgaacaaacatccccaggatctgctcaaaagggaaaaggacagttgacc
tcggtcaatgtggactcctggggacaatcactggaccacctcaatgtgaccaattcctagaattttcagccgatttaattattgagaggcgagaaggaagtgatg
tctgttatcctgggaaattcgtgaatgaagaagctctgaggcaaattctcagagaatcaggcggaattgacaaggaagcaatgggattcacatacagtggaat
aagaactaatggagcaaccagttcatgtaggagatcaggatcttcattctatgcagaaatgaaatggctcctgtcaaacacagataatgctgcattcccgcaga
tgactaagtcatataaaaatacaagaaaaaacccagctctaatagtatggggatccatcattccggatcaactgcagagcaaaccaagctatatgggagtgg
aaacaaactggtgacagttgggagttctaattatcaacaatcttttgtaccgagtccgggagcgagaacacaagttaatggtcaatctggaagaattgactttca
ttggctaatgctaaatcccaatgatacagtcactttcagtttcaatggggctttcatagctccagaccgtgcaagcttcctgagaggaaaatctatgggaatccag
agtggagtacaggttgatgccgattgtgaaggggactgctattatagtggagggacaataataagtaacttgccatttcagaacatagatagcagggcagttgg
aaaatgtccgagatatgttaagcaaaggagtctgctgctagcaacagggatgaagaatgttcctgagattccaaagggaagaggcctatttggtgctatagcg
ggtttcattgaaaatggatgggaaggcctaattgatggttggtatggtttcagacaccagaatgcacagggagagggaactgctgcagattacaaaagcactc
aatcggcaattgatcaaataacaggaaaattaaaccggcttatagaaaaaaccaaccaacaatttgagttgatagacaatgaattcactgaggtagagaagc
aaatcggtaatgtgataaattggaccagagattctataacagaagtgtggtcatacaatgctgaactcttggtagcaatggagaaccagcatacaattgatctg
gctgattcagaaatggacaaactgtacgaacgagtgaaaagacagctgagagagaatgctgaagaagatggcactggttgctttgaaatatttcacaagtgtg
atgatgactgtatggccagcattagaaataacacctatgatcacagcaaatacagggaagaggcaatgcaaaatagaatacagattgacccagtcaaactaa
gcagcggctacaaagatgtgatactttggtttagcttcggggcatcatgtttcatacttctagccattgcaatgggccttgtcttcatatgtgtaaagaatggaaa
c atgcggtgcactatttgtatataa (SEQ ID NO:24)

MNTQILVFALIAIIPTNADKICLGHHAVSNGTKVNTLTERGVEVVNATETVERTNIPRICSKGKRTVDLGQCGLLGTITGPPQCDQ
FLEFSADLIIERREGSDVCYPGKFVNEEALRQILRESGGIDKEAMGFTYSG IRTNGATSSCRRSGSSFYAEMKWLLSNTDNAAFP
QMTKSYKNTRKNPALIVWGIHHSGSTAEQTKLYGSGNKLVTVGSSNYQQSFVPSPGARTQVNGQSGRIDFHWLMLNPNDTV
TFSFNGAFIAPDRASFLRGKSMGIQSGVQVDADCEGDCYYSGGTIISNLPFQNIDSRAVGKCPRYVKQRSLLLATGMKNVPEIP
KGRGLFGAIAGFIENGWEGLIDGWYGFRHQNAQGEGTAADYKSTQSAIDQITGKLNRLIEKTNQQFELIDNEFTEVEKQIGNVI
NWTRDSITEVWSYNAELLVAMENQHTIDLADSEMDKLYERVKRQLRENAEEDGTGCFEIFHKCDDDCMASIRNNTYDHSKY
R EEAMQNRIQIDPVKLSSGYKDVILWFSFGASCFILLAIAMGLVFICVKNGNMRCTICI (SEQ ID NO:25)

NA atgaatccaaatcagaagattctatgcacttcagccactgctatcataataggcgcaatcgcagtactcattggaatagcaaacctaggattgaacataggact
gcatctaaaaccgagctgcaattgctcacactcacaacctgaaacaaccaacacaagccaaacaataataaacaactattataatgaaacaaacatcaccaa
catccaaatggaagagagaacaagcaggaatttcaataacttaactaaagggctctgtactataaattcatggcacatatatgggaaagacaatgcggtaaga
attggagagagctcggatgttttagtcacaagagaaccctatgtttcatgcgacccagatgaatgcaggttctatgctctcagccaaggaacaacaatcagagg
aaaacactcaaacggaacaatacacgataggtcccagtatcgcgccctgataagctggccactatcatcaccgcccacagtgtacaacagcagggtggaatg
cattgggtggtcaagtactagttgccatgatggcaaatccaggatgtcaatatgtatatcaggaccaaacaacaatgcatctgcagtagtatggtacaacagaa
ggcctgttgcagaaattaacacatgggcccgaaacatactaagaacacaggaatctgaatgtgtatgccacaacggcgtatgcccagtagtgttcaccgatgg
gtctgccactggacctgcagacacaagaatatactattttaaagagggggaaaatattgaaatgggagtctctgactggaactgctaagcatattgaagaatgct
catgttacggggaacgaacaggaattacctgcacatgcaaggacaattggcagggctcaaatagaccagtgattcagatagatccagtagcaatgacacaca
ctagtcagtatatatgcagtcctgttcttacagacaatccccgaccgaatgacccaaatataggtaagtgtaatgacccttatccaggtaataataacaatggag
tcaagggattctcatacctggatggggctaacacttggctagggaggacaataagcacagcctcgaggtctggatacgagatgttaaaagtgccaaatgcatt
gacagatgatagatcaaagcccattcaaggtcagacaattgtattaaacgctgactggagtggttacagtggatctttcatggactattgggctgaggggact
gctatcgagcgtgttttatgtggaattgatacgtggaagacccaaggaggataaagtgtggtggaccagcaatagtatagtatcgatgtgttccagtacagaat
tcctgggacaatggaactggcctgatggggctaaaatagagtacttcctctaa (SEQ ID NO:26)

MNPNQKILCTSATAIIIGAIAVLIGIANLGLNIGLHLKPSCNCSHSQPETTNTSQTIINNYYNETNITNIQMEERTSRNFNNLTKGL
CTINSWHIYGKDNAVRIGESSDVLVTREPYVSCDPDECRFYALSQGTTIRG KHSNGTIHDRSQYRALISWPLSSPPTVYNSRVECI
GWSSTSCHDGKSRMSICISGPNNNASAVVWYNRRPVAEINTWARNILRTQESECVCHNGVCPVVFTDGSATGPADTRIYYFK

FIG. 12B

EGKILKWESLTGTAKHIEECSCYGERTGITCTCKDNWQGSNRPVIQIDPVAMTHTSQYICSPVLTDNPRPNDPNIGKCNDPYPG
NNNNGVKGFSYLDGANTWLGRTISTASRSGYEMLKVPNALTDDRSKPIQGQTIVLNADWSGYSGSFMDYWAEGDCYRACF
Y VELIRGRPKEDKVWWTSNSIVSMCSSTEFLGQWNWPDGAKIEYFL (SEQ ID NO:27)

FIG. 12C

Growth kinetics in MDCK cells

HY-#61 includes PB2: M202L F323L, PB1 Q247H, PA K142N, NP R74K, M V97A Y100H and NS K55E mutations.

HY mutations include PB2: M202L F323L, PB1 Q247H, PA K142N, NP R74K, M V97A Y100H and NS K55E mutations.

Schematic diagram of screening high growth mutations in eggs.

Summary of HA assay of individual clones purified from Vero cells

| Groups | Numbers of clone | Fold change | % |
|---|---|---|---|
| WT HA titer = $2^{6.5}$ | 5 | - | 2.3% |
| HA titer =$2^{>9\text{-}9.5}$ | 16 | >5.6 | 7.4% |
| HA titer =$2^{>8\text{-}9}$ | 91 | >2.8 -5.6 | 42.2% |
| HA titer =$2^{6.5\text{-}8}$ | 80 | 1 - 2.8 | 37.0% |
| HA titer < $2^{6.5}$ | 24 | <1 | 11.1% |
| Total | 216 | - | 100% |

*FIG. 16*

Recombinant viruses generated with different PR8 backbone mutants.

| # | Del-HA & NA genes | PB2 | PB1 | PA | NP | M | NS |
|---|---|---|---|---|---|---|---|
| WT | CK/Indo/NC/09 | WT | WT | WT | WT | WT | WT |
| HY-1 | | I504V | M40L G180W | R401K | I116L | WT | A30P R118K |
| HY-2 | | E391Q | | I30T E31K K142N | R74K S377N | WT | S161T |
| HY-3 | | I504V | | K142N | I116L | V97A Y100H | V136M S161T |
| HY-4 | | M202L F323L | | K356R | I116L | V97A Y100H | K55E |
| HY-5 | | | | K356R | R422L | WT | K55E |

FIG. 17

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 1 | M476I | | M202L F323L | | | R293M | | | MDCK | HA titer | 2.8 |
| 2 | F252I | L55S | M202L F323L | | | I116L | | | MDCK | HA titer | 2.8 |
| 3 | | | M202L F323L | | | | | A223E | MDCK | HA titer | 2.8 |
| 4 | L182V | | M202L F323L | | | | | | MDCK | HA titer | 2.8~4 |
| 5 | | | | E112G (PB1-F2 R81G)[5] | | | | | MDCK | HA titer | 2.8 |
| 6 | E136D/ Q179L/ A194V | | | R54I | | | | | MDCK | HA titer | 2.8~4 |
| 7 | K162E | | | I667T/M714T | | | | | MDCK | HA titer | 4 |
| 8 | L182V | | | | | I116L | | R140Q | MDCK | HA titer | 2.8~4 |
| 9 | L182V | | | | | | | | MDCK | HA titer | 2.8~4 |
| 10 | L182V | | M202L F323L | | | | | | MDCK | HA titer | 4 |
| 11 | L182V | | M66R | | | | | | MDCK | HA titer | 2.8~4 |
| 12 | L182V | | M202L F323L | | | | | | MDCK | HA titer | 4 |
| 13 | | | M202L F323L | M507V/V644A | | | | | MDCK | HA titer | 4 |
| 14 | L182V | | I504V | | | R74K/ N417D | | A30P | MDCK | HA titer | 2.8 |
| 15 | K162E | | | E112G (PB1-F2-R81G) | | | | S161T | MDCK | HA titer | 2.8 |
| 16 | | | | I667T | | | | | MDCK | HA titer | 2.8 |
| 17 | K449E | | | M40L/G180W | | | | | MDCK | HA titer | 2.8 |
| 18 | K162E | | | E112G (PB1-F2-R81G)/ L624V | | | | S161T | MDCK | HA titer | 2.8~4 |

FIG. 19A

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 19 | | | | E112G (PB1-F2-R61G) | | | | | MDCK | HA titer | 2.8 |
| 20 | | | | M40L G180W | | | | S161T | MDCK | HA titer | 2.8~4 |
| 21 | | | M202L F323L M243I | R54I | | | | | MDCK | HA titer | 4~5.7 |
| 22 | V184I | | M202L F323L | | F105C | | P90S | | MDCK | HA titer | 2.8~4 |
| 23 | | | M202L F323L | Q247H | | | | | MDCK | HA titer | 2.8~4 |
| 24 | | | M202L F323L | | | N224I | | | MDCK | HA titer | 2.8~4 |
| 25 | M476I | | I504V | | | R74K/ N417D | | | MDCK | HA titer | 2.8~4 |
| 26 | M476I | | M202L F323L | V644A | R401K | | | T49A | MDCK | HA titer | 4~5.7 |
| 27 | F252I | | I504V | V644A | | M371V | | | MDCK | HA titer | 2.8 |
| 28 | M476I | A265V | I504V | T59I G62A A63P V644A N694K L695T | | R74K/ N417D | | | MDCK | HA titer | 2.8 |
| 29 | M476I | | I504V | | | | | | MDCK | HA titer | 2.8~4 |
| 30 | F252I | | I504V | E75V D76G E78P P79V S80G V644A E697P F699L F700L P701H S702R Y705T | | R74K | | | MDCK | HA titer | 2.8~4 |
| 31 | L182V | | I504V | | | R74K | | | MDCK | HA titer | 2.8~4 |
| 32 | F252I | | M202L F323L | V644A | | | | | MDCK | HA titer | 4 |

FIG. 19B

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 33 | | | I57V<br>T58G<br>A59V<br>K61Q<br>E677D<br>D678E<br>P679M | E112G (PB1-F2-R81G)<br>S713C | | | | | MDCK | HA titer | 2.8 |
| 34 | | | | M40I<br>G180W | | | | S161T | MDCK | HA titer | 2.8 |
| 35 | | | R368K | | | | | | MDCK | Viral titer | 2.8 |
| 36 | | | E391K | | | | | | MDCK | Viral titer | 3.8 |
| 37 | | | I504V | | I550L | | | | MDCK | Viral titer | 4.3 |
| 38 | | | | PB1 F2 N66S | | | | | MDCK | Viral titer | 2.78 |
| 39 | | | | PB1 F2 K73R | | | | | MDCK | Viral titer | 3.9 |
| 40 | | | | | K142N | | | | MDCK | Viral titer | 2.1 |
| 41 | | | | | K356R | | | | MDCK | Viral titer | 3.9 |
| 42 | | | | | | R293K | | | MDCK | Viral titer | 3.36 |
| 43 | | | | | | R442K | | | MDCK | Viral titer | 2.4 |
| 44 | | | | | | T442A | | | MDCK | Viral titer | 2.6 |
| 46 | | | | | | | V97A | | MDCK | HA titer | 8 |
| 47 | | | | | | | Y100H | | MDCK | HA titer | 9 |
| 48 | | | | | | | V97A<br>Y100H | | MDCK | HA titer | 9.5 |
| 49 | | | | | | | | K55E | MDCK | Viral titer | 2.1 |
| 50 | | | M202L<br>F323L | M507V<br>V644A | | I116L | | K55E | MDCK | Viral titer<br>HA titer | 9.9<br>4.3 |
| 51 | | | M202L<br>F323L | M507V<br>V644A | K356R | T442A | V97A<br>Y100H | K55E | MDCK | Viral titer<br>HA titer | 1.3<br>3.7 |
| 52 | | | I504V | E112G (PB1-F2-R81G) | I550L | I112L | Y100H | R140Q | MDCK | Viral titer<br>HA titer | 3<br>3 |

FIG. 19C

| Virus number | Surface genes | | UW-PR8 internal gene | | | | | | Growth substrate | Viral titer or HA titer | Fold change |
|---|---|---|---|---|---|---|---|---|---|---|---|
| | HA (H3 numbering) | NA | PB2 | PB1 | PA | NP | M1 | NS1 | | | |
| 53 | | | M202L F323L | M507V V644A | | I116L | Y100H | K55E | MDCK | Viral titer | 9 |
| | | | | | | | | | | HA titer | 6.5 |
| 54 | | | M202L F323L | Q247H | K142N | R74K | V97A Y100H | K55E | MDCK | Viral titer | 4.3 |
| | | | | | | | | | | HA titer | 9.2 |
| 55 | | | I504V | E112G (PB1-F2-R81G) | S225C | R74K N417D | V97A Y100H | K55E | MDCK | Viral titer | 14.9 |
| | | | | | | | | | | HA titer | 6.5 |
| 56 | | | M202L F323L | M40L G180W | S225C | R422K | V97A Y100H | K55E | MDCK | Viral titer | 4.2 |
| | | | | | | | | | | HA titer | 6.5 |
| 57 | | | *C4U* | *C4U* | *C4U* | | | | MDCK | Viral titer | 3.3 |
| | | | | | | | | | | HA titer | 2.1 |
| 58 | X-181 HA &NA (Derived from A/California/ 07/2009 pdmH1N1) | | | G180E S261G S361R Q621R N654S | | | | | MDCK | Viral titer | 3.5 |
| | | | | | | | | | | HA titer | 2.1 |
| 59 | A/Chicken/Indonesia/NC/2009, A/Vietnam/1203/2004, A/Hubei/1/2010, A/Egypt/N03072/2010, A/Indonesia/5/2005, A/Anhui/1/2013, X-181, X-223A | | *C4U* I504V | *C4U* M40L G180W | *C4U* R401K | I116L | | A30P R118K | Vero | Viral titer | 5.1~269 |
| | | | | | | | | | | HA titer | 2.2~134 |
| | | | | | | | | | MDCK | Viral titer | 1.8~29 |
| | | | | | | | | | | HA titer | 1.3~5.5 |
| | | | | | | | | | Eggs | Viral titer | 4.6~172 |
| | | | | | | | | | | HA titer | 1.3~17.7 |
| 60 | A/Chicken/Indonesia/NC/2009 | | C4U I504V | C4U M40L G180W | C4U R401K | I116L | *G1012C, A1013U, U1014A* | A30P R118K | Vero | Viral titer | 2.8 |
| | | | | | | | | | | HA titer | 1.2 |
| | | | | | | | | | Egg | Viral titer | 1.5 |
| | | | | | | | | | | HA titer | 1.6 |

Note: 1. The HA and NA genes of #1-58 come from A/Chicken/Indonesia/NC/2009 (H5N1) or mutant HA and NA of A/Chicken/Indonesia/NC/2009.
2:All the H5N1 HAs used in this study were mutated to remove multibasic cleavage sites to create lowly pathogenicity mutants.

FIG. 19D

- UW-PR8_INDO/05(HA+NA)
- UW-PR8+PR8-HY PB2_INDO/05(HA+NA)
- UW-PR8+PR8-HY PB1_INDO/05(HA+NA)
- UW-PR8+PR8-HY PA_INDO/05(HA+NA)
- UW-PR8+PR8-HY NP_INDO/05(HA+NA)
- UW-PR8+PR8-HY NS_INDO/05(HA+NA)
- UW

- UW-PR8_INDO/05(HA+NA)
- UW-PR8+PR8-HY PB2_INDO/05(HA+NA)
- UW-PR8+PR8-HY PB1_INDO/05(HA+NA)
- UW-PR8+PR8-HY PA_INDO/05(HA+NA)
- UW-PR8+PR8-HY NP_INDO/05(HA+NA)
- UW-PR8+PR8-HY NS_INDO/05(HA+N

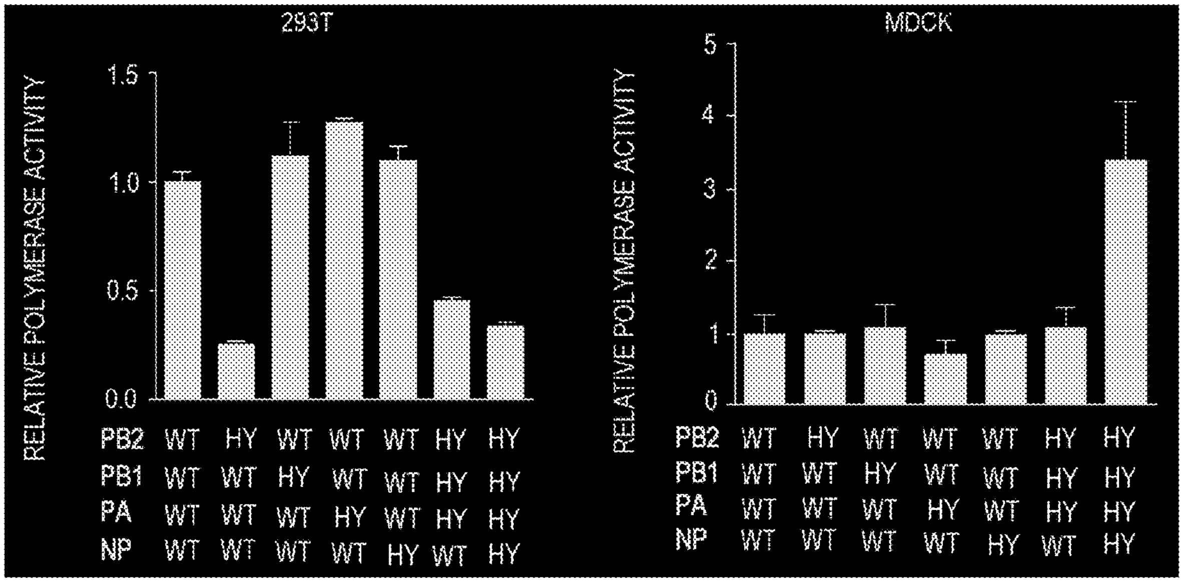
Fig.21A
Fig.21B
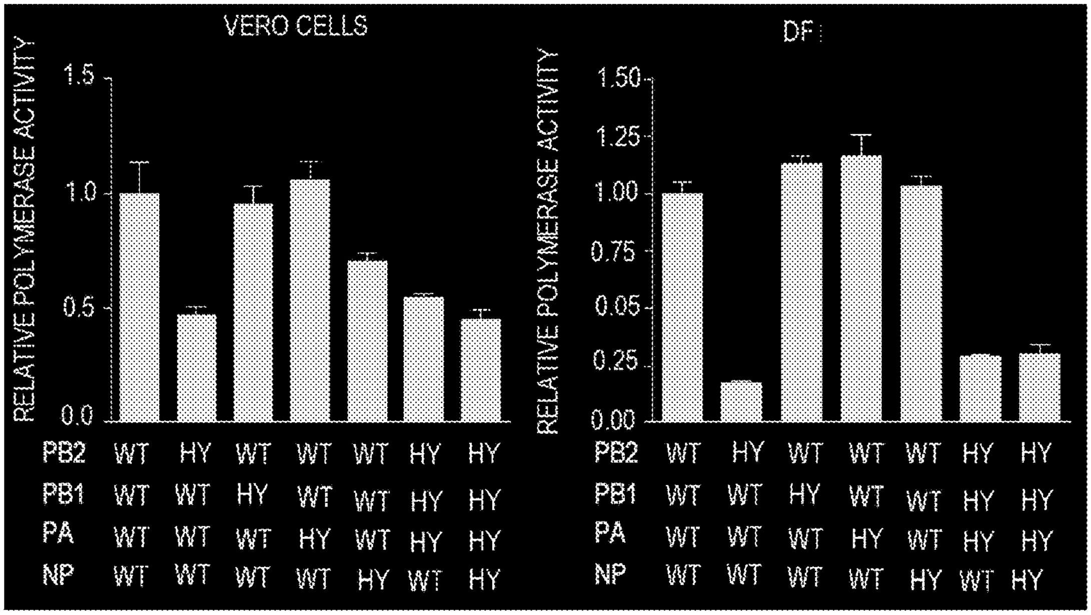
Fig.21C
Fig.21D

- UW-PR8_Indo/05(HA+NA)
- UW-PR8+HY-Vero PB2_Indo/05(HA+NA)
- UW-PR8+HY-Vero PB1_Indo/05(HA+NA)
- UW-PR8+HY-Vero PA_Indo/05(HA+NA)
- UW-PR8+HY-Vero NP_Indo/05(HA+NA)
- UW-PR8+HY-Vero NS_Indo/05(HA+NA)
- UW-PR8+HY-Vero(PB2+PB1+PA)_Indo/05(HA+NA)
- UW-PR8+HY-Vero(PB2+PB1+PA+NP)_Indo/05(HA+NA)
- HY-Vero_Indo/05(HA+NA)

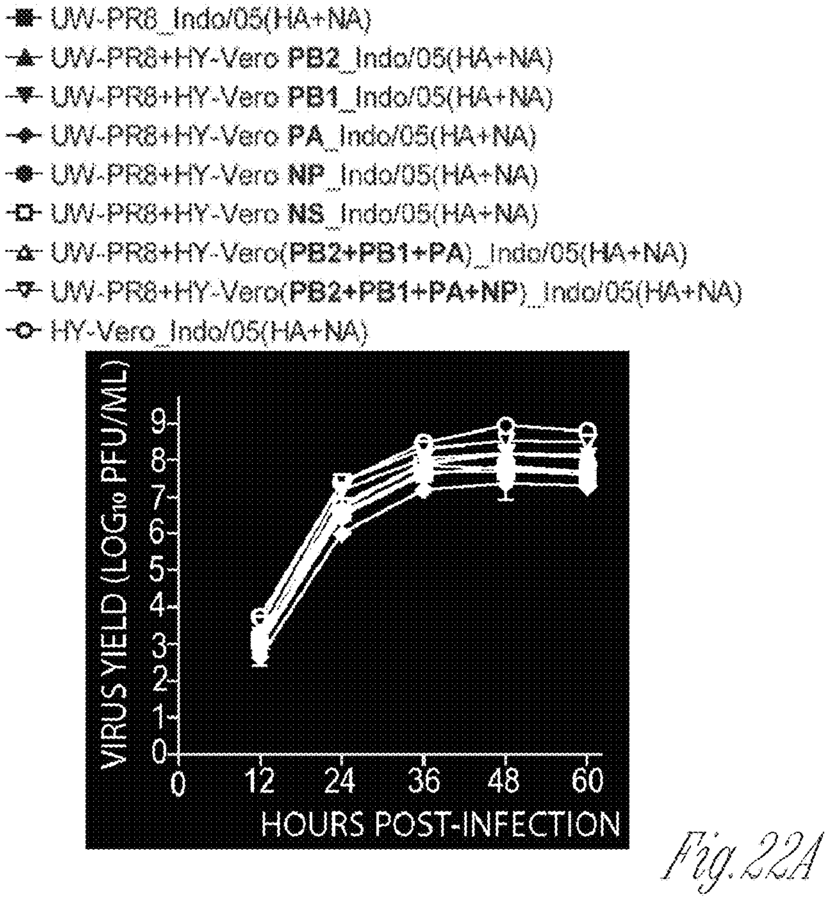

*Fig. 22A*

- HY-Vero_Indo/05(HA+NA)
- HY-Vero+UW-PR8 PB2_Indo/05(HA+NA)
- HY-Vero+UW-PR8 PB1_Indo/05(HA+NA)
- HY-Vero+UW-PR8 PA_Indo/05(HA+NA)
- HY-Vero+UW-PR8 NP_Indo/05(HA+NA)
- HY-Vero+UW-PR8 NS_Indo/05(HA+NA)
- HY-Vero+UW-PR8 (PB2+PB1+PA)_Indo/05(HA+NA)

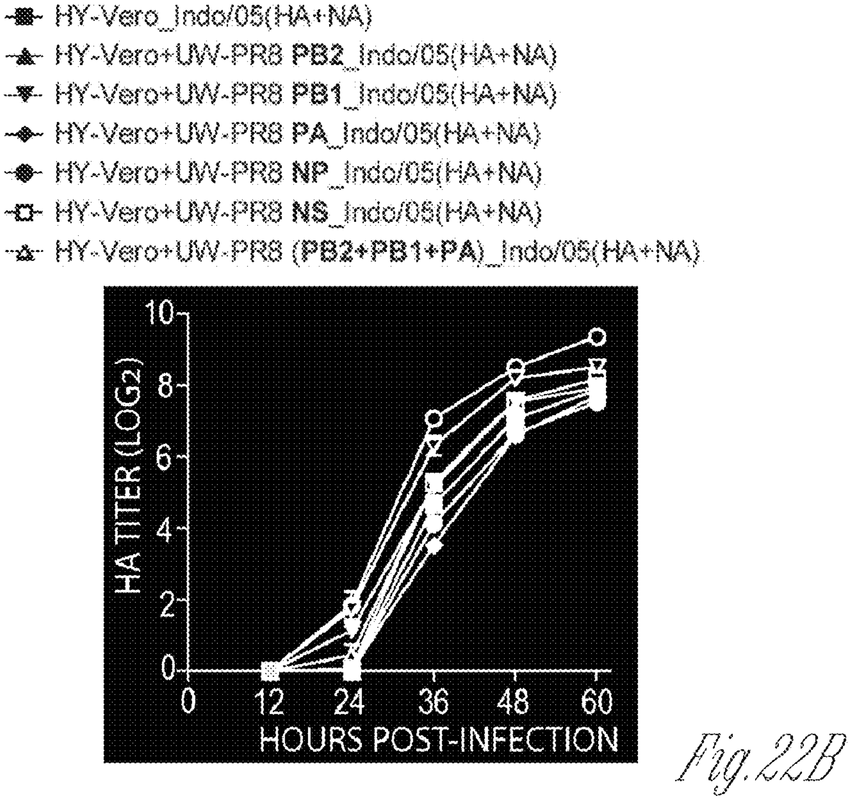

*Fig. 22B*

HY candidate #5,9#,16#,WT,SF-MDCK cells

HY candidate #5,9#,16#,WT,SF-MDCK cells

INFLUENZA VIRUS REPLICATION FOR VACCINE DEVELOPMENT

CROSS-REFERENCE TO RELATED APPLICATIONS

This application claims the benefit of the filing date of U.S. application No. 62/841,491, filed on May 1, 2019, the disclosure of which is incorporated by reference herein.

STATEMENT OF GOVERNMENT RIGHTS

This invention was made with government support under HHSN272201400008C awarded by the National Institutes of Health. The government has certain rights in the invention.

BACKGROUND

Influenza is a major respiratory disease in some mammals and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park et al., 2004).

There are three general types of influenza viruses, Type A, Type B and Type C, which are defined by the absence of serological crossreactivity between their internal proteins. Influenza Type A viruses are further classified into subtypes based on antigenic and genetic differences of their glycoproteins, the HA and NA proteins. Most of all the known HA and NA subtypes (H1 to H16 and N1 to N9) have been isolated from aquatic birds, which are thought to act as a natural reservoir for influenza. The H1 N1 pandemic virus caused a pandemic in 2009. The first vaccine candidates tested in 2009 did not grow to high titers, demonstrating the need to develop vaccine virus backbones that confer efficient replication to vaccine virus candidates.

SUMMARY

Several strategies were employed (including random mutagenesis and the comprehensive testing of potentially growth-enhancing mutations) to develop influenza A/Puerto Rico/8/34 (H1N1; the strain commonly used for the generation of inactivated influenza vaccines) viruses that replicate to high titers in cultured cells and/or embryonated chicken eggs. A number of growth-enhancing mutations were identified that increase the yield of influenza vaccine viruses. Individual growth-enhancing residues in an influenza virus polypeptide may be combined with one or more other growth-enhancing residues in the same influenza virus polypeptide, or with one or more other growth-enhancing residues in other influenza virus polypeptide(s), as well with growth-enhancing nucleotides in viral non-coding regions, e.g., promoter sequences. For example, one or more growth-enhancing residues in a polymerase protein, for instance, 1, 2, 3, 4, 5, 6, 7 or more, growth-enhancing residues in PB2, 1, 2, 3, 4, 5, 6, 7 or more, e.g., up to 12, 13, 14 or 15, growth-enhancing residues in PB1, 1, 2, 3, or 4 or more growth-enhancing residues in PA, or 1, 2, 3, or 4 growth-enhancing residues in NP, 1, 2, 3, or 4 growth-enhancing residues in M, e.g., 1, 2, or 3 growth-enhancing residues in M1, 1, 2, or 3 growth-enhancing residues in NS1, or any combination of growth-enhancing residues or nucleotides in viral non-coding, e.g., promoter sequences, may be combined when preparing influenza virus, e.g., for a vaccine, to enhance viral titers. In one embodiment, growth-enhancing nucleotides in viral promoter sequences may be introduced to a viral segment, or when present in a viral segment may be selected for inclusion in an influenza virus. In one embodiment, growth-enhancing residues in HA and/or in NA may be introduced into, or when present in a HA or NA selected for inclusion in, a HA viral segment or a NA viral segment in an influenza virus. In one embodiment, the one or more growth-enhancing residues may enhance viral growth by at least 1.2, 2, 2.8, 4, 3, 5, 6, 8, 10, 100, or 200 fold or more.

Mutations that increase the replicative ability of viruses in cell culture and/or embryonated chicken eggs are useful to amplify influenza viruses and to establish robust influenza vaccine platforms. Currently, most influenza vaccines are generated in embryonated chicken eggs. Influenza vaccines generated in MDCK cells are now approved for human use in the U.S. and in Europe, and influenza vaccines derived from Vero cells are approved for human use in Europe. Virus libraries possessing random mutations in the 'internal' viral genes (i.e., all viral genes except those encoding the viral surface glycoproteins HA and NA) of a vaccine virus isolate, e.g., UW-PR8 (see Example 1), were generated and passaged in MDCK cells. The identified mutations result in higher virus titers in MDCK cells (and may also increase virus titers in Vero cells and/or embryonated chicken eggs), allowing more efficient influenza virus growth and more cost-effective vaccine production. Moreover, previously described mutations increased the replicative ability of UW-PR8 vaccine backbone virus. In addition to mutations in the coding regions of the six internal viral segments, mutations in non-coding regions were observed to increase viral titers, including promoter mutations, for instance, C-to-U mutations at position 4 from the 3' end of the PB2, PB1, and/or PA vRNA segments. The resulting sequences may be also codon-usage optimized, e.g., optimized for expression in mammalian cells such as canine cells or primate cells, or avian cells, e.g., chicken embryos. The mutations can be used in various combinations, with results influenced by the cell line (or egg) in use and the desired level of improvement in the replication of the virus.

The invention provides isolated recombinant, e.g., reassortant, influenza viruses with selected amino acid residues at one or more specified positions in one or more viral segments for PA, PB1, PB2, NP, M (encoding M1 and M2 proteins), and/or NS (encoding NS1 and NS2 proteins), e.g., in selected amino acid residues at specified positions of PB1, PB2 and NS1; PA, PB1, PB2, NP and NS1; PB1, PB2, NP, M1, and NS1; PA, PB1, PB2, NP and NS1; or PA, PB1, PB2, NP, M1, and NS1, and including HA and NA genes/proteins of interest, e.g., from annual and pandemic strains, which viruses are produced more efficiently and cost-effectively via cell culture (in MDCK or Vero cells) or in embryonated chicken eggs than parental virus. As used herein, a "viral segment" in a virus means an influenza vRNA sequence and a "viral segment" in a transcription cassette for production of a viral segment means a sequence that when introduced into a cell or appropriate cell-free system and transcribed, yields influenza vRNA or cRNA. Recombinant virus may also be obtained by generating influenza viral plus-sense cRNA from a transcription cassette.

In one embodiment, the isolated recombinant influenza virus has PA, PB1, PB2, NP, NS, and M viral segments from a first influenza virus isolate, a heterologous or chimeric influenza virus NA viral segment, and a heterologous or chimeric HA viral segment, wherein the PB1 viral segment encodes a PB1 with a residue other than isoleucine at position 711 or the M viral segment encodes a M1 with a residue other than methionine at position 128, wherein the recombinant influenza virus has enhanced replication, e.g., in MDCK cells, Vero cells or eggs, relative to a corresponding influenza virus having a PB1 viral segment that encodes a PB1 with an isoleucine at position 711 or having a M viral segment that encodes a M1 with methionine at position 128. In one embodiment, the PB1 viral segment encodes a PB1 with a residue other than isoleucine at position 711 and the M viral segment encodes a M1 with a residue other than methionine at position 128. In one embodiment, the PA viral segment encodes a PA with a residue other than phenylalanine at position 105, a residue other than lysine at position 142, a residue other than serine at position 149, a residue other than serine at position 225, a residue other than lysine at position 356, a residue other than threonine at position 357, a residue other than arginine at residue 401, or a residue other than isoleucine at position 550, or any combination thereof. In one embodiment, the PB1 viral segment further encodes a PB1 with a residue other than methionine at position 40, a residue other than glutamic acid at position 112, a residue other than glycine at position 180, or a residue other than glutamine at residue 247, or any combination thereof. In one embodiment, the PB2 viral segment encodes a PB2 a residue other than methionine at position 202, a residue other than phenylalanine at position 323, or a residue other than isoleucine at position 504, or any combination thereof. In one embodiment, the NP viral segment encodes a NP with a residue other than arginine at position 74, a residue other than isoleucine at position 116, or a residue other than asparagine at position 417, or any combination thereof. In one embodiment, the NS viral segment encodes a NS1 with a residue other than alanine at position 30, a residue other than lysine at position 55, or a residue other than arginine at position 118, or any combination thereof. In one embodiment, the recombinant virus has a V, A, L, G, S, T, C, or M at position 711 in PB1, has an A, L, G, V, S, T, I, or C at position 40 in PB1, has an A, L, G, V, S, T, I, or C at position 112 in PB1, has an A, L, W, Y, F, V, S, T, I, or C at position 180 in PB1, has a H, R, K, D, E, D or E at position 247 in PB1, or any combination thereof. In one embodiment, the recombinant virus has a K, H, D, E, Q or N at position 74 in NP, has a L, V, G, A, S, C or T at position 116 in NP, has a D, E, Q, K, or H at position 417 in NP, or any combination thereof. In one embodiment, the recombinant virus has a P, W, F, L, I, V, G, S, C or T at position 30 in NS1, has E, D, Q, or N at position 55, has a K, H, D, E, Q, or N at position 118 in NS1, has a L, I, V, G, A, S, C or T at position 128 in M1, or any combination thereof. In one embodiment, the recombinant virus has a C, L, I, V, G, A, or T at position 142 in PA, has a C, L, I, V, G, A, or T at position 225 in PA, has a K, H, D, E, N or Q at position 401 in PA, or any combination thereof. In one embodiment, the recombinant virus has a V, A, L, G, S, T, C, or M at position 504 in PB2, has a A, L, G, S, T, I, or C at position 202 in PB2, has a A, L, G, S, T, I, or C at position 323 in PB2, or any combination thereof. In one embodiment, the recombinant virus has a V, A, L, G, S, T, C, or M at position 711 in PB1, has a A, L, G, V, S, T, I, or C at position 40 in PB1, has a A, L, W, Y, F, V, S, T, I, or C at position 180 in PB1; has a L, V, G, A, S, C or T at position 116 in NP; has a P, W, F, L, I, V, G, S, C or T at position 30 in NS1, has a K, H, D, E, Q, or N at position 118 in NS1; has a L, I, V, G, A, S, C or T at position 128 in M1; has a K, H, D, E, N or Q at position 401 in PA; has a V, A, L, G, S, T, C, or M at position 504 in PB2; or any combination thereof. In one embodiment, the recombinant virus has 504V in PB2. In one embodiment, the recombinant virus has 74K, 116L or 417D in NP. In one embodiment, the recombinant virus has 30P, 55E or 118K in NS1. In one embodiment, the recombinant virus has 225C or 401K in PA. In one embodiment, the recombinant virus of has a V, A, L, G, S, T, C, or M at position 711 in PB1. In one embodiment, the recombinant virus has a L, I, V, G, A, S, C or T at position 128 in M1. In one embodiment, the recombinant virus has a U at position 4 in the viral segment for any one of PB1, PB2 or PA. In one embodiment, the recombinant virus has a U at position 4 in the viral segment for PB1, PB2 and PA. In one embodiment, the PA, PB1, PB2, NP, NS, and M viral segments comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or P32 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M1 and/or M2 having the amino acid sequence encoded by SEQ ID NO:5 or M1 and/or M2 with at least 95% amino acid sequence identity to the M1 and/or M2 encoded by SEQ ID NO:5; or a NS1 and/or Ns2 having the amino acid sequence encoded by SEQ ID NO:6 or NS1 and/or NS2 with at least 95% amino acid sequence identity to the NS encoded by SEQ ID NO:6 or wherein the PA, PB1, PB2, NP, NS, and M viral segments comprise sequences for at least one of the following: a PB1 having the amino acid sequence encoded by SEQ ID NO:10 or PB1 with at least 95% amino acid sequence identity to the PB1 encoded by SEQ ID NO:10; a PB2 having the amino acid sequence encoded by SEQ ID NO:11 or PB2 with at least 95% amino acid sequence identity to the PB2 encoded by SEQ ID NO:11; a PA having the amino acid sequence encoded by SEQ ID NO:12 or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M1 and/or M2 having the amino acid sequence encoded by SEQ ID NO:14 or M1 and/or M2 with at least 95% amino acid sequence identity to the M1 and/or M2 encoded by SEQ ID NO:14; or a NS1 and/or NS2 having the amino acid sequence encoded by SEQ ID NO:15 or NS1 and/or NS2 with at least 95% amino acid sequence identity to the NS1 and/or NS2 encoded by SEQ ID NO:15. In one embodiment, two of the PA, PB1, PB2, NP, NS, and M viral segments have at least one of the alterations disclosed herein. In one embodiment, three of the PA, PB1, PB2, NP, NS, and M viral segments have at least one of the alterations disclosed herein. In one embodiment, four of the PA, PB1, PB2, NP, NS, and M viral segments have at least one of the alterations disclosed herein. In one embodiment, five of the PA, PB1, P32, NP, NS, and M viral segments have at least one of the alterations disclosed herein. In one embodiment, the PA, PB1, PB2, NP, NS, and M viral segments have at least one of the alterations disclosed herein.

Also provided is a method to prepare influenza virus, comprising: contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, wherein the PB1 DNA encodes a PB1 with a residue other than isoleucine at position 711 or the M DNA encodes a M1 with a residue other than methionine at position 128; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the cell is an avian or a mammalian cell. In one embodiment, the cell is a Vero cell, a human cell or a MDCK cell. The cell is in an avian egg.

Further provided is a method of using the recombinant virus. In one embodiment, an avian or a mammal is administered an amount of the virus effective to induce an immune response.

In one embodiment, the invention provides an isolated recombinant reassortant influenza virus having six "internal" viral segments from a vaccine influenza virus with two or more of the selected amino acid residues at specified positions described herein, and a NA viral segment selected from a first influenza virus isolate, and a HA viral segment from the same isolate or a different isolate.

In one embodiment, the influenza virus of the invention is a recombinant influenza virus having a particular amino acid residue at specified positions, as disclosed herein, in one, two, three or more of PA, PB1, PB2, NP, M1 and/or NS1 and having an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos, 1-6 or 10-15. The residue other than the specified residue may be conservative substitution, Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine or valine-leucine-isoleucine-alanine; phenylalanine-tyrosine; lysine-arginine; alanine-valine; glutamic acid-aspartic acid; and asparagine-glutamine.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue other than R401 in PA, M40 or G180 in PB1, I504 in PB2, I116 in NP, and/or A30 or R118 in NS1, or any combination thereof, as well as a residue other than I711 in PB1 or M128 in M1.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue other than R401 in PA, M40 or G180 in PB1, I504 in PB2, I116 in NP, and/or A30 or R118 in NS1, or any combination thereof, as well as a residue other than I711 in PB1 and M128 in M1.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue that is a non-conservative substitution relative to R401 in PA, M40 or G180 in PB1, I504 in PB2, I116 in NP, and/or A30 or R118 in NS1, or any combination thereof, as well as a conservative substitution relative to I711 in PB1 or a conservative substitution relative to M128 in M1.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue that is a non-conservative substitution relative to R401 in PA, M40 or G180 in PB1, I504 in PB2, I116 in NP, and/or A30 or R118 in NS1, or any combination thereof, as well as a conservative substitution relative to I711 in PB1 and a conservative substitution relative to M128 in M1.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue that is a non-conservative substitution relative to R401 in PA, M40 or G180 in PB1, I504 in PB2, I116 in NP, and/or A30 or R118 in NS1, or any combination thereof, as well as a conservative substitution relative to I711 in PB1 or a non-conservative substitution relative to M128 in M1.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue that is a non-conservative substitution relative to R401 in PA, M40 or G180 in PB1, I504 in PB2, I116 in NP, and/or A30 or R118 in NS1, or any combination thereof, as well as a conservative substitution relative to I711 in PB1 and a non-conservative substitution relative to M128 in M1.

In one embodiment, the influenza virus of the invention is a recombinant influenza virus having a particular amino acid residue at specified positions in PA, PB1, P52, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a conservative residue other than R401 in PA, a non-conservative residue other than M40 or G180 in PB1, a conservative residue other than I504 in PB2 and I116 in NP, a non-conservative residue at A30 or a conservative residue at R118 in NS1, or any combination thereof, as well as a conservative residue other than I711 in PB1 or a non-conservative residue other than M128 in M1.

In one embodiment, the influenza virus of the invention is a recombinant influenza virus having a particular amino acid residue at specified positions in PA, PB1, PB2, NP, M1, and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a conservative residue other than R401 in PA, a non-conservative residue other than M40 or G180 in PB1, a conservative residue other than I504 in PB2 and I116 in NP, a non-conservative residue at A30 or a conservative residue at R118 in NS1, or any combination thereof, as well as a conservative residue other than I711 in PB1 and a non-conservative residue other than M128 in M1.

Also included are any combination of the selected amino acid residues at specified positions described herein.

Viral segments for of PA, PB1, PB2, NP, M and/or NS that have the residues at the specified positions may be combined with a viral segment for HA, e.g., H1, H2, H3, H4, H5, H6, H7, H8, H9, H10, H11, H12, H13, H14, H15, H16, or H17 and a viral segment for NA, e.g., N1, N2, N3, N4, N5, N6, N7, N8, N9, or N10, and any combination of HA and NA, to provide the reassortant vaccine viruses of the invention. In one embodiment, the HA is H1, H5 or H7. In one embodiment the NA is N1 or N9. In one embodiment, the HA viral segment in the reassortant virus is heterologous to the viral segments for PA, PB1, PB2, NP, M and NS. In one embodiment, the NA viral segment in the reassortant virus is heterologous to the viral segments for PA, PB1, PB2, NP, M and NS. In one embodiment, the HA viral segment in the reassortant virus has viral segments for PA, PB1, PB2, NP, M and NS from one influenza virus isolate or strain ("parent"), or a variant thereof, e.g., one with viral segments encoding influenza virus proteins with at least 95%, 96%, 97%, 98%, 99%, or 99.5% amino acid sequence identity, or having 1, 2, 5, 10, or 20 substitutions relative, to sequences in a parent influenza virus isolate or strain. In one embodiment, the parent strain has viral segments with sequences corresponding to SEQ ID Nos. 1-6 or 10-15. In one embodiment, the HA viral segment in the reassortant virus is a chimeric HA viral segment, e.g., a chimera of heterologous HA ectodomain sequences linked to HA signal peptide sequences and/or HA transmembrane domain sequences from the HA viral segment of the parent isolate or strain, or variant thereof. In one embodiment, the NA viral segment in the isolated recombinant virus is a chimeric NA viral segment e.g., a chimera of heterologous NA ectodomain sequences linked to NA transmembrane domain sequences from the NA viral segment of the parent isolate or strain, or variant thereof, and/or stalk sequences from the parent isolate or strain, or variant thereof. In one embodiment, the NA viral segment in the isolated recombinant virus is a chimeric NA viral segment e.g., a chimera of heterologous NA ectodomain sequences linked to NA transmembrane domain sequences from the NA viral segment of the parent isolate or strain, or variant thereof, and/or stalk sequences from a second isolate or strain, or variant thereof. In one embodiment, the isolated recombinant virus has a heterologous HA viral segment, a heterologous NA viral segment, a chimeric HA viral segment, a chimeric NA viral segment, or any combination thereof. The nucleic acid sequences employed to prepare vRNA may be ones that introduce the residues at the specified positions via recombinant methodology or may be selected as having the residues at the specified positions.

A/Puerto Rico/8/34 (H1N1), "PR8," virus serves as the genetic backbone for generation of inactivated influenza vaccines. Occasionally, vaccine strains based on PR8 backbone replicate to relatively low titers in eggs and cell culture resulting in delayed vaccine production and vaccine shortage. To determine if high yield vaccine strain backbones for propagation in MDCK cells, chicken eggs and Vero cells can be prepared to supply the demand of seasonal flu and highly pathogenic pandemic viruses, various mutagenesis strategies were employed. For example, PR8 backbone random mutant libraries were screened for high replicative mutants, e.g., by introducing random mutations to internal PR8 genes by error prone PCR, introducing mutations that confer high replication and high polymerase activity, and optimizing PR8 internal gene via codon bias.

As described herein, virus libraries with random mutations related to an influenza virus isolate useful as a vaccine virus (e.g., A/Puerto Rico/8/34, "PR8," including a specific isolate such as UW-PR8) to carry heterologous viral segments for NA and/or HA, were serially passaged in MDCK cells, e.g., about 10-12-times although fewer passages may be employed, to obtain virus with enhanced replication in those cells. In one embodiment, viruses obtained after serial passage which have enhanced replication, have titers that are at least 1 or 2 logs higher than viruses that were not serially passaged. In one embodiment, viruses obtained after serial passage had substitutions in two or more internal viral segments relative to the parent virus.

Thus, for vaccine viruses that are to be grown or passaged in cells in culture, e.g., MDCK or Vero cells or eggs, selection of sequences with, or replacement of, the disclosed residues at the specified positions in one or more of PA, PB1, PB2, NP, and/or NS1, that confer enhanced growth of the virus in cultured cells when employed with HA and NA sequences of interest, can result in significantly higher viral titers. Thus, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are canine or primate, e.g., human or monkey, cells.

The invention provides a plurality of influenza virus vectors of the invention, e.g., those useful to prepare reassortant viruses including 6:1:1 reassortants, 6:2 reassortants and 7:1 reassortants. A 6:1:1 reassortant within the scope of the present invention is an influenza virus with 6 internal viral segments from a vaccine virus, a NA viral segment from a different (second) viral isolate, and a HA viral segment from a third isolate; a 6:2 reassortant within the scope of the present invention is an influenza virus with 6 internal viral segments from a vaccine virus, and a NA viral segment and a HA viral segment from a different (second) viral isolate; and a 7:1 reassortant within the scope of the present invention is an influenza virus with 6 internal viral segments and a NA viral segment from a vaccine virus, and a HA viral segment from a different viral source than the vaccine virus, or an influenza virus with 6 internal viral segments and a HA viral segment from the vaccine virus, and a NA viral segment is from a different viral source than the vaccine virus.

In one embodiment of the invention, the plurality includes vectors for nRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6® cells and also optionally embryonated eggs, and/or from a vaccine virus, e.g., one that does not cause significant disease in humans. The DNA for nRNA production of NA may be from any NA, e.g., any of N1-N1, and the DNA for vRNA production of HA may be from any HA, e.g., H1-H18. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers in MDCK cells, e.g., titers of at least about $10^5$ PFU/mL, e.g., at least $10^8$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in cells such as MDCK cells, e.g., titers of at least about $10^7$ PFU/mL, e.g., at least $10^8$ PFU/mL, or high titers in two of more of those host cells.

In one embodiment, the titers of the reassortant viruses of the invention in cells such as MDCK cells or Vero cells may be over 1 log, 2 logs, 3 logs, or greater, than titers of the corresponding virus without particular residues at the specified positions.

Other reassortants with internal genes from other PR8 isolates or vaccine viruses may be employed in recombinant reassortant viruses of the invention. In particular, 5:1:2 reassortants having UW-PR8 PB1, PB2, PA, NP, and M ("5") and PR8(Cam) NS ("1"); 6:1:1 reassortants having UW-PR8 NA, PB1, PB2, PA, NP, and M ("6") and PR8 (Cam) NS ("1"), and 7:1 reassortants having UW-PR8 PB1, PB2, PA, NP, M, NA, and NS ("7") may be employed.

In one embodiment, the DNAs for the internal genes for PB1, PB2, PA, NP, M, and NS encode proteins with substantially the same activity as a corresponding polypeptide encoded by one of SEQ ID NOs:1-6 or 10-15. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97%, 98%, or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 10-15 and, in one embodiment, also encodes a polypeptide having at least 80%, e.g., 90%, 92%, 95%, 97%, 98%, or 99%, including any integer between 80 and 99, contiguous amino acid sequence identity to a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide encoded by one of SEQ IS NOs:1-6 or 10-15, and has a characteristic residue in two or more of PA, PB1, PB2, NP, M1, and/or NS1 the residues, relative to a polypeptide encoded by one of SEQ ID NOs:1-6 or 10-15, and has a characteristic residue, as described herein, in two or more of the viral segments for PA, PB1, PB2, NP, M, and/or NS, such as in PA and PB1 viral segments, PB1 and PB2 viral segments, PA, PB1 and PB2 viral segments, or in PA, PB1, PB2 and NP viral segments, or in PA, PB1, PB2 and M viral segments. In one embodiment, the influenza virus polypeptide has one or more, for instance, 2, 3, 4, 5, 6, 7 or 8 conservative and/or nonconservative amino acid substitutions, relative to a polypeptide encoded by one of SEQ ID NOs:1-6 or 10-15, at positions including but not limited to 401 in PA, 40 or 180 and 711 in PB1, 504 in PB2, 116 in NP, 30 or 118 in NS1, or 128 in M1, or any combination thereof.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 18 HA or 11 NA subtypes), B or C DNA (see Fields *Virology* (Fields et al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme, Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, the invention provides a plurality of influenza virus vectors for a reassortant, comprising a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for PB1, PB2, PA, NP, NS, and M are from one or more influenza vaccine seed viruses and contain two or more of the characteristic residues at the specified position(s); and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus N52. In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:1-6 or 10-15, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:1-6 or 10-15. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

In one embodiment, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate cells.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, omithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may be employed with other anti-virals, e.g., amantadine, rimantadine, and/or neuraminidase inhibitors, e.g., may be administered separately in conjunction with those anti-virals, for instance, administered before, during and/or after.

BRIEF DESCRIPTION OF THE FIGURES

FIGS. 1A-1E. Nucleotide sequence for PR8(Cambridge) genes (SEQ ID NOs:10-15).

FIG. 3. Number of clones with random mutations having specified HA titers.

FIG. 4. Titers of clones having selected mutations.

FIG. 6. Summary of mutations that confer high replicative property in MDCK cells.

FIGS. 7A-7B. A) Virus stocks were tested for HA titers (in 2n) and virus titers (in PFU/mL). B) Growth curves in MDCK cells.

FIGS. 9A-9B. A) Comparison of titers of wild type virus (UW-PR8) and high replicative virus with mutations in M1. B) Growth kinetics of wild type virus (UW-PR8) and high replicative virus with mutations in M1.

FIGS. 10A-10M. A) Codon usage table for canines. B) Relative adaptiveness of wild type (UW-PR8) and "rare" codon optimized PB2 viruses. C) Relative adaptiveness of wild type (UW-PR8) and "all" codon optimized PB2 viruses. D) Growth kinetics of PB2 codon optimized viruses. E) Growth kinetics of viruses with codon optimized PB2, PB1, PA, or NP viral segment or combinations of segments. F-M) Sequence of PB2, PB1, PA and NP viral segments of UW-PR8 and sequence of canine codon-usage optimized PB2, PB1, PA and NP viral segments of UW-PR8 (SEQ ID no. 1-4 and 16-19).

FIGS. 11A-11C. A) Nucleotide position 4 of each gene of PR8 and Indo/NC/09. B) All 3'C4U mutant. C) Growth kinetics of a recombinant UW-PR8 virus encoding 'C' at position 4 of the PB2, PB1, and PA genes (black), and a mutant encoding 'U' at position 4 of all eight segments (red).

FIG. 12A-12C. Nucleotide and amino acid sequences for H7 and N9 (SEQ ID Nos. 20-27) which are exemplary sequences for use with the internal viral segment sequences disclosed herein useful to provide high titer influenza viruses for vaccines.

FIG. 16. HA titers of 216 clones isolated from Vero cells.

FIG. 17. Recombinant viruses generated with different PR8 backbone mutations.

FIGS. 19A-19D. Exemplary high yield substitutions (relative to PR8 (UW)).

FIGS. 21A-21H. Viral polymerase activity in mini-replicon assays in 293T, MDCK, Vero, and DF1 cells. The PB2, PB1, PA, and NP proteins were derived from UW-PR8 wild-type (WT) virus or from the high-yield PR8-HY (HY) variant.

FIGS. 22A-22D. HA titer and virus yield for various recombinant viruses and parent reassortant virus in Vero cells.

FIGS. 24A1-24B2. Growth kinetics analysis of HY candidate #9 backbone in SC-MDCK cells (A) and in eggs (B). HY candidate #9 was selected from SC-MDCK cells.

FIGS. 25A1-25C2. Growth kinetics analysis of HY candidate #5, #9, #16 backbone in eggs (A), in SC-MDCK cells (B) and in SF-MDCK cells (C).

DETAILED DESCRIPTION

Definitions

Figure 2:
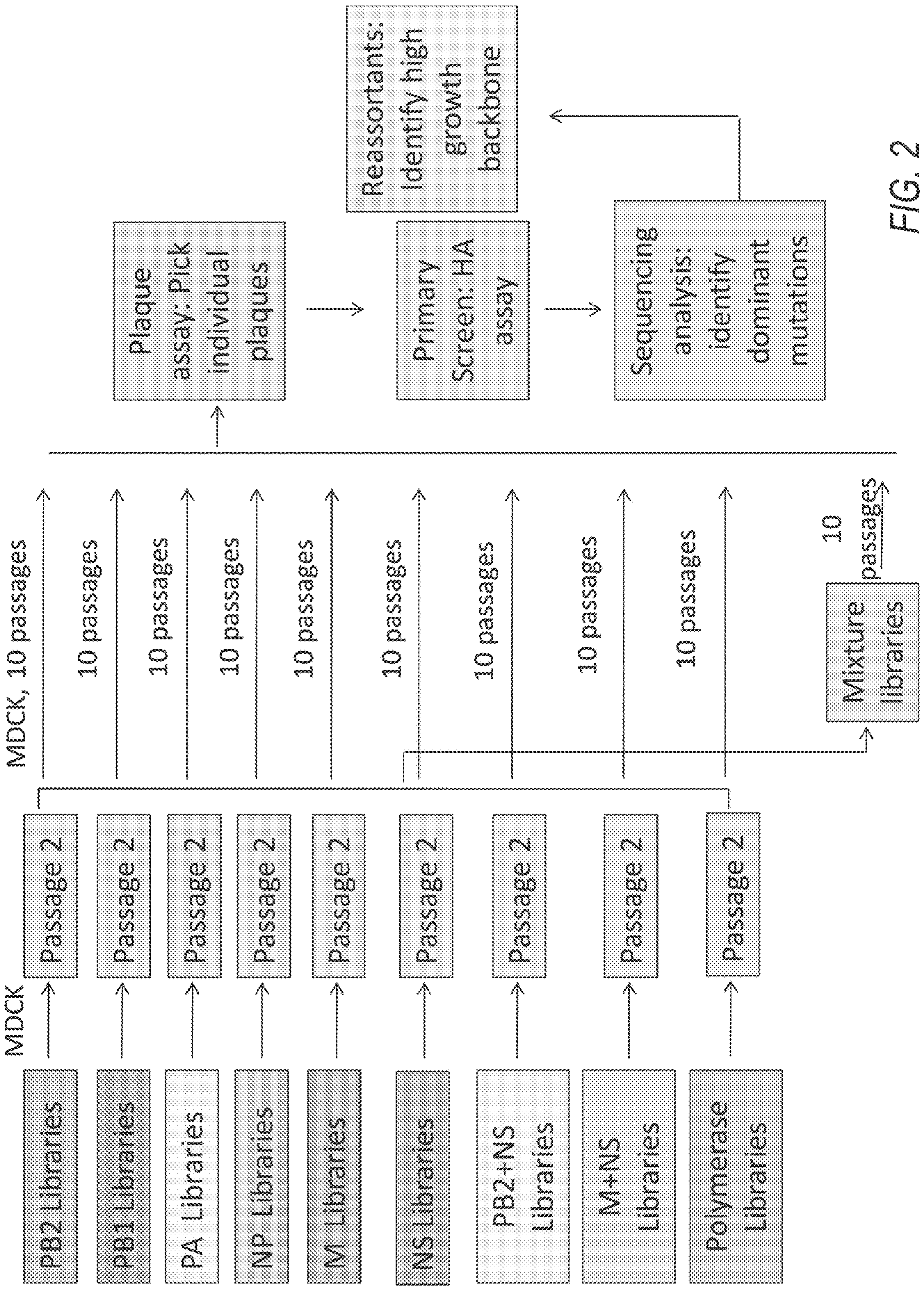
FIG. 2: Overview of library passages and the identification of high-yield candidates.
Figure 5A:
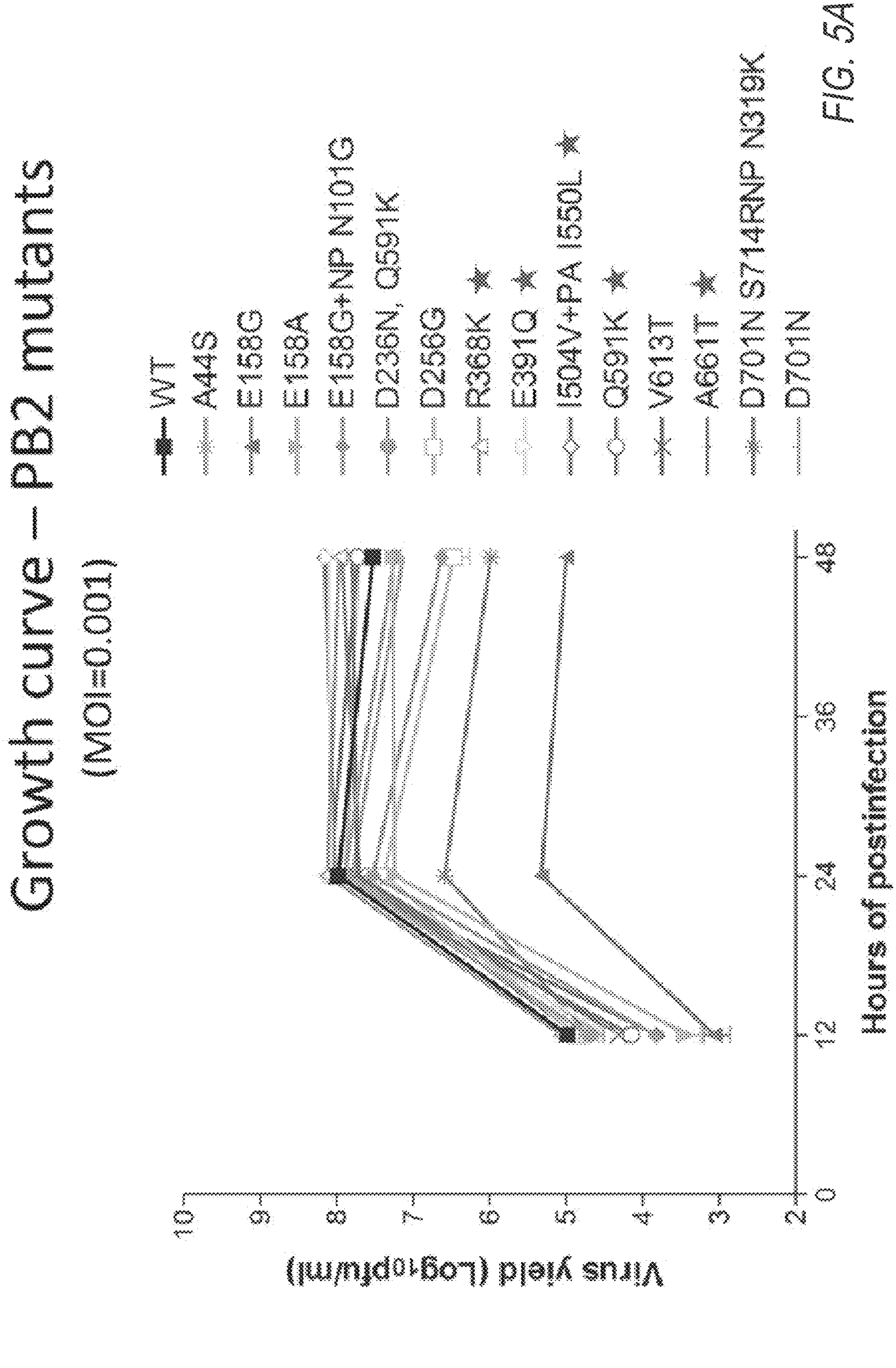
FIGS. 5A-5D. Growth curves of UW-PR8 viruses possessing previously identified mutations in PB2 (A), PB1 or PB1-F2 (B), PA (C), and NP, M or NS1 (D).
Figure 5B:
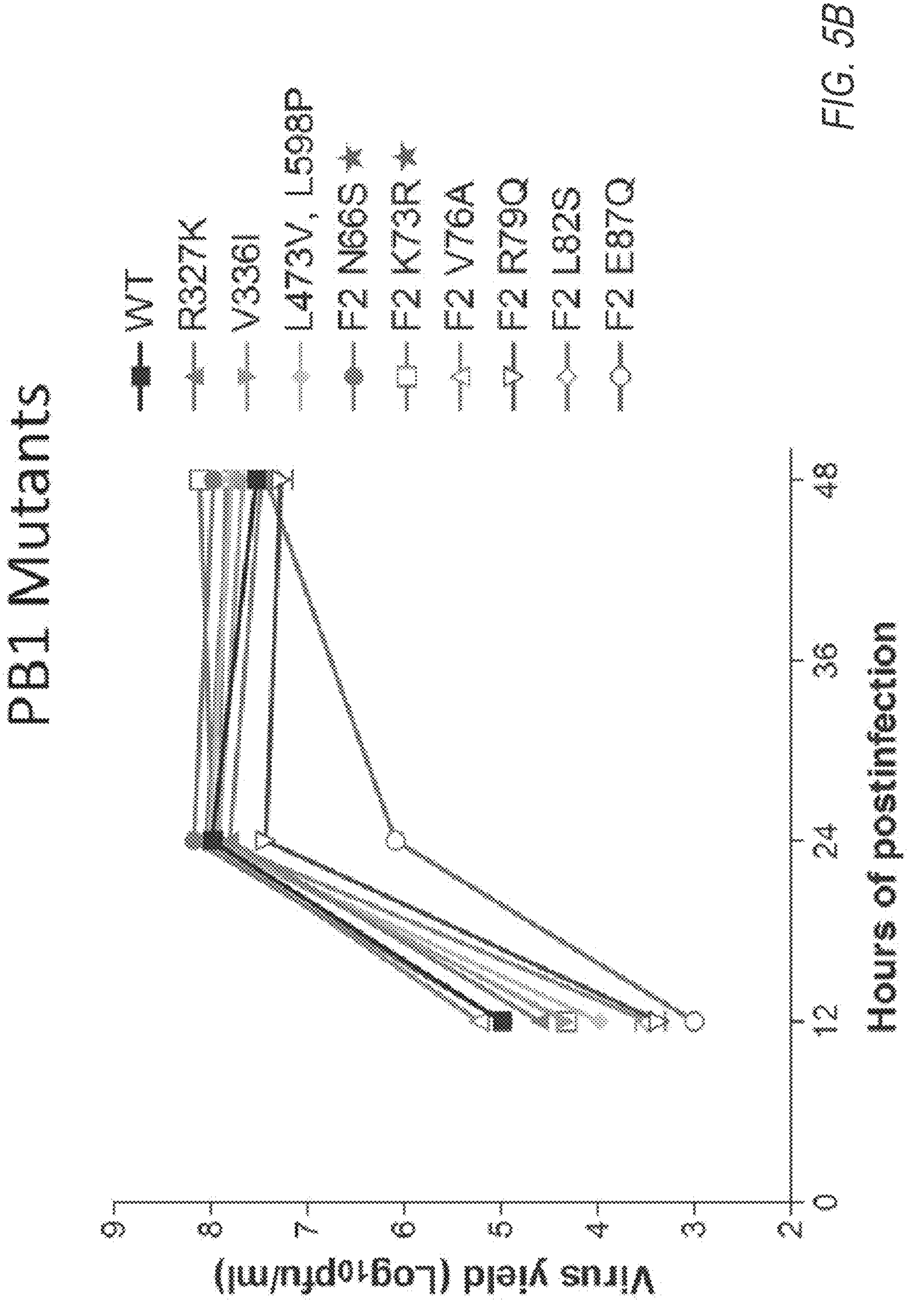
Figure 5C:
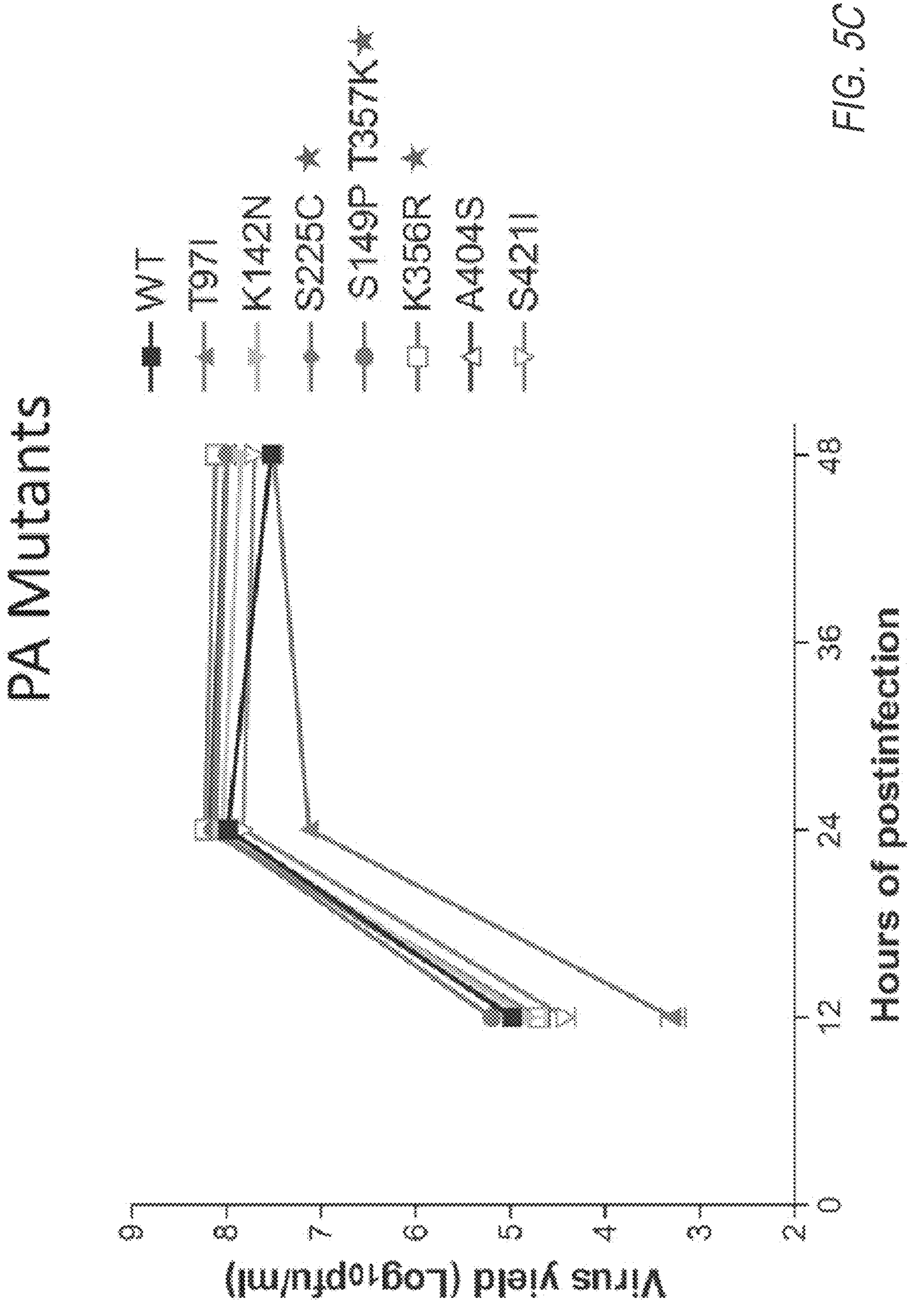
Figure 5D:
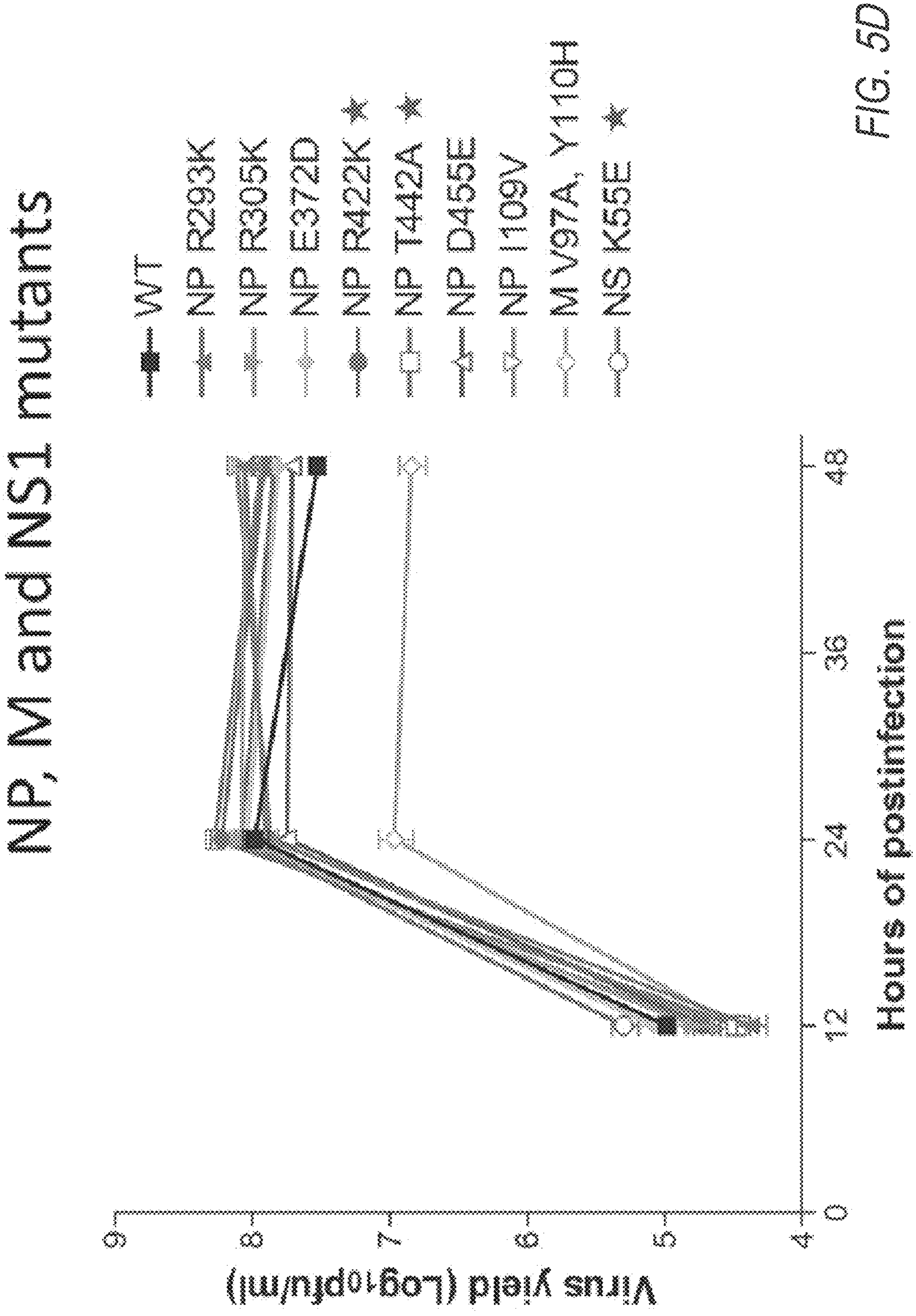

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0,01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.n1m.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus has a viral segment with both NA and NB sequences. Influenza C virus has only seven viral segments.

Cell Lines that can be Used in the Present Invention

Any cell, e.g., any avian or mammalian cell, such as a human, e.g., 293T or PER.C6® cells, or canine, e.g., MDCK, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (layer & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose (lithe attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein, Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α; interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg per component for older children (greater than or equal to 3 years of age), and 7.5 μg per component for children less than 3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

EXEMPLARY EMBODIMENTS

In one embodiment, an isolated influenza virus having PA, PB1, PB2, NP, NS, M, NA and HA viral segments is provided, wherein the PB1 viral segment encodes a PB1 with a residue other than isoleucine at position 711 or the M viral segment encodes a M1 with a residue other than methionine at position 128, wherein the influenza virus has enhanced replication relative to a corresponding influenza virus having a PB1 viral segment that encodes a PB1 with an isoleucine at position 711 or having a M viral segment that encodes a M1 with methionine at position 128. In one embodiment, the NA viral segment is heterologous to the PA, PB1, PB2, NP, NS, and M viral segments. In one embodiment, the NA and HA viral segments are from the same viral isolate. In one embodiment, the PB1 viral segment encodes a PB1 with a residue other than isoleucine at position 711 and the M viral segment encodes a M1 with a residue other than methionine at position 128. In one embodiment, the PA viral segment encodes a PA with a residue other than phenylalanine at position 105, a residue other than lysine at position 142, a residue other than serine at position 149, a residue other than serine at position 225, a residue other than lysine at position 356, a residue other than threonine at position 357, a residue other than arginine at residue 401, or a residue other than isoleucine at position 550, or any combination thereof. In one embodiment, the PB1 viral segment further encodes a PB1 with a residue other than methionine at position 40, a residue other than glutamic acid at position 112, a residue other than glycine at position 180, or a residue other than glutamine at residue 247, or any combination thereof. In one embodiment, the PB2 viral segment encodes a PB2 a residue other than methionine at position 202, a residue other than phenylalanine at position 323, or a residue other than isoleucine at position 504, or any combination thereof. In one embodiment, the NP viral segment encodes a NP with a residue other than arginine at position 74, a residue other than isoleucine at position 116, or a residue other than asparagine at position 417, or any combination thereof. In one embodiment, the NS viral segment encodes a NS1 with a residue other than alanine at position 30, a residue other than lysine at position 55, or a residue other than arginine at position 118, or any combination thereof.

In one embodiment, the PA viral segment encodes a PA with a residue other than phenylalanine at position 105, a residue other than lysine at position 142, a residue other than serine at position 149, a residue other than serine at position 225, a residue other than arginine at position 256, a residue other than asparagine at position 350, a residue other than lysine at position 356, a residue other than threonine at position 357, a residue other than alanine at position 369, a residue other than arginine at residue 401, or a residue other than isoleucine at position 550, or any combination thereof.

In one embodiment, the PB1 viral segment encodes a PB1 with a residue other than methionine at position 40, a residue other than methionine at position 92, a residue other than asparagine at position 105, a residue other than glutamic acid at position 112, a residue other than glutamic acid at position 178, a residue other than glycine at position 180, a residue other than glutamine at residue 247, a residue other than methionine at position 290, a residue other than methionine at position 325, a residue other than isoleucine at position 711, or any combination thereof.

In one embodiment, the PB2 viral segment encodes a PB2 a residue other than arginine at position 62, a residue other than methionine at position 202, a residue other than alanine at position 221, a residue other than phenylalanine at position 323, a residue other than alanine at position 370, a residue other than methionine at position 467, a residue other than isoleucine at position 504, a residue other than tyrosine at position 704, or a residue other than lysine at position 721, or any combination thereof.

In one embodiment, the NP viral segment encodes a NP with a residue other than arginine at position 74, a residue other than lysine at position 103, a residue other than isoleucine at position 116, a residue other than valine at position 194, or a residue other than asparagine at position 417, or any combination thereof. In one embodiment, the M viral segment encodes a M1 with a residue other than serine at position 126, with a residue other than methionine at position 128, a residue other than methionine at position 244, or a M2 with a residue other than tryptophan at position 15, or any combination thereof.

In one embodiment, the NS viral segment encodes a NS1 with a residue other than alanine at position 30, a residue other than lysine at position 55, a residue other than aspartic acid at position 101, or a residue other than arginine at position 118, or any combination thereof.

In one embodiment, the virus has a V, A, L, G, S, T, C, or M at position 711 in PB1, has an A, L, G, V, S, T, I, or C at position 40 in PB1, has an A, L, G, V, S, T, I, or C at position 112 in PB1, has an A, L, W, Y, F, V, S, T, I, or C at position 180 in PB1, has a H, R, K, D or E at position 247 in PB1, has a V, A, L, G, S, T, C, or I at position 290 in PB1, has a V, A, L, G, S, T, C, or I at position 92 in PB1, has a V, A, L, G, S, T, C, or I at position 325 in PB1, has a H, R, K, D, or E at position 105 in PB1, has a H, R, or K at position 178 in PB1, or any combination thereof.

In one embodiment, the virus has a V, A, L, or G at position 711 in PB1, has an A, L, G, V, or I at position 40 in PB1, has an A, L, G, V, S, T, or I at position 112 in PB1, has a W, Y, or F, at position 180 in PB1, has a H, R, K, D or E at position 247 in PB1, has a V, A, L, G, or I at position 290 in PB1, has a V, A, L, G, or I at position 92 in PB1, has a V, A, L, G, or I at position 325 in PB1, has a H, R, or K at position 105 in PB1, has a R or K at position 178 in PB1, or any combination thereof.

In one embodiment, the virus has a K, H, D, E, Q or N at position 74 in NP, has a R or H at position 103 in NP, has a I, A, L, or G at position 194 in NP, has a L, V, G, A, S, or T at position 116 in NP, has a D, E, Q, K, or H at position 417 in NP, or any combination thereof.

In one embodiment, the virus of has a P, W, F, S or T at position 30 in NS1, has E, D, Q, or N at position 55, has a L, I, V, G, A or T at position 101 in NS1, has a K, H, D, E, Q, or N at position 118 in NS1, or any combination thereof.

In one embodiment, the virus has a E, D, H, R or K at position 142 in PA, has a C, L, I, V, G, A, or T at position 225 in PA, has a L, I, V, S, G, A, or T at position 256 in PA, has a L, I, V, G, A, or T at position 350 in PA, has a L, I, V, G, S, or T at position 356 in PA, has a K, H, D, E, N or Q at position 401 in PA, or any combination thereof.

In one embodiment, the virus has a V, A, L, G, S, or T at position 504 in PB2, has a A, L, G, S, T, I, or C at position 202 in PB2, has a A, L, G, S, T, I, or C at position 323 in PB2, has a V, L, G, or I at position 221 in PB2, has a V, L, G, T or I at position 370 in PB2, has a V, L, G, S, T or I at position 62 in PB2, has a V, L, A, G, S, T, or lat position 467 in PB2, has a K, H, D, E, N or Q at position 704 in PB2, has a R, H, D, E, N or Q at position 721 in PB2, or any combination thereof.

In one embodiment, the virus has a V, A, L, G, or T at position 126 in M1, has a V, A, L, G, T, or Sat position 128 in M1, has a R, K, D, E or H at position 244 in M1, has a A, L, G, S, T, or I at position 15 in M2, or any combination thereof.

In one embodiment, the virus has a V, A, L, G, S, T, C, or M at position 711 in PB1, has a A, L, G, V, S, T, I, or C at position 40 in PB1, has a A, L, W, Y, F, V, S, T, I, or Cat position 180 in PB1; has a L, V, G, A, S, C or T at position 116 in NP; has a P, W, F, L, I, V, G, S, C or T at position 30 in NS1, has a K, H, D, E, Q, or N at position 118 in NS1; has a L, I, V, G, A, S, C or T at position 128 in M1; has a K, H, D, E, N or Q at position 401 in PA; has a V, A, L, G, S, T, C, or M at position 504 in PB2; or any combination thereof. In one embodiment, the virus has a V, A, L, G, S, T, C, or M at position 711 in PB1, has a H, R, K, D, E, D or E at position 247 in PB1; has a K, H, D, E, Q or N at position 74 in NP; has E, D, Q, or N at position 55 in NS1; has a L, I, V, G, A, S, C or T at position 128 in M1; has a C, L, I, V, G, A, or T at position 142 in PA; has a A, L, G, S, T, I, or C at position 202 in PB2, has a A, L, G, S, T, I, or C at position 323 in PB2; or any combination thereof. In one embodiment, the virus has a V, A, L, G, S, T, C, or M at position 711 in PB1, has a A, L, G, V, S, T, I, or C at position 112 in PB1; has a K, H, D, E, Q or N at position 74 in NP, has a D, E, Q, K, or H at position 417 in NP; has E, D, Q, or N at position 55; has a L, I, V, G, A, S, C or T at position 128 in M1; has a C, L, I, V, G, A, or T at position 225 in PA; has a V, A, L, G, S, T, C, or M at position 504 in PB2; or any combination thereof. In one embodiment, the virus has 142N, 225C, 356R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or any combination thereof. In one embodiment, the virus has at least one of 202L and/or 323L in PB2, 247H in PB1 or 74K in NP and optionally at least one of 142N in PA1, 55K in NS1 or 97A and/or 100H in M1.

In one embodiment, the virus has at least one of 202L and/or 323L in PB2, 247H in PB1 or 74K in NP and at least one of 142N in PA1, 55K in NS1 or 97A and/or 100H in M1. In one embodiment, the virus has 202L and/or 323L in PB2. In one embodiment, the virus has 247H in PB1, In one embodiment, the virus has 55E in NS1. In one embodiment, the virus has 142C in PA. In one embodiment, the virus has 74K in NP. In one embodiment, the virus has 504V in PB2, In one embodiment, the virus has 74K, 116L or 417D in NP. In one embodiment, the virus has 30P, 55E or 118K in NS1, In one embodiment, the virus has 225C or 401K in PA. In one embodiment, the virus has a V, A, L, G, S, T, C, or M at position 711 in PB1. In one embodiment, the virus has a L, I, V, G, A, S, C or T at position 128 in M1. In one embodiment, the virus has a U at position 4 in the viral segment for any one of PB1, PB2 or PA. In one embodiment, the PA, PB1, PB2, NP, NS, and M viral segments comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or PB2 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M1 and/or M2 having the amino acid sequence encoded by SEQ ID NO:5 or M1 and/or M2 with at least 95% amino acid sequence identity to the M1 and/or M2 encoded by SEQ ID NO:5; or a NS1 and/or NS2 having the amino acid sequence encoded by SEQ ID NO:6 or NS1 and/or NS2 with at least 95% amino acid sequence identity to the NS1 and/or NS2 encoded by SEQ ID NO:6 or wherein the PA, PB1, PB2, NP, NS, and M viral segments comprise sequences for at least one of the following: a PB1 having the amino acid sequence encoded by SEQ ID NO:10 or PB1 with at least 95% amino acid sequence identity to the PB1 encoded by SEQ ID NO:10; a PB2 having the amino acid sequence encoded by SEQ ID NO:11 or PB2 with at least 95% amino acid sequence identity to the PB2 encoded by SEQ ID NO:11; a PA having the amino acid sequence encoded by SEQ ID NO:12 or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M1 and/or M2 having the amino acid sequence encoded by SEQ ID NO:14 or M1 and/or M2 with at least 95% amino acid sequence identity to the M1 and/or M2 encoded by SEQ ID NO:14; or a NS1 and/or NS2 having the amino acid sequence encoded by SEQ ID NO:15 or NS1 and/or NS2 with at least 95% amino acid sequence identity to the NS1 and/or NS2 encoded by SEQ ID NO:15.

A vaccine having the isolated virus is also provided.

In one embodiment, a plurality of influenza virus vectors for preparing a reassortant virus is provided. In one embodiment, the plurality includes but is not limited to a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, wherein the PB1 DNA encodes a PB1 with a residue other than isoleucine at position 711 or the M DNA encodes a M1 with a residue other than methionine at position 128; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, the PB1, PB2, PA, NP, NS, and M DNAs in the vectors for vRNA production have a sequence corresponding to one that encodes a polypeptide having at least 95% amino acid sequence identity to a corresponding polypeptide encoded by SEQ ID NOs:1-6 or 10-15. In one embodiment, the promoter for vRNA vectors is a RNA polymerase I promoter, a RNA polymerase II promoter, a RNA polymerase III promoter, a T3 promoter or a T7 promoter. In one embodiment, the HA is H1, H3, H5, H7 or H9. In one embodiment, the PA, PB1, and PB2 viral segments, and optionally NP, NS, and M viral segments has a promoter C to a mutation.

Further provided is a method to prepare influenza virus, comprising: contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, wherein the PB1 DNA encodes a PB1 with a residue other than isoleucine at position 711 or the M DNA encodes a M1 with a residue other than methionine at position 128; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the cell is an avian or a mammalian cell. In one embodiment, the cell is a Vero cell, a human cell or a MDCK cell. In one embodiment, the PB1, PB2, PA, NP, NS, and M DNAs in the vectors for vRNA productions have a sequence that corresponds to one that encodes a polypeptide having at least 95% amino acid sequence identity to a corresponding polypeptide encoded by SEQ ID NOs:1-6 or 10-15. In one embodiment, the virus is isolated. In one embodiment, the PB1 viral segment encodes a PB1 with a residue other than isoleucine at position 711 and the M viral segment encodes a M1 with a residue other than methionine at position 128. In one embodiment, the PA viral segment encodes a PA with a residue other than phenylalanine at position 105, a residue other than lysine at position 142, a residue other than serine at position 149, a residue other than serine at position 225, a residue other than lysine at position 356, a residue other than threonine at position 357, a residue other than arginine at residue 401, or a residue other than isoleucine at position 550, or any combination thereof; or wherein the PB1 viral segment further encodes a PB1 with a residue other than methionine at position 40, a residue other than glutamic acid at position 112, a residue other than glycine at position 180, or a residue other than glutamine at residue 247, or any combination thereof; or wherein the PB2 viral segment encodes a PB2 a residue other than methionine at position 202, a residue other than phenylalanine at position 323, or a residue other than isoleucine at position 504, or any combination thereof or wherein the NP viral segment encodes a NP with a residue other than arginine at position 74, a residue other than isoleucine at position 116, or a residue other than asparagine at position 417, or any combination thereof; or wherein the NS viral segment encodes a NS1 with a residue other than alanine at position 30, a residue other than lysine at position 55, or a residue other than arginine at position 118, or any combination thereof. In one embodiment, the virus has a V, A, L, G, S, T, C, or M at position 711 in PB1, has a A, L, G, V, S, T, I, or C at position 40 in PB1, has a A, L, G, V, S, T, I, or C at position 112 in PB1, has a A, L, W, Y, F, V, S, T, I, or C at position 180 in PB1, has a H, R, K, D, E, D o E at position 247 in PB1, or any combination thereof; or has a K, H, D, E, Q or N at position 74 in NP, has a L, V, G, A, S, C or T at position 116 in NP, has a D, E, Q, K, or H at position 417 in NP, or any combination thereof; or has a P, W, F, L, I, V, G, S, C or T at position 30 in NS1, has E, D, Q, or N at position 55, has a K, H, D, E, Q, or N at position 118 in NS1, has a L, I, V, G, A, S, C or T at position 128 in M1, or any combination thereof; or has a C, L, I, V, G, A, or T at position 142 in PA, has a C, L, I, V, G, A, or T at position 225 in PA, has a K, H, D, E, N or Q at position 401 in PA, or any combination thereof; or has an V, A, L, G, S, T, C, or M at position 504 in PB2, has a A, L, G, S, T, I, or C at position 202 in PB2, has a A, L, G, S, T, I, or C at position 323 in PB2, or any combination thereof. In one embodiment, the virus has a V, A, L, G, S, T, C, or M at position 711 in PB1, has a A, L, G, V, S, T, I, or C at position 40 in PB1, has a A, L, W, Y, F, V, S, T, I, or C at position 180 in PB1; has a L, V, G, A, S, C or T at position 116 in NP; has a P, W, F, L, I, V, G, S, C or T at position 30 in NS1, has a K, H, D, E, Q, or N at position 118 in NS1; has a L, I, V, G, A, S, C or T a position 128 in M1; has a K, H, D, E, N or Q at position 401 in PA; has an V, A, L, G, S, T, C, or M at position 504 in PB2; or any combination thereof. In one embodiment, the virus has a V, A, L, G, S, T, C, or M at position 711 in PB1, has a H, R, K, D, E, D or E at position 247 in PB1; has a K, H, D, E, Q or N at position 74 in NP; has E, D, Q, or N at position 55 in NS1; has a L, I, V, G, A, S, C or T at position 128 in M1; has a C, L, I, V, G, A, or T at position 142 in PA; has a A, L, G, S, T, I, or C at position 202 in PB2, has a A, L, G, S, T, I, or C at position 323 in PB2; or any combination thereof. In one embodiment, the virus has a V, A, L, G, S, T, C, or M at position 711 in PB1, has a A, L, G, V, S, T, I, or C at position 112 in PB1; has a K, H, D, E, Q or N at position 74 in NP, has a D, E, Q, K, or H at position 417 in NP; has E, D, Q, or N at position 55; has a L, I, V, G, A, S, C or T at position 128 in M1; has a C, L, I, V, G, A, or T at position 225 in PA; has an V, A, L, G, S, T, C, or M at position 504 in PB2; or any combination thereof. In one embodiment, the virus has one or more of 142N, 225C, 356R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or any combination thereof. In one embodiment, the virus has at least one of 202L and/or 323L in PB2, 247H in PB1 or 74K in NP and optionally at least one of 142N in PA1, 55K in NS1 or 97A and/or 100H in M1. In one embodiment, the virus has at least one of 202L and/or 323L in PB2, 247H in PB1 or 74K in NP and at least one of 142N in PA1, 55K in NS1 or 97A and/or 100H in M1. In one embodiment, the virus has 202L and/or 323L in PB2. In one embodiment, the virus has 247H in PB1. In one embodiment, the virus has 55E in NS1, In one embodiment, the virus has 142C in PA. In one embodiment, the virus has 74K in NP. In one embodiment, the virus has 504V in PB2. In one embodiment, the virus has 74K, 116L or 417D in NP. In one embodiment, the virus has 30P, 55E or 118K in NS1. In one embodiment, the virus has 225C or 401K in PA. In one embodiment, the virus has a V, A, L, G, S, T, C, or M at position 711 in PB1. In one embodiment, the virus has a L, I, V, G, A, S, C or T at position 128 in M1. In one embodiment, at least one of PA, PB1, or PB2 viral segments has a C to U promoter mutation.

In other embodiments, the virus has a residue at position 30 or 31 in PA other than the residue encoded by SEQ ID NO:1 or 10; a residue in PB1 other than R54, T59, G62, A63, E75, D76, E78, P79, S80, R327, M507, L624, V644, I667, N694, L695, E697, F699, F700, P701, S702, Y705, S713, and/or M714; a residue in PB2 other than I57, T58, A59, K61, M66, R368, E391, Q591, E677, D678, and/or P679, in PB2; a residue in NP other than I112, N224, R293, M371, R422 or T442; a residue in M1 other than P90, V97, and/or Y100; or a residue in NS1 other than T49, R140, S161 and/or A223. In one embodiment, the PB1 viral segment and/or the NS viral segment encodes a polypeptide having a residue other than glycine, serine, serine, glutamine or asparagine at position 62, 261, 361, 621, and/or 654 in PB1 or a residue other than arginine at position 81 in F2.

In one embodiment, the isolated recombinant influenza virus has PA, PB1, PB2, NP, NS, and M viral segments from a first influenza vaccine virus isolate, a heterologous, recombinant or chimeric influenza virus NA viral segment, and a heterologous, recombinant or chimeric HA viral segment, wherein one, two or more of the PA, PB1, PB2, NP, NS, and M viral segments have selected amino acid residues at positions 30, 31, 105, 142, 149, 225, 356, 357, 401, and/or 550 in PA; positions 40, 54, 59, 62, e.g., 62A, 63, 75, 76, 78, 79, 80, 112, 180, 247, 261, e.g., 161G, 327, 361, e.g., 361R, 507, 621, e.g., 621R, 624, 644, 654, e.g., 654S, 667, 694, 695, 697, 699, 700, 701, 702, 705, 713, and/or 714 in PB1; positions 57, 58, 59, 61, 66, 202, 323, 368, 391, 504, 591, 677, 678, and/or 679, in PB2; positions 74, 112, 116, 224, 293, 371, 377, 417, 422 or 442 in NP; positions 90, 97 and/or 100 in M1; or positions 30, 49, 55, 118, e.g., 118K, 140, 161, and/or 223 in NS1, and optionally an HA with a residue other than glutamic acid, lysine, glutamine, leucine, valine, phenylalanine, lysine or methionine at position 136, 162, 179, 182, 184, 252, 449, or 476, respectively, e.g., a HA segment with one or more of 136D, 162E, 179L, 182V, 184I, 252I, 449E or 476I, or optionally a NA with a residue other than leucine or alanine at residue 55 or 265, respectively, e.g., 55S or 265V. In one embodiment, the isolated virus has 142N, 225C, 356R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or combinations thereof, e.g., has at least one of 202L and/or 323L in PB2, 247H in PB1 or 74K in NP and optionally at least one of 142N in PA1, 55K in NS1 or 97A and/or 100H in M1 or has at least one of 202L and/or 323L in PB2, 247H in PB1 or 74K in NP and at least one of 142N in PA1, 55K in NS1 or 97A and/or 100H in M1. In one embodiment, the virus has at least one of 202L and/or 323L in PB2, 247H in PB1 or 74K in NP and optionally at least one of 142N in PA1, 55K in NS1 or 97A and/or 100H in M1 In one embodiment, the virus has at least one of 202L and/or 323L in PB2, 247H in PB1 or 74K in NP and at least one of 142N in PA1, 55K in NS1 or 97A and/or 100H in M1 In one embodiment, the isolated virus has 202L and/or 323L in PB2, and optionally has 247H in PB1 and optionally 74K in NP. In one embodiment, the isolated virus has 247H in PB1 and optionally 74K in NP. In one embodiment, the isolated virus has 40I, 40L, 112G, 180W, 247H, 507V, or 644A in PB1 and optionally has 202L and/or 323L in PB2, and optionally has 74K, 112L, 116L, 377N, 417D, or 422L in NP, and optionally has 30P, 118K, 161T or 140Q in NS1, and optionally has 142N, 225C, 356R, 401K, or 550L in PA. In one embodiment, the isolated virus has 40I, 40L, 112G, 180W, 247H, 507V, or 644A in PB1. In one embodiment, the isolated virus has 202L and/or 323L in PB2. In one embodiment, the isolated virus has 74K, 112L, 116L, 377N, 417D, or 422L in NP. In one embodiment, the isolated virus has 30P, 118K, 161T or 140Q in NS1. In one embodiment, the isolated virus has 142N, 225C, 356R, 401K, or 550L in PA. In one embodiment, the selected amino acid residues at specified positions in the PA is/are at position(s) 97, 105, 142, 149, 225, 356, 357, 401, 404, and/or 421. In one embodiment, the selected amino acid residues at specified positions in the PB1 is/are at position(s) 12, 40, 54, 59, 62, 63, 66, 75, 76, 78, 79, 80, 180, 247, 507, 624, 644, 694, 695, 697, 699, 700, 701, 705, 713, 714, and/or 762. In one embodiment, the selected amino acid residues at specified positions in the PB2 is/are at position(s) 57, 58, 59, 61, 66, 202, 243, 323, 504, 677, 678, and/or 679. In one embodiment, the selected amino acid residues at specified positions in the NP is/are at position(s) 74, 112, 116, 224, 293, 417, and/or 442. In one embodiment, the selected amino acid residues at specified positions in the M1 is/are at position(s) 90, 97, and/or 100. In one embodiment, the selected amino acid residues at specified positions in the NS1 is/are at position(s) 49, 30, 55, 161, and/or 223, In one embodiment, the selected amino acid residues at specified positions in the PA is/are at position(s) 97, 105, 142, 149, 225, 356, 357, 401, 404, and/or 421; and optionally the selected amino acid residues at specified positions in the PB1 is/are at position(s) 12, 40, 54, 59, 62, 63, 66, 75, 76, 78, 79, 80, 180, 247, 507, 624, 644, 694, 695, 697, 699, 700, 701, 705, 713, 714, and/or 762, in any combination with the selected residues for PA; and optionally the selected amino acid residues at specified positions in the PB2 is/are at position(s) 57, 58, 59, 61, 66, 202, 243, 323, 504, 677, 678, and/or 679 in any combination with the selected residues for PA and/or PB1; and optionally the selected amino acid residues at specified positions in the NP is/are at position(s) 74, 112, 116, 224, 293, 417, and/or 442 any combination with the selected residues for PA, PB1 and/or PB2; and optionally the selected amino acid residues at specified positions in the M1 is/are at position(s) 90, 97, and/or 100 any combination with the selected residues for PA, PB1, PB2, and/or NP; and optionally the selected amino acid residues at specified positions in the NS1 is/are at position(s) 49, 30, 55, 161, and/or 223, or in any combination with the selected residues for PA, PB1, PB2, NP, and/or M1.

For any of the exemplary viruses disclosed above, in one embodiment, the PA, PB1, PB2, NP, NS, and M viral segments comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or PB2 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M1 and/or M2 having the amino acid sequence encoded by SEQ ID NO:5 or M1 and/or M2 with at least 95% amino acid sequence identity to the M1 and/or M2 encoded by SEQ ID NO:5; or a NS1 and/or NS2 having the amino acid sequence encoded by SEQ ID NO:6 or NS1 and/or NS2 with at least 95% amino acid sequence identity to the NS1 and/or NS2 encoded by SEQ ID NO:6, or the PA, PB1, PB2, NP, NS, and M viral segments comprise sequences for at least one of the following: a PB1 having the amino acid sequence encoded by SEQ ID NO:10 or PB1 with at least 95% amino acid sequence identity to the PB1 encoded by SEQ ID NO:10; a PB2 having the amino acid sequence encoded by SEQ ID NO:11 or PB2 with at least 95% amino acid sequence identity to the PB2 encoded by SEQ ID NO:11; a PA having the amino acid sequence encoded by SEQ ID NO:12 or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M1 and/or M2 having the amino acid sequence encoded by SEQ ID NO:14 or M1 and/or M2 with at least 95% amino acid sequence identity to the M1 and/or M2 encoded by SEQ ID NO:14; or a NS1 and/or NS2 having the amino acid sequence encoded by SEQ ID NO:15 or NS1 and/or NS2 with at least 95% amino acid sequence identity to the NS1 and/or NS2 encoded by SEQ ID NO:15.

For any of the exemplary viruses disclosed above, in one embodiment, at least one of the PA, PB1, PB2, NP, NS, and M viral segments has a C to U promoter mutation.

Any of the isolated viruses disclosed herein may be employed in a vaccine.

In one embodiment, the invention provides a plurality of influenza virus vectors for preparing a reassortant. In one embodiment, the plurality includes a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, 30, 31, 105, 142, 149, 225, 356, 357, 401, and/or 550 in PA; 40, 54, 59, 62, 63, 75, 76, 78, 79, 80, 112, 180, 247, 327, 507, 624, 644, 667, 694, 695, 697, 699, 700, 701, 702, 705, 713, or 714 and/or 247 in PB1; 57, 58, 59, 61, 66, 202, 323, 368, 391, 504, 591, 677, 678, or 679, 202 and/or 323 in PB2; 74, 112, 116, 224, 293, 371, 377, 417, 422 and/or 442 in NP; 90, 97 and/or 100 in M1; or 30, 49, 55, 118, 140, 161 and/or 223 in NS; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, the PB1, PB2, PA, NP, NS, and M DNAs in the vectors for vRNA production have a sequence corresponding to one that encodes a polypeptide having at least 95% amino acid sequence identity to a corresponding polypeptide encoded by SEQ ID NOs:1-6 or 10-15. In one embodiment, the promoter for vRNA vectors is a RNA polymerase I promoter, a RNA polymerase II promoter, a RNA polymerase III promoter, a T3 promoter or a T7 promoter. In one embodiment, the NA is N9. In one embodiment, the HA is H7. In one embodiment, the PA, PB1, PB2, NP, NS, and/or M viral segments has/have a promoter C to a mutation.

In one embodiment, the invention provides a method to prepare influenza virus. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, 30, 31, 105, 142, 149, 225, 356, 357, 401, and/or 550 in PA; 40, 54, 59, 62, 63, 75, 76, 78, 79, 80, 112, 180, 247, 327, 507, 624, 644, 667, 694, 695, 697, 699, 700, 701, 702, 705, 713, and/or 714 and/or 247 in PB1; 57, 58, 59, 61, 66, 202, 323, 368, 391, 504, 591, 677, 678, and/or 679, 202 and/or 323 in PB2; 74, 112, 116, 224, 293, 371, 377, 417, 422 and/or 442 in NP; 90, 97 and/or 100 in M1; or 30, 49, 55, 118, 140, 161 or 223 in NS; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the cell is an avian cell or a mammalian cell, e.g., a Vero cell, a human cell or a MDCK cell. In one embodiment, the PB1, PB2, PA, NP, NS, and M DNAs in the vectors for vRNA productions have a sequence that corresponds to one that encodes a polypeptide having at least 95% amino acid sequence identity to a corresponding polypeptide encoded by SEQ ID NOs:1-6 or 10-15. In one embodiment, the method includes isolating the virus. In one embodiment, at least one of PA, PB1, or PB2 viral segments has a C to U promoter mutation.

Further provided is a vector for vRNA or mRNA expression of influenza virus PA having at least 95% amino acid sequence identity to a polypeptide encoded by SEQ ID NO:1 and having a threonine at position 30, a lysine at position 31, cysteine at position 105 or a lysine at position 401; a vector for vRNA or mRNA expression of influenza virus PB1 having at least 95% amino acid sequence identity to a polypeptide encoded by SEQ ID NO:2 and having a leucine at position 40, an alanine or isoleucine at position 54, glycine at position 112, histidine at position 247, valine at position 507, alanine at position 644, or cysteine at position 713; a vector for vRNA or mRNA expression of PB2 having at least 95% amino acid sequence identity to a polypeptide encoded by SEQ ID NO:3 and a leucine at position 202 and/or 323; a vector for vRNA or mRNA expression of influenza virus NP having at least 95% amino acid sequence identity to a polypeptide encoded by SEQ ID NO:4 and having a lysine at position 74, leucine at position 116, isoleucine at position 224, lysine at position 293, asparagine at position 377, or aspartic acid at position 417; a vector for vRNA or mRNA expression of influenza virus NS1 having at least 95% amino acid sequence identity to a NS1 polypeptide encoded by SEQ ID NO:6 and having a proline at position 30, alanine at position 49, lysine at position 118, glutamine at position 140, threonine at position 161, or glutamic acid at position 223; and a vector for vRNA or mRNA expression of influenza virus M1 having at least 95% amino acid sequence identity to a M1 polypeptide encoded by SEQ ID NO:5 and having a serine at position 90.

The invention will be described by the following nonlimiting examples.

Example 1

Methods

Cells and Viruses 293T human embryonic kidney cells are maintained in Dulbecco's modified Eagle's minimal essential medium (DMEM) with 10% fetal calf serum and antibiotics. Madin-Darby canine kidney (MDCK) cells are grown in MEM with 5% newborn calf serum and antibiotics. African green monkey Vero WCB cells, which had been established after biosafety tests for use in human vaccine production (Sugawara et al., 2002), are maintained in serum-free VP-SFM medium (GIBCO-BRL) with antibiotics, Cells are maintained at 37° C. in 5% $CO_2$.

Construction of Plasmids and Reverse Genetics

To generate reassortants of influenza A viruses, a plasmid-based reverse genetics (Neumann et al., 1999) is used. The full-length cDNAs were cloned into a plasmid under control of the human polymerase I promoter and the mouse RNA polymerase I terminator (PolI plasmids).

A previously produced series of PolI constructs, derived from A/WSN/33 (H1N1; WSN) or PR8 strains is used, for reverse genetics (Horimoto et al., 2006; Neumann et al., 1999). The World Health Organization (WHO) recommends A/Puerto Rico/8/34 (H1N1; PR8) as a donor virus, because of its safety in humans (Wood & Robertson, 2004; Webby & Webster, 2003).

Plasmids expressing WSN or PR8 NP, PA, PB1, or PB2 under control of the chicken actin, e.g., beta-actin, promoter are used for all reverse genetics experiments (Horimoto et al., 2006; Neumann et al., 1999). Briefly, PolI plasmids and protein expression plasmids are mixed with a transfection reagent, Trans-IT 293T (Panvera), incubated at room temperature for 15 minutes, and then added to 293T cells. Transfected cells are incubated in Opti-MEM I (GIBCO-BRL) for 48 hours. For reverse genetics in Vero WCB cells, an electroporator (Amaxa) is used to transfect the plasmid mixtures according to the manufacturers instructions, Sixteen hours after transfection, freshly prepared Vero WCB cells were added onto the transfected cells and TPCK-trypsin (1 μg/mL) is added to the culture 6 hours later. Transfected cells are incubated in serum-free VP-SFM for a total of 4 days. Supernatants containing infectious viruses are harvested, and may be biologically cloned by limiting dilution.

A recombinant virus having the HA and NA genes from A/Hong Kong/213/2003 (H5N1) and the remainder of the type A influenza virus genes from PR8(UW) was prepared. The titer of the recombinant virus was $10^{10.67}$ $EID_{50}$/mL, and the HA titer was 1:1600

TABLE 1

| Virus possessing PR8 genes together with the following | HA titer (HAU/mL) in each dilition | | | | | | |
|---|---|---|---|---|---|---|---|
| HA and NA genes | 10-2 | 10-3 | 10-4 | 10-5 | 10-6 | 10-7 | 10-8 |
| WSN-HA NA | 160 | 40 | 40 | 320 | 40 | 640 | <1 |
| HK-HAavir NA | 400 | 800 | 400 | 400 | 400 | 800 | <1 |

The sequences of PR8 (UW) genes are as follows:

PA (SEQ ID NO: 1)

```
AGCGAAAGCA GGTACTGATC CAAAATGGAA GATTTTGTGC GACAATGCTT CAATCCGATG

ATTGTCGAGC TTGCGGAAAA AACAATGAAA GAGTATGGGG AGGACCTGAA AATCGAAACA

AACAAATTTG CAGCAATATG CACTCACTTG GAAGTATGCT TCATGTATTC AGATTTTCAC

TTCATCAATG AGCAAGGCGA GTCAATAATC GTAGAACTTG GTGATCCAAA TGCACTTTTG

AAGCACAGAT TTGAAATAAT CGAGGGAAGA GATCGCACAA TGGCCTGGAC AGTAGTAAAC

AGTATTTGCA ACACTACAGG GGCTGAGAAA CCAAAGTTTC TACCAGATTT GTATGATTAC

AAGGAGAATA GATTCATCGA AATTGGAGTA ACAAGGAGAG AAGTTCACAT ATACTATCTG

GAAAAGGCCA ATAAAATTAA ATCTGAGAAA ACACACATCC ACATTTTCTC GTTCACTGGG

GAAGAAATGG CCACAAAGGC AGACTACACT CTCGATGAAG AAAGCAGGGC TAGGATCAAA

ACCAGACTAT TCACCATAAG ACAAGAAATG GCCAGCAGAG GCCTCTGGGA TTCCTTTCGT

CAGTCCGAGA GAGGAGAAGA GACAATTGAA GAAAGGTTTG AAATCACAGG AACAATGCGC

AAGCTTGCCG ACCAAAGTCT CCCGCCGAAC TTCTCCAGCC TTGAAAATTT TAGAGCCTAT

GTGGATGGAT TCGAACCGAA CGGCTACATT GAGGGCAAGC TGTCTCAAAT GTCCAAAGAA

GTAAATGCTA GAATTGAACC TTTTTTGAAA ACAACACCAC GACCACTTAG ACTTCCGAAT

GGGCCTCCCT GTTCTCAGCG GTCCAAATTC CTGCTGATGG ATGCCTTAAA ATTAAGCATT

GAGGACCCAA GTCATGAAGG AGAGGGAATA CCGCTATATG ATGCAATCAA ATGCATGAGA
```

```
ACATTCTTTG GATGGAAGGA ACCCAATGTT GTTAAACCAC ACGAAAAGGG AATAAATCCA
AATTATCTTC TGTCATGGAA GCAAGTACTG GCAGAACTGC AGGACATTGA GAATGAGGAG
AAAATTCCAA AGACTAAAAA TATGAAGAAA ACAAGTCAGC TAAAGTGGGC ACTTGGTGAG
AACATGGCAC CAGAAAAGGT AGACTTTGAC GACTGTAAAG ATGTAGGTGA TTTGAAGCAA
TATGATAGTG ATGAACCAGA ATTGAGGTCG CTTGCAAGTT GGATTCAGAA TGAGTTTAAC
AAGGCATGCG AACTGACAGA TTCAAGCTGG ATAGAGCTCG ATGAGATTGG AGAAGATGTG
GCTCCAATTG AACACATTGC AAGCATGAGA AGGAATTATT TCACATCAGA GGTGTCTCAC
TGCAGAGCCA CAGAATACAT AATGAAGGGA GTGTACATCA ATACTGCCTT GCTTAATGCA
TCTTGTGCAG CAATGGATGA TTTCCAATTA ATTCCAATGA TAAGCAAGTG TAGAACTAAG
GAGGGAAGGC GAAAGACCAA CTTGTATGGT TTCATCATAA AAGGAAGATC CCACTTAAGG
AATGACACCG ACGTGGTAAA CTTTGTGAGC ATGGAGTTTT CTCTCACTGA CCCAAGACTT
GAACCACATA AATGGGAGAA GTACTGTGTT CTTGAGATAG GAGATATGCT TATAAGAAGT
GCCATAGGCC AGGTTTCAAG GCCCATGTTC TTGTATGTGA GAACAAATGG AACCTCAAAA
ATTAAAATGA AATGGGGAAT GGAGATGAGG CGTTGCCTCC TCCAGTCACT TCAACAAATT
GAGAGTATGA TTGAAGCTGA GTCCTCTGTC AAAGAGAAAG ACATGACCAA AGAGTTCTTT
GAGAACAAAT CAGAAACATG GCCCATTGGA GAGTCCCCCA AAGGAGTGGA GGAAAGTTCC
ATTGGGAAGG TCTGCAGGAC TTTATTAGCA AAGTCGGTAT TCAACAGCTT GTATGCATCT
CCACAACTAG AAGGATTTTC AGCTGAATCA AGAAAACTGC TTCTTATCGT TCAGGCTCTT
AGGGACAACC TGGAACCTGG GACCTTTGAT CTTGGGGGGC TATATGAAGC AATTGAGGAG
TGCCTGATTA ATGATCCCTG GGTTTTGCTT AATGCTTCTT GGTTCAACTC CTTCCTTACA
CATGCATTGA GTTAGTTGTG GCAGTGCTAC TATTTGCTAT CCATACTGTC CAAAAAAGTA
CCTTGTTTCT ACT
PB1
                                                        (SEQ ID NO: 2)
AGCGAAAGCAGGCAAACCATTTGAATGGATGTCAATCCGACCTTACTTTTCTTAAAAGTGCCAGCACAAA
ATGCTATAAGCACAACTTTCCCTTATACTGGAGACCCTCCTTACAGCCATGGGACAGGAACAGGATACAC
CATGGATACTGTCAACAGGACACATCAGTACTCAGAAAAGGGAAGATGGACAACAAACACCGAAACTGG
AGCACCGCAACTCAACCCGATTGATGGGCCACTGCCAGAAGACAATGAACCAAGTGGTTATGCCCAAAC
AGATTGTGTATTGGAGGCGATGGCTTTCCTTGAGGAATCCCATCCTGGTATTTTTGAAAACTCGTGTATT
GAAACGATGGAGGTTGTTCAGCAAACACGAGTAGACAAGCTGACACAAGGCCGACAGACCTATGACTGG
ACTCTAAATAGAAACCAACCTGCTGCAACAGCATTGGCCAACACAATAGAAGTGTTCAGATCAAATGGCC
TCACGGCCAATGAGTCTGGAAGGCTCATAGACTTCCTTAAGGATGTAATGGAGTCAATGAACAAAGAAGA
AATGGGGATCACAACTCATTTTCAGAGAAAGAGACGGGTGAGAGACAATATGACTAAGAAAATGATAACA
CAGAGAACAATGGGTAAAAAGAAGCAGAGATTGAACAAAAGGAGTTATCTAATTAGAGCATTGACCCTGA
ACACAATGACCAAAGATGCTGAGAGAGGGAAGCTAAAACGGAGAGCAATTGCAACCCCAGGGATGCAAA
TAAGGGGGTTTGTATACTTTGTTGAGACACTGGCAAGGAGTATATGTGAGAAACTTGAACAATCAGGGTT
GCCAGTTGGAGGCAATGAGAAGAAAGCAAAGTTGGCAAATGTTGTAAGGAAGATGATGACCAATTCTCA
GGACACCGAACTTTCTTTCACCATCACTGGAGATAACACCAAATGGAACGAAAATCAGAATCCTCGGATG
TTTTTGGCCATGATCACATATATGACCAGAAATCAGCCCGAATGGTTCAGAAATGTTCTAAGTATTGCTCC
AATAATGTTCTCAAACAAAATGGCGAGACTGGGAAAAGGGTATATGTTTGAGAGCAAGAGTATGAAACTT
AGAACTCAAATACCTGCAGAAATGCTAGCAAGCATCGATTTGAAATATTTCAATGATTCAACAAGAAAGAA
```

-continued

GATTGAAAAAATCCGACCGCTCTTAATAGAGGGGACTGCATCATTGAGCCCTGGAATGATGATGGGCAT

GTTCAATATGTTAAGCACTGTATTAGGCGTCTCCATCCTGAATCTTGGACAAAAGAGATACACCAAGACTA

CTTACTGGTGGGATGGTCTTCAATCCTCTGACGATTTTGCTCTGATTGTGAATGCACCCAATCATGAAGG

GATTCAAGCCGGAGTCGACAGGTTTTATCGAACCTGTAAGCTACTTGGAATCAATATGAGCAAGAAAAAG

TCTTACATAAACAGAACAGGTACATTTGAATTCACAAGTTTTTTCTATCGTTATGGGTTTGTTGCCAATTTC

AGCATGGAGCTTCCCAGTTTTGGGGTGTCTGGGATCAACGAGTCAGCGGACATGAGTATTGGAGTTACT

GTCATCAAAAACAATATGATAAACAATGATCTTGGTCCAGCAACAGCTCAAATGGCCCTTCAGTTGTTCAT

CAAAGATTACAGGTACACGTACCGATGCCATATAGGTGACACACAAATACAAACCCGAAGATCATTTGAA

ATAAAGAAACTGTGGGAGCAAACCCGTTCCAAAGCTGGACTGCTGGTCTCCGACGGAGGCCCAAATTTA

TACAACATTAGAAATCTCCACATTCCTGAAGTCTGCCTAAAATGGGAATTGATGGATGAGGATTACCAGG

GGCGTTTATGCAACCCACTGAACCCATTTGTCAGCCATAAAGAAATTGAATCAATGAACAATGCAGTGAT

GATGCCAGCACATGGTCCAGCCAAAAACATGGAGTATGATGCTGTTGCAACAACACACTCCTGGATCCC

CAAAAGAAATCGATCCATCTTGAATACAAGTCAAAGAGGAGTACTTGAGGATGAACAAATGTACCAAAGG

TGCTGCAATTTATTTGAAAAATTCTTCCCCAGCAGTTCATACAGAAGACCAGTCGGGATATCCAGTATGGT

GGAGGCTATGGTTTCCAGAGCCCGAATTGATGCACGGATTGATTTCGAATCTGGAAGGATAAAGAAAGA

AGAGTTCACTGAGATCATGAAGATCTGTTCCACCATTGAAGAGCTCAGACGGCAAAAATAGTGAATTTAG

CTTGTCCTTCATGAAAAAATGCCTTGTTTCTACT

PB2

(SEQ ID NO: 3)

AGCGAAAGCA GGTCAATTAT ATTCAATATG GAAAGAATAA AAGAACTACG AAATCTAATG

TCGCAGTCTC GCACCCGCGA GATACTCACA AAAACCACCG TGGACCATAT GGCCATAATC

AAGAAGTACA CATCAGGAAG ACAGGAGAAG AACCCAGCAC TTAGGATGAA ATGGATGATG

GCAATGAAAT ATCCAATTAC AGCAGACAAG AGGATAACGG AAATGATTCC TGAGAGAAAT

GAGCAAGGAC AAACTTTATG GAGTAAAATG AATGATGCCG GATCAGACCG AGTGATGGTA

TCACCTCTGG CTGTGACATG GTGGAATAGG AATGGACCAA TAACAAATAC AGTTCATTAT

CCAAAAATCT ACAAAACTTA TTTTGAAAGA GTCGAAAGGC TAAAGCATGG AACCTTTGGC

CCTGTCCATT TTAGAAACCA AGTCAAAATA CGTCGGAGAG TTGACATAAA TCCTGGTCAT

GCAGATCTCA GTGCCAAGGA GGCACAGGAT GTAATCATGG AAGTTGTTTT CCCTAACGAA

GTGGGAGCCA GGATACTAAC ATCGGAATCG CAACTAACGA TAACCAAAGA GAAGAAAGAA

GAACTCCAGG ATTGCAAAAT TTCTCCTTTG ATGGTTGCAT ACATGTTGGA GAGAGAACTG

GTCCGCAAAA CGAGATTCCT CCCAGTGGCT GGTGGAACAA GCAGTGTGTA CATTGAAGTG

TTGCATTTGA CTCAAGGAAC ATGCTGGGAA CAGATGTATA CTCCAGGAGG GGAAGTGAGG

AATGATGATG TTGATCAAAG CTTGATTATT GCTGCTAGGA ACATAGTGAG AAGAGCTGCA

GTATCAGCAG ATCCACTAGC ATCTTTATTG GAGATGTGCC ACAGCACACA GATTGGTGGA

ATTAGGATGG TAGACATCCT TAGGCAGAAC CCAACAGAAG AGCAAGCCGT GGATATATGC

AAGGCTGCAA TGGGACTGAG AATTAGCTCA TCCTTCAGTT TTGGTGGATT CACATTTAAG

AGAACAAGCG GATCATCAGT CAAGAGAGAG GAAGAGGTGC TTACGGGCAA TCTTCAAACA

TTGAAGATAA GAGTGCATGA GGGATATGAA GAGTTCACAA TGGTTGGGAG AAGAGCAACA

GCCATACTCA GAAAAGCAAC CAGGAGATTG ATTCAGCTGA TAGTGAGTGG GAGAGACGAA

CAGTCGATTG CCGAAGCAAT AATTGTGGCC ATGGTATTTT CACAAGAGGA TTGTATGATA

AAAGCAGTCA GAGGTGATCT GAATTTCGTC AATAGGGCGA ATCAACGATT GAATCCTATG

CATCAACTTT TAAGACATTT TCAGAAGGAT GCGAAAGTGC TTTTTCAAAA TTGGGGAGTT

-continued

```
GAACCTATCG ACAATGTGAT GGGAATGATT GGGATATTGC CCGACATGAC TCCAAGCATC
GAGATGTCAA TGAGAGGAGT GAGAATCAGC AAAATGGGTG TAGATGAGTA CTCCAGCACG
GAGAGGGTAG TGGTGAGCAT TGACCGTTTT TTGAGAATCC GGGACCAACG AGGAAATGTA
CTACTGTCTC CCGAGGAGGT CAGTGAAACA CAGGGAACAG AGAAACTGAC AATAACTTAC
TCATCGTCAA TGATGTGGGA GATTAATGGT CCTGAATCAG TGTTGGTCAA TACCTATCAA
TGGATCATCA GAAACTGGGA AACTGTTAAA ATTCAGTGGT CCCAGAACCC TACAATGCTA
TACAATAAAA TGGAATTTGA ACCATTTCAG TCTTTAGTAC CTAAGGCCAT TAGAGGCCAA
TACAGTGGGT TTGTAAGAAC TCTGTTCCAA CAAATGAGGG ATGTGCTTGG GACATTTGAT
ACCGCACAGA TAATAAAACT TCTTCCCTTC GCAGCCGCTC CACCAAAGCA AAGTAGAATG
CAGTTCTCCT CATTTACTGT GAATGTGAGG GGATCAGGAA TGAGAATACT TGTAAGGGGC
AATTCTCCTG TATTCAACTA TAACAAGGCC ACGAAGAGAC TCACAGTTCT CGGAAAGGAT
GCTGGCACTT TAACTGAAGA CCCAGATGAA GGCACAGCTG GAGTGGAGTC CGCTGTTCTG
AGGGGATTCC TCATTCTGGG CAAAGAAGAC AAGAGATATG GGCCAGCACT AAGCATCAAT
GAACTGAGCA ACCTTGCGAA AGGAGAGAAG GCTAATGTGC TAATTGGGCA AGGAGACGTG
GTGTTGGTAA TGAAACGGAA ACGGGACTCT AGCATACTTA CTGACAGCCA GACAGCGACC
AAAAGAATTC GGATGGCCAT CAATTAGTGT CGAATAGTTT AAAAACGACC TTGTTTCTAC T
```

NP

```
                                                         (SEQ ID NO: 4)
AGCAAAAGCA GGGTAGATAA TCACTCACTG AGTGACATCA AAATCATGGC GTCTCAAGGC
ACCAAACGAT CTTACGAACA GATGGAGACT GATGGAGAAC GCCAGAATGC CACTGAAATC
AGAGCATCCG TCGGAAAAAT GATTGGTGGA ATTGGACGAT TCTACATCCA AATGTGCACC
GAACTCAAAC TCAGTGATTA TGAGGGACGG TTGATCCAAA ACAGCTTAAC AATAGAGAGA
ATGGTGCTCT CTGCTTTTGA CGAAAGGAGA AATAAATACC TTGAAGAACA TCCCAGTGCG
GGGAAAGATC CTAAGAAAAC TGGAGGACCT ATATACAGGA GAGTAAACGG AAAGTGGATG
AGAGAACTCA TCCTTTATGA CAAAGAAGAA ATAAGGCGAA TCTGGCGCCA AGCTAATAAT
GGTGACGATG CAACGGCTGG TCTGACTCAC ATGATGATCT GGCATTCCAA TTTGAATGAT
GCAACTTATC AGAGGACAAG AGCTCTTGTT CGCACCGGAA TGGATCCCAG GATGTGCTCT
CTGATGCAAG GTTCAACTCT CCCTAGGAGG TCTGGAGCCG CAGGTGCTGC AGTCAAAGGA
GTTGGAACAA TGGTGATGGA ATTGGTCAGA ATGATCAAAC GTGGGATCAA TGATCGGAAC
TTCTGGAGGG GTGAGAATGG ACGAAAAACA AGAATTGCTT ATGAAAGAAT GTGCAACATT
CTCAAAGGGA AATTTCAAAC TGCTGCACAA AAAGCAATGA TGGATCAAGT GAGAGAGAGC
CGGAACCCAG GGAATGCTGA GTTCGAAGAT CTCACTTTTC TAGCACGGTC TGCACTCATA
TTGAGAGGGT CGGTTGCTCA CAAGTCCTGC CTGCCTGCCT GTGTGTATGG ACCTGCCGTA
GCCAGTGGGT ACGACTTTGA AAGGGAGGGA TACTCTCTAG TCGGAATAGA CCCTTTCAGA
CTGCTTCAAA ACAGCCAAGT GTACAGCCTA ATCAGACCAA ATGAGAATCC AGCACACAAG
AGTCAACTGG TGTGGATGGC ATGCCATTCT GCCGCATTTG AAGATCTAAG AGTATTAAGC
TTCATCAAAG GGACGAAGGT GCTCCCAAGA GGGAAGCTTT CCACTAGAGG AGTTCAAATT
GCTTCCAATG AAAATATGGA GACTATGGAA TCAAGTACAC TTGAACTGAG AAGCAGGTAC
TGGGCCATAA GGACCAGAAG TGGAGGAAAC ACCAATCAAC AGAGGGCATC TGCGGGCCAA
ATCAGCATAC AACCTACGTT CTCAGTACAG AGAAATCTCC CTTTTGACAG AACAACCATT
ATGGCAGCAT TCAATGGGAA TACAGAGGGG AGAACATCTG ACATGAGGAC CGAAATCATA
```

-continued

AGGATGATGG AAAGTGCAAG ACCAGAAGAT GTGTCTTTCC AGGGGCGGGG AGTCTTCGAG

CTCTCGGACG AAAAGGCAGC GAGCCCGATC GTGCCTTCCT TTGACATGAG TAATGAAGGA

TCTTATTTCT TCGGAGACAA TGCAGAGGAG TACGACAATT AAAGAAAAAT ACCCTTGTTT CTACT

M (SEQ ID NO: 5)

AGCAAAAGCA GGTAGATATT GAAAGATGAG TCTTCTAACC GAGGTCGAAA CGTACGTACT

CTCTATCATC CCGTCAGGCC CCCTCAAAGC CGAGATCGCA CAGAGACTTG AAGATGTCTT

TGCAGGGAAG AACACCGATC TTGAGGTTCT CATGGAATGG CTAAAGACAA GACCAATCCT

GTCACCTCTG ACTAAGGGGA TTTTAGGATT TGTGTTCACG CTCACCGTGC CCAGTGAGCG

AGGACTGCAG CGTAGACGCT TTGTCCAAAA TGCCCTTAAT GGGAACGGGG ATCCAAATAA

CATGGACAAA GCAGTTAAAC TGTATAGGAA GCTCAAGAGG GAGATAACAT TCCATGGGGC

CAAAGAAATC TCACTCAGTT ATTCTGCTGG TGCACTTGCC AGTTGTATGG GCCTCATATA

CAACAGGATG GGGGCTGTGA CCACTGAAGT GGCATTTGGC CTGGTATGTG CAACCTGTGA

ACAGATTGCT GACTCCCAGC ATCGGTCTCA TAGGCAAATG GTGACAACAA CCAATCCACT

AATCAGACAT GAGAACAGAA TGGTTTTAGC CAGCACTACA GCTAAGGCTA TGGAGCAAAT

GGCTGGATCG AGTGAGCAAG CAGCAGAGGC CATGGAGGTT GCTAGTCAGG CTAGACAAAT

GGTGCAAGCG ATGAGAACCA TTGGGACTCA TCCTAGCTCC AGTGCTGGTC TGAAAAATGA

TCTTCTTGAA AATTTGCAGG CCTATCAGAA ACGAATGGGG GTGCAGATGC AACGGTTCAA

GTGATCCTCT CACTATTGCC GCAAATATCA TTGGGATCTT GCACTTGACA TTGTGGATTC

TTGATCGTCT TTTTTTCAAA TGCATTTACC GTCGCTTTAA ATACGGACTG AAAGGAGGGC

CTTCTACGGA AGGAGTGCCA AAGTCTATGA GGGAAGAATA TCGAAAGGAA CAGCAGAGTG

CTGTGGATGC TGACGATGGT CATTTTGTCA GCATAGAGCT GGAGTAAAAA ACTACCTTGT TTCTACT

NS (SEQ ID NO: 6)

AGCAAAAGCA GGGTGACAAA AACATAATGG ATCCAAACAC TGTGTCAAGC TTTCAGGTAG

ATTGCTTTCT TTGGCATGTC CGCAAACGAG TTGCAGACCA AGAACTAGGC GATGCCCCAT

TCCTTGATCG GCTTCGCCGA GATCAGAAAT CCCTAAGAGG AAGGGGCAGT ACTCTCGGTC

TGGACATCAA GACAGCCACA CGTGCTGGAA AGCAGATAGT GGAGCGGATT CTGAAAGAAG

AATCCGATGA GGCACTTAAA ATGACCATGG CCTCTGTACC TGCGTCGCGT TACCTAACTG

ACATGACTCT TGAGGAAATG TCAAGGGACT GGTCCATGCT CATACCCAAG CAGAAAGTGG

CAGGCCCTCT TTGTATCAGA ATGGACCAGG CGATCATGGA TAAGAACATC ATACTGAAAG

CGAACTTCAG TGTGATTTTT GACCGGCTGG AGACTCTAAT ATTGCTAAGG GCTTTCACCG

AAGAGGGAGC AATTGTTGGC GAAATTTCAC CATTGCCTTC TCTTCCAGGA CATACTGCTG

AGGATGTCAA AAATGCAGTT GGAGTCCTCA TCGGAGGACT TGAATGGAAT GATAACACAG

TTCGAGTCTC TGAAACTCTA CAGAGATTCG CTTGGAGAAG CAGTAATGAG AATGGGAGAC

CTCCACTCAC TCCAAAACAG AAACGAGAAA TGGCGGGAAC AATTAGGTCA GAAGTTTGAA

GAAATAAGAT GGTTGATTGA AGAAGTGAGA CACAAACTGA AGATAACAGA GAATAGTTTT

GAGCAAATAA CATTTATGCA AGCCTTACAT CTATTGCTTG AAGTGGAGCA AGAGATAAGA

ACTTTCTCGT TTCAGCTTAT TTAGTACTAA AAAACACCCT TGTTTCTACT

HA (SEQ ID NO: 7)

AGCAAAAGCAGGGGAAAATAAAAACAACCAAAATGAAGGCAAACCTACTGGTCCTGTTATGTGCACTTGC

AGCTGCAGATGCAGACACAATATGTATAGGCTACCATGCGAACAATTCAACCGACACTGTTGACACAGTA

CTCGAGAAGAATGTGACAGTGACACACTCTGTTAACCTGCTCGAAGACAGCCACAACGGAAAACTATGTA

-continued

GATTAAAAGGAATAGCCCCACTACAATTGGGGAAATGTAACATCGCCGGATGGCTCTTGGGAAACCCAG

AATGCGACCCACTGCTTCCAGTGAGATCATGGTCCTACATTGTAGAAACACCAAACTCTGAGAATGGAAT

ATGTTATCCAGGAGATTTCATCGACTATGAGGAGCTGAGGGAGCAATTGAGCTCAGTGTCATCATTCGAA

AGATTCGAAATATTTCCCAAAGAAAGCTCATGGCCCAACCACAACACAAACGGAGTAACGGCAGCATGCT

CCCATGAGGGGAAAAGCAGTTTTTACAGAAATTTGCTATGGCTGACGGAGAAGGAGGGCTCATACCCAA

AGCTGAAAAATTCTTATGTGAACAAAAAAGGGAAAGAAGTCCTTGTACTGTGGGGTATTCATCACCCGCC

TAACAGTAAGGAACAACAGAATCTCTATCAGAATGAAAATGCTTATGTCTCTGTAGTGACTTCAAATTATA

ACAGGAGATTTACCCCGGAAATAGCAGAAAGACCCAAAGTAAGAGATCAAGCTGGGAGGATGAACTATT

ACTGGACCTTGCTAAAACCCGGAGACACAATAATATTTGAGGCAAATGGAAATCTAATAGCACCAATGTA

TGCTTTCGCACTGAGTAGAGGCTTTGGGTCCGGCATCATCACCTCAAACGCATCAATGCATGAGTGTAAC

ACGAAGTGTCAAACACCCCTGGGAGCTATAAACAGCAGTCTCCCTTACCAGAATATACACCCAGTCACAA

TAGGAGAGTGCCCAAAATACGTCAGGAGTGCCAAATTGAGGATGGTTACAGGACTAAGGAACATTCCGT

CCATTCAATCCAGAGGTCTATTTGGAGCCATTGCCGGTTTTATTGAAGGGGGATGGACTGGAATGATAGA

TGGATGGTATGGTTATCATCATCAGAATGAACAGGGATCAGGCTATGCAGCGGATCAAAAAAGCACACAA

AATGCCATTAACGGGATTACAAACAAGGTGAACACTGTTATCGAGAAAATGAACATTCAATTCACAGCTGT

GGGTAAAGAATTCAACAAATTAGAAAAAAGGATGGAAAATTTAAATAAAAAAGTTGATGATGGATTTCTGG

ACATTTGGACATATAATGCAGAATTGTTAGTTCTACTGGAAAATGAAAGGACTCTGGATTTCCATGACTCA

AATGTGAAGAATCTGTATGAGAAAGTAAAAAGCCAATTAAAGAATAATGCCAAAGAAATCGGAAATGGAT

GTTTTGAGTTCTACCACAAGTGTGACAATGAATGCATGGAAAGTGTAAGAAATGGGACTTATGATTATCC

CAAATATTCAGAAGAGTCAAAGTTGAACAGGGAAAAGGTAGATGGAGTGAAATTGGAATCAATGGGGATC

TATCAGATTCTGGCGATCTACTCAACTGTCGCCAGTTCACTGGTGCTTTTGGTCTCCCTGGGGGCAATCA

GTTTCTGGATGTGTTCTAATGGATCTTTGCAGTGCAGAATATGCATCTGAGATTAGAATTTCAGAGATATG

AGGAAAAACACCCTTGTTTCTACT

NA (SEQ ID NO: 8)

AGCAAAAGCAGGGGTTTAAAATGAATCCAAATCAGAAAATAATAACCATTGGATCAATCTGTCTGGTAGTC

GGACTAATTAGCCTAATATTGCAAATAGGGAATATAATCTCAATATGGATTAGCCATTCAATTCAAACTGG

AAGTCAAAACCATACTGGAATATGCAACCAAAACATCATTACCTATAAAAATAGCACCTGGGTAAAGGACA

CAACTTCAGTGATATTAACCGGCAATTCATCTCTTTGTCCCATCCGTGGGTGGGCTATATACAGCAAAGA

CAATAGCATAAGAATTGGTTCCAAAGGAGACGTTTTTGTCATAAGAGAGCCCTTTATTTCATGTTCTCACT

TGGAATGCAGGACCTTTTTTCTGACCCAAGGTGCCTTACTGAATGACAAGCATTCAAGTGGGACTGTTAA

GGACAGAAGCCCTTATAGGGCCTTAATGAGCTGCCCTGTCGGTGAAGCTCCGTCCCCGTACAATTCAAG

ATTTGAATCGGTTGCTTGGTCAGCAAGTGCATGTCATGATGGCATGGGCTGGCTAACAATCGGAATTTCA

GGTCCAGATAATGGAGCAGTGGCTGTATTAAAATACAACGGCATAATAACTGAAACCATAAAAAGTTGGA

GGAAGAAAATATTGAGGACACAAGAGTCTGAATGTGCCTGTGTAAATGGTTCATGTTTTACTATAATGACT

GATGGCCCGAGTGATGGGCTGGCCTCGTACAAAATTTTCAAGATCGAAAAGGGGAAGGTTACTAAATCA

ATAGAGTTGAATGCACCTAATTCTCACTATGAGGAATGTTCCTGTTACCCTGATACCGGCAAAGTGATGT

GTGTGTGCAGAGACAATTGGCATGGTTCGAACCGGCCATGGGTGTCTTTCGATCAAAACCTGGATTATC

AAATAGGATACATCTGCAGTGGGGTTTTCGGTGACAACCCGCGTCCCGAAGATGGAACAGGCAGCTGTG

GTCCAGTGTATGTTGATGGAGCAAACGGAGTAAAGGGATTTTCATATAGGTATGGTAATGGTGTTTGGAT

AGGAAGGACCAAAAGTCACAGTTCCAGACATGGGTTTGAGATGATTTGGGATCCTAATGGATGGACAGA

-continued

GACTGATAGTAAGTTCTCTGTGAGGCAAGATGTTGTGGCAATGACTGATTGGTCAGGGTATAGCGGAAG

TTTCGTTCAACATCCTGAGCTGACAGGGCTAGACTGTATGAGGCCGTGCTTCTGGGTTGAATTAATCAGG

GGACGACCTAAAGAAAAAACAATCTGGACTAGTGCGAGCAGCATTTCTTTTTGTGGCGTGAATAGTGATA

CTGTAGATTGGTCTTGGCCAGACGGTGCTGAGTTGCCATTCAGCATTGACAAGTAGTCTGTTCAAAAAAC

TCCTTGTTTCTACT

High-titer A/PR/8/34 (H1N1, PR8(UW)) virus grows 10 times better than other A/PR/8/34 PR8 strains in eggs ($10^{10}$ $EID_{50}$/mL; HA titer:1:8,000). Thus, replacement of the HA and NA genes of PR8(UW) with those of a currently circulating strain of influenza virus results in a vaccine strain that can be safely produced, and validates the use of PR8 (UW) as a master vaccine strain.

Figures 1, 24A:
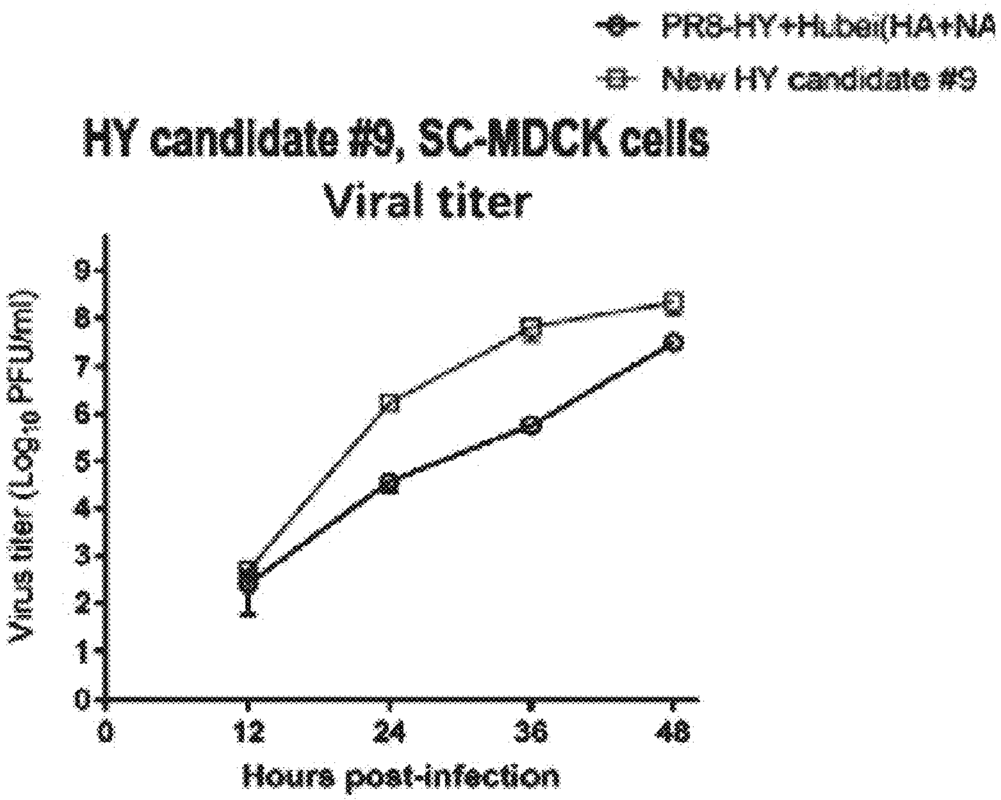
Figures 2, 24A:
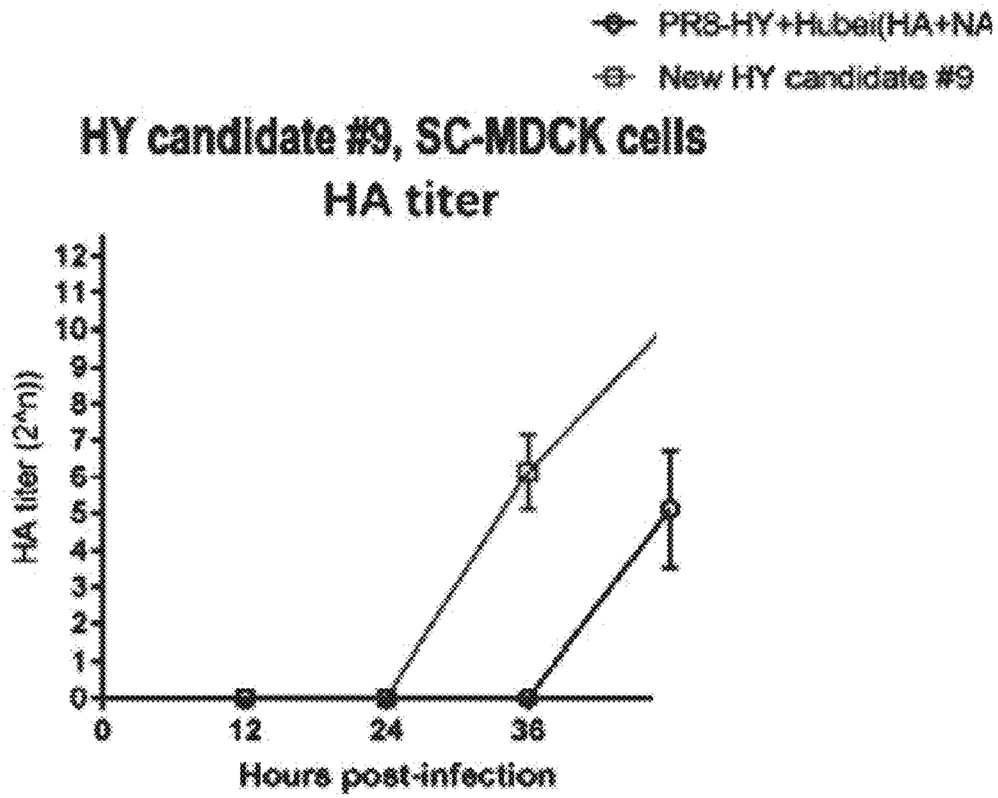
Figures 1, 24B:
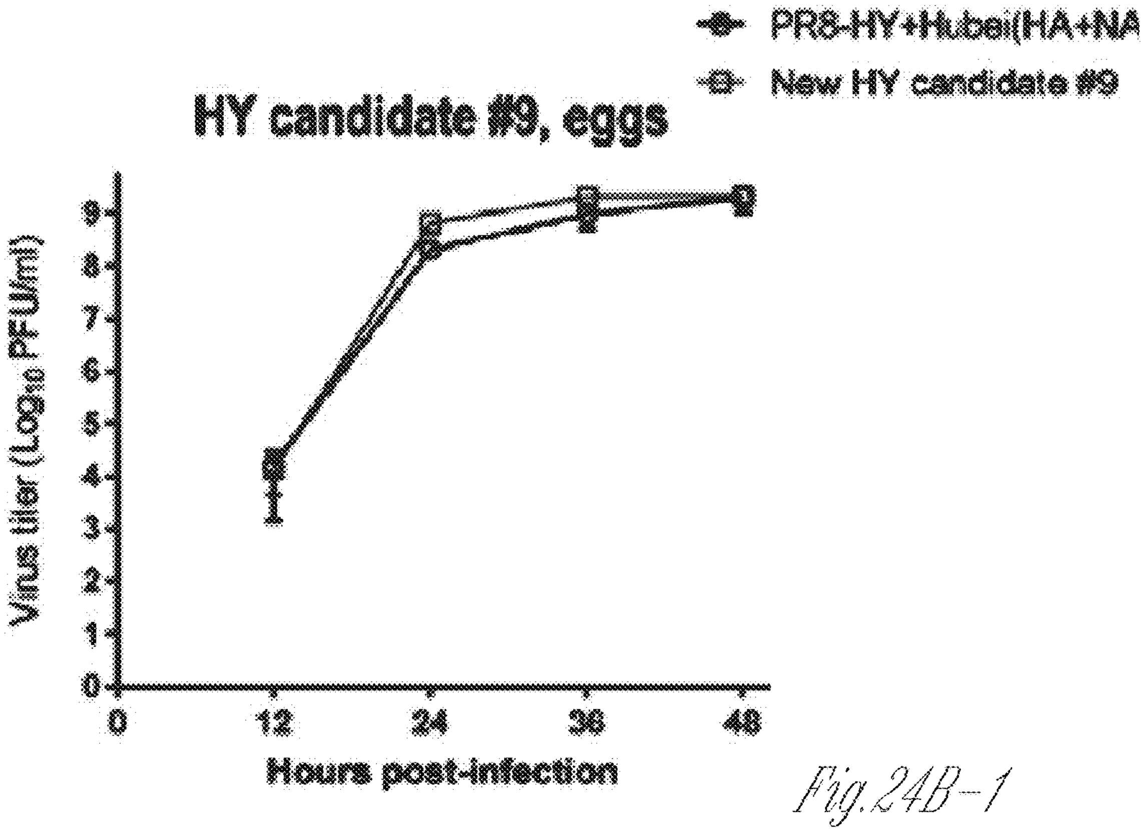
Figures 2, 24B:
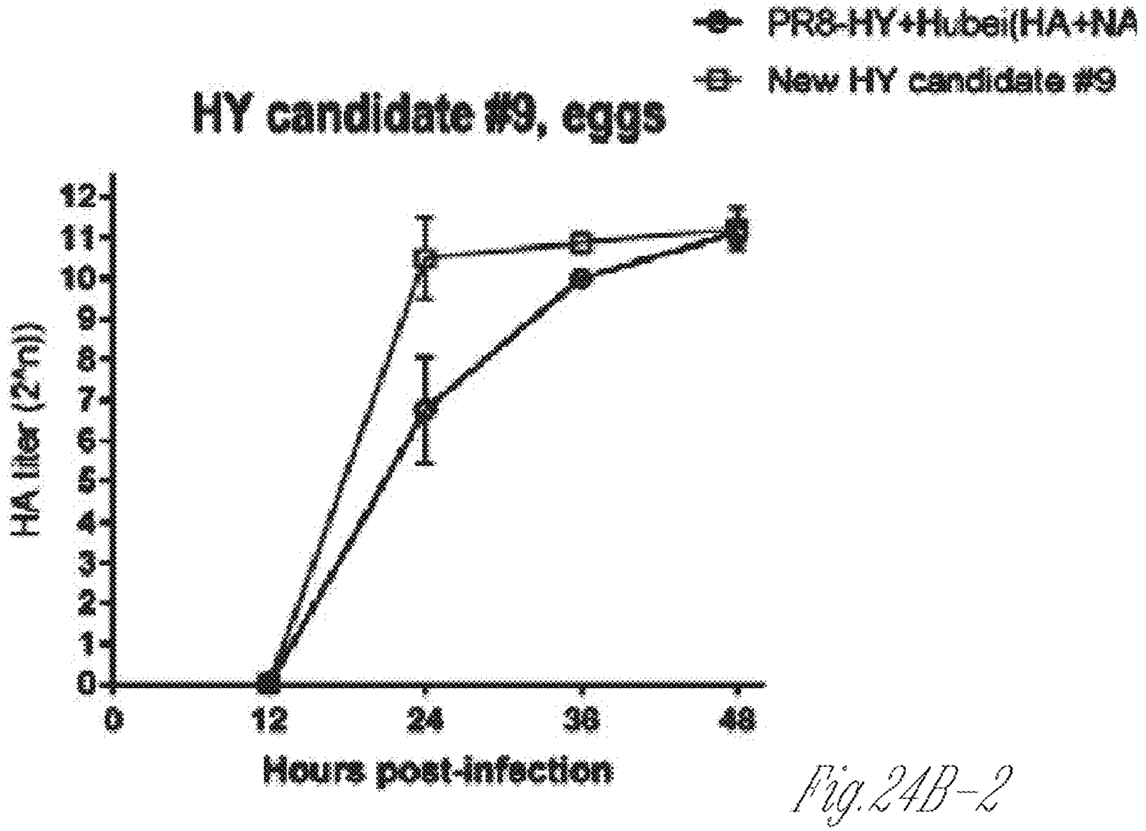
Figures 1, 25A:
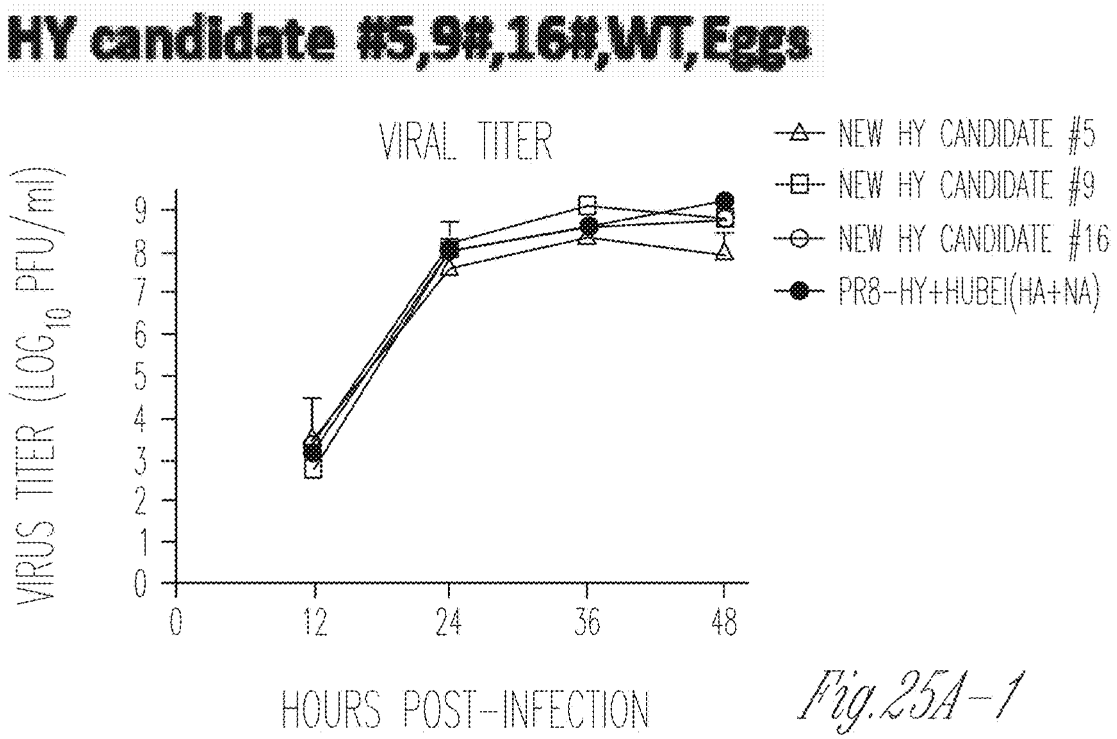
Figures 2, 25A:
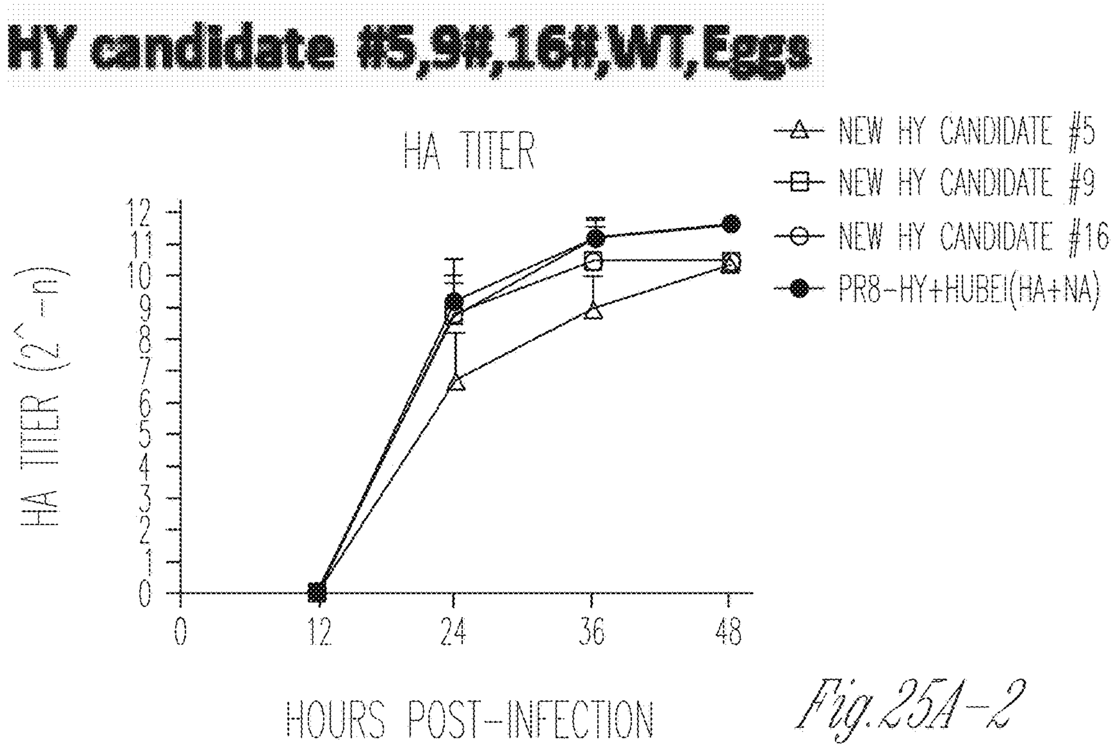
Figures 1, 25B:
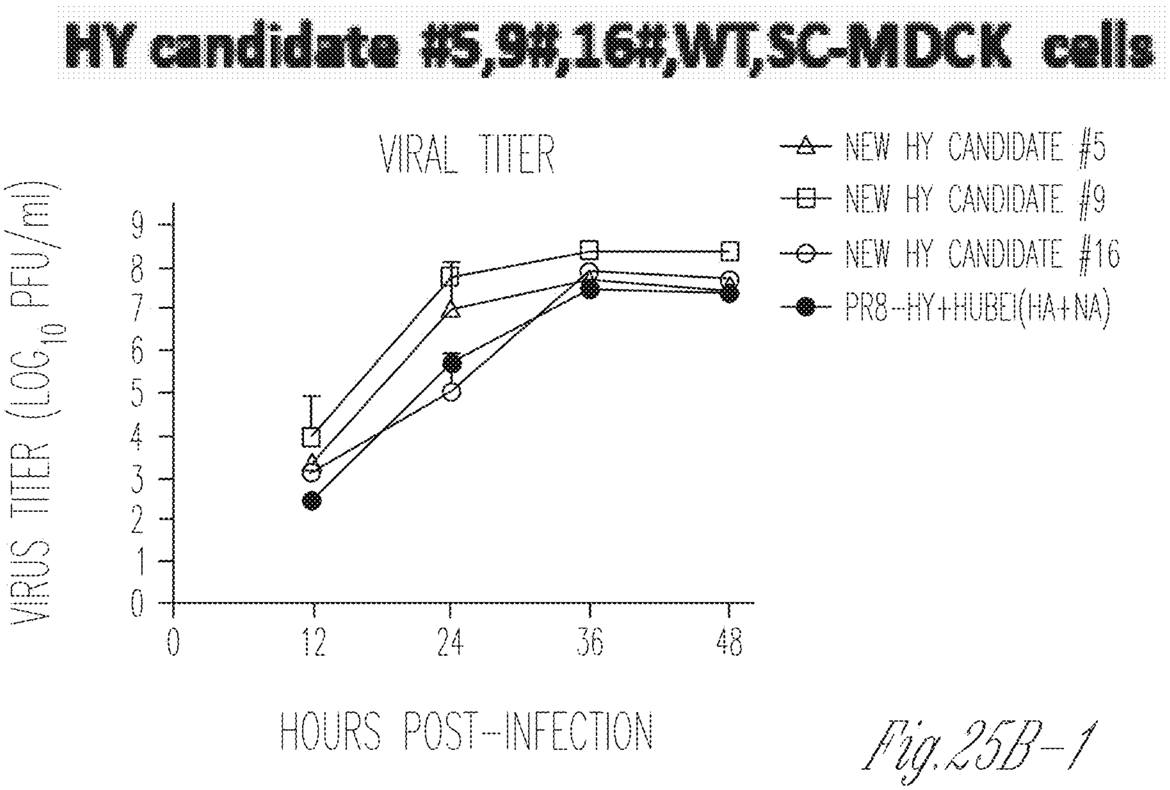
Figures 2, 25B:
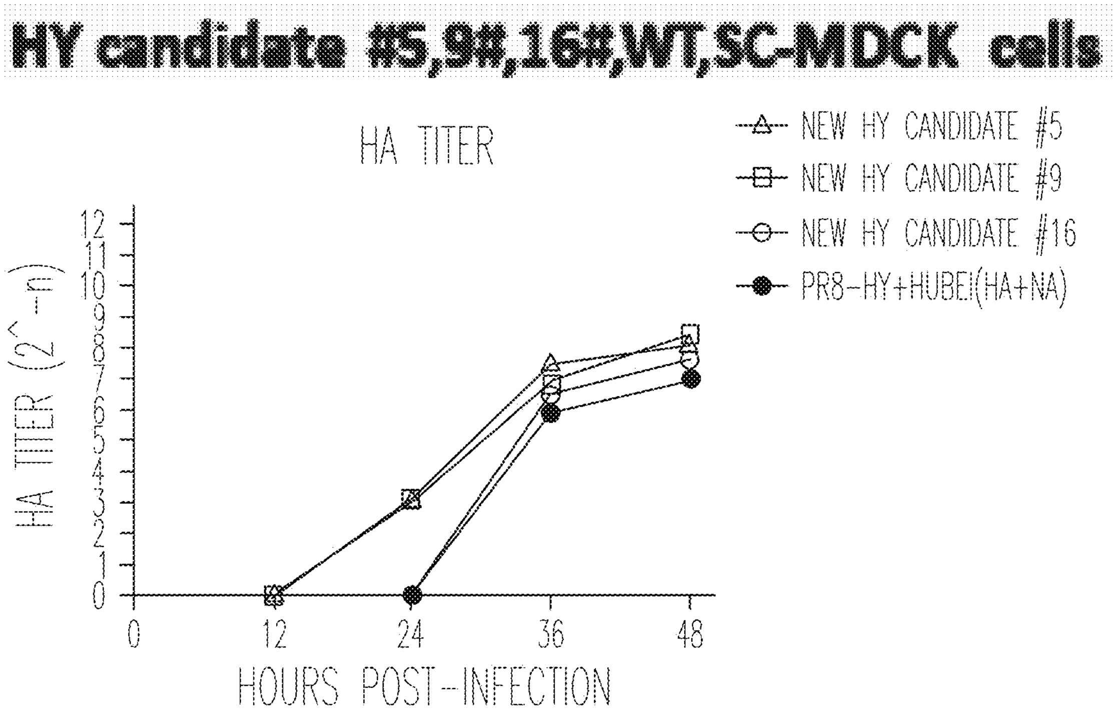
Figures 1, 25C:
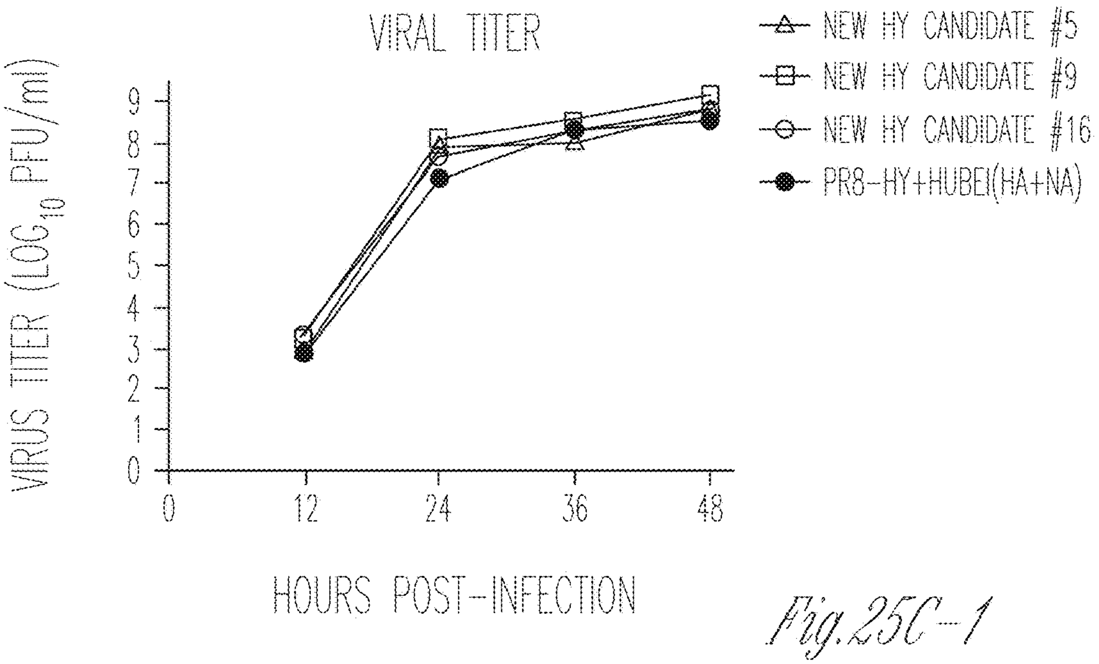
Figures 2, 25C:
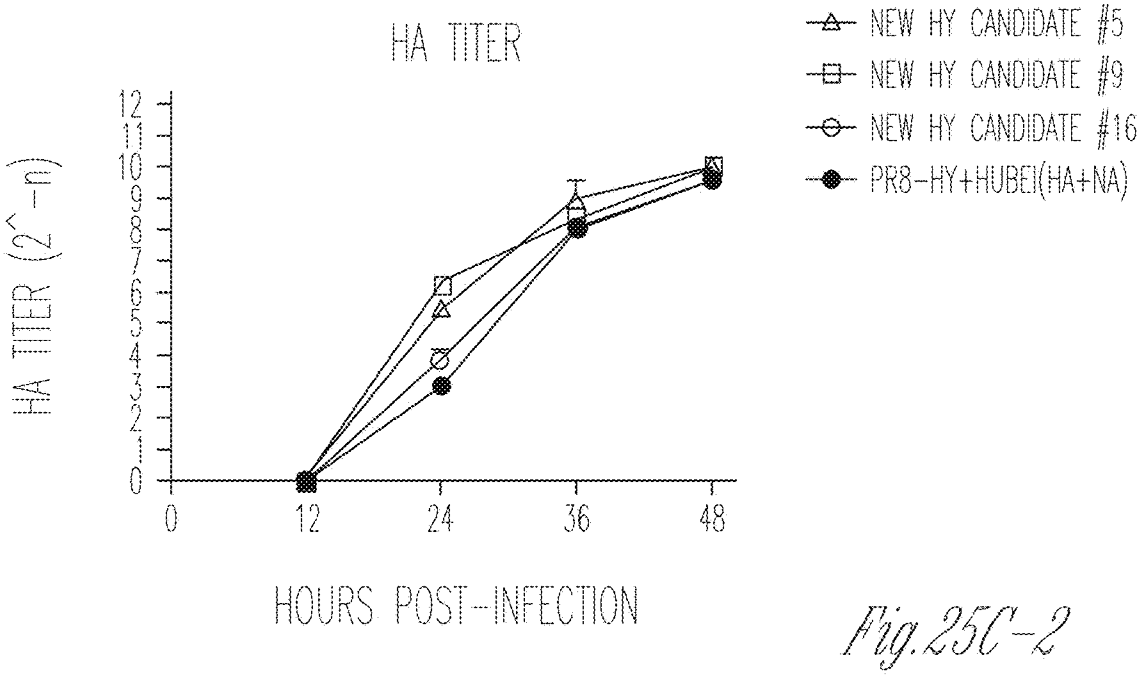

Genes that contribute to different growth properties between PR8(UW) and PR8 (Cambridge), which provides the non-HA and -NA genes of the NIBRG-14 vaccine strain (FIG. 1), were determined. Higher titers in eggs were obtained when the majority of internal genes were from PR8(UW). Highest titers were with the M viral segment of PR8(UW) and the NS gene of PR8 (Cambridge). The NS gene in PR8(UW) has a K (lysine) at residue 55 while the NS gene in PR8(Cam) has a E (glutamic acid), The polymerase subunit (PA, PB1, and PB2) and NP genes of PR8(UW) enhanced the growth of an H5N1 vaccine seed virus in chicken embryonated eggs, and the NS gene of PR8(Cambridge) enhanced the growth of an HSN1 vaccine seed virus in chicken embryonated eggs. A tyrosine (Y) at position 360 in PB2 of PR8(UW) likely contributes to the high growth rate of that virus in MDCK cells.

Example 2

To develop an high-yield A/PR/8/34 (H1N1; PR8) virus backbone for growth of vaccine virus in specific host cells, random mutagenesis of the internal genes of PR8(HG) (PR8UW) was conducted. Random mutations were introduced into the UW-PR8 (Example 1) internal genes by error-prone PCR, after which plasmid libraries were prepared that possessed the random mutations in an individual UW-PR8 internal gene. Then virus libraries (PR8/H5N1) were generated that possessed random mutations in an individual UW-PR8 internal gene, along with the other wild type internal genes and the NA and 'detoxified' HA genes of A/chicken/Indonesia/NC/09 (H5N1) virus (Table 1), to generate "6+2" recombinant viruses. Consecutive passages of the virus in MDCK cells were employed to select for variants with high-growth properties.

TABLE 1

Virus libraries generated

| Number | Gene library (Internal genes) | Other internal genes (Internal genes) | HA + NA | Titer of virus library (pfu/ml) |
|---|---|---|---|---|
| Control | | PR8 wild type | NC/09/H5N1 | $3 \times 10^6$ |
| 1 | PB2 | 5 UW-PR8 genes | NC/09/H5N1 | $2.1 \times 10^2$ |
| 2 | PB1 | 5 UW-PR8 genes | NC/09/H5N1 | $1.6 \times 10^5$ |
| 3 | PA | 5 UW-PR8 genes | NC/09/H5N1 | $7 \times 10^3$ |
| 4 | NP | 5 UW-PR8 genes | NC/09/H5N1 | $1.5 \times 10^3$ |
| 5 | M | 5 UW-PR8 genes | NC/09/H5N1 | $1 \times 10^6$ |
| 6 | NS | 5 UW-PR8 genes | NC/09/H5N1 | $1.8 \times 10^6$ |
| 7 | PB2 + PB1 + PA | 3UW-PR8 genes | NC/09/H5N1 | 75 |
| 8 | PB2 + PB1 + PA + NP | 2UW-PR8 genes | NC/09/H5N1 | 33 |
| 9 | PB2 + NS | 4UW-PR8 genes | NC/09/H5N1 | $2 \times 10^2$ |
| 10 | M + NS | 4UW-PR8 genes | NC/09/H5N1 | $5.7 \times 10^5$ |

Virus libraries were passaged 12 times in MDCK cells or, after 2 passages, the libraries were mixed and 10 more passages were carried out (FIG. 2).

After 10 to about 12 consecutive passages in MDCK cells, plaque assays were performed and over 1,400 individual plaques were picked. FIG. 3 shows the numbers of clones with various HA titers. Growth-enhancing mutations included: PB2: M202L; F323L, I504V, PB1: E112G, V644A, NP: R74K; N417D, I116L, and NS1: S161T. FIG. 4 provides the titers of recombinant viruses generated from selected mutations.

36 viruses with the highest HA titers from the random mutagenesis libraries were sequenced (Table 2)

TABLE 2

Sequences of viruses with the highest HA titers

| Clone # | Library | HA titer ($2^n$) | PB2 | PB1 | PA | HA (H3 numbering) | NP | NA | M | NS |
|---|---|---|---|---|---|---|---|---|---|---|
| WT | | 7 | | | | | | | | |
| 329 | Mix | 9 | M202L F323L | | | L182V | | | | |
| 154 | Mix | 8.5~9 | M202L F323L | | | L182V | | | | |
| 347 | Mix | 9 | M202L F323L | | | L182V | | | | |
| 94 | Mix | 8.5 | M202L F323L | | | F252I | I116L | L55S | | |

TABLE 2-continued

Sequences of viruses with the highest HA titers

| Clone # | Library | HA titer $(2^n)$ | PB2 | PB1 | PA | HA (H3 numbering) | NP | NA | M | NS |
|---|---|---|---|---|---|---|---|---|---|---|
| 1045 | Mix | 9 | M202L<br>F323L | V644A | | F252I | | | | |
| 965 | Mix | 8.5~9 | M202L<br>F323L | | F105C | V184I | | | P90S | |
| 50 | Mix | 8.5 | M202L<br>F323L | | | M148I<br>(HA2) | R293M | | | |
| 1005 | Mix | 9~9.5 | M202L<br>F323L | V644A | R401K | M148I<br>(HA2) | | | | T49A |
| 134 | Mix | 8.5 | M202L<br>F323L | | | | | | | A223E |
| 387 | Mix | 9 | M202L<br>F323L | M507V<br>V644A | | | | | | |
| 852 | Mix | 9~9.5 | M202L<br>F323L<br>M243I | R54I | | | | | | |
| 981 | Mix | 8.5~9 | M202L<br>F323L | Q247H | | | | | | |
| 993 | Mix | 8.5~9 | M202L<br>F323L | | | | N224I | | | |
| 1043 | Mix | 8.5~9 | I504V | | | L182V | R74K | | | |
| 398 | Mix | 8.5 | I504V | | | L182V | R74K,<br>N417D | | | A30P |
| 1007 | Mix | 8.5 | I504V | V644A | | F252I | M371V | | | |
| 1042 | Mix | 8.5~9 | I504V | E75V<br>D76G<br>E78P<br>P79V<br>S80G<br>V644A<br>E697P<br>F699L<br>F700L<br>P701H<br>S702R<br>Y705T | | F252I | R74K | | | |
| 999 | Mix | 8.5~9 | I504V | | | M148I<br>(HA2) | R74K,<br>N417D | | | |
| 1014 | Mix | 8.5 | I504V | T59I<br>G62X<br>A63P<br>V644A<br>N694K<br>L695T | | M148I<br>(HA2) | R74K,<br>N417D | A265V | | |
| 1016 | Mix | 8.5~9 | I504V | | | M148I<br>(HA2) | | | | |
| 540 | PB1 | 8.5 | | E112G<br>(PB1-F2-<br>R81G) | | K162E | | | | S161T |
| 548 | PB1 | 8.5~9 | | E112G<br>(PB1-F2-<br>R81G)<br>L624V | | K162E | | | | S161T |
| 191 | PB1 | 8~8.5 | | E112G<br>(PB1-F2-<br>R81G) | | | | | | |
| 571 | PB1 | 9~9.5 | | E112G<br>(PB1-F2-<br>R81G) | | | | | | |
| 572 | PB1 | 8.5 | | E112G<br>(PB1-F2-<br>R81G) | | | | | | |
| 573 | PB1 | 8.5 | | E112G<br>(PB1-F2-<br>R81G) | | | | | | |
| 1404 | PB1 | 8.5 | I57V<br>T58G<br>A59V<br>K61Q<br>E677D<br>D678E<br>P679M | E112G<br>(PB1-F2-<br>R81G)<br>S713C | | | | | | |
| 1408 | PB1 | 8.5 | | M40I<br>G180W | | | | | | S161T |

TABLE 2-continued

Sequences of viruses with the highest HA titers

| Clone # | Library | HA titer ($2^n$) | PB2 | PB1 | PA | HA (H3 numbering) | NP | NA | M | NS |
|---|---|---|---|---|---|---|---|---|---|---|
| 582 | PB1 | 8.5~9 | | M40L, G180W | | | | | | S161T |
| 545 | PB1 | 8.5 | | M40L, G180W | | K121E (HA2) | | | | |
| 543 | PB1 | 8.5 | | I667T | | | | | | |
| 219 | PB1 | 9 | | I667T, M714T | | K162E | | | | |
| 344 | Mix | 8.5~9 | M66R | | | L182V | | | | |
| 312 | Mix | 8.5~9 | | | | L182V | I116L | | | R140Q |
| 320 | Mix | 8.5 | | | | L182V | | | | |
| 209 | PB1 | 8.5~9 | | R54I | | E136D, Q179L, A194V | | | | |

In a second approach, potentially growth-enhancing mutations described in the literature were introduced into the background of UW-PRS virus (see Table 3 for virus stock titers) and tested for replicative ability. FIGS. 5A-D show growth curves for various viruses.

TABLE 3

UW-PR8 viruses possessing mutation(s) identified in the literature

| Gene | Mutation(s) | Virus stock titer (Pfu/ml) |
|---|---|---|
| WT | — | $2 \times 10^7$ |
| PB2 | A44S | $4.5 \times 10^7$ |
| | E158G | $3.2 \times 10^4$ |
| | E158G + NP N101G | $7.5 \times 10^4$ |
| | E158A | $8.3 \times 0^6$ |
| | D253N + Q591K | $8.3 \times 10^6$ |
| | D256G | $2.8 \times 10^7$ |
| | R368K | $3.1 \times 10^7$ |
| | E391Q | $1.4 \times 10^8$ |
| | I504V + PA I550L | $1.1 \times 10^8$ |
| | Q591K | $4.4 \times 10^7$ |
| | V613T | $1.8 \times 10^7$ |
| | A661T | $2.2 \times 10^7$ |
| | D701N + S714R + NP N319K | $1 \times 10^6$ |
| | D701N | $2.1 \times 10^7$ |
| PB1 | R327K | $1.3 \times 10^7$ |
| | V336I | $2.3 \times 10^7$ |
| | L473V + L598P | $3.9 \times 10^6$ |

TABLE 3-continued

UW-PR8 viruses possessing mutation(s) identified in the literature

| Gene | Mutation(s) | Virus stock titer (Pfu/ml) |
|---|---|---|
| PB1F2 | F2 N66S | $1.6 \times 10^8$ |
| | F2 K73R | $1.1 \times 10^8$ |
| | F2 V76A | $4.4 \times 10^7$ |
| | F2 R79Q | $6.2 \times 10^6$ |
| | F2 L82S | $2.7 \times 10^7$ |
| | F2 E87Q | $1.5 \times 10^6$ |
| PA | T97I | $1.6 \times 10^7$ |
| | K142N | $3.3 \times 10^7$ |
| | S225C | $6.7 \times 10^7$ |
| | S149P + T357K | $3.4 \times 10^8$ |
| | K356R | $8.5 \times 10^7$ |
| | A404S | $5.2 \times 10^7$ |
| | S421I | $2.7 \times 10^7$ |
| WT | — | $2 \times 10^7$ |
| NP | R293K | $4.7 \times 10^7$ |
| | R305K | $7.2 \times 10^7$ |
| | E372D | $2.2 \times 10^7$ |
| | R422K | $1.3 \times 10^8$ |
| | T442A | $5 \times 10^7$ |
| | D455E | $2.2 \times 10^7$ |
| | I109V | $3.9 \times 10^7$ |
| M | V97A + Y100H | $1.4 \times 10^7$ |
| NS1 | K55E | $1.6 \times 10^7$ |

In a third approach, candidates from approaches 1 and 2 were combined and HA titers and PFU/mL determined (Table 4).

TABLE 4

High-growth candidates identified in approaches 1 and 2 were tested in various combinations.

| | Gene origin | | | | | | | | Virus stock titer | |
|---|---|---|---|---|---|---|---|---|---|---|
| # | HA | NA | PB2 | PB1 | PA | NP | M | NS | HA ($2^n$) | Pfu/ml |
| WT | Indo/NC/09 (detoxified) | Indo/NC/09 | UW-PR8 | UW-PR8 | UW-PR8 | UW-PR8 | UW-PR8 | UW-PR8 | 7 | 3.00E+07 |
| 1 | | | M202L F323L | M507V V644A | | I116L | | K55E | 9~9.5 | 2.00E+08 |
| 2 | | | M202L F323L | R54I | | N224I | | K55E | 5 | 1.00E+05 |
| 3 | | | M202L F323L | Q247H | R401K | | | T49A | 9 | 1.00E+08 |
| 4 | | | M202L F323L | M507V V644A | K356R | T442A | V97A Y100H | K55E | 10~10.5 | 1.60E+08 |
| 5 | | | I504V | M507V V644A | I550L | R74K N417D | | K55E | 8~8.5 | 5.70E+07 |

TABLE 4-continued

High-growth candidates identified in approaches 1 and 2 were tested in various combinations.

| | Gene origin | | | | | | | | Virus stock titer | |
|---|---|---|---|---|---|---|---|---|---|---|
| | | | | | | | | | HA | |
| # | HA | NA | PB2 | PB1 | PA | NP | M | NS | $(2^n)$ | Pfu/ml |
| 6 | | | I504V | M507V V644A | I550L | R74K N417D | V97A Y100H | K55E | 9~9.5 | 4.40E+07 |
| 7 | | | I505V | E112G | I550L | R74K | | S161T | 9 | 1.60E+08 |
| 8 | | | M202L F323L | I667T M714T | | I116L | | R140Q | <1 | <1E3 |
| 9 | | | M202L F323L | E112G (PB1-F2-R81G) | | | | S161T | 8.5 | 1.30E+08 |
| 10 | | | M66R | M40I G180W | | R74K | | S161T | 8~8.5 | 2.30E+07 |
| 12 | | | R368K | PB1 F2 N66S | K356R | R422K | | K55E | 5.5 | 9.00E+02 |
| 13 | | | E391Q | R327K | S149P T357K | R293K | | | 3 | 1.60E+06 |
| 14 | | | Q591K | PB1 F2 K73R | S225C | R422K | | K55E | 7.5 | 2.00E+07 |
| 23 | | | | | | | V97A | | 8.5~9 | 1.50E+07 |
| 24 | | | | | | | Y100H | | 9~9.5 | 2.90E+07 |
| 25 | NCR 15-19 nt mut[1] | Indo/NC/09 | M202L F323L | M507V V644A | K356R | R422K | V97A Y100H | K55E | 9.5~10 | 7.50E+07 |
| 26 | Indo/NC/09 | Indo/NC/09 | | | | | | A30P | 6.5~7 | 1.00E+07 |
| 27 | (detoxified) | | | | | | | T49A | 6.5~7 | 2.00E+07 |
| 28 | | | | | | | | R140Q | 8 | 4.00E+07 |
| 29 | | | | | | | | S161T | 7~7.5 | 1.40E+07 |
| 30 | | | | | | | | A223E | 7.5 | 1.00E+07 |
| 31 | | | | I667T M714T | | | | | 3.5 | 4.00E+05 |
| 32 | NCR 15-19 nt mut | UW-PR8 | M202L F323L | V644A | K356R | T442A | Y100H | K55E | 7~7.5 | 4.30E+06 |
| 33 | Indo/NC/09 (detoxified) | Indo/NC/09 | M202L F323L | E112G (PB1-F2-R81G) | K356R | R74K | Y100H | K55E | 9~9.5 | 7.00E+07 |
| 34 | NCR 15-19 nt mut | UW-PR8 | I504V | M507V V644A | | | V97A Y100H | K55E | 7 | 2.00E+05 |
| 35 | Indo/NC/09 (detoxified) | Indo/NC/09 | M202L F323L | M507V V644A | R401K | T442A | Y100H | R140Q | 9 | 3.20E+07 |
| 36 | | | I504V | E112G (PB1-F2-R81G) | I550L | I112L | Y100H | R140Q | 9.5 | 1.30E+08 |
| 37 | | | M202L F323L | E112G (PB1-F2-R81G) | S149P T357K | T442A | Y100H | K55E | 0 | 0.00E+00 |
| 38 | | | M202L F323L | M507V V644A | | I116L | Y100H | K55E | 10.1 | 2.30E+08 |
| 39 | | | M202L F323L | M507V V644A | K356R | T442A | Y100H | K55E | 9.8 | 1.00E+08 |
| 40 | | | I504V | M507V V644A | I550L | T442A | Y100H | K55E | 9.2 | 6.00E+07 |
| 41 | | | I504V | I112G | I550L | R74K | Y100H | K55E | 9.2 | 7.50E+07 |
| P17 | | | I504V | E112G (PB1-F2-R81G) | S225C | R74K N417D | V97A Y100H | K55E | 9.5~10 | 5.80E+08 |
| P26 | | | M202L F323L | M40L G180W | S225C | R422K | V97A Y100H | K55E | 10 | 3.00E+08 |
| P61 | | Indo/NC/09 NA P263T[2] | M202L F323L | Q247H | K142N | R74K | V97A Y100H | K55E | 10~10.5 | 2.00E+08 |

[1]Mutation in the HA gene noncoding region;

[2]A P263T mutation was detected in the NA protein of this virus clone

Figure 7B:
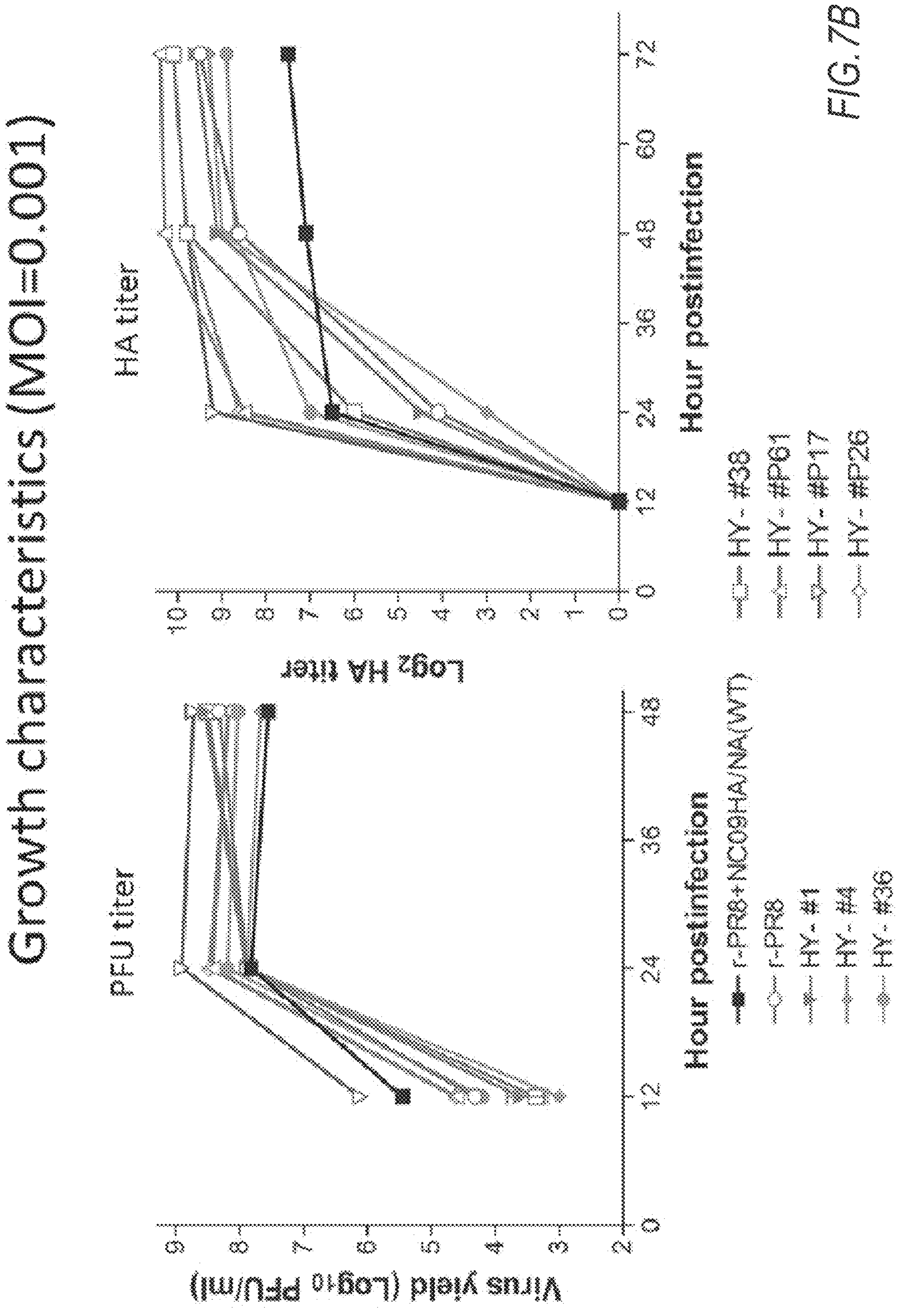
Figure 8A:
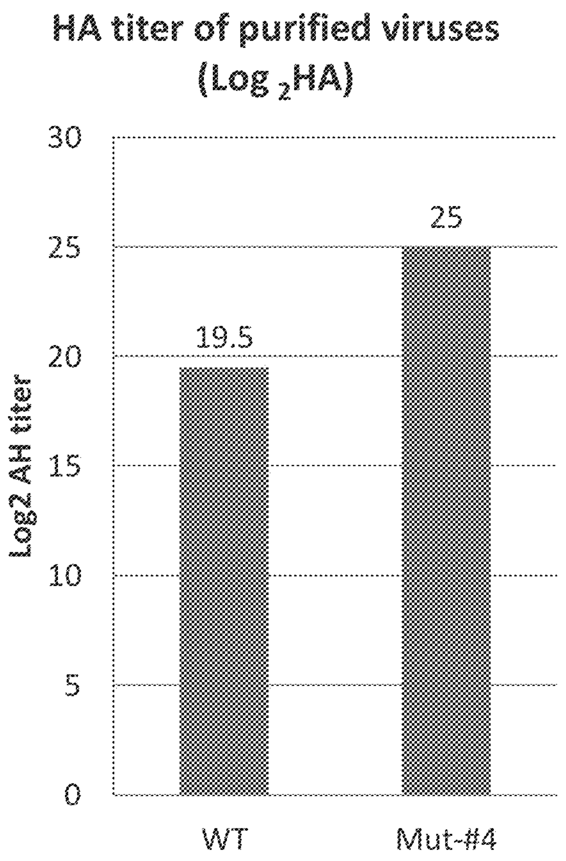
FIGS. 8A-8C. A) HA titer of wild type (UW-PR8) and clone #4. B) Viral protein for wild type (UW-PR8) and #4. C) SDS-PAGE analysis of viral proteins of wild type and #4.
Figure 8B:
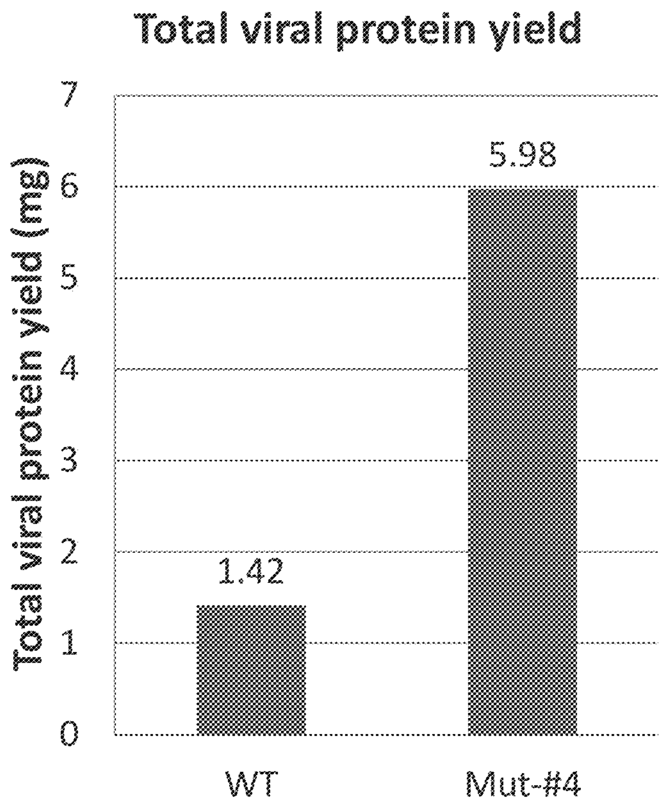
Figure 8C:
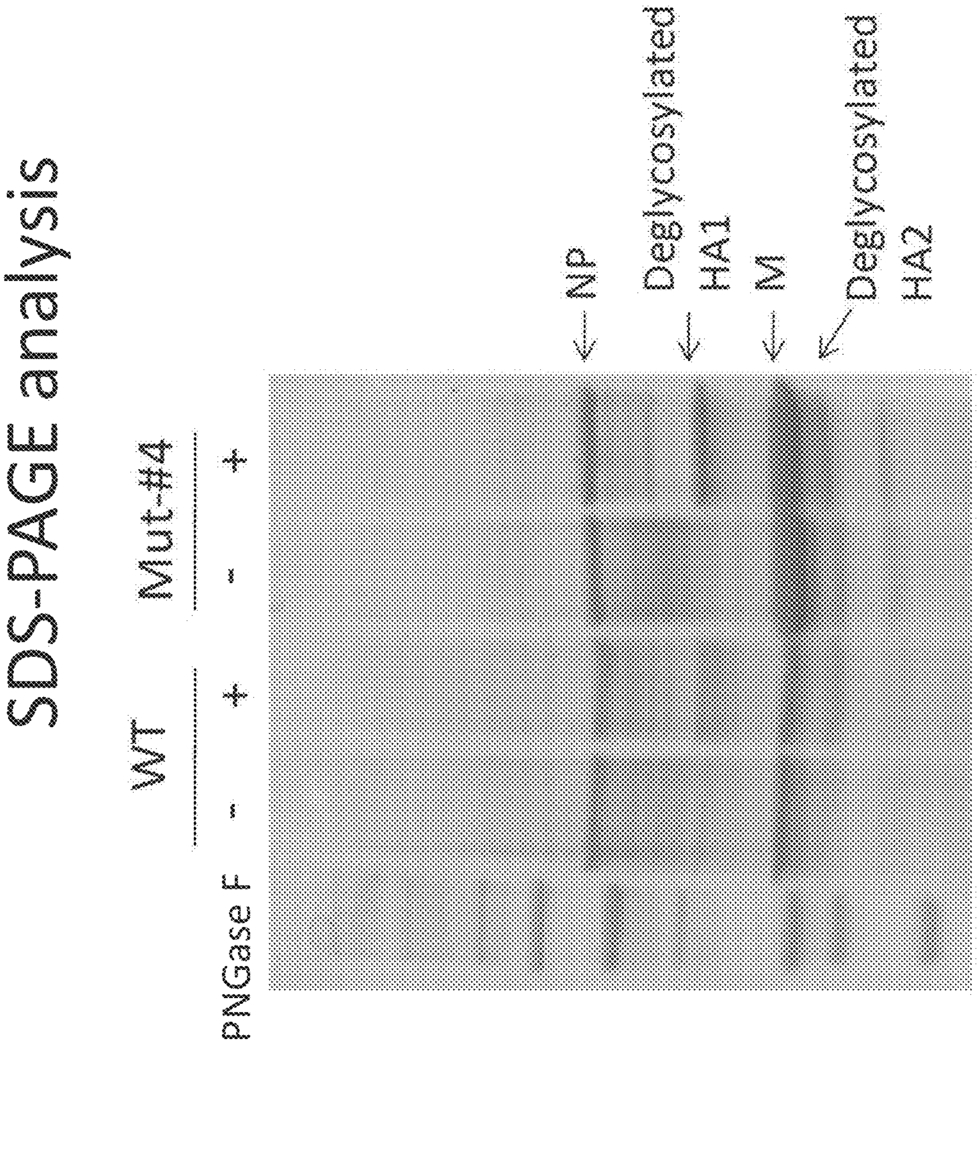
Figure 9B:
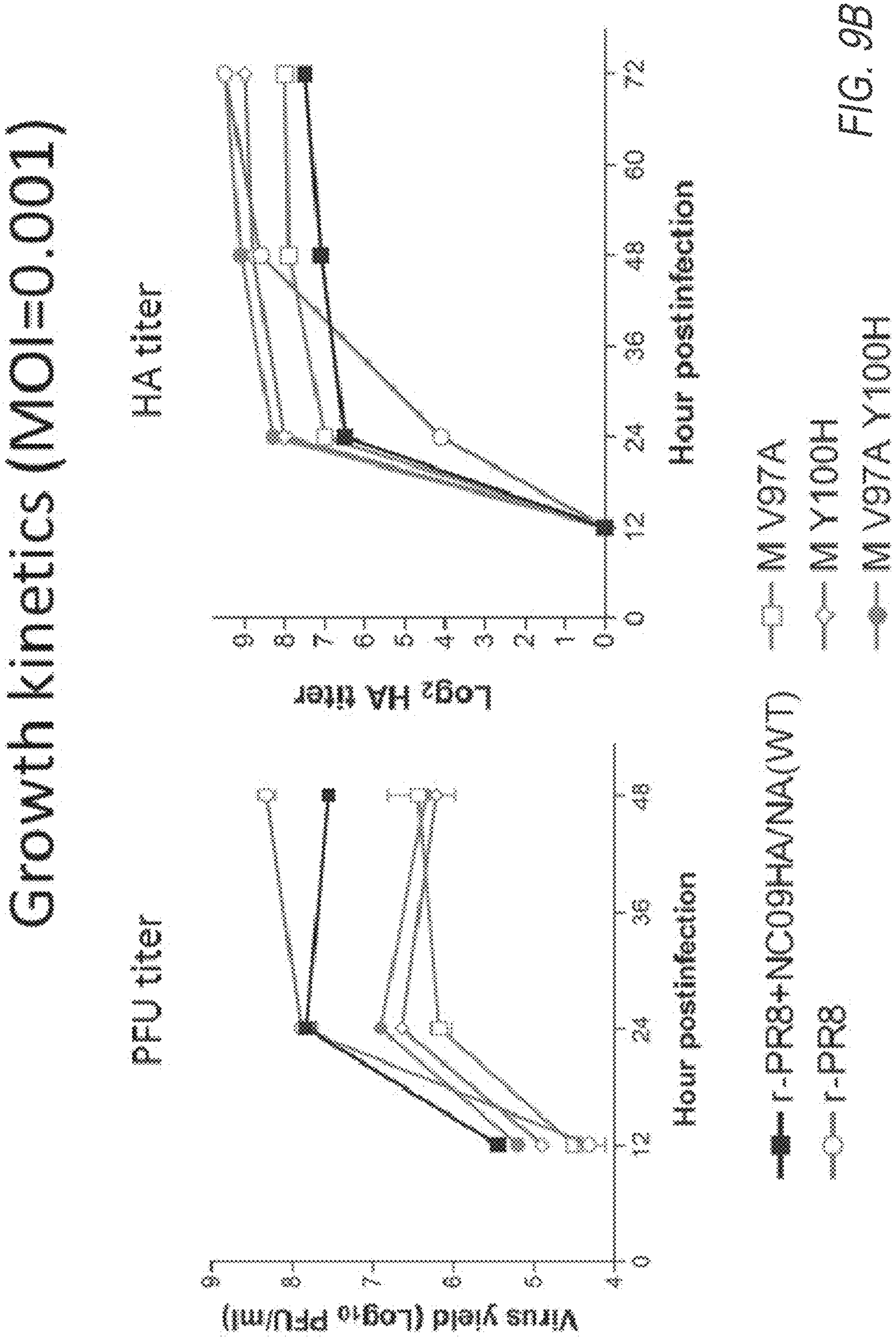

As shown in Table 4, several recombinant viruses were identified that replicated better than wild type, such as #1, #4, #36, #38, P17, P16, and P61. To identify the growth characteristics of these viruses, growth kinetics in MDCK cells were determined (FIG. 7). For one candidate, virus was purified on sucrose gradients and HA content and viral total protein evaluated. FIG. 8A shows HA titer of wild type (UW-PR8) and #4, FIG. 8B shows viral protein for wild type (UW-PR8) and #4, and FIG. 8BC is a SDS-PAGE analysis of viral proteins of wild type (UW-PR8) and #4. Further analysis demonstrated that viruses possessing the V97A/Y100H mutations in M1 yielded higher HA titers than the parental virus, although the virus titer was lower (see FIGS. 9A-B). The V97A/Y100H mutations in M1 may result in particles with a larger surface into which more HA protein can be incorporated. Since inactivated influenza viruses are dosed based on their HA content, variants with high HA content are attractive vaccine candidates.

Figure 11C:
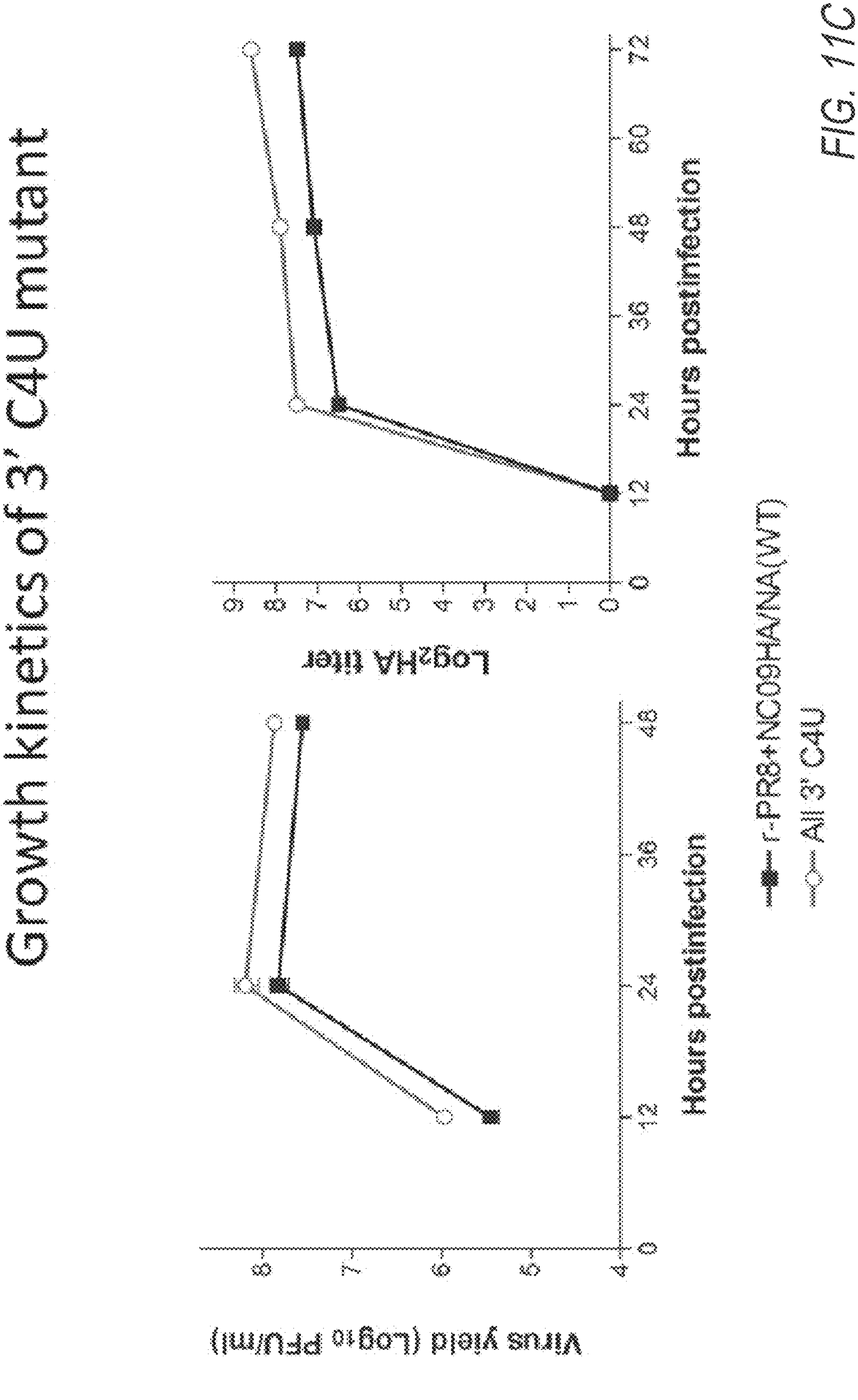

To identify mutations in the influenza promoter region that provide for enhanced replication, viruses possessing a 'U' at position 4 at the 3' end of all eight vRNA segments were prepared in the UW-PR8 PA, PB1 and PB2 internal genes (the UW-PR8 PB2, PB1, and PA segments possess a 'C' at position 4). The growth curves of the resulting viruses are shown in FIG. 11C.

Viruses possessing combinations of promoter mutations and amino acid changes were prepared and titers determined (Table 5).

|  | Gene backbone |  |  |  |  |  |  |  | Virus stock titer |  |
|---|---|---|---|---|---|---|---|---|---|---|
| Virus | HA | NA | PB2 | PB1 | PA | NP | M | NS | HA (2ⁿ) | pfu/ml |
| Wild type | WT | WT | WT | WT | WT | WT | WT | WT | 7~7.5 | 3.5E+07 |
| PB2 codon optimization-1 | WT | WT | Rare codon optimized PB2 | WT | WT | WT | WT | WT | 9 | 2.1E+08 |
| PB2 codon optimization-2 | WT | WT | All Codon optimized PB2 | WT | WT | WT | WT | WT | 3 | 9.0E+05 |

Figure 10B:
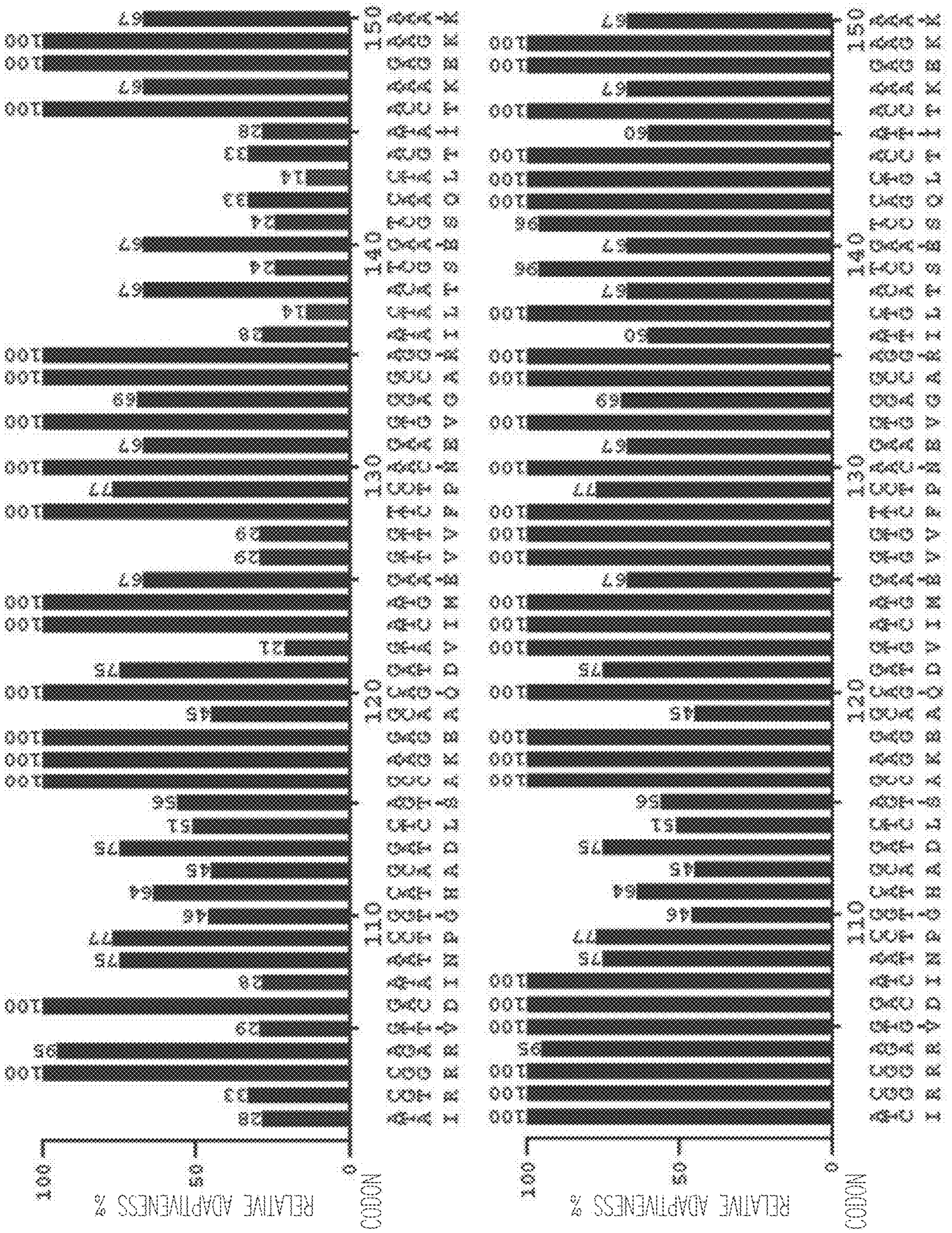
Figure 10C:
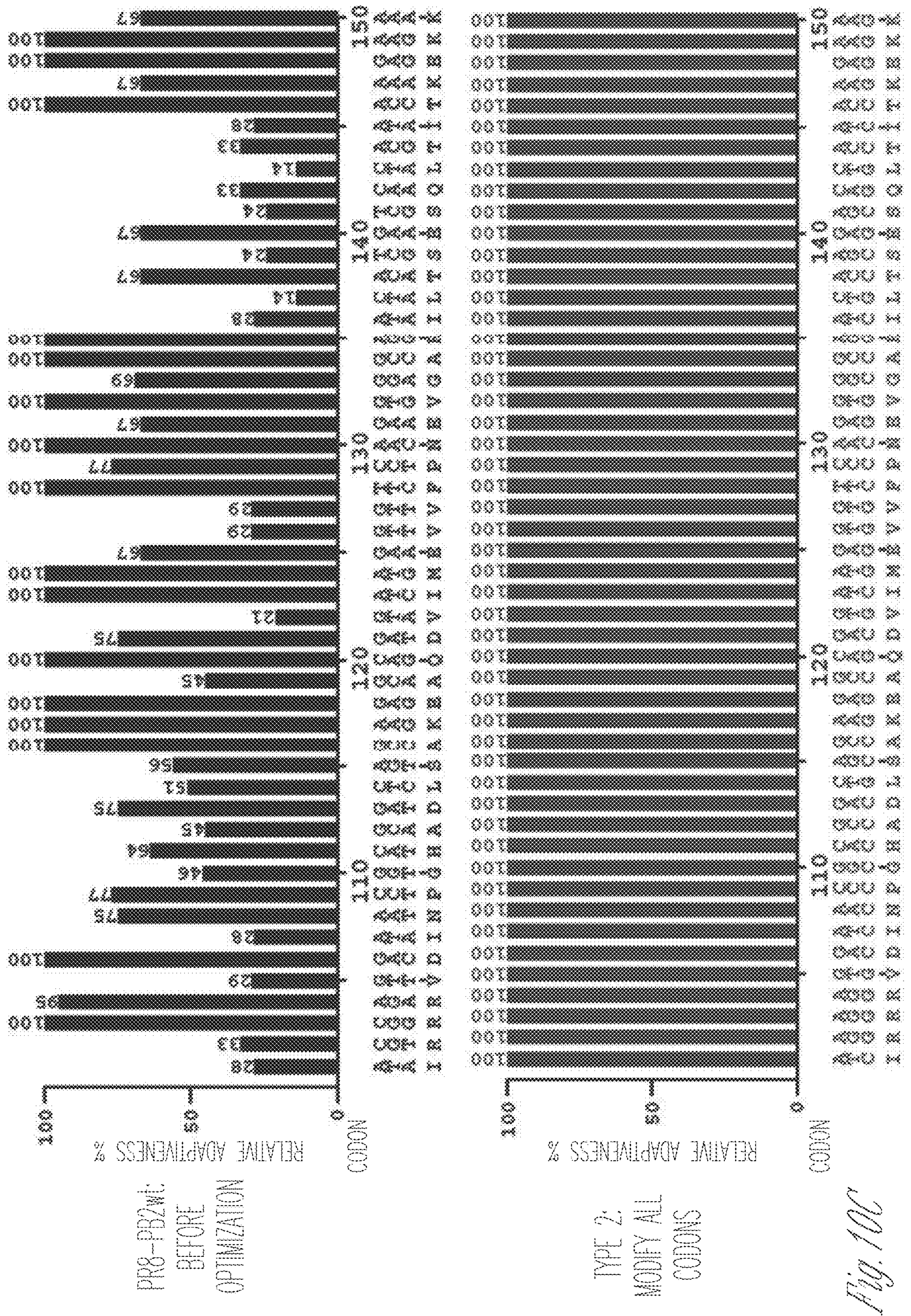
Figure 10D:
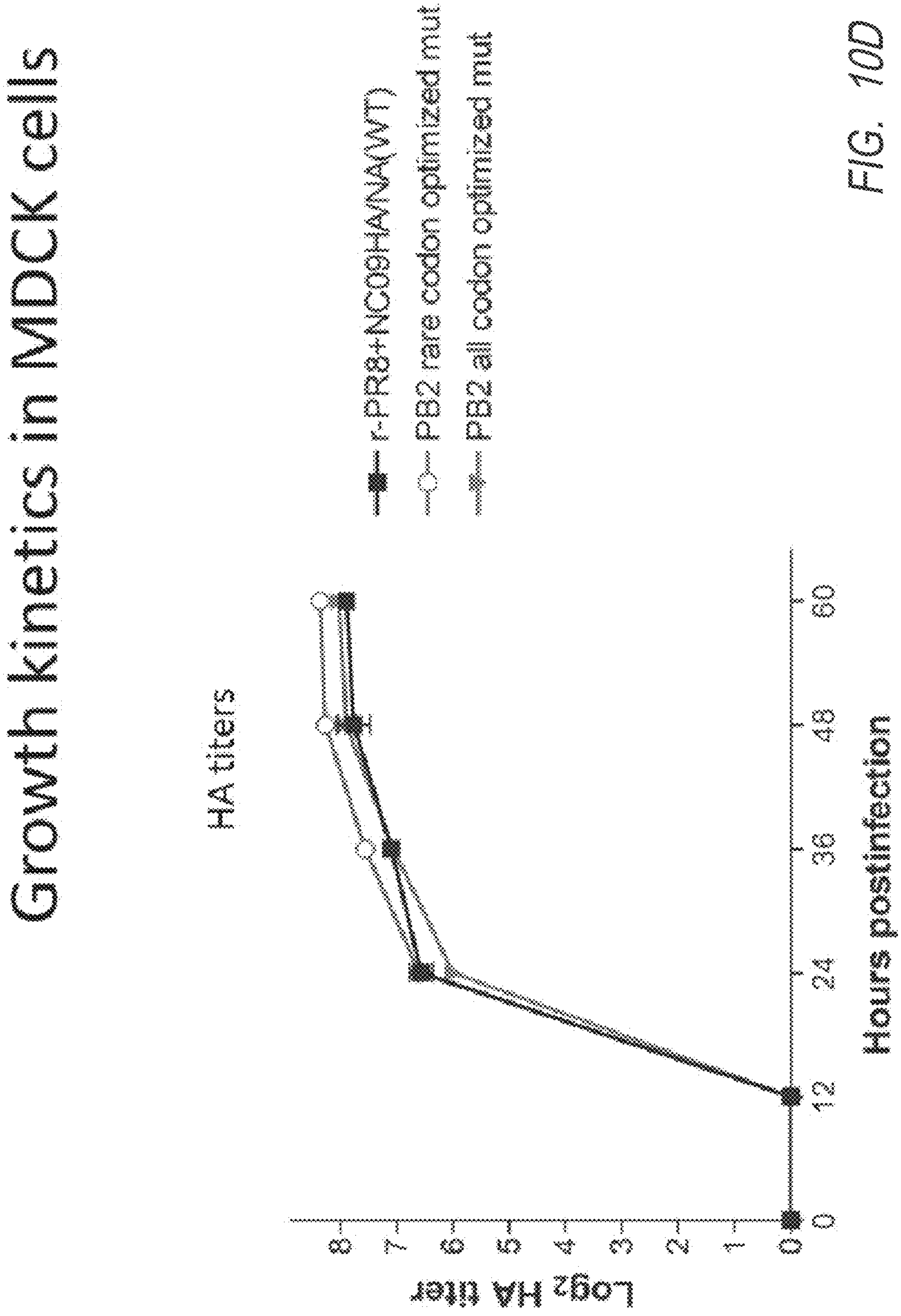
Figure 10E:
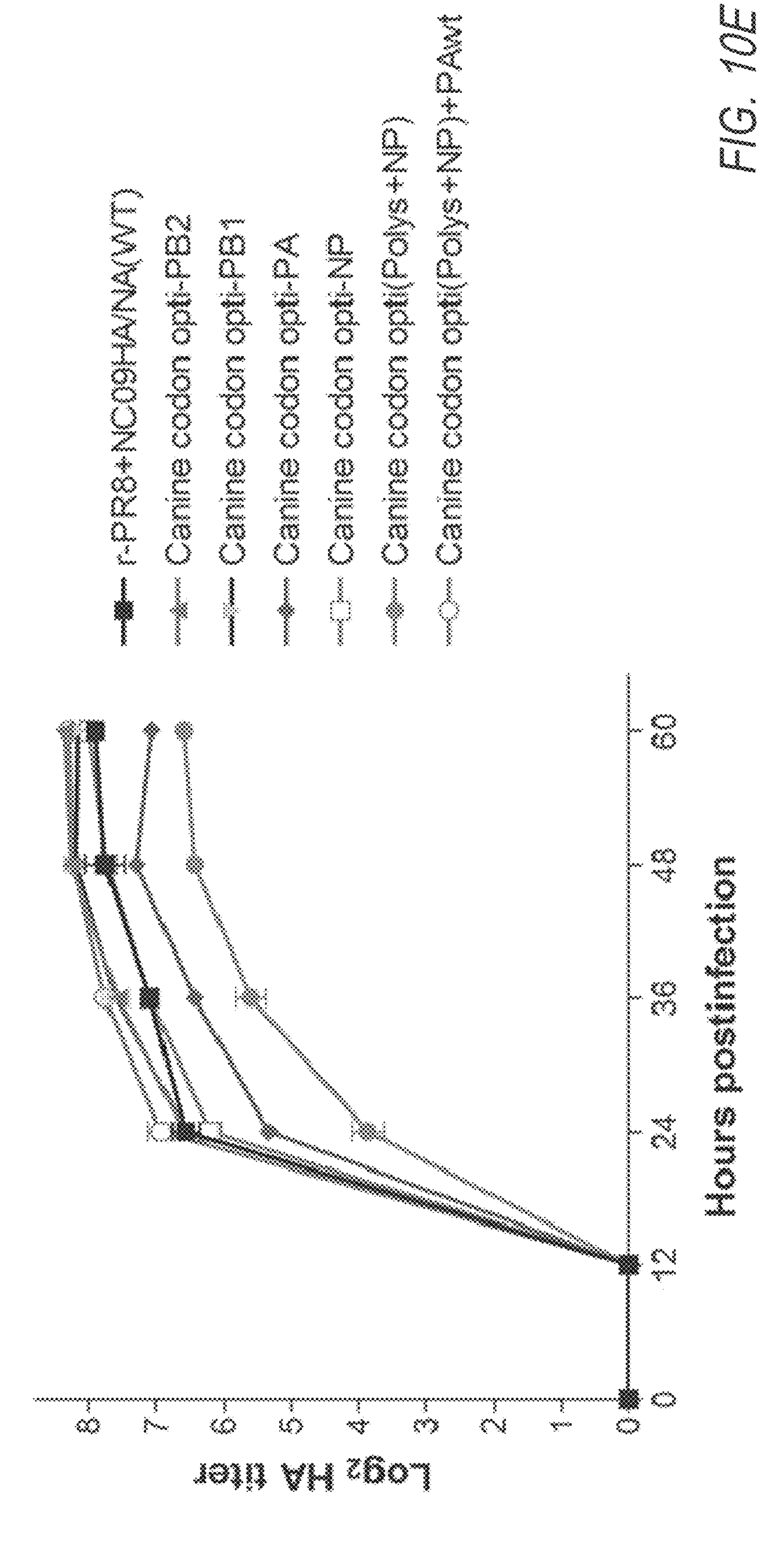

Optimization of rare codons in PB2 resulted in increased titers compared to wild type virus (UW-PR8) (see FIG. 10D), Other viral segments were codon optimized and titers of viruses with those segments or combinations of optimized segments were determined (FIG. 10E).

Figure 13A:
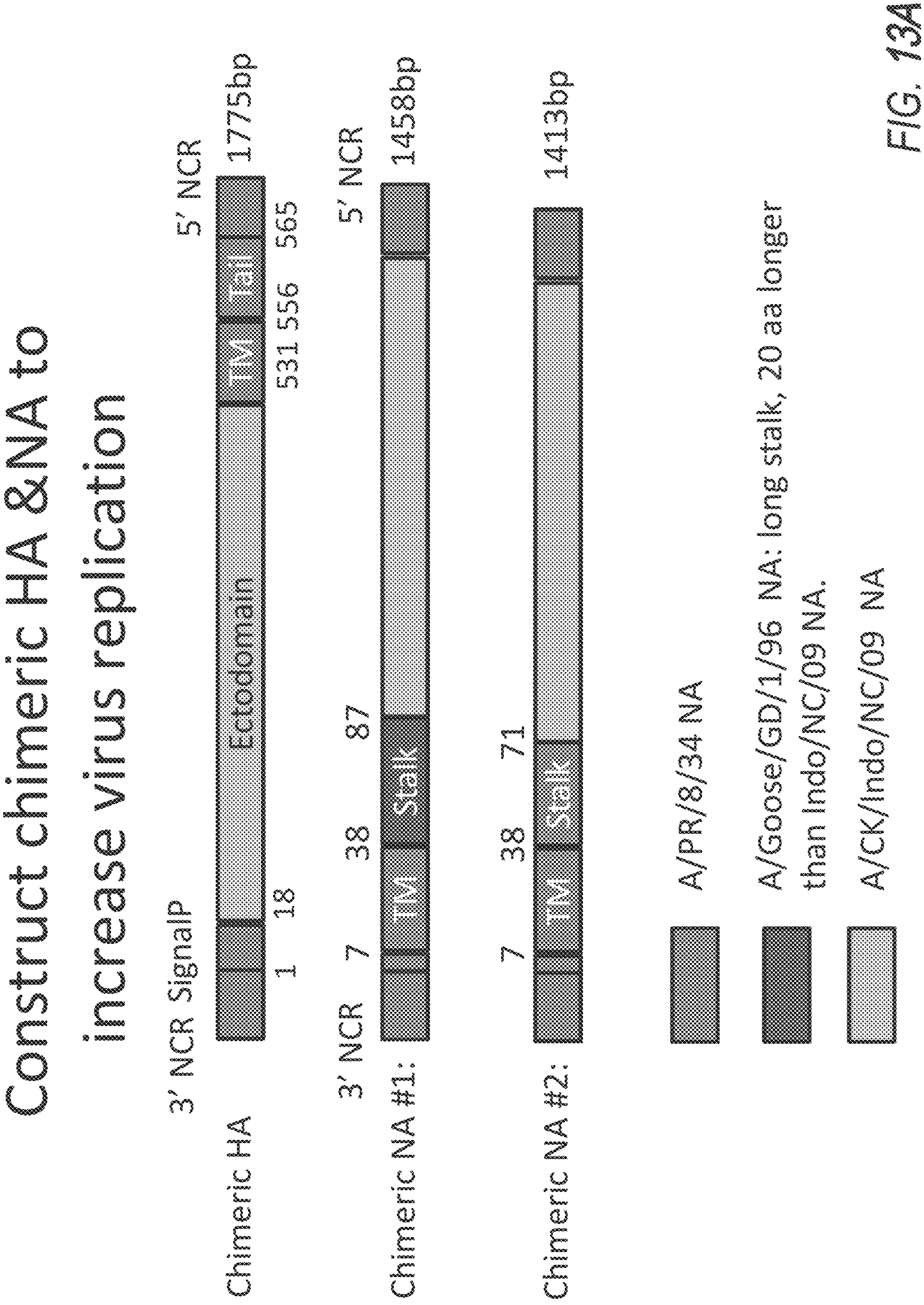
FIGS. 13A-13B. A) Schematic of chimeric HA and NA genes to increase virus titer. B) Growth kinetics of chimeric viruses.
Figure 13B:
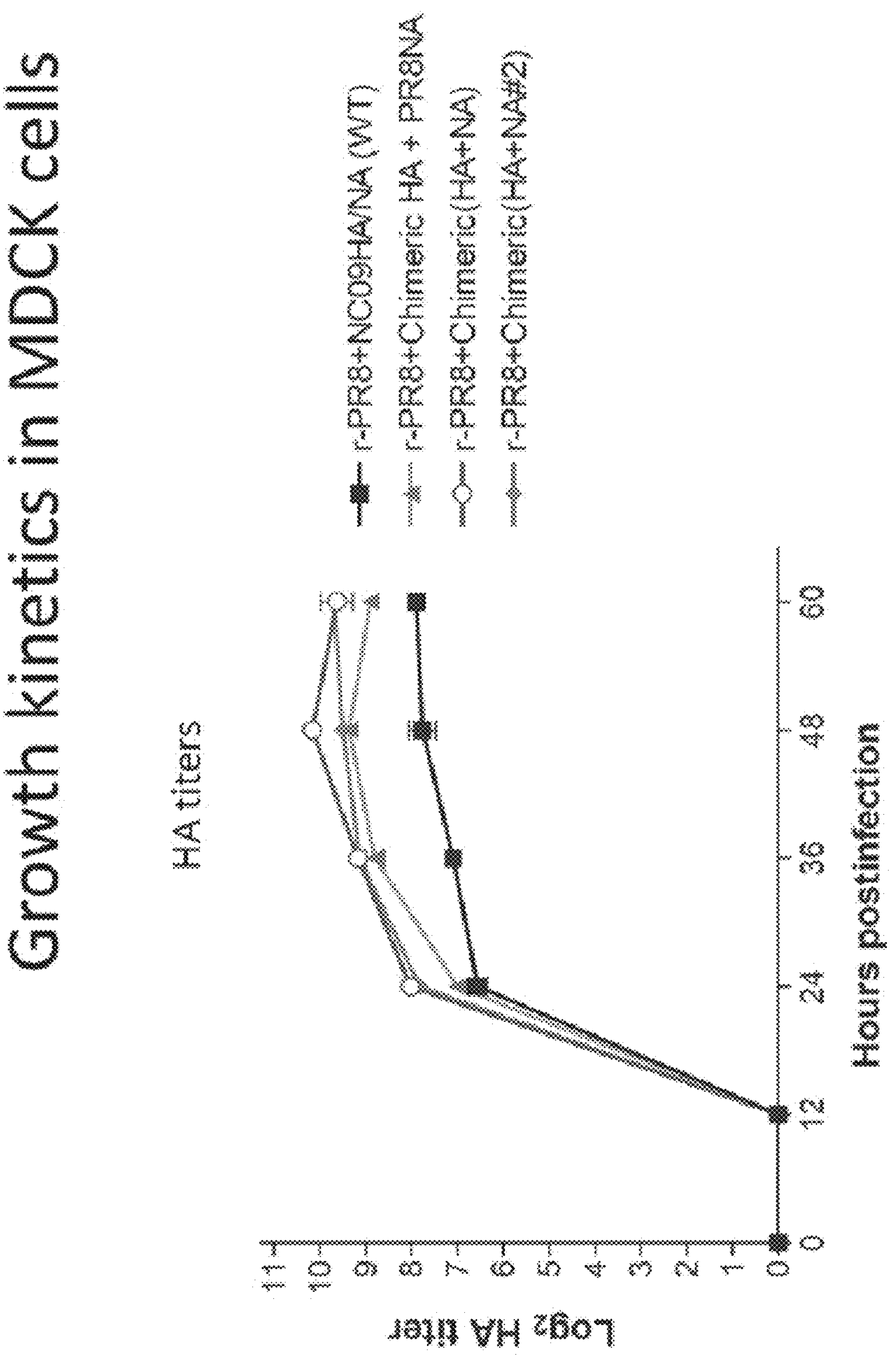

In another approach to increase virus titer in MDCK cells, chimeric HA and NA genes were prepared (FIG. 13A) and titers of viruses having those genes were determined (FIG. 13B).

Figure 14A:
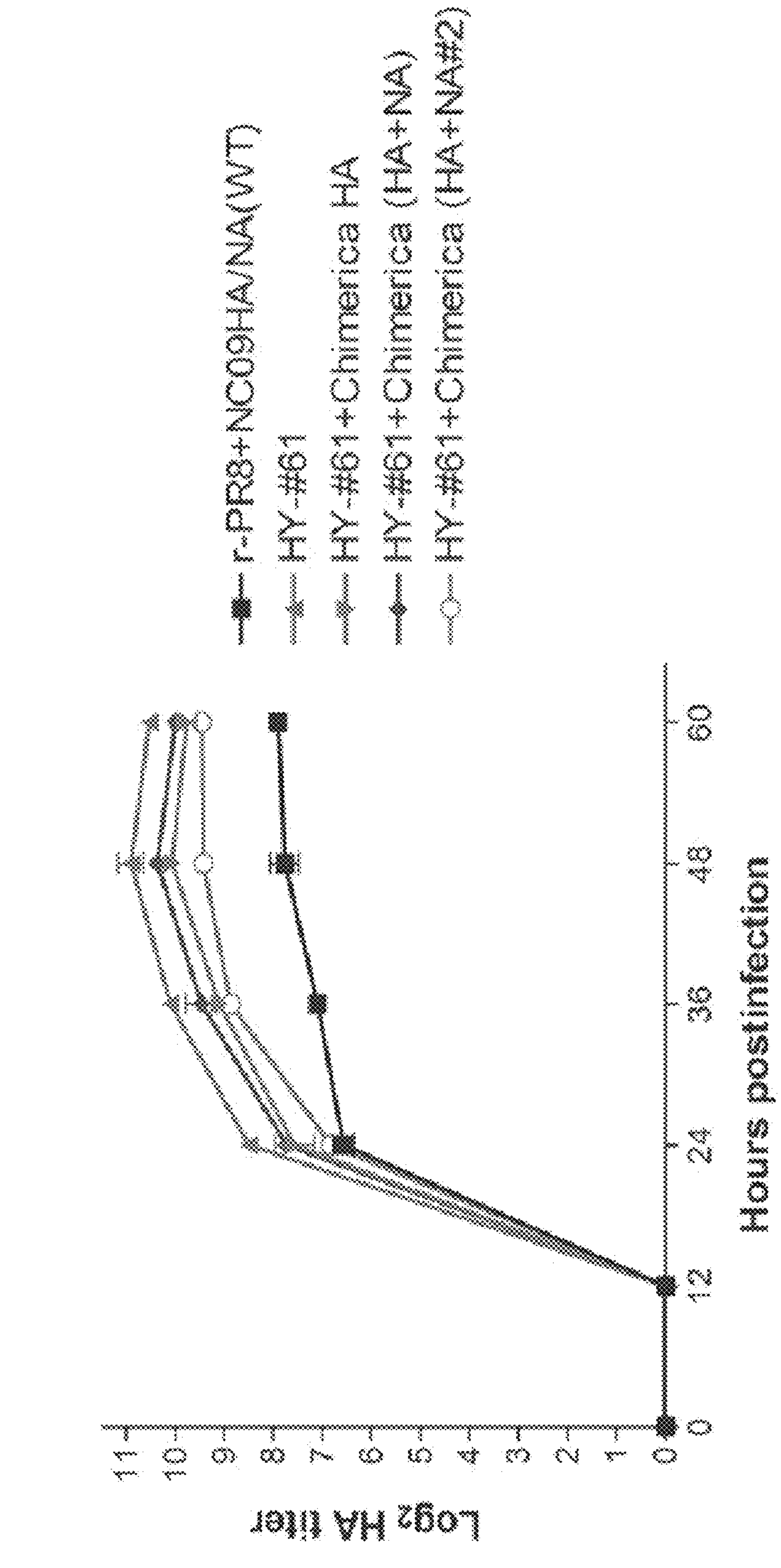
FIGS. 14A-14B. A) Growth kinetics of viruses with combinations of mutations. B) PFU and HA titers of viruses with combinations of mutations.
Figure 14B:
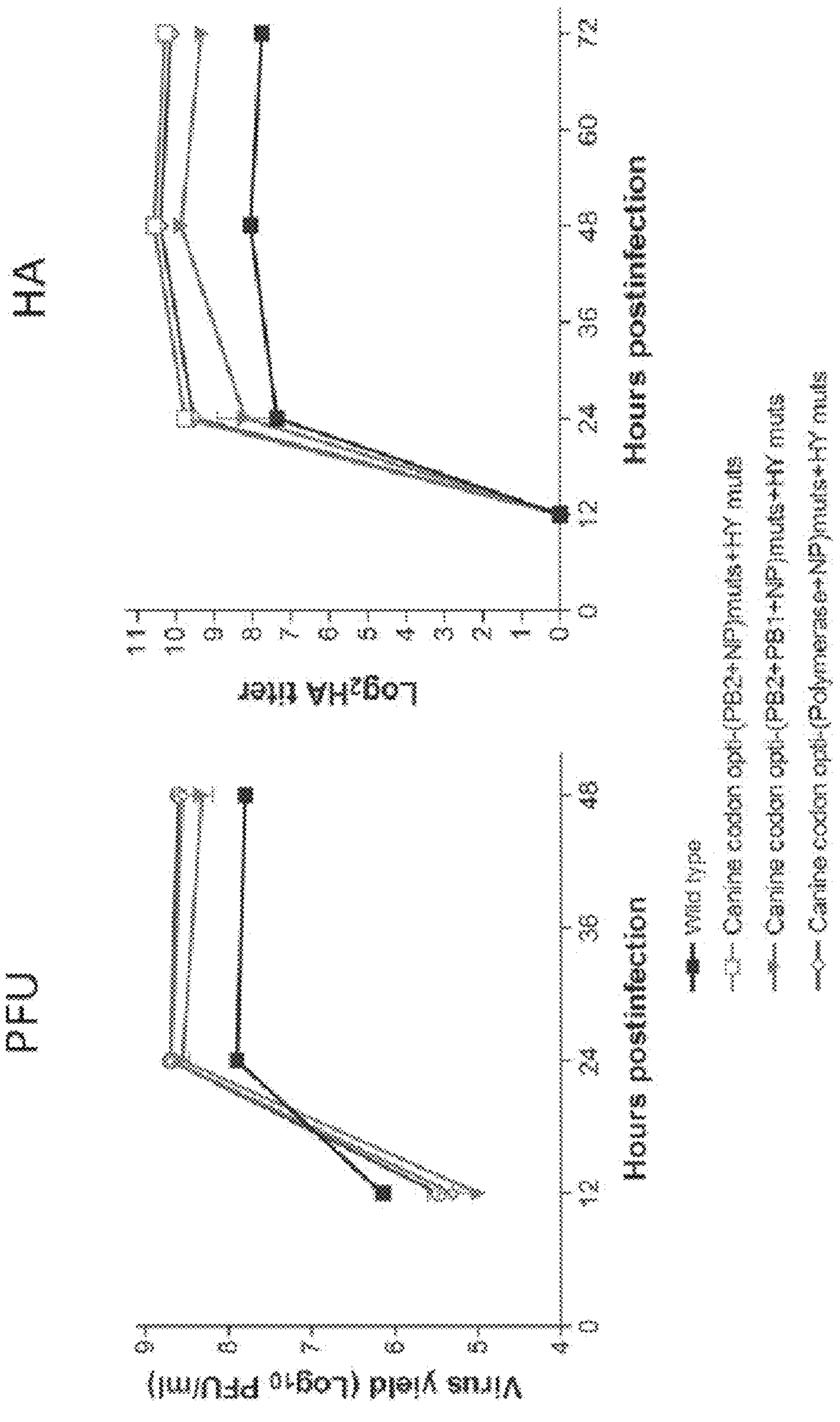

Viruses with combinations of the above-mentioned mutations (high growth backbone mutations, promoter mutations, chimeric HA and NA genes and canine codon optimization) were prepared and growth kinetics, PFU and HA titers of those viruses were determined (see FIG. 14). An exemplary set of backbone mutations are canine codon opti-PB2+C4U+M202L, F323L; PB1: C4U+Q247H; PA: C4U+K142N; NP: Canine codon opti-NP+R74K; M: V97A, Y100H; and NS: K55E.

Figure 15:
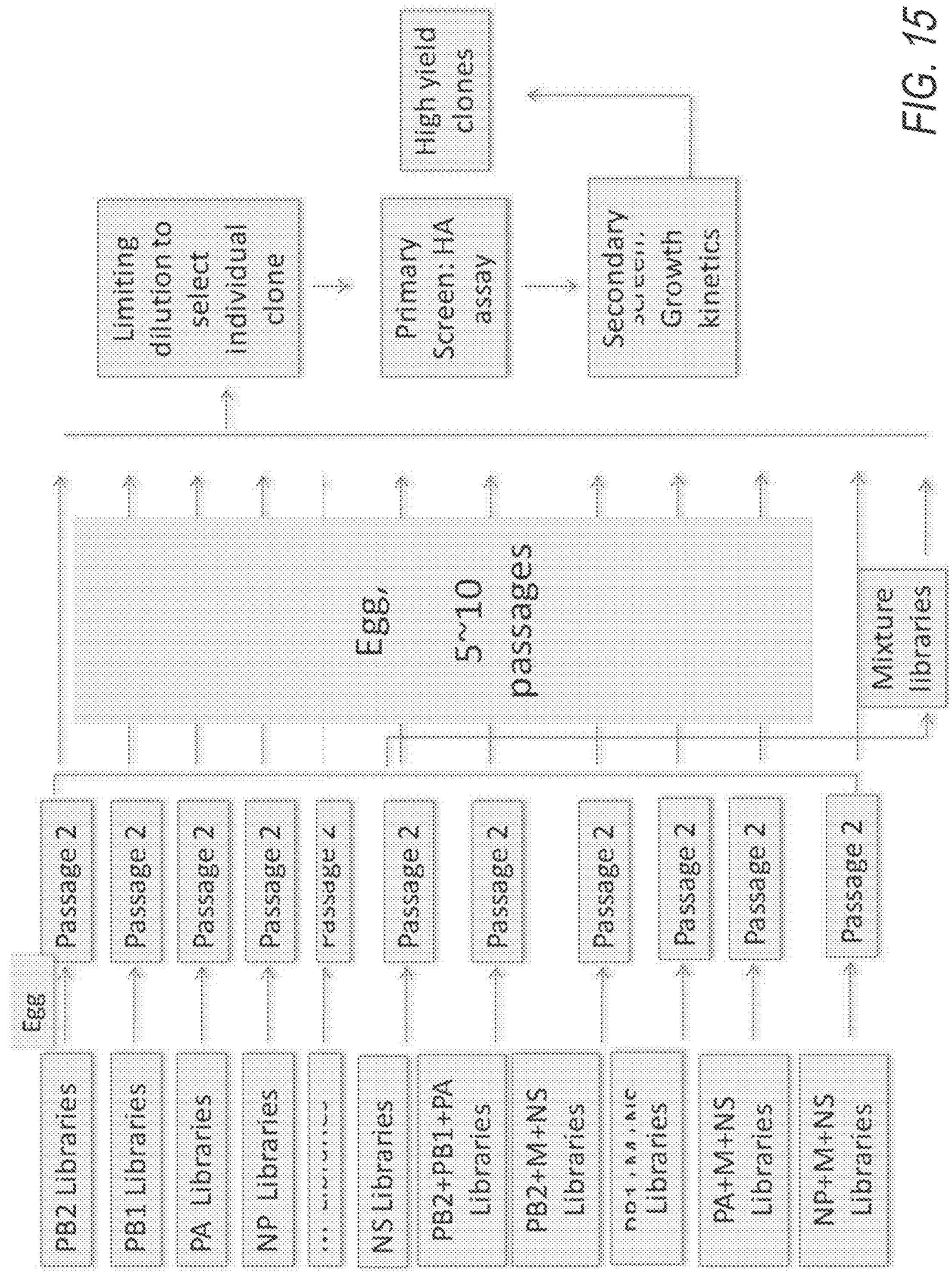
FIG. 15. Screening in eggs.
Figure 18A:
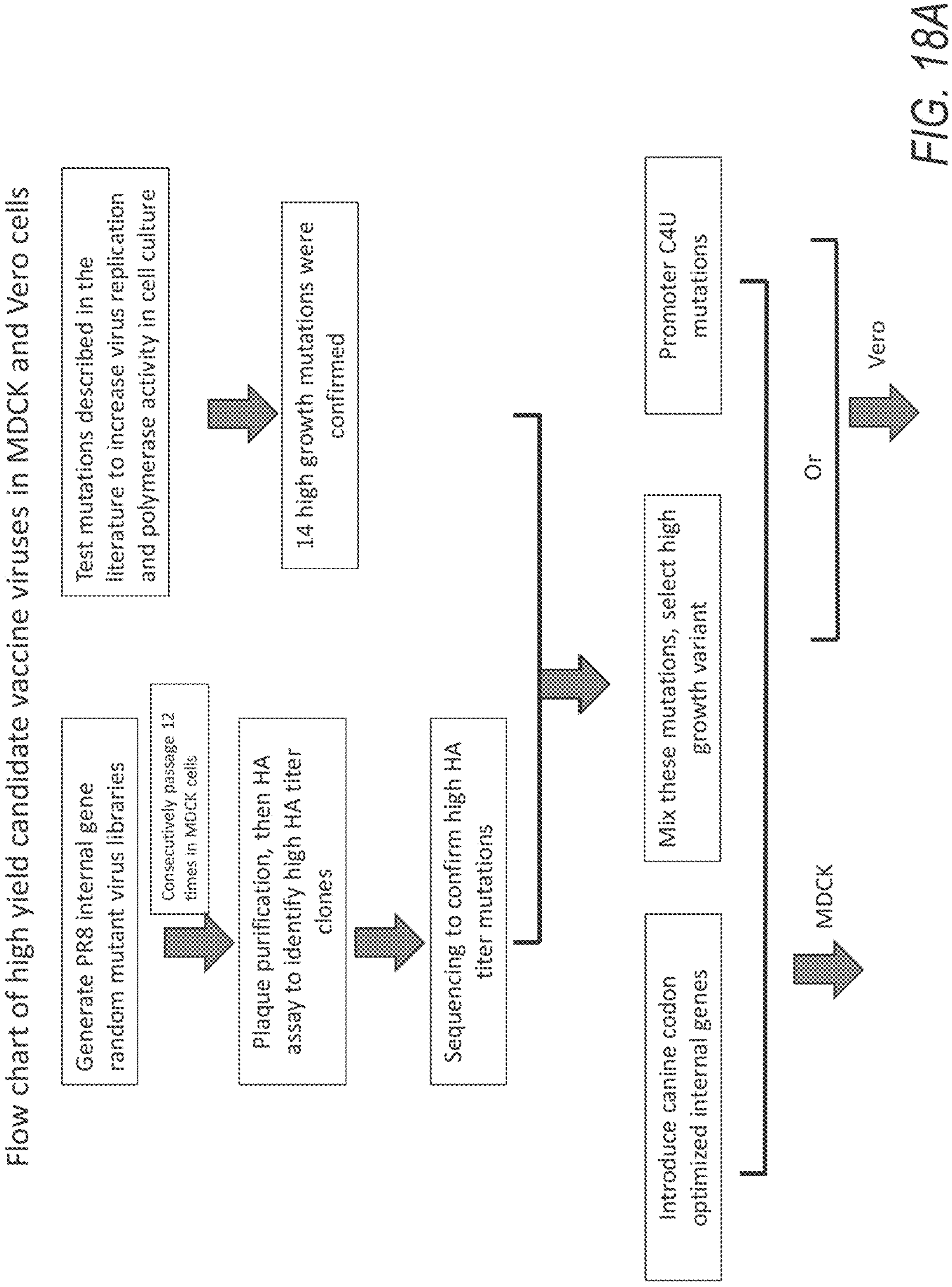
FIGS. 18A-18B. Overview of generation of viruses with enhanced growth in MDCK cells and Vero cells.
Figure 18B:
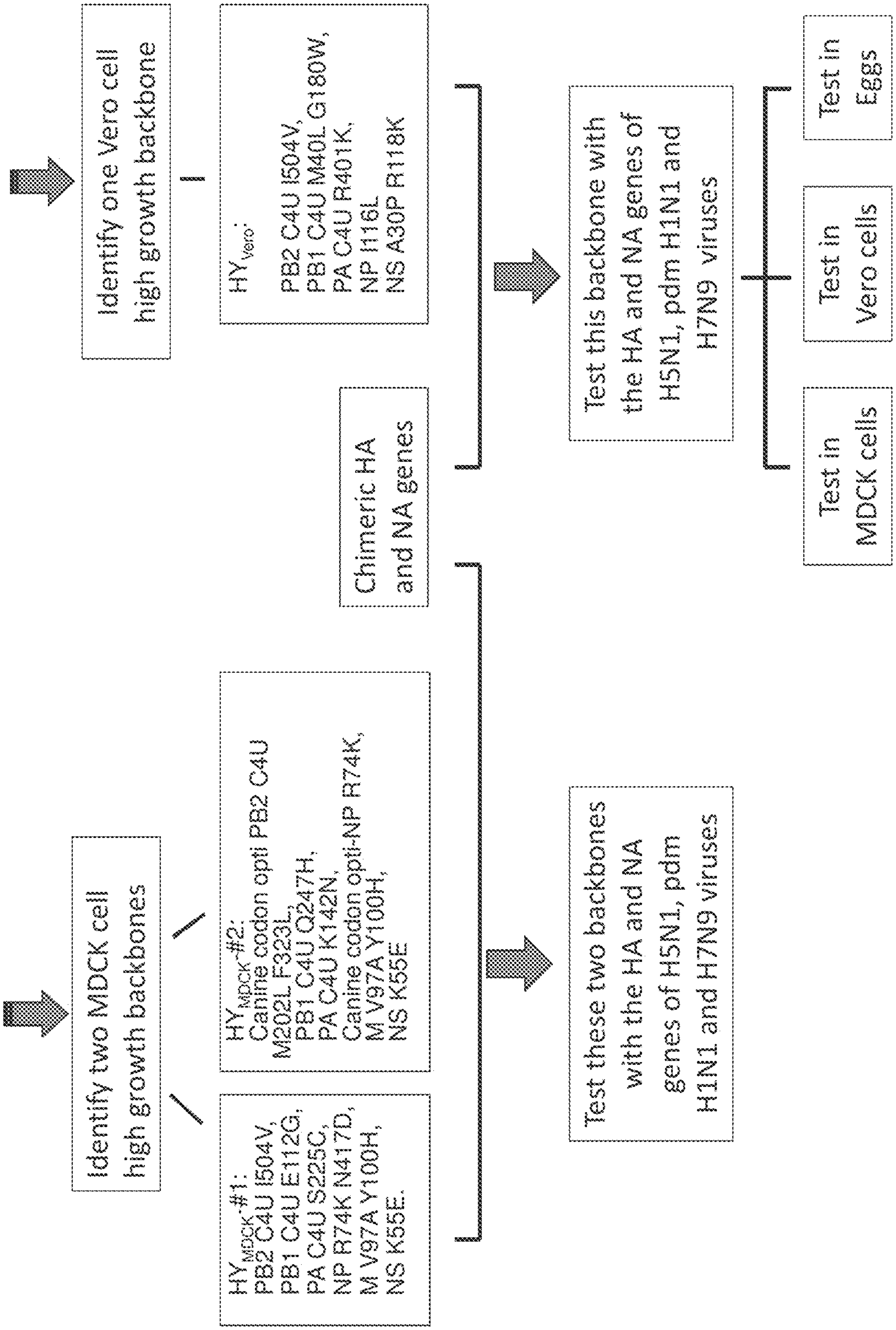
Figure 20A:
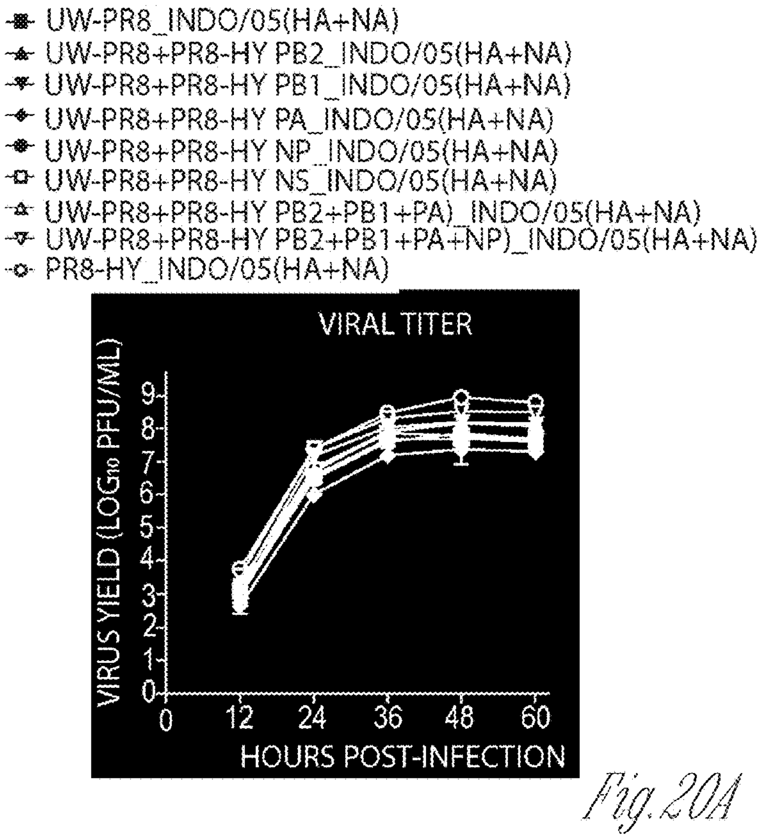
FIGS. 20A-20F. Growth kinetics and HA titers of reassortant viruses possessing one or several vRNAs of PR8-HY virus.
Figure 20B:
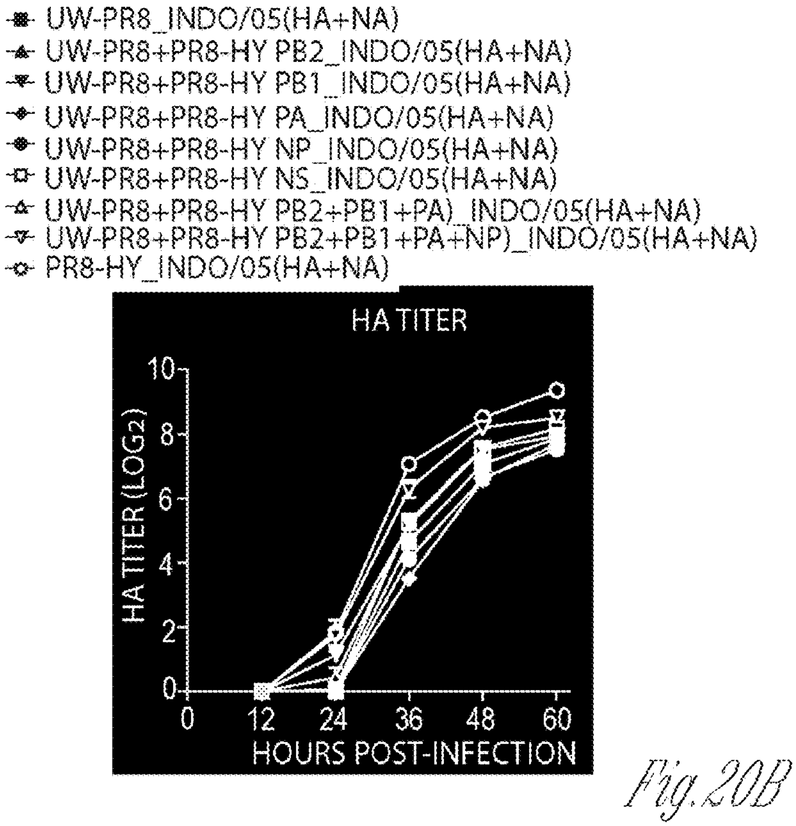
Figure 20C:
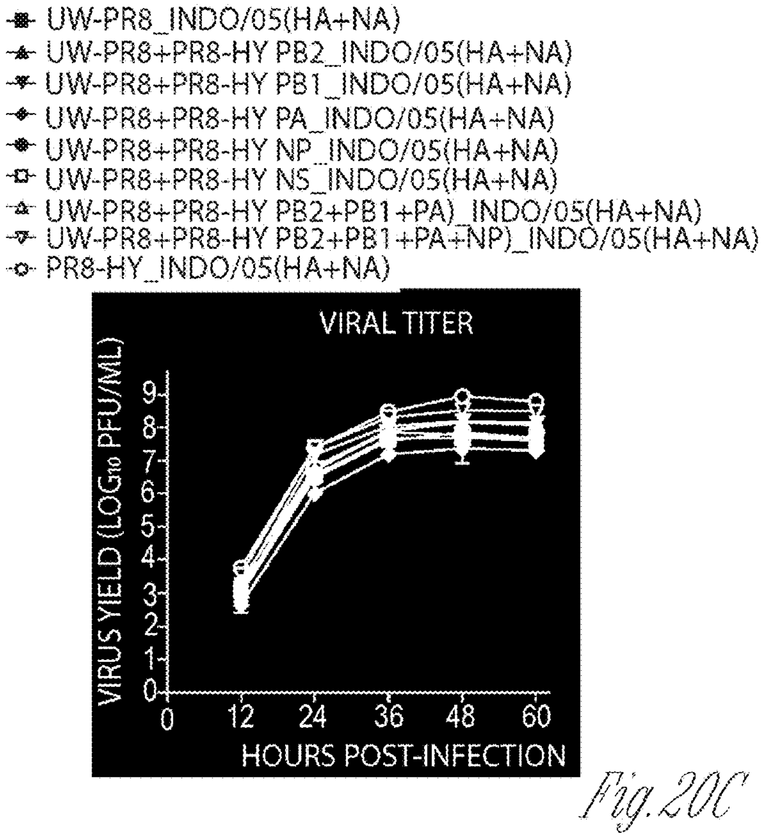
Figure 20D:
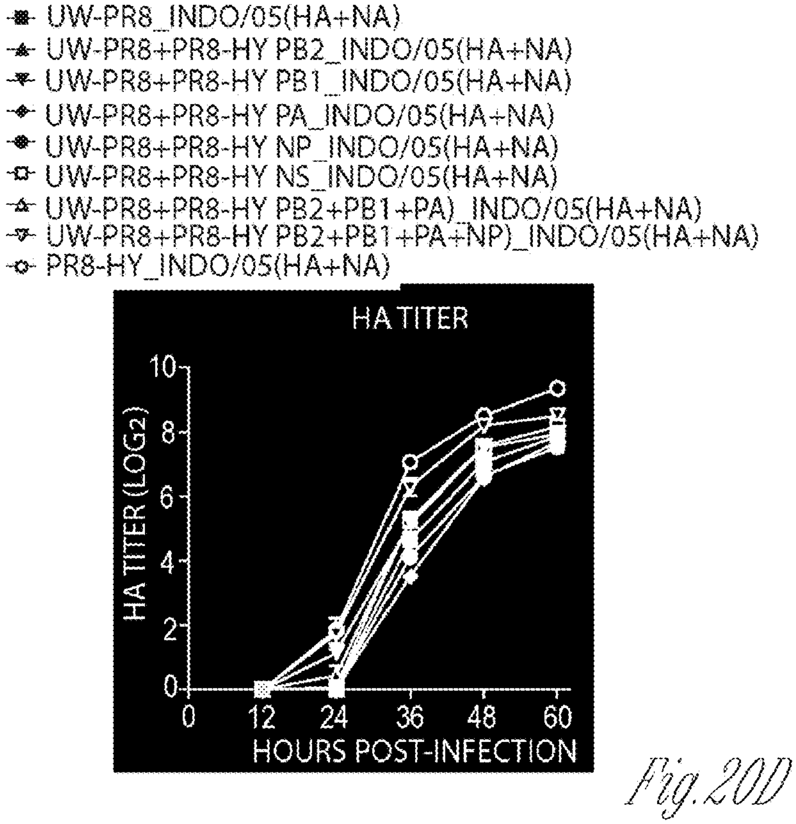
Figure 20E:
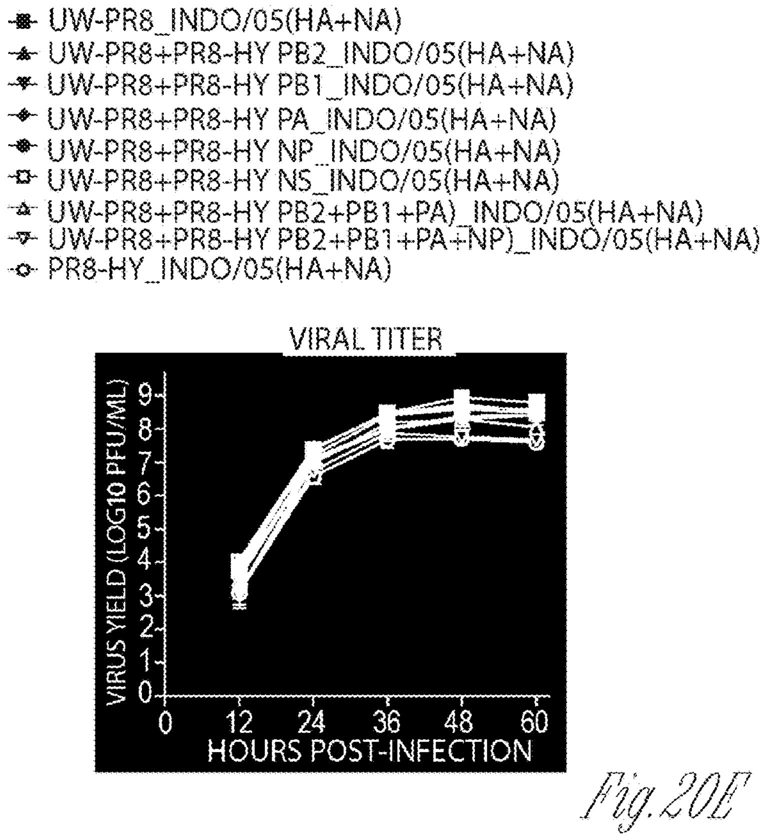
Figure 20F:
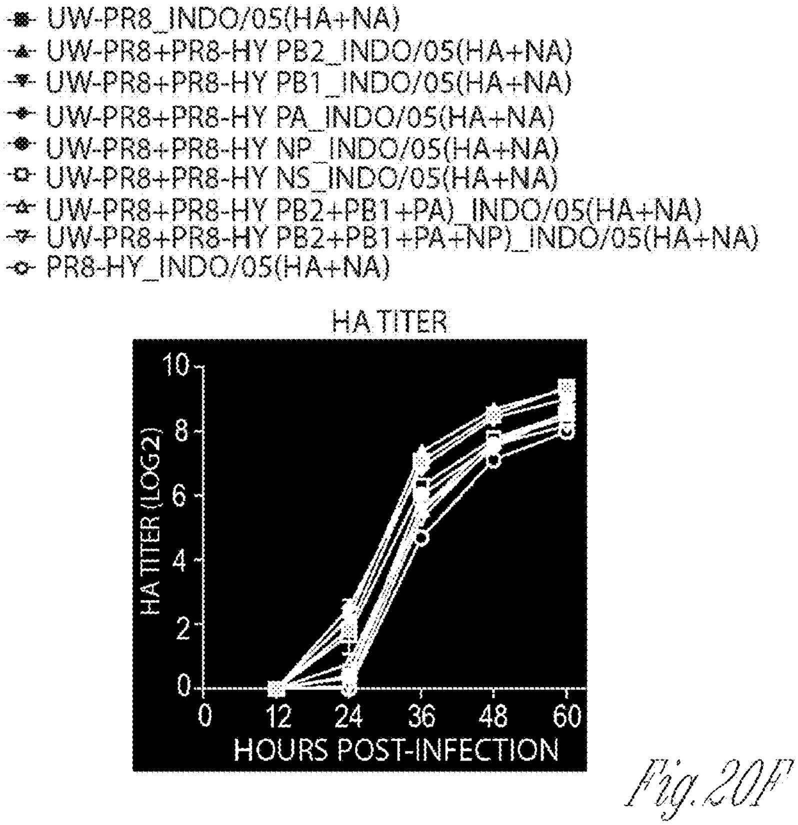
Figure 21E:
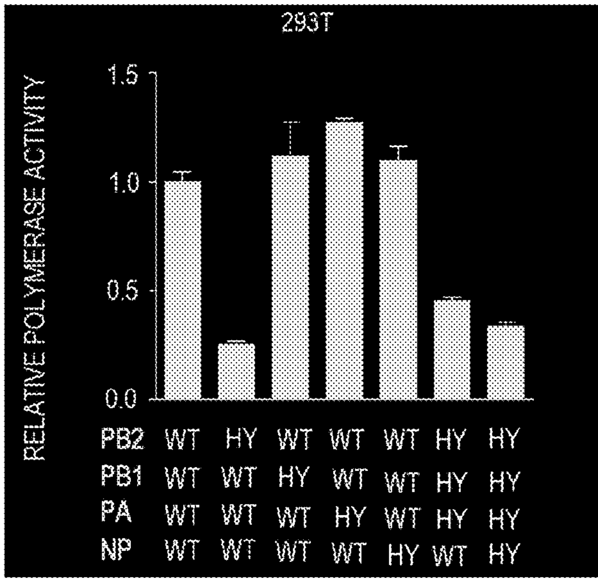
Figure 21F:
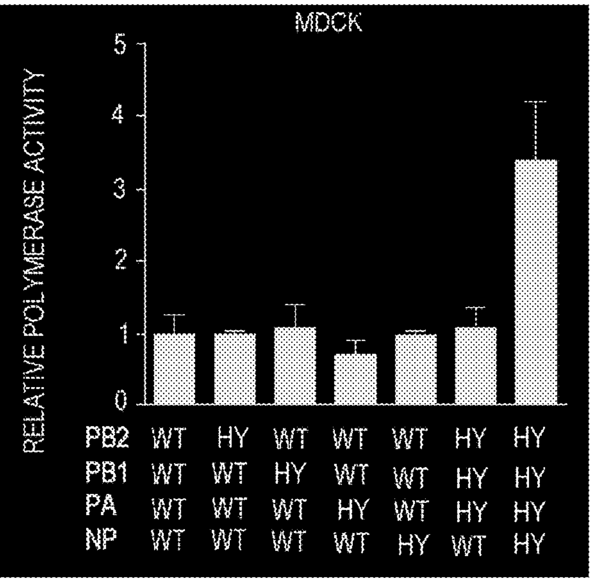
Figure 21G:
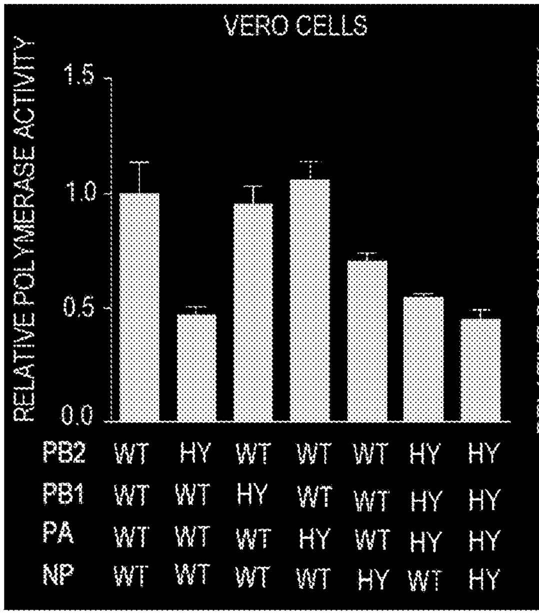
Figure 21H:
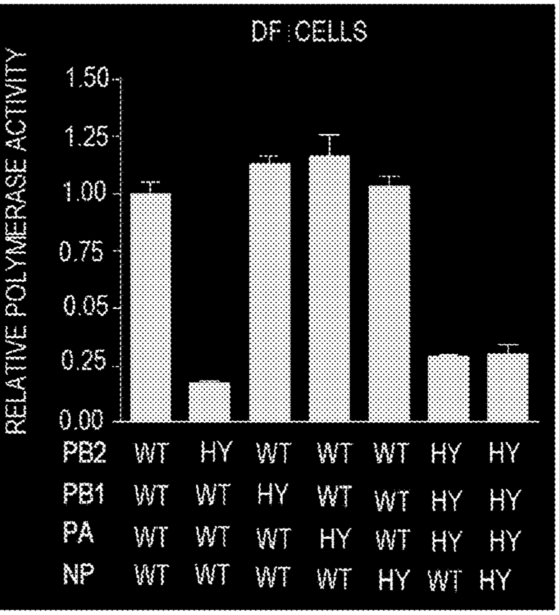
Figure 22C:
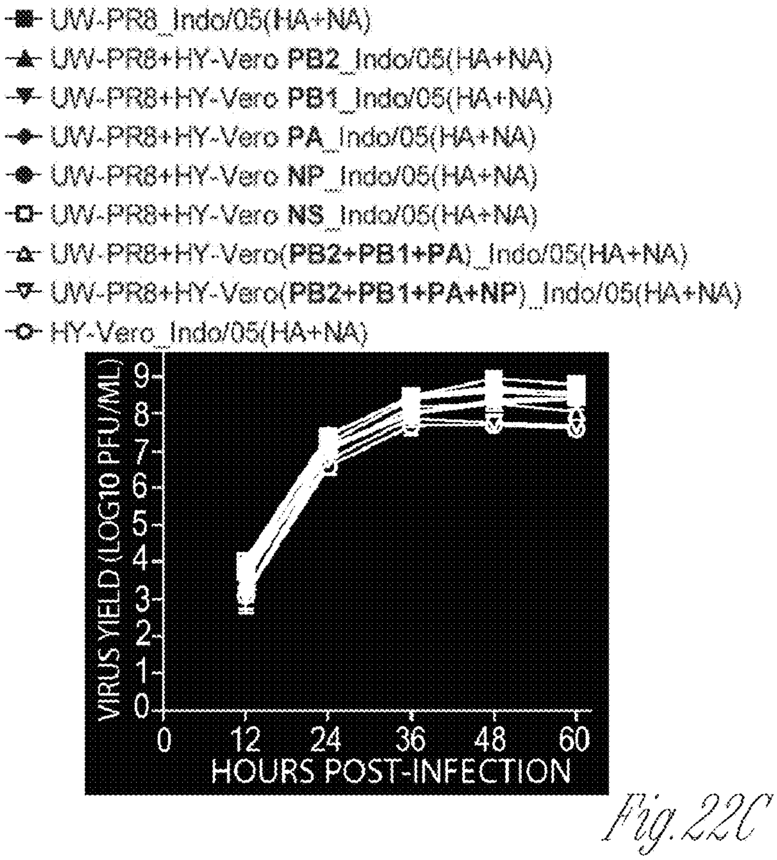
Figure 22D:
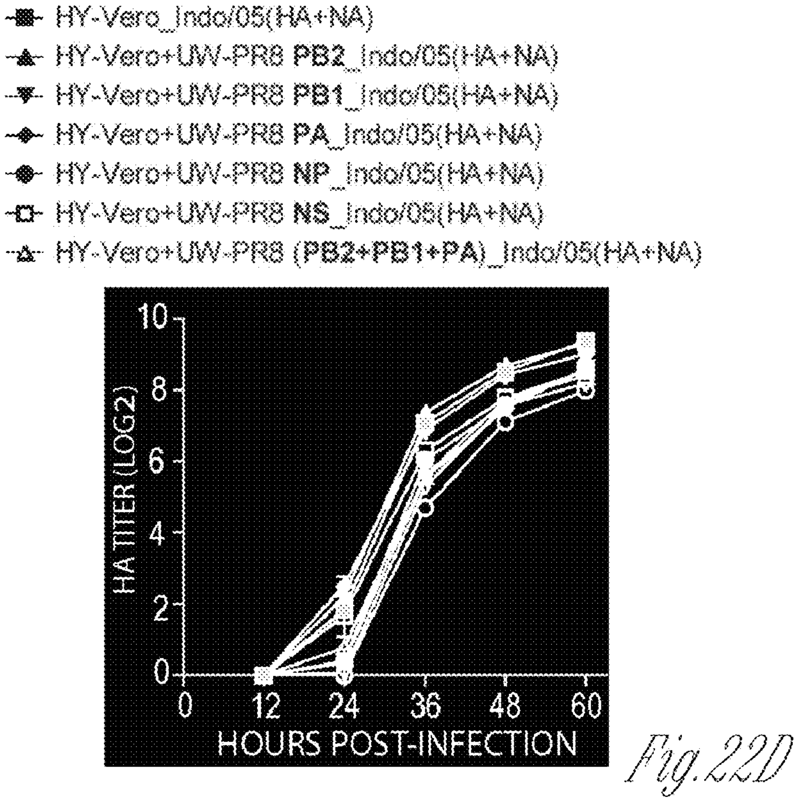

Any of the mutations described herein, or any combination thereof, may be combined with, for instance, seasonal H1N1 and H3N2, H3N2 Variant, PdmH1N1, H5N1, H7N9 or H9N2, or other clades or candidate vaccine strains. For example, HA and NA genes from A/California/04/2009(pdm H1N1) were combined with the six internal genes of UW-PR/8 to generate "6+2" recombinant viruses. Eleven virus libraries were generated and passaged 10 times in eggs. Three rounds of limiting dilution were performed to screen for high growth mutants (FIG. 15). In one embodiment, a variant with high growth properties in MDCK cells has a PB2 viral segment with a promoter mutation (C4U) and a mutation that results in I504V (relative to the parental virus); a PB1 viral segment with a promoter mutation (C4U) and a mutation that results in E112G; a PA viral segment with a promoter mutation (C4U) and a mutation that results in S225C; a NP viral segment with mutations that result in R74K and N417D; a M viral segment with mutations that result in V97A and Y100H, and a NS viral segment with a mutation that results in K55E, where optionally the sequence of one or more viral segments, e.g., the NP viral segment, is modified to include canine codon optimized codons. In one embodiment, a variant with high growth properties in MDCK cells has a canine codon optimized PB2 viral segment with a promoter mutation (C4U) and muta-tions that result in M202L and F323L; a PB1 viral segment with a promoter mutation (C4U) and a mutation that results in Q247H; a PA viral segment with a promoter mutation (C4U) and a mutation that results in K142N; a canine codon optimized NP viral segment with a mutation that results in R74K; a M viral segment with mutations that result in V97A Y100H; and a NS viral segment with a mutation that results in K55E.

Similar experiments were conducted in Vero cells, e.g., after about 3 to 5 passages in Vero cells, using clones with high replicative properties in MDCK cells (see FIG. 16), FIG. 17 shows 5 viruses likely to have high replicative properties in Vero cells. In one embodiment, a PR8(UW) variant with high-growth properties in Vero cells has the following mutations that may be used in various combinations to increase the replicative ability of PR8(UW) viruses: PB2 segment: C4U (promoter mutation), I504V (amino acid change); PB1 segment: C4U (promoter mutation); M40L (amino acid change), G180W (amino acid change); PA segment: C4U (promoter mutation), R401K (amino acid change); NP segment: I116L (amino acid change); NS segment: A30P (amino acid change in NS1), or R118K (amino acid change in NS1).

In one embodiment, a PR8(UW) variant with high-growth properties has the following residues that may be used in various combinations with each other and/or other residues, e.g., those that enhance virus replication, to increase the replicative ability of reassortants having PR8(UW) viral segment(s): a HA segment with one or more of 136D, 162E, 179L, 182V, 184I, 252I, 449E, and/or 476I: a NA segment with 55S and/or 265V; a NS segment with NS1 having 118K; F2 with 81G; a PB1 segment with 62A, 261G, 361R, 621R, and/or 654S, and/or viral segment promoters with the growth-enhancing nucleotides described herein, e.g., having one or more of the nucleotide changes G10120, A1013U, or U1014A in the M viral segment.

Example 3

To assess the contribution of individual viral RNA (vRNA) segments to high-yield properties, a series of reassortant viruses was generated that possessed one or several vRNA segments of a high-yield PR8 (PR8-HY) variant in the background of the parental virus [UW-PR8_Indo/05 (HA+NA)]. Vero cells were infected in triplicate with the indicated viruses at a MOI of 0.005 and incubated at 37° C. in the presence of trypsin. At the indicated time points, virus titers and HA titers were determined by performing plaque or HA assays, respectively. The results are shown in FIG. 20. These data indicated that several vRNA segments contribute to the properties of PR8-HY virus. In particular, the PB2+

PB1+PA+NP vRNAs of PR8-HY virus conferred an appreciable increase in virus and HA titers, evidencing the enhanced replicative ability of this virus.

To further assess which component of the viral replication complex that provides for high-yield properties, wild-type or high-yield PB2, PB1, PA, and NP proteins were tested in various combinations in minireplicon assays in human 293T, canine MDCK, African green monkey Vero, and avian DF1 cells. The results are shown in FIG. 21. Interestingly, the PB2, PB1, PA, and NP proteins of PR8-HY virus attenuated the viral replicative ability in 293T, Vero, and DF1 cells; this effect was primarily conferred by the PB2 protein. In contrast, the combination of PB2+PB1+PA+NP proteins derived from PR8-HY virus conferred a substantial increase in replicated ability in canine MDCK cells, which were used for the selection of PR8-HY virus. The findings suggested host-dependent mechanisms underlying the high yield of PR8-HY virus. For example, the combination of PB1+PA+NP proteins, or a subset thereof, derived from PR8-HY may confer enhanced viral replicative ability in 293T, Vero, and DF1 cells.

Libraries were screened in serum-free (SF) medium, serum-containing (SC) medium, and eggs. To identify a variant that replicates efficiently in all growth media tested, viruses were passaged under changing conditions:

SF to SC to Eggs, SF to Eggs to SC

SC to SF to Eggs, SC to Eggs to SF

Eggs to SF to SC, Eggs to SC to SF

Figure 23A:
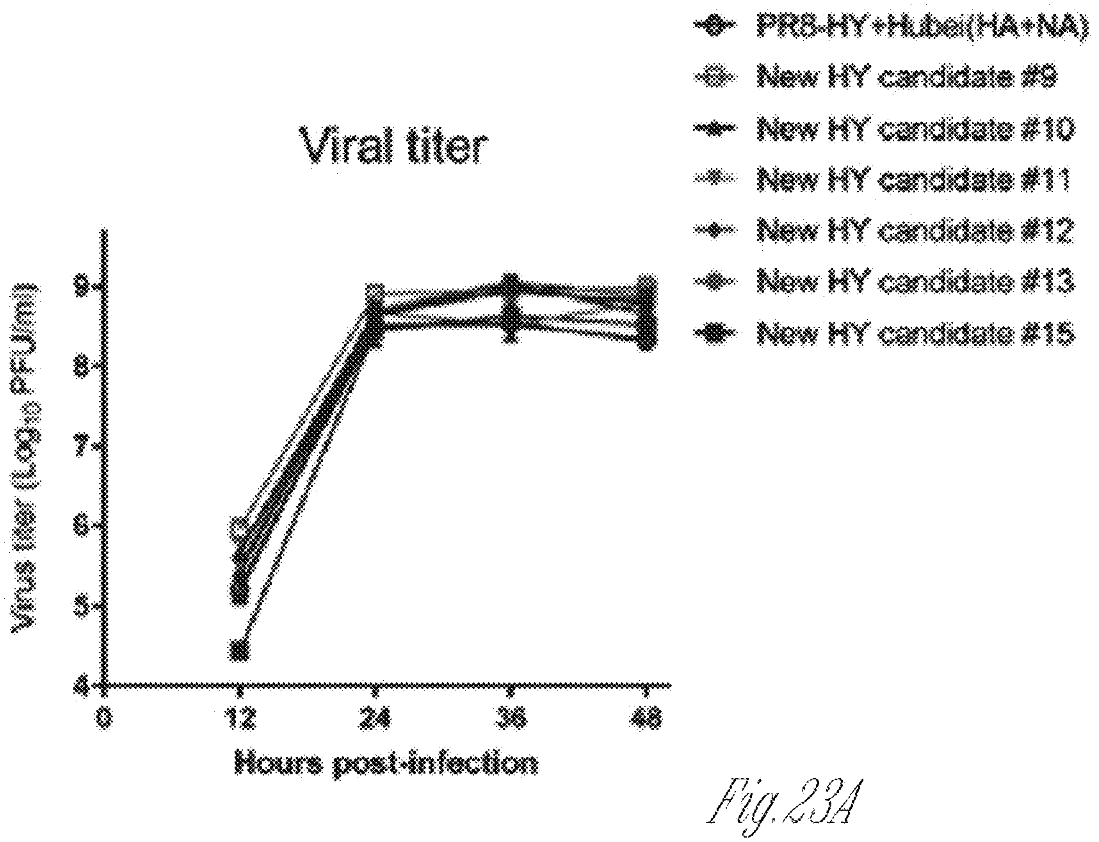
FIGS. 23A-23B. Growth kinetics analysis of Hubei/1/10 (H5N1) high yield candidates in serum-free (SF)-MDCK cells.
Figure 23B:
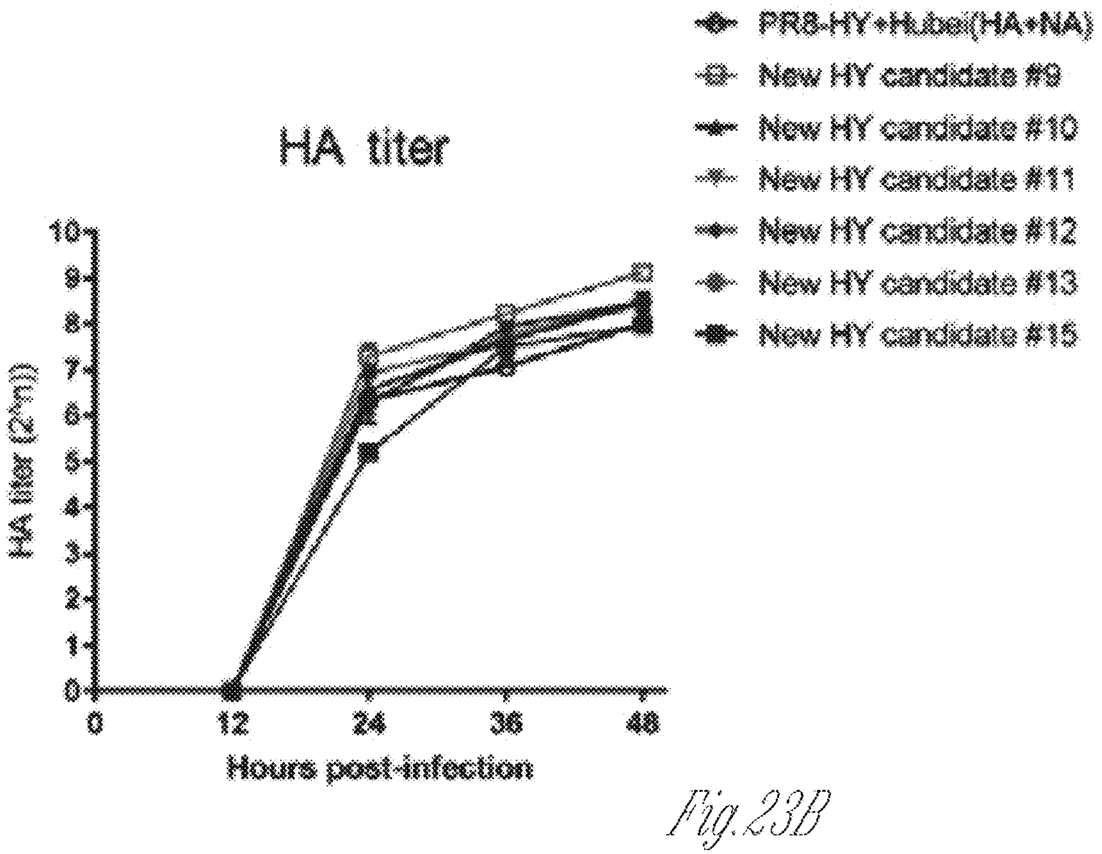

For example, other identified mutations that further improve the replication of influenza virus in cultured cells and/or embryonated chicken eggs are I711V in PB1 and M128L in the M1 protein, and those may be combined with any of the mutations disclosed herein, and in any combination (see FIGS. 23-25 and Tables 8-9). The viral titers for HY candidate #9 were 5.5-fold, 2.4-fold, 2.6-fold, 4.4-fold higher than those of the parental high yield backbone recombinant virus at 12 h, 24 h, 36 h and 48 h. HY candidate #9 contains the following mutations: PB2: C4U I504V; PB1: C4U M40L/G180W/I711V; PA: C4U R401K; NP: I116L; M1: M128L; NS1: A30P/R118K.

TABLE 8

Top 8 high HA titer clones selected from SF-MDCK PR8-HY + Hubei/1/10(H5N1) virus libraries

| | Virus stock titer | | Mutations | | | | | | | |
|---|---|---|---|---|---|---|---|---|---|---|
| Virus | HA titer (2^n) | PFU/ml | PB2 | PB1 | PA | NP | M1 | NS1 | HA (H3 numbering) | NA |
| WT | — | — | C4U I504V | C4U M40L/ G180W | C4U R401K | I116L | | A30P/ R118K | | |
| SF-14 | 10 | 1.44 × 10^9 | | +I711V | | | +M128L | | K216N | |
| SF-22 | 9.4 | 6.6 × 10^8 | | +I711V | | | | | K216N | |
| SF-37 | 9.6 | 8.7 × 10^8 | | +I711V | | | | | K216N | |
| SF-46 | 9.3 | 8.3 × 10^8 | +M467I/ K721R | | | | | | K22T/ G326R | |
| SF-42 | 9.5 | 8.7 × 10^8 | | +I711V | +R256G | | | | K216N | |
| SF-57 | 9.6 | 1 × 10^9 | | | | | | | K222T | |
| SF#15 | 10 | 1.24 × 10^9 | +Y704H | | | | | | K222T | |
| SF-E-85 | 9.6 | 9 × 10^8 | | | +N350I/ A369T | | | | K222T | |

TABLE 9

Top 12 HA titer clones selected from one round of passage of second generation mixed library (SC = serum containing; SF-serum-free.

| Medium | Plaque # | HA liter (2^n) | HA & NA | PB2 | PB1 | PA | NP | M1 | M2 | NS1 | NS2 |
|---|---|---|---|---|---|---|---|---|---|---|---|
| | WT | | Detoxified-A/Hubei/1/2010(HA + NA) | C4UI504V | C4UM40L/ G180W | C4UR401K | I116L | | | A30P/ R118K | |
| SC ↓ Egg | 11 | 7.5 | | C4UI504V + A221V | C4UM40L/ G180W | C4UR401K | I116L + K103R + V194I | S126G + 244 (mixture) M/R | W15G | A30P/ R118K + D101V | 176M |
| ↓ SF | 14 | 7.5 | | C4UI504V + A221V | C4UM40L/ G180W + I711V | C4UR401K | I116L + K103R + V194I | M128L + 244 (mixture) M/R | W15G | A30P/ R118K | E820 |
| | 23 | 8.0 | | C4UI504V + R62S + A370T | C4UM40L/ G180W + I711V | C4UR401K | I116L + K103R + V194I | F62L + 244 (mixture) M/R | W15G | A30P/ R118K | |
| | 27 | 7.5 | | C4UI504V + R62S | C4UM40L/ G180W + E178K + M290I | C4UR401K | I116L | S126G | W15G | A30P/ R118K | |
| | 33 | 7.5 | | C4UI504V | C4UM40L/ G180W + I711V | C4UR401K + K142E | I116L | S126G + 244 (mixture) M/R | W15G | A30P/ R118K + D101V | I76M |

TABLE 9-continued

Top 12 HA titer clones selected from one round of passage of second generation mixed library (SC = serum containing; SF-serum-free.

| Medium | Plaque # | HA liter (2^n) | HA & NA | PB2 | PB1 | PA | NP | M1 | M2 | NS1 | NS2 |
|---|---|---|---|---|---|---|---|---|---|---|---|
| SC ↓ SF ↓ Egg | 1 | 7.5 | | C4UI504V + R62S + A370T | C4UM40L/ G180W + M92I | C4UR401K + R256G | I116L | S126G + 244 (mixture) M/R | W15G | A30P/ R118K | N92D |
| | 2 | 7.5 | | C4UI504V + A221V | C4UM40L/ G180W + M92I | C4UR401K + R256G | I116L | M128L + 244 (mixture) M/R | | A30P/ R118K + D101V | I76M |
| | 4 | 7.5 | | C4UI504V + R62S | C4UM40L/ G180W + M325V | C4UR401K + R256G | I116L | 244(mixture) M/R | W15G | A30P/ R118K | |
| | 5 | 8.0 | | C4UI504V + A221V | C4UM40L/ G180W + M92I | C4UR401K + K142E | I116L | S126G + 244 (mixture) M/R | W15G | A30P/ R118K | E82D |
| | 13 | 8.0 | | C4UI504V | C4UM40L/ G180W + M92I | C4UR401K + K142E | I116L + K103R + V194I | M128L + 244 (mixture) M/R | W15G | A30P/ R118K | N92D |
| | 24 | 8.0 | | C4UI504V+ R62S + A370T | C4UM40L/ G180W | C4UR401K + K142E | I116L + K103R + V194I | M128L + 244 (mixture) M/R | W15G | A30P/ R118K | E82D |
| | 25 | 7.5 | | C4UI504V | C4UM40L/ G180W + M92I + N105H | C4UR401K | I116L + K103R + V194I | S126G + 244 (mixture) M/R | W15G | A30P/ R118K | N92D |

REFERENCES

*Avery's Drug Treatment: Principles and Practice of Clinical Pharmacology and Therapeutics*. 3rd edition, ADIS Press, Ltd., Williams and Wilkins, Baltimore, Md. (1987).

Aymard-Henry et al., *Virology: A Practical Approach*, Oxford IRL Press, Oxford, 119-150 (1985).

Bachmeyer, *Intervirology*, 5:260 (1975).

Berkow et al., eds., *The Merck Manual*, 16th edition, Merck & Co., Rahway, N.J. (1992).

Hatta et al., *Science*, 293:1840 (2001).

Horimoto et al., *J. Virol.*, 68:3120 (1994).

Horimoto et al., *Vaccine*, 24:3669 (2006).

Keitel et al., in Textbook of Influenza, eds. Nickolson, K. G., Webster, R. G., and Hay, A, (Blackwell, Oxford), pp. 373-390 (1998), Laver & Webster, *Virology*, 69:511 (1976), Neumann et al., *Adv. Virus Res.*, 53:265 (1999).

Neumann et al., *J, Gen, Virol.*, 83:2635 (2002),

Neumann et al., *J, Virol.*, 71:9690 (1997),

Neumann et al., *Proc, Natl. Acad, Sci, USA*, 96:9345 (1999),

Neumann et al., *Virology*, 287:243 (2001).

Osol (ed.), *Remington's Pharmaceutical Sciences*, Mack Publishing Co., Easton, Pa. 1324-1341 (1980).

Sugawara et al., *Biologicals*, 30:303 (2002).

Webby & Webster et al., *Science*, 302:1519 (2003).

Wood & Robertson, *Nat. Rev. Microbiol.*, 2:842 (2004).

World Health Organization TSR No. 673 (1982).

World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated recombinant influenza virus having PA, PB1, PB2, NP, NS, M, NA and HA viral segments, wherein the PB1 viral segment encodes a PB1 with a residue other than isoleucine at position 711 or the M viral segment encodes a M1 with a residue other than methionine at position 128, wherein the recombinant influenza virus has enhanced replication relative to a corresponding influenza virus having a PB1 viral segment that encodes a PB1 with an isoleucine at position 711 or having a M viral segment that encodes a M1 with methionine at position 128.

2. The recombinant virus of claim 1 wherein the PB1 viral segment encodes a PB1 with a residue other than isoleucine at position 711 and the M viral segment encodes a M1 with a residue other than methionine at position 128; or the PA viral segment encodes a PA with a residue other than phenylalanine at position 105, a residue other than lysine at position 142, a residue other than serine at position 149, a residue other than serine at position 225, a residue other than lysine at position 356, a residue other than threonine at position 357, a residue other than arginine at residue 401, or a residue other than isoleucine at position 550, or any combination thereof, or the PB1 viral segment further encodes a PB1 with a residue other than methionine at position 40, a residue other than glutamic acid at position 112, a residue other than glycine at position 180, or a residue other than glutamine at residue 247, or any combination thereof; or the PB2 viral segment encodes a PB2 a residue other than methionine at position 202, a residue other than phenylalanine at position 323, or a residue other than isoleucine at position 504, or any combination thereof; or the NP viral segment encodes a NP with a residue other than arginine at position 74, a residue other than isoleucine at position 116, or a residue other than asparagine at position 417, or any combination thereof; or the NS viral segment encodes a NS1 with a residue other than alanine at position 30, a residue other than lysine at position 55, or a residue other than arginine at position 118, or any combination thereof.

3. The recombinant virus of claim 1 which has a V, A, L, G, S, T, C, or M at position 711 in PB1, has an A, L, G, V, S, T, I, or Cat position 40 in PB1, has an A, L, G, V, S, T, I, or C at position 112 in PB1, has an A, L, W, Y, F, V, S, T, I, or C at position 180 in PB1, has a H, R, K, D, E, D or E at position 247 in PB1, or any combination thereof; or which has a K, H, D, E, Q or N at position 74 in NP, has a L, V, G, A, S, C or T at position 116 in NP, has a D, E, Q, K, or H at position 417 in NP, or any combination thereof; or which has a P, W, F, L, I, V, G, S, C or T at position 30 in NS1, has E, D, Q, or N at position 55, has a K, H, D, E, Q, or N at position 118 in NS1, has a L, I, V, G, A, S, C or T at position 128 in M1, or any combination thereof; or which has a C, L, I, V, G, A, or T at position 142 in PA, has a C, L, I, V, G, A, or T at position 225 in PA, has a K, H, D, E, N or Q at position 401 in PA, or any combination thereof; or which has an V, A, L, G, S, T, C, or M at position 504 in PB2, has a A, L, G, S, T, I, or C at position 202 in PB2, has a A, L, G, S, T, I, or C at position 323 in PB2, or any combination thereof; or which has a V, A, L, G, S, T, C, or M at position 711 in PB1, has an A, L, G, V, S, T, I, or C at position 40 in PB1, has an A, L, W, Y, F, V, S, T, I, or C at position 180 in PB1; has a L, V, G, A, S, C or T at position 116 in NP; has a P, W, F, L, I, V, G, S, C or T at position 30 in NS1, has a K, H, D, E, Q, or N at position 118 in NS1; has a L, I, V, G, A, S, C or T at position 128 in M1; has a K, H, D, E, N or Q at position 401 in PA; has a V, A, L, G, S, T, C, or M at position 504 in PB2; or any combination thereof; or which has a V, A, L, G, S, T, C, or Mat position 711 in PB1, has a H, R, K, D, E, DoE at position 247 in PB1; has a K, H, D, E, Q or N at position 74 in NP; has E, D, Q, or N at position 55 in NS1; has a L, I, V, G, A, S, C or T at position 128 in M1; has a C, L, I, V, G, A, or T at position 142 in PA; has an A, L, G, S, T, I, or C at position 202 in PB2, has a A, L, G, S, T, I, or C at position 323 in PB2; or any combination thereof; or which has a V, A, L, G, S, T, C, or Mat position 711 in PB1, has a A, L, G, V, S, T, I, or C at position 112 in PB1; has a K, H, D, E, Q or N at position 74 in NP, has a D, E, Q, K, or H at position 417 in NP; has E, D, Q, or N at position 55; has a L, I, V, G, A, S, C or T at position 128 in M1; has a C, L, I, V, G, A, or T at position 225 in PA; has an V, A, L, G, S, T, C, or M at position 504 in PB2; or any combination thereof.

4. The recombinant virus of claim 1 which has 142N, 225C, 356R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or any combination thereof; or which has at least one of 202L and/or 323L in PB2, 247H in PB1 or 74K in NP and optionally at least one of 142N in PA1, 55K in NS1 or 97A and/or 100H in M1; or which has at least one of 202L and/or 323L in PB2, 247H in PB1 or 74K in NP and at least one of 142N in PA1, 55K in NS1 or 97A and/or 100H in M1.

5. The recombinant virus of claim 1 which has 504V or 202L and/or 323L in PB2; or which has 40L and 180W or 247H in PB1; or which has 30P and 118K or 55E in NS1; or which has 401K or 142C in PA; or which has 116L or 74K in NP; or which has 504V in PB2, 116L in NP; 30P or 118K in NS1 and 401K in PA; and which has a V, A, L, G, S, T, C, or Mat position 711 in PB1 or a L, I, V, G, A, S, C or T at position 128 in M1.

6. The recombinant virus of claim 1 which has a U at position 4 in the viral segment for any one of PB1, PB2 or PA.

7. The recombinant virus of claim 1 which has V, A, L, G, or T at position 711 in PB1 and a L, I, V, G, A, or T at position 128 in M1.

8. The recombinant virus of claim 1 wherein the PA, PB1, PB2, NP, NS, and M viral segments comprise sequences for at least one of the following: a PB1 having the amino acid sequence encoded by SEQ ID NO: 2 or PB1 with at least 95% amino acid sequence identity to the PB1 encoded by SEQ ID NO: 2; a PB2 having the amino acid sequence encoded by SEQ ID NO:3 or PB2 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M1 and/or M2 having the amino acid sequence encoded by SEQ ID NO:5 or M1 and/or M2 with at least 95% amino acid sequence identity to the M1 and/or M2 encoded by SEQ ID NO:5; or a NS1 and/or NS2 having the amino acid sequence encoded by SEQ ID NO: 6 or NS1 and/or NS2 with at least 95% amino acid sequence identity to the NS1 and/or NS2 encoded by SEQ ID NO: 6 or wherein the PA, PB1, PB2, NP, NS, and M viral segments comprise sequences for at least one of the following: a PB1 having the amino acid sequence encoded by SEQ ID NO: 10 or PB1 with at least 95% amino acid sequence identity to the PB1 encoded by SEQ ID NO: 10; a PB2 having the amino acid sequence encoded by SEQ ID NO: 11 or PB2 with at least 95% amino acid sequence identity to the PB2 encoded by SEQ ID NO: 11; a PA having the amino acid sequence encoded by SEQ ID NO: 12 or PA with at least 95% amino acid sequence identity to the PA encoded by SEQ ID NO: 12; a NP having the amino acid sequence encoded by SEQ ID NO:13 or NP with at least 95% amino acid sequence identity to the NP encoded by SEQ ID NO:13; a M1 and/or M2 having the amino acid sequence encoded by SEQ ID NO:14 or M1 and/or M2 with at least 95% amino acid sequence identity to the M1 and/or M2 encoded by SEQ ID NO:14; or a NS1 and/or NS2 having the amino acid sequence encoded by SEQ ID NO:15 or NS1 and/or NS2 with at least 95% amino acid sequence identity to the NS1 and/or NS2 encoded by SEQ ID NO:15.

9. A vaccine having the isolated recombinant virus of claim 1.

10. A method to prepare influenza virus, comprising: contacting a cell with:

a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, wherein the PB1 DNA encodes a PB1 with a residue other than isoleucine at position 711 or the M DNA encodes a M1 with a residue other than methionine at position 128; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2;

in an amount effective to yield infectious influenza virus.

11. The method of claim 10 wherein the cell is a Vero cell, a human cell or a MDCKcell.

12. The method of claim 10 wherein the PB1 viral segment encodes a PB1 with a residue other than isoleucine at position 711 and the M viral segment encodes a M1 with a residue other than methionine at position 128; or wherein the PA viral segment encodes a PA with a residue other than phenylalanine at position 105, a residue other than lysine at position 142, a residue other than serine at position 149, a residue other than serine at position 225, a residue other than lysine at position 356, a residue other than threonine at position 357, a residue other than arginine at residue 401, or a residue other than isoleucine at position 550, or any combination thereof; or wherein the PB1 viral segment further encodes a PB1 with a residue other than methionine at position 40, a residue other than glutamic acid at position 112, a residue other than glycine at position 180, or a residue other than glutamine at residue 247, or any combination thereof; or wherein the PB2 viral segment encodes a PB2 a residue other than methionine at position 202, a residue other than phenylalanine at position 323, or a residue other than isoleucine at position 504, or any combination thereof or wherein the NP viral segment encodes a NP with a residue other than arginine at position 74, a residue other than isoleucine at position 116, or a residue other than asparagine at position 417, or any combination thereof; or wherein the NS viral segment encodes a NS1 with a residue other than alanine at position 30, a residue other than lysine at position 55, or a residue other than arginine at position 118, or any combination thereof.

13. The method of claim 10 wherein the virus has a V, A, L, G, S, T, C, or Mat position 711 in PB1, has a A, L, G, V, S, T, I, or C at position 40 in PB1, has a A, L, W, Y, F, V, S, T, I, or C at position 180 in PB1; has a L, V, G, A, S, C or T at position 116 in NP; has a P, W, F, L, I, V, G, S, C or Tat position 30 in NS1, has a K, H, D, E, Q, or N at position 118 in NS1; has a L, I, V, G, A, S, C or T at position 128 in M1; has a K, H, D, E, N or Q at position 401 in PA; has a V, A, L, G, S, T, C, or M at position 504 in PB2; or any combination thereof; or wherein the virus has a V, A, L, G, S, T, C, or M at position 711 in PB1, has a H, R, K, D, E, D or E at position 247 in PB1; has a K, H, D, E, Q or N at position 74 in NP; has E, D, Q, or N at position 55 in NS1; has a L, I, V, G, A, S, C or T at position 128 in M1; has a C, L, I, V, G, A, or T at position 142 in PA; has a A, L, G, S, T, I, or C at position 202 in PB2, has a A, L, G, S, T, I, or C at position 323 in PB2; or any combination thereof.

14. The method of claim 10 wherein the virus has a V, A, L, G, S, T, C, or Mat position 711 in PB1, has a A, L, G, V, S, T, I, or C at position 112 in PB1; has a K, H, D, E, Q or N at position 74 in NP, has a D, E, Q, K, or H at position 417 in NP; has E, D, Q, or N at position 55; has a L, I, V, G, A, S, C or T at position 128 in M1; has a C, L, I, V, G, A, or T at position 225 in PA; has an V, A, L, G, S, T, C, or M at position 504 in PB2; or any combination thereof; or wherein the virus has one or more of 142N, 225C, 356R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or any combination thereof.

15. The method of claim 10 wherein the virus has at least one of 202L and/or 323L in PB2, 247H in PB1 or 74K in NP and optionally at least one of 142N in PA1, 55K in NS1 or 97A and/or 100H in M1; or wherein the virus has at least one of 202L and/or 323L in PB2, 247H in PB1 or 74K in NP and at least one of 142N in PA1, 55K in NS1 or 97A and/or 100H in M1; or wherein the virus has 202L and/or 323L in PB2; or wherein the virus has 247H in PB1; or wherein the virus has 55E in NS1; or wherein the virus has 142C in PA; or wherein the virus has 74K in NP; or wherein the virus has 504V in PB2; or wherein the virus has 74K, 116L or 417D in NP; or wherein the virus has 30P, 55E or 118K in NS1; or wherein the virus has 225C or 401K in PA; or wherein the virus has a V, A, L, G, S, T, C, or Mat position 711 in PB1.

16. The method of claim 10 wherein the virus has a L, I, V, G, A, S, C or T at position 128 in M1.

17. A method of immunizing an avian or a mammal, comprising: administering to the avian or the mammal an effective amount of a composition comprising the recombinant virus of claim 1.

18. The method of claim 17 wherein the mammal is a human.

19. The method of claim 17 wherein the composition is injected.

20. The method of claim 17 wherein the composition is administered to the upper respiratory tract.

* * * * *

SEQUENCE LISTING

<160> NUMBER OF SEQ ID NOS: 27

<210> SEQ ID NO 1
<211> LENGTH: 2233
<212> TYPE: DNA
<213> ORGANISM: Influenza virus

<400> SEQUENCE: 1
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300

-continued

```
agtatttgca acactacagg ggctgagaaa ccaaagtttc taccagattt gtatgattac    360
aaggagaata gattcatcga aattggagta acaaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag gagatatgct tataagaagt   1680
gccataggcc aggtttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aaggagtgga ggaaagttcc   1920
attgggaagg tctgcaggac tttattagca aagtcggtat tcaacagctt gtatgcatct   1980
ccacaactag aaggattttc agctgaatca agaaaactgc ttcttatcgt tcaggctctt   2040
agggacaacc tggaacctgg gacctttgat cttgggggc tatatgaagc aattgaggag    2100
tgcctgatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233
```

<210> SEQ ID NO 2
<211> LENGTH: 2340
<212> TYPE: DNA
<213> ORGANISM: Influenza virus

<400> SEQUENCE: 2

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
```

-continued

```
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaacacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact tccttaagga tgtaatggag    540
tcaatgaaca aagaagaaat ggggatcaca actcattttc agagaaagag acgggtgaga    600
gacaatatga ctaagaaaat gataacacag agaacaatgg gtaaaaagaa gcagagattg    660
aacaaaagga gttatctaat tagagcattg accctgaaca caatgaccaa agatgctgag    720
agagggaagc taaaacggag agcaattgca accccaggga tgcaaataag gggttttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata acaccaaatg gaacgaaaat    960
cagaatcctc ggatgttttt ggccatgatc acatatatga ccagaaatca gcccgaatgg   1020
ttcagaaatg ttctaagtat tgctccaata atgttctcaa acaaaatggc gagactggga   1080
aaagggtata tgtttgagag caagagtatg aaacttagaa ctcaaatacc tgcagaaatg   1140
ctagcaagca tcgatttgaa atatttcaat gattcaacaa gaaagaagat tgaaaaaatc   1200
cgaccgctct taatagaggg gactgcatca ttgagccctg gaatgatgat gggcatgttc   1260
aatatgttaa gcactgtatt aggcgtctcc atcctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taaagaaact gtgggagcaa acccgttcca aagctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa aagaaatcga   2040
tccatcttga tacaagtcaa agaggagtac ttgaggatga acaaatgtac caaaggtgct   2100
gcaatttatt tgaaaaattc ttccccagca gttcatacag aagaccagtc gggatatcca   2160
gtatggtgga ggctatggtt tccagagccc gaattgatgc acggattgat ttcgaatctg   2220
gaaggataaa gaaagaagag ttcactgaga tcatgaagat ctgttccacc attgaagagc   2280
tcagacggca aaaatagtga atttagcttg tccttcatga aaaaatgcct tgtttctact   2340
```

<210> SEQ ID NO 3
<211> LENGTH: 2341
<212> TYPE: DNA
<213> ORGANISM: Influenza virus -continued

<400> SEQUENCE: 3

```
agcgaaagca ggtcaattat attcaatatg gaaagaataa aagaactacg aaatctaatg      60
tcgcagtctc gcacccgcga gatactcaca aaaaccaccg tggaccatat ggccataatc     120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgccg gatcagaccg agtgatggta     300
tcacctctgg ctgtgacatg gtggaatagg aatggaccaa taacaaatac agttcattat     360
ccaaaaatct acaaaactta ttttgaaaga gtcgaaaggc taaagcatgg aacctttggc     420
cctgtccatt ttagaaacca agtcaaaata cgtcggagag ttgacataaa tcctggtcat     480
gcagatctca gtgccaagga ggcacaggat gtaatcatgg aagttgtttt ccctaacgaa     540
gtgggagcca ggatactaac atcggaatcg caactaacga taaccaaaga gaagaaagaa     600
gaactccagg attgcaaaat ttctcctttg atggttgcat acatgttgga gagagaactg     660
gtccgcaaaa cgagattcct cccagtggct ggtggaacaa gcagtgtgta cattgaagtg     720
ttgcatttga ctcaaggaac atgctgggaa cagatgtata ctccaggagg ggaagtgagg     780
aatgatgatg ttgatcaaag cttgattatt gctgctagga acatagtgag aagagctgca     840
gtatcagcag atccactagc atctttattg gagatgtgcc acagcacaca gattggtgga     900
attaggatgg tagacatcct taggcagaac ccaacagaag agcaagccgt ggatatatgc     960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatatgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtca gaggtgatct gaatttcgtc aatagggcga atcaacgatt gaatcctatg    1320
catcaacttt taagacattt tcagaaggat gcgaaagtgc tttttcaaaa ttggggagtt    1380
gaacctatcg acaatgtgat gggaatgatt gggatattgc ccgacatgac tccaagcatc    1440
gagatgtcaa tgagaggagt gagaatcagc aaaatgggtg tagatgagta ctccagcacg    1500
gagagggtag tggtgagcat tgaccgtttt ttgagaatcc gggaccaacg aggaaatgta    1560
ctactgtctc ccgaggaggt cagtgaaaca cagggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca aagtagaatg    1920
cagttctcct catttactgt gaatgtgagg ggatcaggaa tgagaatact tgtaaggggc    1980
aattctcctg tattcaacta taacaaggcc acgaagagac tcacagttct cggaaaggat    2040
gctggcactt taactgaaga cccagatgaa ggcacagctg gagtggagtc cgctgttctg    2100
aggggattcc tcattctggg caaagaagac aagagatatg ggccagcact aagcatcaat    2160
gaactgagca accttgcgaa aggagagaag gctaatgtgc taattgggca aggagacgtg    2220
gtgttggtaa tgaaacggaa acgggactct agcatactta ctgacagcca gacagcgacc    2280
aaaagaattc ggatggccat caattagtgt cgaatagttt aaaaacgacc ttgtttctac    2340
```

t 2341

<210> SEQ ID NO 4
<211> LENGTH: 1565
<212> TYPE: DNA
<213> ORGANISM: Influenza virus

<400> SEQUENCE: 4
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 5
<211> LENGTH: 1027
<212> TYPE: DNA
<213> ORGANISM: Influenza virus

<400> SEQUENCE: 5
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180

-continued

```
gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttgggactca tcctagctcc agtgctggtc tgaaaaatga    720

tcttcttgaa aatttgcagg cctatcagaa acgaatgggg gtgcagatgc aacggttcaa    780

gtgatcctct cactattgcc gcaaatatca ttgggatctt gcacttgaca ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027
```

<210> SEQ ID NO 6
<211> LENGTH: 890
<212> TYPE: DNA
<213> ORGANISM: Influenza virus

<400> SEQUENCE: 6

```
agcaaaagca gggtgacaaa aacataatgg atccaaacac tgtgtcaagc tttcaggtag     60

attgctttct ttggcatgtc cgcaaacgag ttgcagacca agaactaggc gatgccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaga atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact               890
```

<210> SEQ ID NO 7
<211> LENGTH: 1775
<212> TYPE: DNA
<213> ORGANISM: Influenza virus

<400> SEQUENCE: 7

```
agcaaaagca ggggaaaata aaaacaacca aaatgaaggc aaacctactg gtcctgttat     60

gtgcacttgc agctgcagat gcagacacaa tatgtatagg ctaccatgcg aacaattcaa    120
```

```
ccgacactgt tgacacagta ctcgagaaga atgtgacagt gacacactct gttaacctgc    180
tcgaagacag ccacaacgga aaactatgta gattaaaagg aatagcccca ctacaattgg    240
ggaaatgtaa catcgccgga tggctcttgg gaaacccaga atgcgaccca ctgcttccag    300
tgagatcatg gtcctacatt gtagaaacac caaactctga gaatggaata tgttatccag    360
gagatttcat cgactatgag gagctgaggg agcaattgag ctcagtgtca tcattcgaaa    420
gattcgaaat atttcccaaa gaaagctcat ggcccaacca caacacaaac ggagtaacgg    480
cagcatgctc ccatgagggg aaaagcagtt tttacagaaa tttgctatgg ctgacggaga    540
aggagggctc atacccaaag ctgaaaaatt cttatgtgaa caaaaaaggg aaagaagtcc    600
ttgtactgtg ggtattcat cacccgccta acagtaagga acaacagaat ctctatcaga    660
atgaaaatgc ttatgtctct gtagtgactt caaattataa caggagattt accccggaaa    720
tagcagaaag acccaaagta agagatcaag ctgggaggat gaactattac tggaccttgc    780
taaaacccgg agacacaata atatttgagg caaatggaaa tctaatagca ccaatgtatg    840
ctttcgcact gagtagaggc tttgggtccg gcatcatcac ctcaaacgca tcaatgcatg    900
agtgtaacac gaagtgtcaa acacccctgg gagctataaa cagcagtctc ccttaccaga    960
atatacaccc agtcacaata ggagagtgcc caaaatacgt caggagtgcc aaattgagga   1020
tggttacagg actaaggaac attccgtcca ttcaatccag aggtctattt ggagccattg   1080
ccggttttat tgaagggga tggactggaa tgatagatgg atggtatggt tatcatcatc   1140
agaatgaaca gggatcaggc tatgcagcgg atcaaaaaag cacacaaaat gccattaacg   1200
ggattacaaa caaggtgaac actgttatcg agaaaatgaa cattcaattc acagctgtgg   1260
gtaaagaatt caacaaatta gaaaaaagga tggaaaattt aaataaaaaa gttgatgatg   1320
gatttctgga catttggaca tataatgcag aattgttagt tctactggaa aatgaaagga   1380
ctctggattt ccatgactca aatgtgaaga atctgtatga gaaagtaaaa agccaattaa   1440
agaataatgc caaagaaatc ggaaatggat gttttgagtt ctaccacaag tgtgacaatg   1500
aatgcatgga aagtgtaaga aatgggactt atgattatcc caaatattca gaagagtcaa   1560
agttgaacag ggaaaaggta gatggagtga aattggaatc aatggggatc tatcagattc   1620
tggcgatcta ctcaactgtc gccagttcac tggtgctttt ggtctccctg gggcaatca   1680
gtttctggat gtgttctaat ggatctttgc agtgcagaat atgcatctga gattagaatt   1740
tcagagatat gaggaaaaac acccttgttt ctact                              1775
```

<210> SEQ ID NO 8
<211> LENGTH: 1413
<212> TYPE: DNA
<213> ORGANISM: Influenza virus

<400> SEQUENCE: 8

```
agcaaaagca ggggtttaaa atgaatccaa atcagaaaat aataaccatt ggatcaatct     60
gtctggtagt cggactaatt agcctaatat tgcaaatagg gaatataatc tcaatatgga    120
ttagccattc aattcaaact ggaagtcaaa accatactgg aatatgcaac caaaacatca    180
ttacctataa aaatagcacc tggtaaagg acacaacttc agtgatatta accggcaatt    240
catctctttg tcccatccgt gggtgggcta tatacagcaa agacaatagc ataagaattg    300
gttccaaagg agacgttttt gtcataagag agccctttat ttcatgttct cacttggaat    360
gcaggacctt ttttctgacc caaggtgcct tactgaatga caagcattca agtgggactg    420
```

```
ttaaggacag aagcccttat agggccttaa tgagctgccc tgtcggtgaa gctccgtccc    480

cgtacaattc aagatttgaa tcggttgctt ggtcagcaag tgcatgtcat gatggcatgg    540

gctggctaac aatcggaatt tcaggtccag ataatggagc agtggctgta ttaaaataca    600

acggcataat aactgaaacc ataaaaagtt ggaggaagaa aatattgagg acacaagagt    660

ctgaatgtgc ctgtgtaaat ggttcatgtt ttactataat gactgatggc ccgagtgatg    720

ggctggcctc gtacaaaatt ttcaagatcg aaaaggggaa ggttactaaa tcaatagagt    780

tgaatgcacc taattctcac tatgaggaat gttcctgtta ccctgatacc ggcaaagtga    840

tgtgtgtgtg cagagacaat tggcatggtt cgaaccggcc atgggtgtct ttcgatcaaa    900

acctggatta tcaaatagga tacatctgca gtggggtttt cggtgacaac ccgcgtcccg    960

aagatggaac aggcagctgt ggtccagtgt atgttgatgg agcaaacgga gtaaagggat   1020

tttcatatag gtatggtaat ggtgtttgga taggaaggac caaaagtcac agttccagac   1080

atgggtttga gatgatttgg gatcctaatg gatggacaga gactgatagt aagttctctg   1140

tgaggcaaga tgttgtggca atgactgatt ggtcagggta tagcggaagt ttcgttcaac   1200

atcctgagct gacagggcta gactgtatga ggccgtgctt ctgggttgaa ttaatcaggg   1260

gacgacctaa agaaaaaaca atctggacta gtgcgagcag catttctttt tgtggcgtga   1320

atagtgatac tgtagattgg tcttggccag acggtgctga gttgccattc agcattgaca   1380

agtagtctgt tcaaaaaact ccttgtttct act                                1413
```

<210> SEQ ID NO 9

<400> SEQUENCE: 9

000

<210> SEQ ID NO 10
<211> LENGTH: 2342
<212> TYPE: DNA
<213> ORGANISM: Influenza virus

<400> SEQUENCE: 10

```
agcgaaagca ggcaaaccat ttgaatggat gtcaatccga ccttactttt cttaaaagtg     60

ccagcacaaa atgctataag cacaactttc ccttataccg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaagcaatg    300

gctttccttg aggaatccca tcctggtatt tttgaaaact cgtgtattga aacgatggag    360

gttgttcagc aaacactgag tagacaagct gacacaaggc cgacagacct atgactggac    420

tttaaataga aaccagcctg ctgcaacagc attggccaac acaatagaag tgttcagatc    480

aaatggcctc acggccaatg agtcaggaag gctcatagac ttccttaagg atgtaatgga    540

gtcaatgaaa aaagaagaaa tggggatcac aactcatttt cagagaaaga gacgggtgag    600

agacaatatg actaagaaaa tgataacaca gagaacaata ggtaaaagga aacagagatt    660

gaacaaaagg ggttatctaa ttagagcatt gaccctgaac acaatgacca aagatgctga    720

gagagggaag ctaaaacgga gagcaattgc aaccccaggg atgcaaataa gggggtttgt    780

atactttgtt gagacactgg caaggagtat atgtgagaaa cttgaacaat cagggttgcc    840

agttggaggc aatgagaaga aagcaaagtt ggcaaatgtt gtaaggaaga tgatgaccaa    900
```

ttctcaggac accgaacttt ctttcaccat cactggagat aacaccaaat ggaacgaaaa 960
tcagaatcct cggatgtttt tggccatgat cacatatatg accagaaatc agcccgaatg 1020
gttcagaaat gttctaagta ttgctccaat aatgttctca aacaaaatgg cgagactggg 1080
aaaagggtat atgtttgaga gcaagagtat gaaacttaga actcaaatac ctgcagaaat 1140
gctagcaagc attgatttga aatatttcaa tgattcaaca agaaagaaga ttgaaaaaat 1200
ccgaccgctc ttaatagagg ggactgcatc attgagccct ggaatgatga tgggcatgtt 1260
caatatgtta agcactgtat taggcgtctc catcctgaat cttggacaaa agagatacac 1320
caagactact tactggtggg atggtcttca atcctctgac gattttgctc tgattgtgaa 1380
tgcacccaat catgaaggga ttcaagccgg agtcgacagg ttttatcgaa cctgtaagct 1440
acttggaatc aatatgagca agaaaaagtc ttacataaac agaacaggta catttgaatt 1500
cacaagtttt ttctatcgtt atgggtttgt tgccaatttc agcatggagc ttcccagttt 1560
tggggtgtct gggatcaacg agtcagcgga catgagtatt ggagttactg tcatcaaaaa 1620
caatatgata aacaatgatc ttggtccagc aacagctcaa atggcccttc agttgttcat 1680
caaagattac aggtacacgt accgatgcca tagaggtgac acacaaatac aaacccgaag 1740
atcatttgaa ataaagaaac tgtgggagca aacccgttcc aaagctggac tgctggtctc 1800
cgacggaggc ccaaatttat acaacattag aaatctccac attcctgaag tctgcctaaa 1860
atgggaattg atggatgagg attaccaggg gcgtttatgc aacccactga acccatttgt 1920
cagccataaa gaaattgaat caatgaacaa tgcagtgatg atgccagcac atggtccagc 1980
caaaaacatg gagtatgatg ctgttgcaac aacacactcc tggatcccca aaagaaatcg 2040
atccatcttg aatacaagtc aaagaggagt acttgaagat gaacaaatgt accaaaggtg 2100
ctggaattta tttgaaaaat tcttccccag cagttcatac agaagaccag tcgggatatc 2160
cagtatggtg gaggctatgg tttccagagc ccgaattgat gcacggattg atttcgaatc 2220
tggaaggata aagaaagaag agttcactga gatcatgaag atctgttcca ccattgaaga 2280
gctcagacgg caaaaatagt gaatttagct tgtccttcat gaaaaaatgc cttgtttcta 2340
ct 2342

<210> SEQ ID NO 11
<211> LENGTH: 2341
<212> TYPE: DNA
<213> ORGANISM: Influenza virus

<400> SEQUENCE: 11
agcgaaagca ggtcaattat attcaatatg gaaagaataa aagaactaag aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcaaggac aaactttatg gagtaaaatg aatgatgccg gatcagaccg agtgatggta 300
tcacctctgg ctgtgacatg gtggaatagg aatggaccaa tgacaaatac agttcattat 360
ccaaaaatct acaaaactta ttttgaaaga gtcgaaaggc taaagcatgg aacctttggc 420
cctgtccatt ttagaaacca agtcaaaata cgtcggagag ttgacataaa tcctggtcat 480
gcagatctca gtgccaagga ggcacaggat gtaatcatgg aagttgtttt ccctaacgaa 540
gtgggagcca ggatactaac atcggaatcg caactaacga taaccaaaga gaagaaagaa 600
gaactccagg attgcaaaat ttctcctttg atggttgcat acatgttgga gagagaactg 660

```
gtccgcaaaa cgagattcct cccagtggct ggtggaacaa gcagtgtgta cattgaagtg    720

ttgcatttga ctcaaggaac atgctgggaa cagatgtata ctccaggagg ggaagtgaag    780

aatgatgatg ttgatcaaag cttgattatt gctgctagga acatagtgag aagagctgca    840

gtatcagcag acccactagc atctttattg gagatgtgcc acagcacaca gattggtgga    900

attaggatgg tagacatcct taagcagaac ccaacagaag agcaagccgt ggatatatgc    960

aaggctgcaa tgggactgag aattagctca tccttcagtt ttggtggatt cacatttaag   1020

agaacaagcg gatcatcagt caagagagag gaagaggtgc ttacgggcaa tcttcaaaca   1080

ttgaagataa gagtgcatga gggatctgaa gagttcacaa tggttgggag aagagcaaca   1140

gccatactca gaaaagcaac caggagattg attcagctga tagtgagtgg gagagacgaa   1200

cagtcgattg ccgaagcaat aattgtggcc atggtatttt cacaagagga ttgtatgata   1260

aaagcagtta gaggtgatct gaatttcgtc aatagggcga atcagcgact gaatcctatg   1320

catcaacttt taagacattt tcagaaggat gcgaaagtgc tttttcaaaa ttggggagtt   1380

gaacctatcg acaatgtgat gggaatgatt gggatattgc ccgacatgac tccaagcatc   1440

gagatgtcaa tgagaggagt gagaatcagc aaaatgggtg tagatgagta ctccagcacg   1500

gagagggtag tggtgagcat tgaccggttc ttgagagtca gggaccaacg aggaaatgta   1560

ctactgtctc ccgaggaggt cagtgaaaca cagggaacag agaaactgac aataacttac   1620

tcatcgtcaa tgatgtggga gattaatggt cctgaatcag tgttggtcaa tacctatcaa   1680

tggatcatca gaaactggga aactgttaaa attcagtggt cccagaaccc tacaatgcta   1740

tacaataaaa tggaatttga accatttcag tctttagtac ctaaggccat tagaggccaa   1800

tacagtgggt ttgtaagaac tctgttccaa caaatgaggg atgtgcttgg gacatttgat   1860

accgcacaga taataaaact tcttcccttc gcagccgctc caccaaagca aagtagaatg   1920

cagttctcct catttactgt gaatgtgagg ggatcaggaa tgagaatact tgtaaggggc   1980

aattctcctg tattcaacta caacaaggcc acgaagagac tcacagttct cggaaaggat   2040

gctggcactt taaccgaaga cccagatgaa ggcacagctg gagtggagtc cgctgttctg   2100

aggggattcc tcattctggg caaagaagac aggagatatg ggccagcatt aagcatcaat   2160

gaactgagca accttgcgaa aggagagaag gctaatgtgc taattgggca aggagacgtg   2220

gtgttggtaa tgaaacgaaa acgggactct agcatactta ctgacagcca gacagcgacc   2280

aaaagaattc ggatggccat caattagtgt cgaatagttt aaaaacgacc ttgtttctac   2340

t                                                                   2341
```

<210> SEQ ID NO 12
<211> LENGTH: 2234
<212> TYPE: DNA
<213> ORGANISM: Influenza virus

<400> SEQUENCE: 12

```
agcgaaagca ggtactgatt caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agatttccac    180

ttcatcaatg agcaaggcga gtcaataatc gtagaacttg gtgatcctaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360
```

```
aaggaaaata gattcatcga aattggagta acaaggagag aagttcacat atactatctg    420
gaaaaggcca ataaaattaa atctgagaaa acacacatcc acattttctc gttcactggg    480
gaagaaatgg ccacaagggc cgactacact ctcgatgaag aaagcagggc taggatcaaa    540
accaggctat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaaaaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagttcaac   1260
aaggcatgcg aactgacaga ttcaagctgg atagagcttg atgagattgg agaagatgtg   1320
gctccaattg aacacattgc aagcatgaga aggaattatt tcacatcaga ggtgtctcac   1380
tgcagagcca cagaatacat aatgaagggg gtgtacatca atactgcctt acttaatgca   1440
tcttgtgcag caatggatga tttccaatta attccaatga taagcaagtg tagaactaag   1500
gagggaaggc gaaagaccaa cttgtatggt ttcatcataa aggaagatc ccacttaagg    1560
aatgacaccg acgtggtaaa ctttgtgagc atggagtttt ctctcactga cccaagactt   1620
gaaccacaca aatgggagaa gtactgtgtt cttgagatag gagatatgct tctaagaagt   1680
gccataggcc aggtttcaag gcccatgttc ttgtatgtga ggacaaatgg aacctcaaaa   1740
attaaaatga aatggggaat ggagatgagg cgttgtctcc tccagtcact tcaacaaatt   1800
gagagtatga ttgaagctga gtcctctgtc aaagagaaag acatgaccaa agagttcttt   1860
gagaacaaat cagaaacatg gcccattgga gagtctccca aggagtgga ggaaagttcc    1920
attggggaag gtctgcagga ctttattagc aaagtcggta tttaacagct tgtatgcatc   1980
tccacaacta gaaggatttt cagctgaatc aagaaaactg cttcttatcg ttcaggctct   2040
tagggacaat ctggaacctg ggacctttga tcttgggggg ctatatgaag caattgagga   2100
gtgcctaatt aatgatccct gggttttgct taatgcttct tggttcaact ccttccttac   2160
acatgcattg agttagttgt ggcagtgcta ctatttgcta tccatactgt ccaaaaaagt   2220
accttgtttc tact                                                     2234
```

<210> SEQ ID NO 13
<211> LENGTH: 1565
<212> TYPE: DNA
<213> ORGANISM: Influenza virus

<400> SEQUENCE: 13

```
agcaaaagca gggtagataa tcactcactg agtgacatca aaatcatggc gtcccaaggc     60
accaaacggt cttacgaaca gatggagact gatggagaac gccagaatgc cactgaaatc    120
agagcatccg tcggaaaaat gattggtgga attggacgat tctacatcca aatgtgcaca    180
gaacttaaac tcagtgatta tgagggacgg ttgatccaaa acagcttaac aatagagaga    240
```

```
atggtgctct ctgcttttga cgaaaggaga aataaatacc tggaagaaca tcccagtgcg    300
gggaaagatc ctaagaaaac tggaggacct atatacagaa gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag ggctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag ggaatgctga gttcgaagat ctcacttttc tagcacggtc tgcactcata    840
ttgagagggt cggttgctca caagtcctgc ctgcctgcct gtgtgtatgg acctgccgta    900
gccagtgggt acgactttga aagagaggga tactctctag tcggaataga ccctttcaga    960
ctgcttcaaa acagccaagt gtacagccta atcagaccaa atgagaatcc agcacacaag   1020
agtcaactgg tgtggatggc atgccattct gccgcatttg aagatctaag agtattgagc   1080
ttcatcaaag ggacgaaggt ggtcccaaga gggaagcttt ccactagagg agttcaaatt   1140
gcttccaatg aaaatatgga gactatggaa tcaagtacac ttgaactgag aagcaggtac   1200
tgggccataa ggaccagaag tggaggaaac accaatcaac agagggcatc tgcgggccaa   1260
atcagcatac aacctacgtt ctcagtacag agaaatctcc cttttgacag aacaaccgtt   1320
atggcagcat tcactgggaa tacagagggg agaacatctg acatgaggac cgaaatcata   1380
aggatgatgg aaagtgcaag accagaagat gtgtctttcc aggggcgggg agtcttcgag   1440
ctctcggacg aaaaggcagc gagcccgatc gtgccttcct ttgacatgag taatgaagga   1500
tcttatttct tcggagacaa tgcagaggag tacgacaatt aaagaaaaat acccttgttt   1560
ctact                                                               1565
```

<210> SEQ ID NO 14
<211> LENGTH: 1027
<212> TYPE: DNA
<213> ORGANISM: Influenza virus

<400> SEQUENCE: 14

```
agcaaaagca ggtagatatt gaaagatgag tcttctaacc gaggtcgaaa cgtacgttct     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg gggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
```

-continued tcttcttgaa aatttgcagg cctatcagaa acgaatgggg gtgcagatgc aacggttcaa 780
gtgatcctct cgctattgcc gcaaatatca ttgggatctt gcacttgata ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctact 1027

<210> SEQ ID NO 15
<211> LENGTH: 890
<212> TYPE: DNA
<213> ORGANISM: Influenza virus

<400> SEQUENCE: 15
agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aaggggcagc actcttggtc 180
tggacatcga gacagccaca cgtgctggaa agcagatagt ggagcggatt ctgaaagaag 240
aatccgatga ggcacttaaa atgaccatgg cctctgtacc tgcgtcgcgt tacctaaccg 300
acatgactct tgaggaaatg tcaagggaat ggtccatgct catacccaag cagaaagtgg 360
caggccctct ttgtatcaga atggaccagg cgatcatgga taaaaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga aggtaacaga gaatagtttt 780
gagcaaataa catttatgca agccttacat ctattgcttg aagtggagca agagataaga 840
actttctcat ttcagcttat ttaataataa aaaacaccct tgtttctact 890

<210> SEQ ID NO 16
<211> LENGTH: 2341
<212> TYPE: DNA
<213> ORGANISM: Influenza virus

<400> SEQUENCE: 16
agcgaaagca ggtcaattat attcaatatg gaaagaataa aagaactacg aaatctaatg 60
tcgcagtctc gcacccgcga gatactcaca aaaaccaccg tggaccatat ggccataatc 120
aagaagtaca catcaggaag acaggagaag aacccagcac tgaggatgaa atggatgatg 180
gcaatgaaat atccaattac agcagacaag aggatcaccg aaatgattcc tgagagaaat 240
gagcagggac agactctgtg gagtaaaatg aatgatgccg gatcagaccg agtgatggtg 300
tcacctctgg ctgtgacatg gtggaatagg aatggaccaa tcacaaatac agtgcattat 360
ccaaaaatct acaaaactta ttttgaaaga gtcgaaaggc tgaagcatgg aacctttggc 420
cctgtccatt ttagaaacca ggtcaaaatc cggcggagag tggacatcaa tcctggtcat 480
gcagatctca gtgccaagga ggcacaggat gtgatcatgg aagtggtgtt ccctaacgaa 540
gtgggagcca ggattctgac atccgaatcc cagctgacca ttaccaaaga gaagaaagaa 600
gaactccagg attgcaaaat ttctcctctg atggtggcat acatgctgga gagagaactg 660

-continued

```
gtccgcaaaa caagattcct cccagtggct ggtggaacaa gcagtgtgta cattgaagtg    720

ctgcatctga ctcagggaac atgctgggaa cagatgtata ctccaggagg ggaagtgagg    780

aatgatgatg tggatcagag cctgattatt gctgctagga acattgtgag aagagctgca    840

gtgtcagcag atccactggc atctctgctg gagatgtgcc acagcacaca gattggtgga    900

attaggatgg tggacatcct gaggcagaac ccaacagaag agcaggccgt ggatatttgc    960

aaggctgcaa tgggactgag aattagctca tccttcagtt ttggtggatt cacatttaag   1020

agaacaagcg gatcatcagt caagagagag gaagaggtgc tgaccggcaa tctgcagaca   1080

ctgaagatca gagtgcatga gggatatgaa gagttcacaa tggtggggag aagagcaaca   1140

gccatcctca gaaaagcaac caggagactg attcagctga tcgtgagtgg gagagacgaa   1200

cagtccattg ccgaagcaat tattgtggcc atggtgtttt cacaggagga ttgtatgatt   1260

aaagcagtca gaggtgatct gaatttcgtc aatagggcca atcagcgact gaatcctatg   1320

catcagctgc tgagacattt tcagaaggat gccaaagtgc tgtttcagaa ttggggagtg   1380

gaacctatcg acaatgtgat gggaatgatt gggatcctgc ccgacatgac tccaagcatc   1440

gagatgtcaa tgagaggagt gagaatcagc aaaatgggtg tggatgagta ctccagcacc   1500

gagagggtcg tggtgagcat tgacagattt ctgagaatcc gggaccagcg aggaaatgtg   1560

ctcctgtctc ccgaggaggt cagtgaaaca cagggaacag agaaactgac aattacttac   1620

tcatcctcaa tgatgtggga gattaatggt cctgaatcag tgctggtcaa tacctatcag   1680

tggatcatca gaaactggga aactgtgaaa attcagtggt cccagaaccc tacaatgctg   1740

tacaataaaa tggaatttga accatttcag tctctggtgc ctaaggccat tagaggccag   1800

tacagtgggt ttgtgagaac tctgttccag cagatgaggg atgtgctggg gacatttgat   1860

accgcacaga ttattaaact gctgcccttc gcagccgctc caccaaagca gagtagaatg   1920

cagttctcct catttactgt gaatgtgagg ggatcaggaa tgagaatcct ggtgaggggc   1980

aattctcctg tgttcaacta taacaaggcc accaagagac tcacagtgct cggaaaggat   2040

gctggcactc tgactgaaga cccagatgaa ggcacagctg gagtggagtc cgctgtgctg   2100

aggggattcc tcattctggg caaagaagac aagagatatg ggccagcact gagcatcaat   2160

gaactgagca acctggccaa aggagagaag gctaatgtgc taattgggca aggagacgtg   2220

gtgttggtaa tgaaacggaa acgggactct agcatactta ctgacagcca gacagcgacc   2280

aaaagaattc ggatggccat caattagtgt cgaatagttt aaaaacgacc ttgtttctac   2340

t                                                                   2341
```

```
<210> SEQ ID NO 17
<211> LENGTH: 2341
<212> TYPE: DNA
<213> ORGANISM: Influenza virus

<400> SEQUENCE: 17

agcgaaagca ggcaaaccat ttgaatggat gtcaatccga ccttactttt cttaaaagtg     60

ccagcacaaa atgctataag cacaactttc ccttatactg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360
```

gttgttcagc aaacacgagt ggacaagctg acacagggcc gacagaccta tgactggact 420
ctgaatagaa accagcctgc tgcaacagca ctggccaaca caatcgaagt gttcagatca 480
aatggcctca ccgccaatga gtctggaagg ctcatcgact tcctgaagga tgtgatggag 540
tcaatgaaca aagaagaaat ggggatcaca actcattttc agagaaagag acgggtgaga 600
gacaatatga ctaagaaaat gattacacag agaacaatgg gtaaaaagaa gcagagactg 660
aacaaaagga gttatctgat tagagcactg accctgaaca caatgaccaa agatgctgag 720
agagggaagc tgaaacggag agcaattgca accccaggga tgcagattag ggggtttgtg 780
tactttgtgg agacactggc aaggagtatt tgtgagaaac tggaacagtc agggctgcca 840
gtgggaggca atgagaagaa agcaaagctg gcaaatgtgg tgaggaagat gatgaccaat 900
tctcaggaca ccgaactgtc tttcaccatc actggagata acaccaaatg gaacgaaaat 960
cagaatcctc ggatgtttct ggccatgatc acatatatga ccagaaatca gcccgaatgg 1020
ttcagaaatg tgctgagtat tgctccaatt atgttctcaa acaaaatggc cagactggga 1080
aaagggtata tgtttgagag caagagtatg aaactgagaa ctcagattcc tgcagaaatg 1140
ctggcaagca tcgatctgaa atatttcaat gattcaacaa gaaagaagat tgaaaaaatc 1200
cgacccctcc tgattgaggg gactgcatca ctgagccctg gaatgatgat gggcatgttc 1260
aatatgctga gcactgtgct gggcgtctcc atcctgaatc tgggacagaa gagatacacc 1320
aagactactt actggtggga tggtctgcag tcctctgacg attttgctct gattgtgaat 1380
gcacccaatc atgaagggat tcaggccgga gtcgacaggt tttatcgaac ctgtaagctg 1440
ctgggaatca atatgagcaa gaaaaagtct tacatcaaca gaacaggtac atttgaattc 1500
acaagttttt tctatcgcta tgggtttgtg gccaatttca gcatggagct gcccagtttt 1560
ggggtgtctg ggatcaacga gtcagccgac atgagtattg gagtgactgt catcaaaaac 1620
aatatgatca acaatgatct gggtccagca acagctcaga tggccctgca gctgttcatc 1680
aaagattaca ggtacaccta ccgatgccat atcggtgaca cacagattca gacccgaaga 1740
tcatttgaaa tcaagaaact gtgggagcag acccgctcca aagctggact gctggtctcc 1800
gacggaggcc caaatctgta caacattaga aatctccaca ttcctgaagt ctgcctgaaa 1860
tgggaactga tggatgagga ttaccagggg cgcctgtgca acccactgaa cccatttgtc 1920
agccataaag aaattgaatc aatgaacaat gcagtgatga tgccagcaca tggtccagcc 1980
aaaaacatgg agtatgatgc tgtggcaaca acacactcct ggatccccaa aagaaatcga 2040
tccatcctga atacaagtca gagaggagtg ctggaggatg aacagatgta ccagaggtgc 2100
tgcaatctgt ttgaaaaatt cttccccagc agttcataca gaagaccagt cgggatctcc 2160
agtatggtgg aggctatggt gtccagagcc cgaattgatg cacggattga tttcgaatct 2220
ggaaggatca agaaagaaga gttcactgag atcatgaaga tctgttccac cattgaagag 2280
ctcagacggc aaaaatagtg aatttagctt gtccttcatg aaaaaatgcc ttgtttctac 2340
t 2341

<210> SEQ ID NO 18
<211> LENGTH: 2233
<212> TYPE: DNA
<213> ORGANISM: Influenza virus

<400> SEQUENCE: 18
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120

-continued

```
aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gattcatcga aattggagta acaaggagag aagttcacat atactatctg    420

gaaaaggcca ataaaattaa atctgagaaa acacacatcc acattttctc gttcactggg    480

gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc ttttctgaaa acaacaccac gaccactgag actgcccaat    840

gggcctccct gttctcagcg gtccaaattc ctgctgatgg atgccctgaa actgagcatt    900

gaggacccaa gtcatgaagg agagggaatt cccctgtatg atgcaatcaa atgcatgaga    960

acattctttg gatggaagga acccaatgtg gtgaaaccac acgaaaaggg aatcaatcca   1020

aattatctgc tgtcatggaa gcaggtgctg gcagaactgc aggacattga gaatgaggag   1080

aaaattccaa agactaaaaa tatgaagaaa acaagtcagc tgaagtgggc actgggtgag   1140

aacatggcac cagaaaaggt ggactttgac gactgtaaag atgtgggtga tctgaagcag   1200

tatgatagtg atgaaccaga actgaggtcc ctggcaagtt ggattcagaa tgagtttaac   1260

aaggcatgcg aactgacaga ttcaagctgg attgagctcg atgagattgg agaagatgtg   1320

gctccaattg aacacattgc aagcatgaga aggaattatt tcacatcaga ggtgtctcac   1380

tgcagagcca cagaatacat catgaaggga gtgtacatca atactgccct gctgaatgca   1440

tcttgtgcag caatggatga tttccagctg attccaatga tcagcaagtg tagaactaag   1500

gagggaaggc gaaagaccaa cctgtatggt ttcatcatca aaggaagatc ccacctgagg   1560

aatgacaccg acgtggtgaa ctttgtgagc atggagtttt ctctcactga cccaagactg   1620

gaaccacata aatgggagaa gtactgtgtg ctggagattg gagatatgct gatcagaagt   1680

gccattggcc aggtgtcaag gcccatgttc ctgtatgtga gaacaaatgg aacctcaaaa   1740

attaaaatga aatggggaat ggagatgagg cgctgcctcc tccagtcact gcagcagatt   1800

gagagtatga ttgaagctga gtcctctgtc aaagagaaag acatgaccaa agagttcttt   1860

gagaacaaat cagaaacatg gcccattgga gagtccccca aggagtggaa ggaaagttcc   1920

attgggaagg tctgcaggac tctgctggca aagtccgtgt tcaacagcct gtatgcatct   1980

ccacagctgg aaggattttc agctgaatca agaaaactgc tgctgatcgt gcaggctctg   2040

agggacaacc tggaacctgg gacctttgat ctgggggggc tgtatgaagc aattgaggag   2100

tgcctgatta atgatccctg ggtgctgctg aatgcttctt ggttcaactc cttccttaca   2160

catgcattga gttagttgtg gcagtgctac tatttgctat ccatactgtc caaaaaagta   2220

ccttgtttct act                                                       2233
```

<210> SEQ ID NO 19
<211> LENGTH: 1565
<212> TYPE: DNA
<213> ORGANISM: Influenza virus

<400> SEQUENCE: 19
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca gatgtgcacc 180
gaactcaaac tcagtgatta tgagggacgg ctgatccaga acagcctgac aatcgagaga 240
atggtgctct ctgcttttga cgaaaggaga aataaatacc tggaagaaca tcccagtgcc 300
gggaaagatc ctaagaaaac tggaggacct atctacagga gagtgaacgg aaagtggatg 360
agagaactca tcctgtatga caaagaagaa atcaggcgaa tctggcgcca ggctaataat 420
ggtgacgatg caaccgctgg tctgactcac atgatgatct ggcattccaa tctgaatgat 480
gcaacttatc agaggacaag agctctggtg cgcaccggaa tggatcccag gatgtgctct 540
ctgatgcagg gttcaactct ccctaggagg tctggagccg caggtgctgc agtcaaagga 600
gtgggaacaa tggtgatgga actggtcaga atgatcaaaa gagggatcaa tgatcggaac 660
ttctggaggg gtgagaatgg acgaaaaaca agaattgctt atgaaagaat gtgcaacatt 720
ctcaaaggga aatttcagac tgctgcacag aaagcaatga tggatcaggt gagagagagc 780
cggaacccag ggaatgctga gttcgaagat ctcacttttc tggcacggtc tgcactcatc 840
ctgagagggt ccgtggctca caagtcctgc ctgcctgcct gtgtgtatgg acctgccgtg 900
gccagtgggt acgactttga aagggaggga tactctctgg tcggaattga ccctttcaga 960
ctgctgcaga acagccaggt gtacagcctg atcagaccaa atgagaatcc agcacacaag 1020
agtcagctgg tgtggatggc atgccattct gccgcatttg aagatctgag agtgctgagc 1080
ttcatcaaag ggaccaaggt gctcccaaga gggaagctgt ccactagagg agtgcagatt 1140
gcttccaatg aaaatatgga gactatggaa tcaagtacac tggaactgag aagcaggtac 1200
tgggccatca ggaccagaag tggaggaaac accaatcagc agagggcatc tgccggccag 1260
atcagcattc agcctacctt ctcagtgcag agaaatctcc cttttgacag aacaaccatt 1320
atggcagcat tcaatgggaa tacagagggg agaacatctg acatgaggac cgaaatcatc 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 20
<211> LENGTH: 1684
<212> TYPE: DNA
<213> ORGANISM: Influenza virus

<400> SEQUENCE: 20
atgaacactc aaatcctggt attcgctctg attgcgatca ttccaacaaa tgcagacaaa 60
atctgcctcg gacatcatgc cgtgtcaaac ggaaccaaag taaacacatt aactgaaaga 120
ggagtggaag tcgtcaatgc aactgaaaca gtggaacgaa caaacatccc caggatctgc 180
tcaaaaggga aaaggacagt tgacctcggt caatgtggac tcctggggac aatcactgga 240
ccacctcaat gtgaccaatt cctagaattt tcagccgatt taattattga gaggcgagaa 300
ggaagtgatg tctgttatcc tgggaaattc gtgaatgaag aagctctgag gcaaattctc 360
agagaatcag gcggaattga caaggaagca atgggattca catacagtgg aataagaact 420
aatggagcaa ccagtgcatg taggagatca ggatcttcat tctatgcaga aatgaaatgg 480

```
ctcctgtcaa acacagataa tgctgcattc ccgccagatg actaagtcat ataaaaatac    540

aagaaaaagc ccagctctaa tagtatgggg gatccatcat tccgtatcaa ctgcagagca    600

aaccaagcta tatgggagtg gaaacaaact ggtgacagtt gggagttcta attatcaaca    660

atcttttgta ccgagtccag gagcgagacc acaagttaat ggtctatctg gaagaattga    720

ctttcattgg ctaatgctaa atcccaatga tacagtcact ttcagtttca atggggcttt    780

catagctcca gaccgtgcaa gcttcctgag aggaaaatct atgggaatcc agagtggagt    840

acaggttgat gccaattgtg aaggggactg ctatcatagt ggagggacaa taataagtaa    900

cttgccattt cagaacatag atagcagggc agttggaaaa tgtccgagat atgttaagca    960

aaggagtctg ctgctagcaa cagggatgaa gaatgttcct gagattccaa agggaagagg   1020

cctatttggt gctatagcgg gtttcattga aaatggatgg gaaggcctaa ttgatggttg   1080

gtatggtttc agacaccaga atgcacaggg agagggaact gctgcagatt acaaaagcac   1140

tcaatcggca attgatcaaa taacaggaaa attaaaccgg cttatagaaa aaaccaacca   1200

acaatttgag ttgatagaca atgaattcaa tgaggtagag aagcaaatcg gtaatgtgat   1260

aaattggacc agagattcta taacagaagt gtggtcatac aatgctgaac tcttggtagc   1320

aatggagaac cagcatacaa ttgatctggc tgattcagaa atggacaaac tgtacgaacg   1380

agtgaaaaga cagctgagag agaatgctga agaagatggc actggttgct ttgaaatatt   1440

tcacaagtgt gatgatgact gtatggccag tattagaaat aacacctatg atcacagcaa   1500

atacagggaa gaggcaatgc aaaatagaat acagattgac ccagtcaaac taagcagcgg   1560

ctacaaagat gtgatacttt ggtttagctt cggggcatca tgtttcatac ttctagccat   1620

tgtaatgggc cttgtcttca tatgtgtaaa gaatggaaac atgcggtgca ctatttgtat   1680

ataa                                                                1684
```

<210> SEQ ID NO 21
<211> LENGTH: 560
<212> TYPE: PRT
<213> ORGANISM: Influenza virus

<400> SEQUENCE: 21

```
Met Asn Thr Gln Ile Leu Val Phe Ala Leu Ser Lys Gly Lys Arg Thr
1               5                   10                  15

Val Asp Leu Gly Ile Ala Ile Ile Pro Thr Asn Ala Asp Lys Gln Cys
            20                  25                  30

Gly Leu Leu Gly Thr Ile Thr Gly Ile Cys Leu Gly His His Ala Val
        35                  40                  45

Ser Asn Pro Pro Gln Cys Asp Gln Phe Leu Glu Phe Gly Thr Lys Val
    50                  55                  60

Asn Thr Leu Thr Glu Arg Ser Ala Asp Leu Ile Ile Glu Arg Arg Glu
65                  70                  75                  80

Gly Val Glu Val Val Asn Ala Thr Glu Thr Gly Ser Asp Val Cys Tyr
                85                  90                  95

Pro Gly Lys Phe Val Glu Arg Thr Asn Ile Pro Arg Ile Cys Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
```

-continued

```
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560
```

<210> SEQ ID NO 22

<211> LENGTH: 1398
<212> TYPE: DNA
<213> ORGANISM: Influenza virus

<400> SEQUENCE: 22

```
atgaatccaa atcagaagat tctatgcact tcagccactg ctatcataat aggcgcaatc     60
gcagtactca ttggaatagc aaacctagga ttgaacatag gactgcatct aaaaccgggc    120
tgcaattgct cacactcaca acctgaaaca accaacacaa gccaaacaat aataaacaac    180
tattataatg aaacaaacat caccaacatc caaatggaag agagaacaag caggaatttc    240
aataacttaa ctaaagggct ctgtactata aattcatggc acatatatgg gaaagacaat    300
gcagtaagaa ttggagagag ctcggatgtt ttagtcacaa gagaacccta tgtttcatgc    360
gacccagatg aatgcaggtt ctatgctctc agccaaggaa caacaatcag agggaaacac    420
tcaaacggaa caatacacga taggtcccag tatcgcgccc tgataagctg gccactatca    480
tcaccgccca cagtgtacaa cagcagggtg gaatgcattg ggtggtcaag tactagttgc    540
catgatggca aatccaggat gtcaatatgt atatcaggac caaacaacaa tgcatctgca    600
gtagtatggt acaacagaag gcctgttgca gaaattaaca catgggcccg aaacatacta    660
agaacacagg aatctgaatg tgtatgccac aacggcgtat gcccagtagt gttcaccgat    720
gggtctgcca ctggacctgc agacacaaga atatactatt ttaaagaggg gaaaatattg    780
aaatgggagt ctctgactgg aactgctaag catattgaag aatgctcatg ttacggggaa    840
cgaacaggaa ttacctgcac atgcagggac aattggcagg gctcaaatag accagtgatt    900
cagatagacc cagtagcaat gacacacact agtcaatata tatgcagtcc tgttcttaca    960
gacaatcccc gaccgaatga cccaaatata ggtaagtgta atgaccctta tccaggtaat   1020
aataacaatg gagtcaaggg attctcatac ctggatgggg ctaacacttg gctagggagg   1080
acaataagca cagcctcgag gtctggatac gagatgttaa aagtgccaaa tgcattgaca   1140
gatgatagat caaagcccat tcaaggtcag acaattgtat taaacgctga ctggagtggt   1200
tacagtggat ctttcatgga ctattgggct gaaggggact gctatcgagc gtgtttttat   1260
gtggagttga tacgtggaag acccaaggaa gataaagtgt ggtggaccag caatagtata   1320
gtatcgatgt gttccagtac agaattcctg ggacaatgga actggcctga tggggctaaa   1380
atagagtact tcctctaa                                                 1398
```

<210> SEQ ID NO 23
<211> LENGTH: 464
<212> TYPE: PRT
<213> ORGANISM: Influenza virus

<400> SEQUENCE: 23

```
Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95
```

```
Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Ile Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Phe Lys Glu Gly
                245                 250                 255

Lys Ile Leu Lys Trp Glu Ser Leu Thr Gly Thr Ala Lys His Ile Glu
            260                 265                 270

Glu Cys Ser Cys Tyr Gly Glu Arg Thr Gly Ile Thr Cys Thr Cys Arg
        275                 280                 285

Asp Asn Trp Gln Gly Ser Asn Arg Pro Val Ile Gln Ile Asp Pro Val
    290                 295                 300

Ala Met Thr His Thr Ser Gln Tyr Ile Cys Ser Pro Val Leu Thr Asp
305                 310                 315                 320

Asn Pro Arg Pro Asn Asp Pro Asn Ile Gly Lys Cys Asn Asp Pro Tyr
                325                 330                 335

Pro Gly Asn Asn Asn Asn Gly Val Lys Gly Phe Ser Tyr Leu Asp Gly
            340                 345                 350

Ala Asn Thr Trp Leu Gly Arg Thr Ile Ser Thr Ala Ser Arg Ser Gly
        355                 360                 365

Tyr Glu Met Leu Lys Val Pro Asn Ala Leu Thr Asp Asp Arg Ser Lys
    370                 375                 380

Pro Ile Gln Gly Gln Thr Ile Val Leu Asn Ala Asp Trp Ser Gly Tyr
385                 390                 395                 400

Ser Gly Ser Phe Met Asp Tyr Trp Ala Glu Gly Asp Cys Tyr Arg Ala
                405                 410                 415

Cys Phe Tyr Val Glu Leu Ile Arg Gly Arg Pro Lys Glu Asp Lys Val
            420                 425                 430

Trp Trp Thr Ser Asn Ser Ile Val Ser Met Cys Ser Ser Thr Glu Phe
        435                 440                 445

Leu Gly Gln Trp Asn Trp Pro Asp Gly Ala Lys Ile Glu Tyr Phe Leu
    450                 455                 460
```

<210> SEQ ID NO 24
<211> LENGTH: 1683
<212> TYPE: DNA
<213> ORGANISM: Influenza virus

<400> SEQUENCE: 24

```
atgaacactc aaatcctggt attcgctctg attgcgatca ttccaacaaa tgcagacaaa     60
```

```
atctgcctcg gacatcatgc tgtgtcaaac ggaaccaaag taaacacatt aactgaaaga    120

ggagtggaag tcgtcaatgc aactgaaaca gtggaacgaa caaacatccc caggatctgc    180

tcaaaaggga aaaggacagt tgacctcggt caatgtggac tcctggggac aatcactgga    240

ccacctcaat gtgaccaatt cctagaattt tcagccgatt taattattga gaggcgagaa    300

ggaagtgatg tctgttatcc tgggaaattc gtgaatgaag aagctctgag gcaaattctc    360

agagaatcag gcggaattga caaggaagca atgggattca catacagtgg aataagaact    420

aatggagcaa ccagttcatg taggagatca ggatcttcat tctatgcaga aatgaaatgg    480

ctcctgtcaa acacagataa tgctgcattc ccgcagatga ctaagtcata taaaaataca    540

agaaaaaacc cagctctaat agtatggggg atccatcatt ccggatcaac tgcagagcaa    600

accaagctat atgggagtgg aaacaaactg gtgacagttg ggagttctaa ttatcaacaa    660

tcttttgtac cgagtccggg agcgagaaca caagttaatg gtcaatctgg aagaattgac    720

tttcattggc taatgctaaa tcccaatgat acagtcactt tcagtttcaa tggggctttc    780

atagctccag accgtgcaag cttcctgaga ggaaaatcta tgggaatcca gagtggagta    840

caggttgatg ccgattgtga aggggactgc tattatagtg gagggacaat aataagtaac    900

ttgccatttc agaacataga tagcagggca gttggaaaat gtccgagata tgttaagcaa    960

aggagtctgc tgctagcaac agggatgaag aatgttcctg agattccaaa gggaagaggc   1020

ctatttggtg ctatagcggg tttcattgaa aatggatggg aaggcctaat tgatggttgg   1080

tatggtttca gacaccagaa tgcacaggga gagggaactg ctgcagatta caaaagcact   1140

caatcggcaa ttgatcaaat aacaggaaaa ttaaaccggc ttatagaaaa aaccaaccaa   1200

caatttgagt tgatagacaa tgaattcact gaggtagaga agcaaatcgg taatgtgata   1260

aattggacca gagattctat aacagaagtg tggtcataca atgctgaact cttggtagca   1320

atggagaacc agcatacaat tgatctggct gattcagaaa tggacaaact gtacgaacga   1380

gtgaaaagac agctgagaga gaatgctgaa gaagatggca ctggttgctt tgaaatattt   1440

cacaagtgtg atgatgactg tatggccagc attagaaata acacctatga tcacagcaaa   1500

tacagggaag aggcaatgca aaatagaata cagattgacc cagtcaaact aagcagcggc   1560

tacaaagatg tgatactttg gtttagcttc ggggcatcat gtttcatact tctagccatt   1620

gcaatgggcc ttgtcttcat atgtgtaaag aatggaaaca tgcggtgcac tatttgtata   1680

taa                                                                 1683
```

<210> SEQ ID NO 25
<211> LENGTH: 560
<212> TYPE: PRT
<213> ORGANISM: Influenza virus

<400> SEQUENCE: 25

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80
```

-continued

```
Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ser Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asn Pro Ala Leu Ile Val Trp Gly Ile His
            180                 185                 190

His Ser Gly Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Thr Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asp Cys Glu Gly
        275                 280                 285

Asp Cys Tyr Tyr Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Val Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495
```

```
Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Ala Met Gly Leu
    530                 535                 540

Val Phe Ile Cys Val Lys Asn Gly Asn Met Arg Cys Thr Ile Cys Ile
545                 550                 555                 560


<210> SEQ ID NO 26
<211> LENGTH: 1398
<212> TYPE: DNA
<213> ORGANISM: Influenza virus

<400> SEQUENCE: 26

atgaatccaa atcagaagat tctatgcact tcagccactg ctatcataat aggcgcaatc      60

gcagtactca ttggaatagc aaacctagga ttgaacatag gactgcatct aaaaccgagc     120

tgcaattgct cacactcaca acctgaaaca accaacacaa gccaaacaat aataaacaac     180

tattataatg aaacaaacat caccaacatc caaatggaag agagaacaag caggaatttc     240

aataacttaa ctaaagggct ctgtactata aattcatggc acatatatgg gaaagacaat     300

gcggtaagaa ttggagagag ctcggatgtt ttagtcacaa gagaacccta tgtttcatgc     360

gacccagatg aatgcaggtt ctatgctctc agccaaggaa caacaatcag aggaaaacac     420

tcaaacggaa caatacacga taggtcccag tatcgcgccc tgataagctg gccactatca     480

tcaccgccca cagtgtacaa cagcagggtg gaatgcattg ggtggtcaag tactagttgc     540

catgatggca aatccaggat gtcaatatgt atatcaggac caaacaacaa tgcatctgca     600

gtagtatggt acaacagaag gcctgttgca gaaattaaca catgggcccg aaacatacta     660

agaacacagg aatctgaatg tgtatgccac aacggcgtat gcccagtagt gttcaccgat     720

gggtctgcca ctggacctgc agacacaaga atatactatt ttaaagaggg gaaaatattg     780

aaatgggagt ctctgactgg aactgctaag catattgaag aatgctcatg ttacggggaa     840

cgaacaggaa ttacctgcac atgcaaggac aattggcagg gctcaaatag accagtgatt     900

cagatagatc cagtagcaat gacacacact agtcagtata tatgcagtcc tgttcttaca     960

gacaatcccc gaccgaatga cccaaatata ggtaagtgta atgaccctta tccaggtaat    1020

aataacaatg gagtcaaggg attctcatac ctggatgggg ctaacacttg gctagggagg    1080

acaataagca cagcctcgag gtctggatac gagatgttaa aagtgccaaa tgcattgaca    1140

gatgatagat caaagcccat tcaaggtcag acaattgtat taaacgctga ctggagtggt    1200

tacagtggat ctttcatgga ctattgggct gagggggact gctatcgagc gtgtttttat    1260

gtggaattga tacgtggaag acccaaggag gataaagtgt ggtggaccag caatagtata    1320

gtatcgatgt gttccagtac agaattcctg ggacaatgga actggcctga tggggctaaa    1380

atagagtact tcctctaa                                                  1398


<210> SEQ ID NO 27
<211> LENGTH: 462
<212> TYPE: PRT
<213> ORGANISM: Influenza virus

<400> SEQUENCE: 27

Met Asn Pro Asn Gln Lys Ile Leu Cys Thr Ser Ala Thr Ala Ile Ile
1               5                   10                  15
```

-continued

```
Ile Gly Ala Ile Ala Val Leu Ile Gly Ile Ala Asn Leu Gly Leu Asn
            20                  25                  30

Ile Gly Leu His Leu Lys Pro Ser Cys Asn Cys Ser His Ser Gln Pro
        35                  40                  45

Glu Thr Ile Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Ile Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Trp Trp Tyr Asn Arg Arg Pro Val
        195                 200                 205

Ala Glu Ile Asn Thr Trp Ala Arg Asn Ile Leu Arg Thr Gln Glu Ser
    210                 215                 220

Glu Cys Val Cys His Asn Gly Val Cys Pro Trp Phe Thr Asp Gly Ser
225                 230                 235                 240

Ala Thr Gly Pro Ala Asp Thr Arg Ile Tyr Tyr Phe Lys Glu Gly Lys
                245                 250                 255

Leu Lys Trp Glu Ser Leu Thr Gly Thr Ala Lys His Ile Glu Glu Cys
            260                 265                 270

Ser Cys Tyr Gly Glu Arg Thr Gly Ile Thr Cys Thr Cys Lys Asp Asn
        275                 280                 285

Trp Gln Gly Ser Asn Arg Pro Val Ile Gln Ile Asp Pro Val Ala Met
    290                 295                 300

Thr His Thr Ser Gln Tyr Ile Cys Ser Pro Val Leu Thr Asp Asn Pro
305                 310                 315                 320

Arg Pro Asn Asp Pro Asn Ile Gly Lys Cys Asn Asp Pro Tyr Pro Gly
                325                 330                 335

Asn Asn Asn Asn Gly Val Lys Gly Phe Ser Tyr Leu Asp Gly Ala Asn
            340                 345                 350

Thr Trp Leu Gly Arg Thr Ile Ser Thr Ala Ser Arg Ser Gly Tyr Glu
        355                 360                 365

Met Leu Lys Val Pro Asn Ala Leu Thr Asp Asp Arg Ser Lys Pro Ile
    370                 375                 380

Gln Gly Gln Thr Ile Val Leu Asn Ala Asp Trp Ser Gly Tyr Ser Gly
385                 390                 395                 400
```

-continued

```
Ser Phe Met Asp Tyr Trp Ala Glu Gly Asp Cys Tyr Arg Ala Cys Phe
                405                 410                 415

Tyr Val Glu Leu Ile Arg Gly Arg Pro Lys Glu Asp Lys Val Trp Trp
            420                 425                 430

Thr Ser Asn Ser Ile Val Ser Met Cys Ser Ser Thr Glu Phe Leu Gly
        435                 440                 445

Gln Trp Asn Trp Pro Asp Gly Ala Lys Ile Glu Tyr Phe Leu
    450                 455                 460
```